US011612577B2

(12) United States Patent
Cornelius et al.

(10) Patent No.: US 11,612,577 B2
(45) Date of Patent: Mar. 28, 2023

(54) BIOMARKERS OF METAP2 INHIBITORS AND APPLICATIONS THEREOF

(71) Applicant: SynDevRx, Inc., Cambridge, MA (US)

(72) Inventors: Peter Cornelius, Framingham, MA (US); James Shanahan, Cambridge, MA (US)

(73) Assignee: SynDevRx, Inc., Cambridge, MA (US)

( * ) Notice: Subject to any disclaimer, the term of this patent is extended or adjusted under 35 U.S.C. 154(b) by 230 days.

(21) Appl. No.: 16/666,249

(22) Filed: Oct. 28, 2019

(65) Prior Publication Data

US 2020/0129457 A1     Apr. 30, 2020

Related U.S. Application Data

(60) Provisional application No. 62/844,271, filed on May 7, 2019, provisional application No. 62/751,335, filed on Oct. 26, 2018.

(51) Int. Cl.
*A61K 31/164* (2006.01)
*A61P 3/10* (2006.01)
*A61K 31/336* (2006.01)

(52) U.S. Cl.
CPC .............. *A61K 31/164* (2013.01); *A61P 3/10* (2018.01)

(58) Field of Classification Search
CPC ........ A61K 31/164; A61K 31/336; A61P 3/10
USPC ................................. 514/620; 549/546, 561
See application file for complete search history.

(56) References Cited

U.S. PATENT DOCUMENTS

| | | | |
|---|---|---|---|
| 4,997,878 A | 3/1991 | Bock et al. |
| 5,037,883 A | 8/1991 | Kopecek et al. |
| 5,037,957 A | 8/1991 | Grubb et al. |
| 5,166,172 A | 11/1992 | Kishimoto et al. |
| 5,258,453 A | 11/1993 | Kopecek et al. |
| 5,773,522 A | 6/1998 | Angelucci et al. |
| 6,063,812 A | 5/2000 | Hong et al. |
| 6,291,671 B1 | 9/2001 | Inoue et al. |
| 6,306,819 B1 | 10/2001 | Rubnick et al. |
| 6,436,912 B1 | 8/2002 | Inoue et al. |
| 6,464,850 B1 | 10/2002 | Zhang et al. |
| 6,548,477 B1 | 4/2003 | Olson et al. |
| 6,759,509 B1 | 7/2004 | King et al. |
| 6,803,438 B1 | 10/2004 | Brocchini et al. |
| 6,811,788 B2 | 11/2004 | Yu |
| 6,811,996 B1 | 11/2004 | Inoue et al. |
| 6,835,807 B1 | 12/2004 | Susaki et al. |
| 6,949,584 B2 | 9/2005 | Folkman et al. |
| 7,041,818 B2 | 5/2006 | Susaki et al. |
| 7,091,186 B2 | 8/2006 | Senter et al. |
| 7,223,837 B2 | 5/2007 | De Groot et al. |
| 7,332,523 B2 | 2/2008 | Folkman et al. |
| 7,553,816 B2 | 6/2009 | Senter et al. |
| 7,700,280 B2 | 4/2010 | Al-Murrani |
| 7,943,569 B2 | 5/2011 | Gemeinhart et al. |
| 8,349,891 B2 | 1/2013 | Crawford et al. |
| 8,367,721 B2 | 2/2013 | Huges et al. |
| 8,399,512 B2 | 3/2013 | Akullian et al. |
| 9,067,913 B2 | 6/2015 | Vath |
| 9,173,956 B2 | 11/2015 | Petersen |
| 9,320,805 B2 | 4/2016 | Petersen |
| 9,433,600 B2 | 9/2016 | Petersen |
| 9,585,909 B2 | 3/2017 | Petersen |
| 9,730,955 B2 | 8/2017 | Petersen |
| 9,750,737 B2 | 9/2017 | Petersen |
| 9,757,373 B2 | 9/2017 | Petersen |
| 9,969,722 B2 | 5/2018 | Petersen et al. |
| 10,010,544 B2 | 7/2018 | Petersen et al. |
| 10,159,692 B2 | 12/2018 | Petersen et al. |
| 11,273,142 B2 | 3/2022 | Shanahan et al. |
| 2002/0076442 A1 | 6/2002 | Burke et al. |
| 2004/0001801 A1 | 1/2004 | Madison et al. |
| 2004/0116348 A1 | 6/2004 | Chau et al. |
| 2004/0229945 A1 | 11/2004 | Satchi-Fainaro et al. |
| 2005/0036948 A1 | 2/2005 | Kasina et al. |
| 2006/0206948 A1 | 9/2006 | Zhao |
| 2006/0276512 A1 | 12/2006 | Han et al. |
| 2007/0142302 A1 | 6/2007 | Mitra et al. |
| 2007/0287680 A1 | 12/2007 | Cuchelkar et al. |
| 2008/0112919 A1 | 5/2008 | Satchi-Fainaro et al. |
| 2008/0248030 A1 | 10/2008 | Folkman et al. |

(Continued)

FOREIGN PATENT DOCUMENTS

| | | |
|---|---|---|
| CA | 1305053 | 7/1992 |
| EP | 0673258 B1 | 5/2003 |

(Continued)

OTHER PUBLICATIONS

Anderson, "The Process of Structure-Baed Drug Design", Chemistry & Biology, 2003, vol. 10, p. 787-797.
André et al. "Alpelisib (ALP) 1 fulvestrant (FUL) for advanced breast cancer (ABC): Results of the phase III SOLAR-1 trial", Annals of Oncology, 2018, vol. 29, Suppl. 8, 1 page.
Andre et al. "SOLAR-1: A phase III study of alpelisib + fulvestrant in men and postmenopausal women with HR+/HER2-advanced breast cancer (BC) progressing on or after prior aromatase inhibitor therapy.", Journal of Clinical Oncology, 2016, Clinical trial information: NCT02437318, 2016, 1 page.

(Continued)

*Primary Examiner* — Joseph R Kosack
*Assistant Examiner* — Sagar Patel
(74) *Attorney, Agent, or Firm* — Cooley LLP; Matthew Pavao; Robert Powers

(57) ABSTRACT

The present disclosure relates to small molecule or polymer conjugated MetAP2 inhibitors. The present disclosure also relates to methods of treating, or ameliorating at least one symptom of metabolic dysfunction associated with a treatment in a subject having a disease, such as cancer. The present disclosure also relates to methods of treating, or ameliorating at least one symptom of cancer comprising administering a combination of a polymer conjugated MetAP2 inhibitors and at least one second agent wherein the second agent may induce metabolic dysfunction.

14 Claims, 47 Drawing Sheets

(56) References Cited

U.S. PATENT DOCUMENTS

| | | |
|---|---|---|
| 2009/0093014 A1 | 4/2009 | Burnet et al. |
| 2010/0111894 A1 | 5/2010 | Benny-Ratsaby et al. |
| 2011/0263561 A1 | 10/2011 | Heinrich et al. |
| 2011/0294952 A1 | 12/2011 | Petersen |
| 2013/0064832 A1 | 3/2013 | Aikawa et al. |
| 2013/0137831 A1 | 5/2013 | Petersen |
| 2013/0216494 A1 | 8/2013 | Petersen |
| 2014/0308235 A1 | 10/2014 | Petersen |
| 2015/0141580 A1 | 5/2015 | Petersen et al. |
| 2015/0374657 A1 | 12/2015 | Petersen |
| 2016/0184345 A1 | 6/2016 | Petersen |
| 2016/0256483 A1 | 9/2016 | Petersen |
| 2016/0346244 A1 | 12/2016 | Petersen |
| 2017/0028014 A1 | 2/2017 | Petersen |
| 2017/0196830 A1 | 7/2017 | Shanahan et al. |
| 2017/0258925 A1 | 9/2017 | Petersen |
| 2018/0271856 A1 | 9/2018 | Petersen et al. |
| 2018/0291010 A1 | 10/2018 | Petersen et al. |
| 2022/0280470 A1 | 9/2022 | Shanahan et al. |

FOREIGN PATENT DOCUMENTS

| | | |
|---|---|---|
| WO | WO 99/57098 A2 | 11/1999 |
| WO | WO 2003/086382 A1 | 10/2003 |
| WO | WO 2004/110358 A2 | 12/2004 |
| WO | WO 2008/011114 | 1/2008 |
| WO | WO 2009/036108 A1 | 3/2009 |
| WO | WO 2009/051706 A2 | 4/2009 |
| WO | WO 2009/073445 | 6/2009 |
| WO | WO 2009/141826 A2 | 11/2009 |
| WO | WO 2010/003475 A2 | 1/2010 |
| WO | WO 2010/065877 A2 | 6/2010 |
| WO | WO 2010/096603 A2 | 8/2010 |
| WO | WO 2011/127304 A2 | 10/2011 |
| WO | WO 2011/150022 A2 | 12/2011 |
| WO | WO 2011/150088 A1 | 12/2011 |
| WO | WO 2012/122264 A1 | 9/2012 |
| WO | WO 2014/169026 A1 | 10/2014 |
| WO | WO 2017/100553 | 6/2017 |
| WO | WO 2017/123603 | 7/2017 |
| WO | WO 2018/027084 | 2/2018 |

OTHER PUBLICATIONS

Ansari et al. "The Programmed Death-1 (PD-1) Pathway Regulates Autoimmune Diabetes in Nonobese Diabetic (NOD) Mice", J. Exp. Med. 2003, vol. 198, No. 1, p. 63-69.
Arico-Muendel, C.C. et al., "Carbamate Analogues of Fumagillin as Potent, Targeted Inhibitors of Methionine Aminopeptidase-2", J. Med. Chem., 52:8047-8056 (2009).
Bae, J. Diabetes and its Complications, (2016) v. 30, pp. 212-220.
Baillargeon et al. "Transient Hyperglycemia in Hispanic Children With Acute Lymphoblastic Leukemia", Pediatr Blood Cancer, 2005, vol. 45, p. 960-963.
Banerji et al. "A Phase I Open-Label Study to Identify a Dosing Regimen of the Pan-AKT Inhibitor AZD5363 for Evaluation in Solid Tumors and in PIK3CA-Mutated Breast and Gynecologic Cancers", Clinical Cancer Research, 2018, vol. 24, No. 9, p. 2050-2059.
Berge et al. "Pharmaceutical Salts" J. Pharm. Sci., 1977, vol. 66, No. 1, p. 1-19.
Bernier, S.G. et al., "Fumagillin class inhibitors of methionine aminopeptidase-2", Drugs of the Future, 30(5):497-508 (2005).
Blencowe, C.A. et al., "Self-immolative linkers in polymeric delivery systems", Polym. Chem., 2:773-790 (2011).
Brahmer et al. "Safety and Activity of Anti-PD-L1 Antibody in Patients with Advanced Cancer", The New England Journal of Medicine, 2012, vol. 366, No. 26, p. 2455-2465.
Brakenhielm et al. "Angiogenesis Inhibitor, TNP-470, Prevents Diet-Induced and Genetic Obesity in Mice", Circulation Research, 2004, vol. 94, p. 1579-1588.
Busaidy et al. "Management of Metabolic Effects Associated With Anticancer Agents Targeting the PI3K-Akt-mTOR Pathway", Journal of Clinical Oncology, 2012, vol. 30, No. 23, p. 2919-2928.

Chang, "Common TherapeuticTarget for Both Cancer and Obesity", World Journal of Biological Chemistry, 2017, vol. 8, No. 2, p. 102-107.
Chau, Y. et al., "Antitumor efficacy of a novel polymer-peptide-drug conjugate in human tumor xenograft models", Int. J. Cancer, 118:1519-1526 (2006).
Clements et al. "Frontline Science: High fat diet and leptin promote tumor progression by inducingmyeloid-derived suppressor cells", Journal of Leukocyte Biology, 2018, vol. 103, p. 395-407.
Davies et al. "The Role of the PI3K-AKT Pathway in Melanoma", The Cancer Journal, 2012, vol. 18, No. 2, p. 142-147.
D'Souza, A.J.M. et al., "Release from Polymeric Prodrugs: Linkages and Their Degradation", J. Pharm. Sci., 93(8):1962-1979 (2004).
Ducry, L. and Stump, B., "Antibody-Drug Conjugates: Linking Cytotoxic Payloads to Monoclonal Antibodies", Bioconj. Chem., 21:5-13 (2010).
Esposito et al. "The metabolic syndrome and inflammation: association or causation?" Nutr. Metab. Cardiovasc. Dis. 14(5):228-232 (2004).
Feng et al. "Secondary diabetes associated with 5-fluorouracil-based chemotherapy regimens in non-diabetic patients with colorectal cancer: results from a single-centre cohort study", Colorectal Disease, 2012, vol. 15, p. 27-33.
Golub et al. "Molecular Classification of Cancer: Class Discovery and Class Prediction by Gene Expression Monitoring", Science, vol. 286, (1999), pp. 531-537.
Goktas et al., "Prostate Cancer and Adiponectin", Adult Urology, 2005, 65 (6), p. 1168-1172.
Goncalves et al. "Phosphatidylinositol 3-Kinase, Growth Disorders, and Cancer", The New England Journal of Medicine, 2018, vol. 379, p. 2052-2062.
Han, C.K. et al., "Design and synthesis of highly potent fumagillin analogues from homology modeling for a human MetAP-2", Biorg. Med. Chem. Lett., 10:39-43 (2000).
Herbst, R.S. et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology, 20(22):4440-4447 (2002).
Hopkins et al. "Suppression of insulin feedback enhances the efficacy of PI3K inhibitors", Nature, 2018, vol. 560, No. 7719, p. 499-503.
Hori et al. "Control of Regulatory T Cell Development by the Transcription Factor Foxp3", Science, 2003, vol. 299, p. 1057-1061.
Hudes et al. "Temsirolimus, Interferon Alfa, or Both for Advanced Renal-Cell Carcinoma", The New England Journal of Medicine, 2007, vol. 356, p. 2271-2281.
Hughes, Thomas. ZGN-201 (ZGN), a Methionine Aminopeptidase 2 (MetAP2) Inhibitor, Durably Eliminates Excess Body Fat in Obese Mice Through Regulation of Fat Metabolism and Food Intake. American Diabetes Association. 2010. Abstract No. 1803-P.
Hughes et al. "Precipitation of Autoimmune Diabetes With Anti-PD-1 Immunotherapy", Diabetes Care, 2015, vol. 38, p, e55-e57.
Hwangbo et al. "Acute Hyperglycemia Associated with Anti-Cancer Medication", Endocrinology Metab., 2017, vol. 32, p. 23-29.
Janku et al. "PIK3CA Mutations in Patients with Advanced Cancers Treated with PI3K/AKT/mTOR Axis Inhibitors", Molecular Cancer Therapeutics, 2011, vol. 10, No. 3, p. 558-565.
Jeong, B-S. et al., "Total synthesis and antiangiogenic activity of cyclopentane analogues of fumagillol", Bioorganic and Medicinal Chemistry Letters, 15:3580-3583 (2005).
Joharapurkar et al. "Inhibition of the methionine aminopeptidase 2 enzyme for the treatment of obesity." Diabetes, Metaboloic Syndrome & Obesity: Targets and Therapy, 2014:7, pp. 73-84.
Jones et al. "Capivasertib (AZD5363) plus fulvestrant versus placebo plus fulvestrant after relapse or progression on an aromatase inhibitor in metastatic ER-positive breast cancer (FAKTION): A randomized, double-blind, placebocontrolled, phase II trial", Journal of Clinical Oncology, 2019, vol. 37, No. 15, p. 1005-1006.
Kahn et al., "Mechanisms linking obesity to insulin resistance and type 2 diabetes," Nature, v. 444, 2006, pp. 840-846.

(56) References Cited

OTHER PUBLICATIONS

Kim et al., "5-Demethoxyfumagillol, a Potent Angiogenesis Inhibitor Isoloated from Aspergillus fumigatus", Chem. Pharm. Bull., 52(4): 447-450 (2004).
Kim et al. "Assessment of the anti-obesity effects of the TNP-470 analog, CKD-732", Journal of Molecular Endocrinology, 2007, vol. 38, p. 455-465.
Klok M. D. et al., "The role of leptin and ghrelin in the regulation of food intake and body weight in humans: a review", Obesity Reviews (2007), vol. 8, pp. 21-34.
Law and Tung, "Proteolysis: A Biological Process Adapted in Drug Delivery, Therapy, and Imaging", Bioconjugate Chem., 20:1683-1695 (2009).
Lee, H.W. et al., "Design, Synthesis, and Antiangiogenic Effects of a Series of Potent Novel Fumagillin Analogues", Chem. Pharm. Bull., 55(7):1024-1029 (2007).
Lijnen et al. "Fumagillin Reduces Adipose Tissue Formation in Murine Models of Nutritionally Induced Obesity", Obesity, 2010, vol. 18, No. 12, p. 2241-2246.
Mann-Steinberg and Satchi-Fainaro, "TNP-470: The Resurrection of the First Synthetic Angiogenesis Inhibitor", Folkman and Figg, Angiogenesis: An Integrative Approach from Science to Medicine, 35:395-414 (2008).
Martyn et al. "Obesity-Induced Insulin Resistance and Hyperglycemia: Etiological Factors and Molecular Mechanisms", Anesthesiology, 2008, vol. 109, No. 1, p. 137-148.
Mason and Joyce. "Proteolytic Networks in Cancer." Trends in Cell Biology. 21(4) pp. 228-237 (2011).
Motzer et al. "Efficacy of everolimus in advanced renal cell carcinoma: a double-blind, randomised, placebo-controlled phase III trial", Lancet 2008, vol. 372, p. 449-456.
Murphy et al. "Cutting Edge: Elevated Leptin during Diet-Induced Obesity Reduces the Efficacy of Tumor Immunotherapy", The Journal of Immunology, 2018, p. 1837-1841.
Okwan-Duodu D. et al. "Obesity-driven inflammation and cancer risk: role of myeloid derived suppressor cells and alternately activated macrophages", Am J Cancer Res 2013, vol. 3, No. 1, p. 21-33.
Ostrand-Rosenberg "Myeloid derived-suppressor cells: their role in cancer and obesity", Science Direct, Current Opinion in Immunology, 2018, vol. 51, p. 68-75.
Popovic et al. "Arginine and Immunity", The Journal of Nutrition, 6th Amino Acid Assessment Workshop, 2007, p. 1681S-1686S.
Satchi-Fainaro, R. et al., "Targeting angiogenesis with a conjugate of HPMA copolymer and TNP-470", Nature Med., 10(3): 255-261 (2004).
Segal, E. et al., "Design and development of polymer conjugates as anti-angiogenic agents", Adv. Drug. Reviews, 61 (13): 1159-1176 (2009).
Shimizu et al. "Immune suppression and reversal of the suppressive tumor microenvironment", International Immunology, 2018, vol. 30, No. 10, pp. 445-455.
Shiose, Y. et al., "Relationship between Drug Release of DE-310, Macromolecular Prodrug of DX-8951f, and Cathepsins Activity in Several Tumors", Biol. Pharm. Bull., 30(12):2365-2370 (2007).
Shiose, Y. et al., "Systematic Research of Peptide Spacers Controlling Drug Release from Macromolecular Prodrug System, Carboxymethyldextran Polyalcohol-Peptide-Drug Conjugates", Bioconjugate Chem., 20(1):60-70 (2009).
Silha et al. "Angiogenic factors are elevated in overweight and obese individuals", International Journal of Obesity, 2005, vol. 29, p. 1308-1314.
Siviero-Miachon et al. "Hyperglycemia in Cancer Survivors: From Diagnosis through Survivorship", J Metabolic Synd, 2013, vol. 3, Issue 1, 2 pages.
Spinola-Castro et al. "Transient Hyperglycemia During Childhood Acute Lymphocytic Leukemia Chemotherapy: An Old Event Revisited", Clinical Advances in Hematology & Oncology, 2009, vol. 7, Issue 7, p. 465-472.
Strong et al. "Leptin produced by obese adipose stromal/stem cells enhances proliferation and metastasis of estrogen", Breast Cancer Research, 2015, vol. 17, 16 pages.
Subr, V. et al., "Poly[M-)2-hydroxypropyl)methacrylamide] Conjugates of Methotrexate Synthesis and in vitro Drug Release", J Controlled Release, 49:123-132 (1997).
Sutherland, J. et al. "The Metabolic Syndrome and Inflammation" Metabolic Syndrome and Related Disorders 2(2):82-104 (2004).
Thiel, "Structure-aided drug design's next generation", Nature Biotechnology, 2004, vol. 22, No. 5, p. 513-519.
Tran et al. "Clinical and pharmacokinetic study of TNP-470, an angiogenesis inhibitor, in combination with paclitaxel and carboplatin in patients with solid tumors", Cancer Chemother Pharmacol, 2004, vol. 54, p. 308-314.
Weber et al. "Myeloid-Derived Suppressor Cells Hinder the Anti-Cancer Activity of immune Checkpoint inhibitors", Frontiers in Immunology, 2018, vol. 9, Article 1310, 9 pages.
Wunderlich et al. "Mechanisms of chronic JAK-STAT3-SOCS3 signaling in obesity", Landes Bioscience, 213, vol. 2, e23878-1, 7 pages.
Xavier et al. "One-week intervention period led to improvements in glycemic control and reduction in DNA damage levels in patients with type 2 diabetes mellitus", Diabetes Research and Clinical Practice, 2014, vol. 105, p. 356-363.
Yu et al. "Present and future of cancer immunotherapy: A tumor microenvironment perspective (Review)", Oncology Letters, 2018, vol. 16, p. 4105-4113.
Zhang et al. "Cell cycle inhibition by the anti-angiogenic agent TNP-470 is mediated by p53 and p21", PNAS, 2000, vol. 97, No. 12, p. 6427-6432.

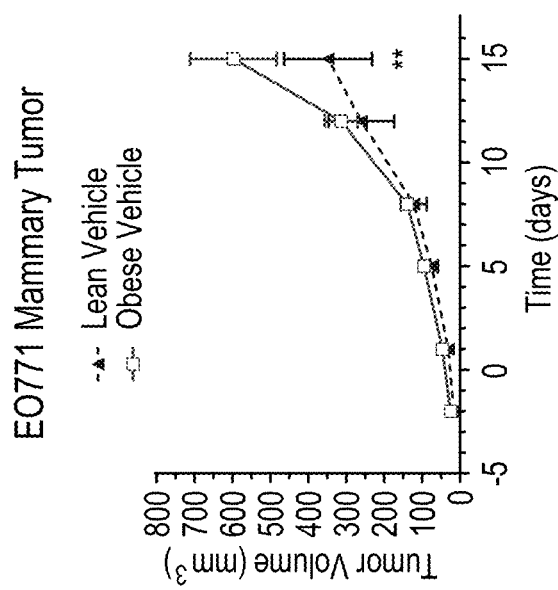

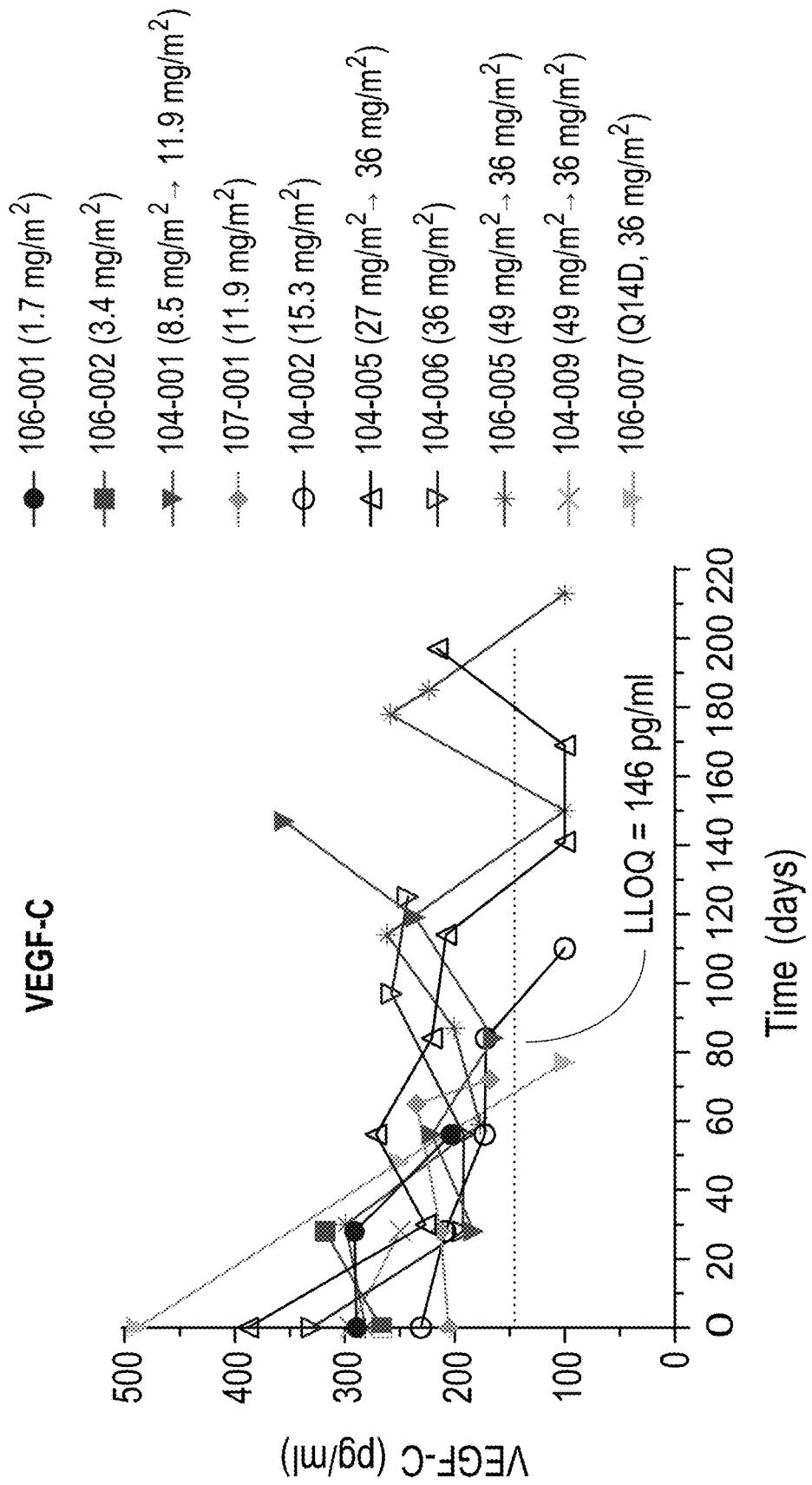

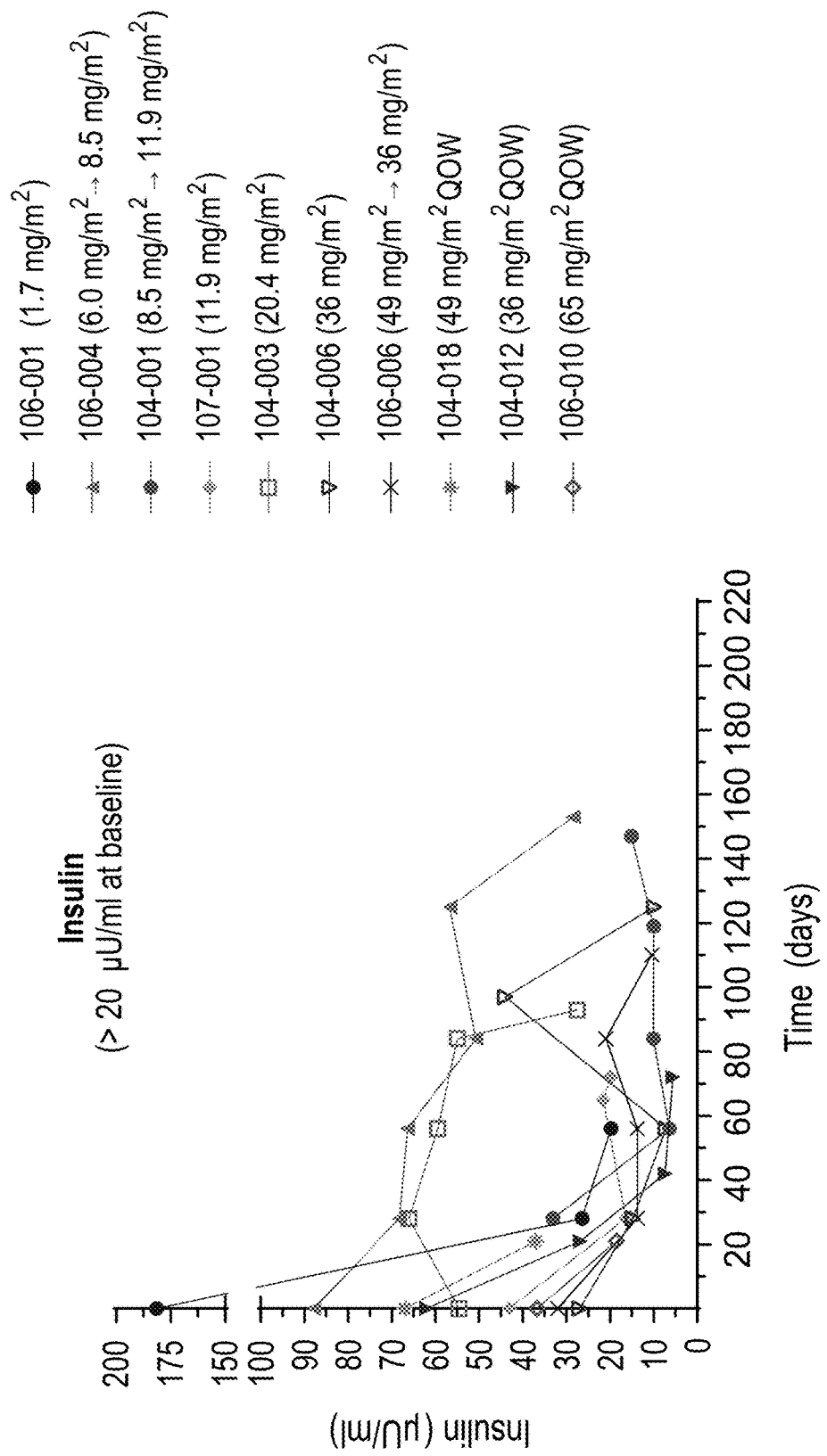

Small molecule fumagillin derivative of the invention showing temporal effects on cell survival (apoptosis) at increasing concentrations over 24 hours

BIOMARKERS OF METAP2 INHIBITORS AND APPLICATIONS THEREOF

RELATED APPLICATIONS

This application claims priority to, and the benefit of, U.S. Provisional Application No. 62/751,335, filed Oct. 26, 2018 and U.S. Provisional Application No. 62/844,271, filed May 7, 2019. The contents of each of the aforementioned patent applications are incorporated herein by reference in their entireties.

BACKGROUND OF THE INVENTION

Obesity and metabolic dysfunction are common disease states for populations around the world. This chronic state of disease leads to systemic inflammation, is pro-angiogenesis, pro-fibrotic and confers an immuno-suppressive state in many patients which complicates treatment for other co-morbidities, such as cancer. While the problem of obesity is increasing, an aging population is further complicating treatments as patient populations with multiple concomitant diseases require both methods of identifying which factors associated with obesity negatively impact upon other diseases and of offering therapeutics that may slow the progression or reverse these factors.

Traditional chemotherapies and targeted therapies have been shown to be less effective in obese cancer patients (Incio et al., Cancer Discov; (2016) 6(8); 852-69, Kruger et al., British Journal of Cancer (2018) 119:832-839). Recently, a new class of cancer treatments has emerged—immunotherapy—that shows clinical benefit in a significant percent of cancer patients. However, and quite unexpectedly, the majority of cancer patients still show resistance to immunotherapy treatments (Yu & Cui, 2018, Oncol. Lett. 16: 4105-41130). What is becoming clear is that cancer patients with obesity and/or metabolic dysfunction do not respond to treatments—including traditional chemotherapy and emerging therapies such as immunotherapy—in the same manner as their non-obese counterparts (Murphy et al., J Immunol 2018; 201:1837-1841). A major challenge is to identify which obesity-associated factor or factors are the key contributors to this unexpected treatment resistance and to reverse them.

Certain targeted treatments for cancer and other diseases lose their efficacy after a relatively short period of time. Recently, one mechanism explaining this loss of activity is "induced metabolic dysfunction"-including hyperglycemia leading to hyperinsulinemia—by the treatments themselves or by co-administered agents. Here, we show that treatment with Compounds of the instant disclosure improve the induced metabolic dysfunction, allowing for continued treatment with the therapeutic agent.

Metabolic dysfunction can be induced by cancer therapeutics, potentially limiting their efficacy. Hyperglycemia during chemotherapy occurs in approximately 10% to 30% of patients. Glucocorticoids and L-asparaginase are well known to cause acute hyperglycemia during chemotherapy. Long-term hyperglycemia is also frequently observed, especially in patients with hematologic malignancies treated with L-asparaginase-based regimens and total body irradiation. Glucocorticoid-induced hyperglycemia often develops because of increased insulin resistance, diminished insulin secretion, and exaggerated hepatic glucose output. depending on the type, dose, and delivery of the glucocorticoid formulation. The incidence of hyperglycemia (defined as blood glucose >200 mg/dL) in hospitalized patients treated with glucocorticoids without a known history of diabetes is >50%. Mammalian target of rapamycin (mTOR) inhibitors are associated with a high incidence of hyperglycemia, ranging from 13% to 50%. Immunotherapy induces hyperglycemia in patients treated with pembrolizumab, hyperglycemic events were reported in 45% to 49% of patients, and 3% to 6% experienced grade 3 or 4 hyperglycemia (Hwangbo et al., Endocrinol Metab (Seoul) 2017 March; 32(1): 23-29).

Cancer cells get much of their energy from glucose. To satisfy their increased need for glucose, the PI3K/AKT/mTOR pathway is frequently up-regulated (amplified) or mutated. There is a concerted effort to develop treatments that inhibit or down-regulate this pathway. However, inhibition of this pathway leads to on-target toxicities that stymie their efficacy by creating a hyperglycemia/hyperinsulinemia feedback loop, which leads to treatment failure.

Obesity increases circulating estrogen, insulin, IGF, and causes chronic, low-grade inflammation. These diverse effects converge either directly or indirectly to induce well-recognised tumor pathways, and contribute to the accumulation of myeloid derived suppressor cells, while re-programming macrophages to the alternatively activated, pro-inflammatory and immunosuppressive M2 phenotype. Among the many pathways affected by obesity are the pro-angiogenic factors VEGF, bFGF, IGF and PLGF (Silha et al., International Journal of Obesity (2005) 29, 1308-1314), and critical transcription factors including STAT3 (Wunderlich et al., (2013) Mechanisms of chronic JAK-STAT3-SOCS3 signaling in obesity, JAK-STAT, 2:2, e23878), plus multiple immune-suppressive factors, including myeloid-derived suppressor cells (MDSCs) (Ostrand-Rosenberg (2018) Myeloid derived-suppressor cells their role in cancer and obesity Current Opinion in Immunology 51:68-75). MDSCs and M2 macrophages are a major source of immunosuppression that allows for tumors to escape from effective host immune surveillance and resist anti-cancer treatments (Weber et al, *Front. Immunol.* 9:1310.doi: 10.3389/fimmu.2018.01310). The induction and preferential shift of macrophages towards the immunosuppressive M2 phenotype may be a primary physiologic and metabolic adaptive response to insulin insensitivity, as well a secondary consequence of an immune process in the setting of chronic, low grade inflammation. These processes may be modulated by tumor cells to promote angiogenesis, tumor cell motility and invasion, as well as metastasis and results in poor treatment outcomes (Okwan-Duodu et al., 2013).

A number of proteins responsible for limiting the clinical benefits of immunotherapy treatments have been identified. These include the enzymes indoleamine-pyrrole 2,3-dioxygenase (IDO-1) and arginase-1 (Arg-1), the cytokine IL-10 as well as the adipokine, leptin. Furthermore, infiltration of tumors by regulatory T cells (Tregs), alternately polarized ("M2") macrophages as well as myeloid-derived suppressor cells (MDSCs) are associated with tumor escape from immune surveillance and subsequent disease progression (Shimizu et al, *International Immunology*, 30(10): 445-455).

MetAP2 inhibitors have a long clinical history showing anti-tumor and anti-metabolic effects in animal studies as well as in human clinical trials (Tran et al, *Cancer Chemother. Pharmacol.* (2004) 54: 308-314; Joharapurkar et al, *Diabetes, Metabolic Syn. and Obesity: Targets and Therapy*, (2014), 7:73-84). Here, we show that the administration of MetAP2 inhibitors can suppress or reverse the expression or amount of some of these biomarkers, which is expected to result in improved clinical benefit for cancer patients who are obese and who may have metabolic dysfunction.

Recent work also implicates the adipokine leptin as a contributor to enhanced tumor growth in mouse models of obesity-accelerated breast cancer (Strong et al, Breast Cancer Research (2015) 17:112-27), as well as a mediator of obesity-associated resistance to immune therapy in a separate mouse model of obesity-accelerated renal cancer (Murphy et al, J. Immunol., 2018; 201:1837-41). One mechanism by which leptin facilitates obesity-accelerated cancer is by increasing the abundance of MDSCs (Clements et al, *J Leukoc Biol.* 2018; 103:395-407).

SUMMARY OF THE INVENTION

The present disclosure provides methods of modifying the expression of cells, tissues and/or proteins that otherwise impede the clinical activity of a variety of cancer treatments. In certain aspects, the subject is overweight, obese or has metabolic dysfunction.

The present disclosure provides a method for treating, or ameliorating at least one symptom of, cancer in a subject in need thereof comprising administering a therapeutically effective amount of at least one compound of the Formula

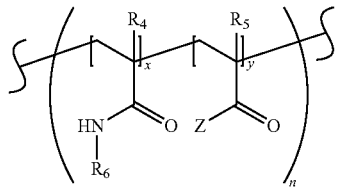

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

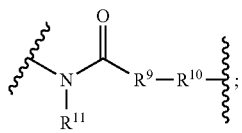

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, in combination with a therapeutically effective amount of at least one second active agent, wherein the at least one compound and the at least one second active agent are administered in amounts sufficient to treat, or ameliorate at least one symptom of, the cancer.

The present disclosure provides a combination comprising at least one compound of the Formula

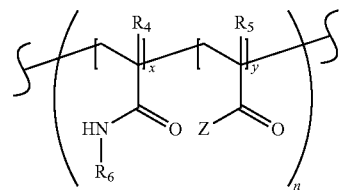

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

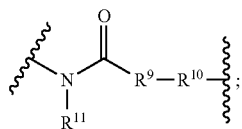

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, and at least one second active agent for use in a method for the treatment of, or amelioration of at least one symptom of, cancer in a subject, wherein the at least one compound and the at least one second active agent are for the administration to the subject in amounts sufficient to treat, or ameliorate at least one symptom of, the cancer.

The present disclosure provides a method of reducing the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof in a subject comprising administering a therapeutically effective amount of at least one compound of the Formula

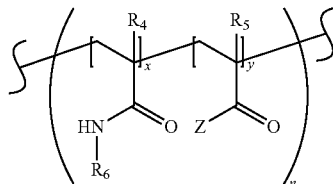

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —NH$_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

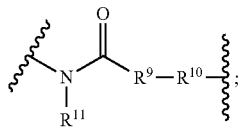

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, in combination with a therapeutically effective amount of at least one second active agent, wherein the at least one compound and the at least one second active agent are administered in amounts sufficient to reduce the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof.

The present disclosure provides a combination comprising at least one compound of the Formula

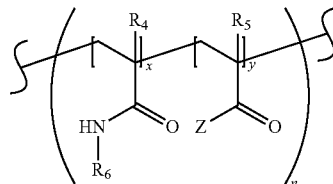

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —NH$_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

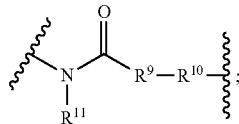

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, and at least one second active agent for use in a method of reducing the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof in a subject having cancer, wherein the at least one compound and the at least one second active agent are for the administration to the subject in amounts sufficient to reduce the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof.

The present disclosure provides a method for treating, or ameliorating at least one symptom of, cancer in a subject in need thereof comprising administering a therapeutically effective amount of at least one compound, or a pharmaceutically acceptable salt, prodrug, metabolite, analog or derivative thereof, represented by: Z-Q-X—Y—C(O)—W, wherein, independently for each occurrence, Z is —H, —$H_2N$-$AA_3$-$AA_4$-$AA_5$-$AA_6$-C(O)— or Z is $H_2N$-$AA_5$-$AA_6$-C(O); $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is alanine, asparagine, citrulline, glutamine, glycine, leucine, methionine, phenylalanine, serine, threonine, tryptophan, tyrosine, valine or $H_2N(CH_2)_mCO_2H$, wherein m is 2, 3, 4 or 5; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

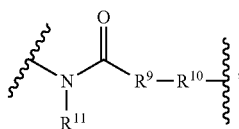

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety; p is 0 to 20; q is 2 or 3; and r is 1, 2, 3, 4, 5, or 6; in combination with a therapeutically effective amount of at least one second active agent wherein the at least one compound and the at least one second active agent are administered in amounts sufficient to treat, or ameliorate at least one symptom of, the cancer.

The present disclosure provides a combination comprising at least one compound, or a pharmaceutically acceptable salt, prodrug, metabolite, analog or derivative thereof, represented by: Z-Q-X—Y—C(O)—W, wherein, independently for each occurrence, Z is —H, —$H_2N$-$AA_3$-$AA_4$-$AA_5$-$AA_6$-C(O)— or Z is $H_2N$-$AA_5$-$AA_6$-C(O); $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is alanine, asparagine, citrulline, glutamine, glycine, leucine, methionine, phenylalanine, serine, threonine, tryptophan, tyrosine, valine or $H_2N(CH_2)_mCO_2H$, wherein m is 2, 3, 4 or 5; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

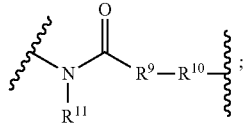

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety; p is 0 to 20; q is 2 or 3; and r is 1, 2, 3, 4, 5, or 6, and at least one second active agent for use in a method for the treatment of, or amelioration of at least one symptom of, cancer in a subject, wherein the at least one compound, or a pharmaceutically acceptable salt, prodrug, metabolite, analog or derivative thereof, and the at least one second active agent are for the administration to the subject in amounts sufficient to treat, or ameliorate at least one symptom of, the cancer.

The present disclosure provides a method of reducing the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof in a subject comprising administering a therapeutically effective amount of at least one compound, or a pharmaceutically acceptable salt, prodrug, metabolite, analog or derivative thereof, represented by: Z-Q-X—Y—C(O)—W, wherein, independently for each occurrence, Z is —H, —$H_2N$-$AA_3$-$AA_4$-$AA_5$-$AA_6$-C(O)— or Z is $H_2N$-$AA_5$-$AA_6$-C(O); $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

AA$_5$ is a bond, or glycine, valine, tyrosine, tryptophan, phenylalanine, methionine, leucine, isoleucine, or asparagine; AA$_6$ is alanine, asparagine, citrulline, glutamine, glycine, leucine, methionine, phenylalanine, serine, threonine, tryptophan, tyrosine, valine or H$_2$N(CH$_2$)$_m$CO$_2$H, wherein m is 2, 3, 4 or 5; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, C$_5$-C$_8$ cycloalkyl, aryl, heteroaryl, NR, O, or S; Y is NR, O, or S; R is H or alkyl; V is a bond or

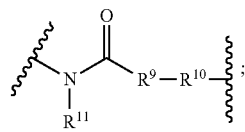

R$^9$ is alkyl, aryl, aralkyl, or a bond; or R$^9$ taken together with Y forms a heterocyclic ring; R$^{10}$ is amido or a bond; R$^{11}$ is H or alkyl; W is a MetAP2 inhibitor moiety; p is 0 to 20; q is 2 or 3; and r is 1, 2, 3, 4, 5, or 6, in combination with a therapeutically effective amount of at least one second active agent wherein the at least one compound and the at least one second active agent are administered in amounts sufficient to reduce the amount of at least one of IL-10, arginase-1, myeloid-derived suppressor cells (MDSC), regulatory T cells, leptin, PD-1, PD-L1, CTLA-4, a growth factor or any combination thereof.

The present disclosure provides a combination comprising at least one compound, or a pharmaceutically acceptable salt, prodrug, metabolite, analog or derivative thereof, represented by: Z-Q-X—Y—C(O)—W, wherein, independently for each occurrence, Z is —H, —H$_2$N-AA$_3$-AA$_4$-AA$_5$-AA$_6$-C(O)— or Z is H$_2$N-AA$_5$-AA$_6$-C(O); AA$_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_5$ is a bond, or glycine, valine, tyrosine, tryptophan, phenylalanine, methionine, leucine, isoleucine, or asparagine; AA$_6$ is alanine, asparagine, citrulline, glutamine, glycine, leucine, methionine, phenylalanine, serine, threonine, tryptophan, tyrosine, valine or H$_2$N(CH$_2$)$_m$CO$_2$H, wherein m is 2, 3, 4 or 5; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, C$_5$-C$_8$ cycloalkyl, aryl, heteroaryl, NR, O, or S; Y is NR, O, or S; R is H or alkyl; V is a bond or

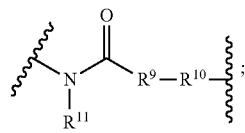

R$^9$ is alkyl, aryl, aralkyl, or a bond; or R$^9$ taken together with Y forms a heterocyclic ring; R$^{10}$ is amido or a bond; R$^{11}$ is H or alkyl; W is a MetAP2 inhibitor moiety; p is 0 to 20; q is 2 or 3; and r is 1, 2, 3, 4, 5, or 6, and at least one second active agent for use in a method of reducing the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof in a subject having cancer, wherein the at least one compound, or a pharmaceutically acceptable salt, prodrug, metabolite, analog or derivative thereof, and the at least one second active agent are for administration to the subject in amounts sufficient to reduce the amount of at least one of IL-10, arginase-1, myeloid-derived suppressor cells (MDSC), regulatory T cells, leptin, PD-1, PD-L1, CTLA-4, a growth factor or any combination thereof.

The present disclosure provides a method for treating, or ameliorating at least one symptom of, cancer in a subject in need thereof comprising administering a therapeutically effective amount of at least one compound of the Formula

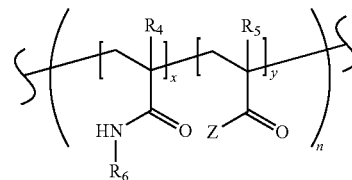

wherein, independently for each occurrence, R$_4$ is H or C$_1$-C$_6$ alkyl; R$_5$ is H or C$_1$-C$_6$ alkyl; R$_6$ is C$_2$-C$_6$ hydroxyalkyl; Z is —NH-AA$_1$-AA$_2$-AA$_3$-AA$_4$-AA$_5$-AA$_6$-C(O)-L or —NH-AA$_1$-AA$_2$-AA$_3$-AA$_4$-AA$_5$-AA$_6$-C(O)-Q-X—Y—C(O)—W; AA$_1$ is glycine, alanine, or H$_2$N(CH$_2$)$_m$CO$_2$H, wherein m is 2, 3, 4 or 5; AA$_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_5$ is a bond, or glycine, valine, tyrosine, tryptophan, phenylalanine, methionine, leucine, isoleucine, or asparagine; AA$_6$ is a bond, or alanine, asparagine, citrulline, glutamine, glycine, leucine, methionine, phenylalanine, serine, threonine, tryptophan, tyrosine, valine, or H$_2$N(CH$_2$)$_m$CO$_2$H, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —NH$_2$, —NH(C$_2$-C$_6$ hydroxyalkyl), halide or perfluoroalkyloxy; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, C$_5$-C$_8$ cycloalkyl, aryl, heteroaryl, NR, O, or S; Y is NR, O, or S; R is H or alkyl; V is a bond or

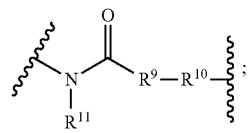

R$^9$ is alkyl, aryl, aralkyl, or a bond; or R$^9$ taken together with Y forms a heterocyclic ring; R$^{10}$ is amido or a bond; R$^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, wherein the compound is administered in an amount sufficient to reduce the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof.

The present disclosure provides at least one compound of the Formula

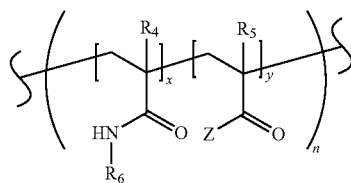

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

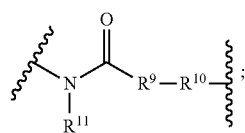

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, for use in the treatment of, or amelioration of at least one symptom of, cancer in a subject, wherein the at least one compound, or a pharmaceutically acceptable salt, prodrug, metabolite, analog or derivative thereof is for administration to the subject in an amount sufficient to reduce the amount of at least one of IL-10, arginase-1, myeloid-derived suppressor cells (MDSC), regulatory T cells, leptin, PD-1, PD-L1, CTLA-4, a growth factor or any combination thereof in a tumor, a tumor microenvironment, in plasma, or any combination thereof.

The present disclosure provides a method for treating, or ameliorating at least one symptom of, metabolic dysfunction associated with treatment in a subject having cancer comprising administering a therapeutically effective amount of at least one compound of the Formula

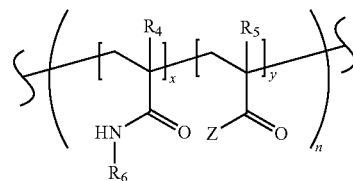

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

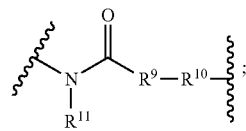

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, wherein the compound is administered in an amount sufficient to treat, or ameliorate at least one symptom of, metabolic dysfunction associated with treatment in a subject having cancer.

The present disclosure provides at least one compound of the Formula

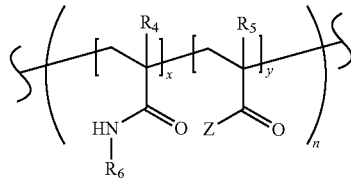

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

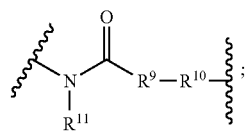

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, for use in the treatment of, or the amelioration of at least one symptom of, metabolic dysfunction associated with a treatment in a subject having cancer, wherein the at least one compound, or a pharmaceutically acceptable salt, prodrug, metabolite, analog or derivative thereof, is for administration to the subject in an amount sufficient to treat, or ameliorate at least one symptom of, metabolic dysfunction associated with the treatment.

The present disclosure provides a method of reducing the amount of at least one of IL-10, arginase-1, myeloid-derived suppressor cells, regulatory T cells, leptin, PD-1, PD-L1, CTLA-4, a growth factor or any combination thereof in a tumor, a tumor microenvironment, in plasma, or any combination thereof in a subject having cancer comprising administering a therapeutically effective amount of at least one compound of the Formula

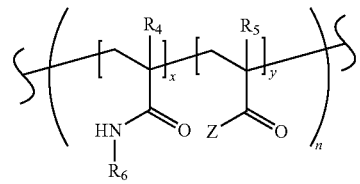

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

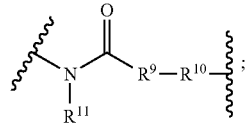

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, wherein the amount of at least one of IL-10, arginase-1, myeloid-derived suppressor cells, regulatory T cells, leptin, PD-1, PD-L1, CTLA-4, a growth factor or any combination thereof in a tumor, a tumor microenvironment, in plasma, or any combination thereof is reduced.

The present disclosure provides at least one compound of the Formula

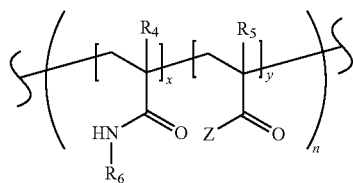

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

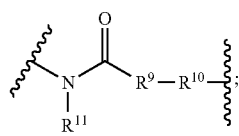

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; r is 1, 2, 3, 4, 5, or 6; or a pharmaceutically acceptable salt, prodrug, metabolite, analog or derivative thereof, for use in a method for reducing the amount of at least one of IL-10, arginase-1, myeloid-derived suppressor cells, regulatory T cells, leptin, PD-1, PD-L1, CTLA-4, a growth factor or any combination thereof in a tumor, a tumor microenvironment, in plasma, or any combination thereof in a subject having cancer, wherein the at least one compound, or a pharmaceutically acceptable salt, prodrug, metabolite, analog or derivative thereof, is for administration to the subject in an amount sufficient to reduce the amount of at least one of IL-10, arginase-1, myeloid-derived suppressor cells, regulatory T cells, leptin, PD-1, PD-L1, CTLA-4, a growth factor or any combination thereof in a tumor, a tumor microenvironment, in plasma, or any combination thereof.

The present disclosure provides a method for treating, or ameliorating at least one symptom of, cancer in a subject in need thereof comprising administering at least one therapeutically effective amount of at least one MetAP2 inhibitor in combination with at least one therapeutically effective amount of at least one PI3K inhibitor. The present disclosure also provides a combination comprising at least one MetAP2 inhibitor and at least one PI3K inhibitor for use in the treatment of, or amelioration of at least one symptom of, cancer in a subject. The present disclosure also provides a combination comprising at least one MetAP2 inhibitor and at least one PI3K inhibitor for use in the manufacture of a medicament for treating, or ameliorating at least one symptom of, cancer in a subject.

The present disclosure provides a method for treating, or ameliorating at least one symptom of, cancer in a subject in need thereof comprising administering at least one therapeutically effective amount of at least one MetAP2 inhibitor in combination with at least one therapeutically effective amount of at least one AKT inhibitor. The present disclosure also provides a combination comprising at least one MetAP2 inhibitor and at least one AKT inhibitor for use in the treatment of, or amelioration of at least one symptom of, cancer in a subject. The present disclosure also provides a combination comprising at least one MetAP2 inhibitor and at least one AKT inhibitor for use in the manufacture of a medicament for treating, or ameliorating at least one symptom of, cancer in a subject.

The present disclosure provides a method for treating, or ameliorating at least one symptom of, cancer in a subject in need thereof comprising administering at least one therapeutically effective amount of at least one MetAP2 inhibitor in combination with at least one therapeutically effective amount of at least one mTOR inhibitor. The present disclosure also provides a combination comprising at least one MetAP2 inhibitor and at least one mTOR inhibitor for use in the treatment of, or amelioration of at least one symptom of, cancer in a subject. The present disclosure also provides a combination comprising at least one MetAP2 inhibitor and at least one mTOR inhibitor for use in the manufacture of a medicament for treating, or ameliorating at least one symptom of, cancer in a subject.

The present disclosure provides a method for treating, or ameliorating at least one symptom of, a metabolic dysfunction induced by a cancer treatment in a subject comprising administering at least one therapeutically effective amount of at least one MetAP2 inhibitor. The present disclosure provides at least one MetAP2 inhibitor for use in the treatment of or amelioration of at least one symptom of a metabolic dysfunction induced by a cancer treatment in a subject. A cancer treatment can comprises the administration of a PI3K inhibitor, an AKT inhibitor, an mTOR inhibitor or a PI3K/AKT/mTOR pathway inhibitor or any combination thereof.

In some aspects of the preceding methods, combinations and uses, the at least one MetAP2 inhibitor can be any conjugate or compound of the present disclosure, or a pharmaceutically acceptable salt, prodrug, metabolite, analog or derivative of any conjugate or compound of the present disclosure. In some aspects, the at least one MetAP2 inhibitor can be a conjugate or compound of the formula

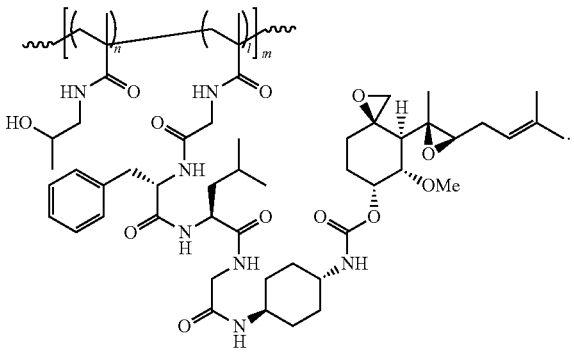

In some aspects of the preceding methods, combinations and uses, the at least one MetAP2 inhibitor can be ZGN-1061 or Beloranib.

In some aspects of the preceding methods, combinations and uses, the at least one compound or the at least one MetAP2 inhibitor can be a compound of the Formula

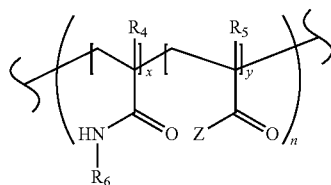

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, $C_5$-$C_8$ cycloalkyl, aryl, heteroaryl, NR, O, or S; Y is NR, O, or S; R is H or alkyl; V is a bond or

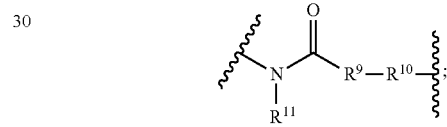

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; and r is 1, 2, 3, 4, 5, or 6. In some aspects, Z can be represented by a formula selected from the group consisting of

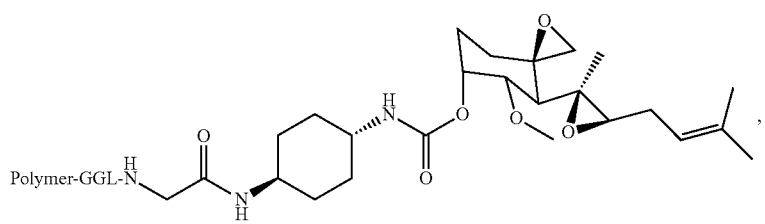

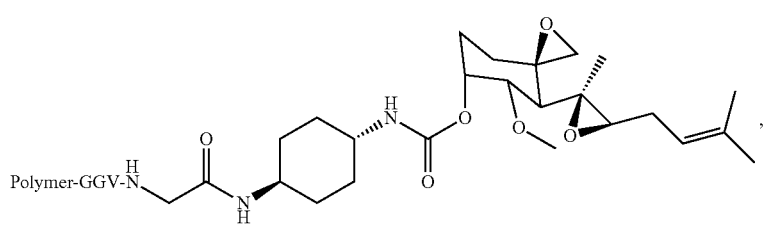

-continued
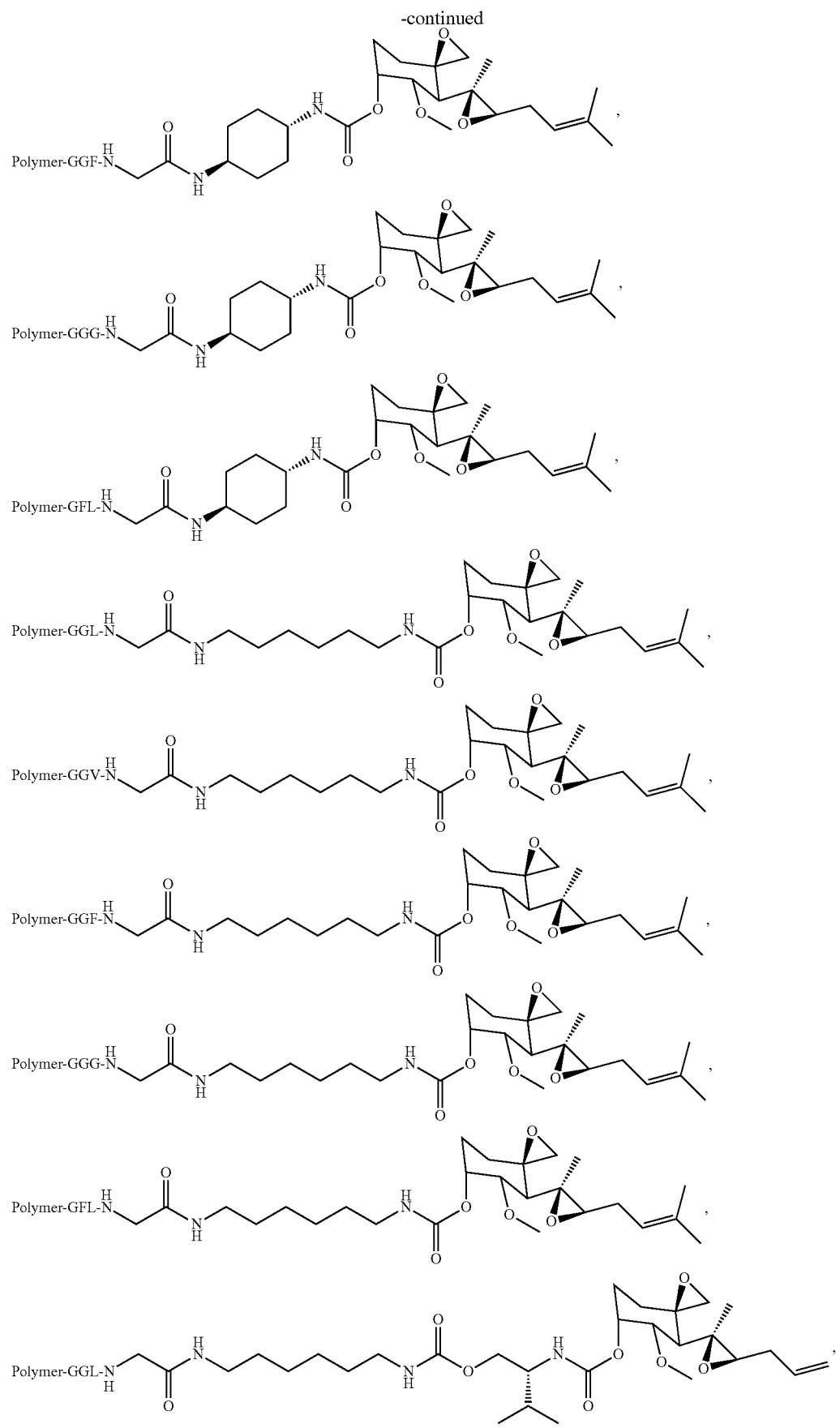

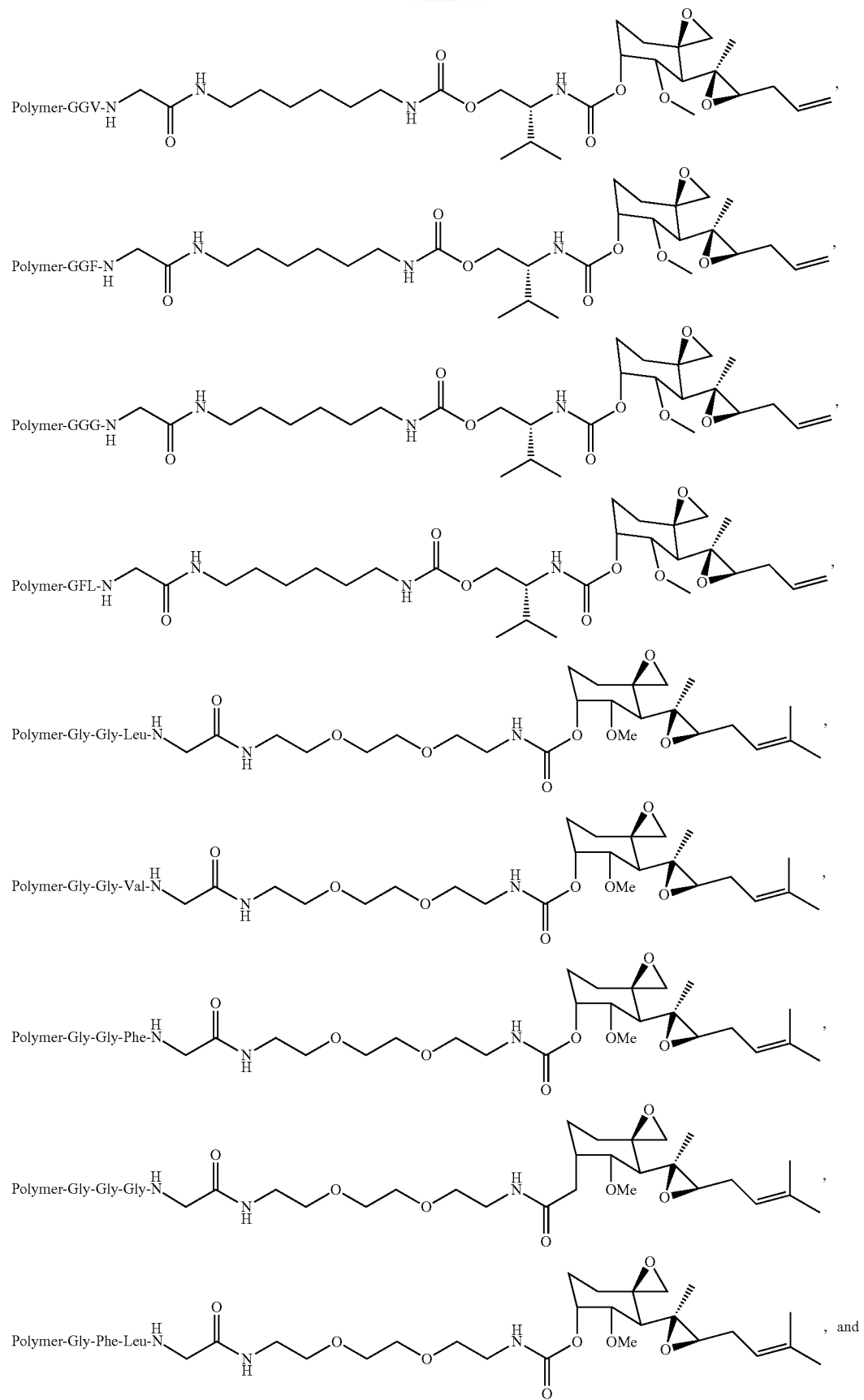

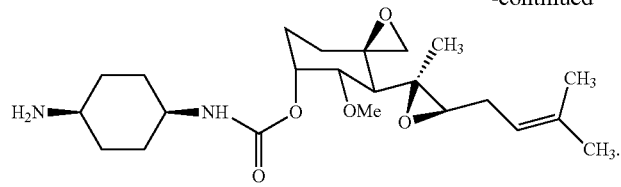

In some aspects, $R_4$ can be methyl. In some aspects, $R_5$ can be methyl. In some aspects $R_6$ can be 2-hydroxypropyl. In some aspects, Z can be —NH-$AA_6$-C(O)-Q-X—Y—C(O)—W. In some aspects, $AA_6$ can be glycine. In some aspects, Z can be —NH-$AA_5$-$AA_6$-C(O)-Q-X—Y—C(O)—W. In some aspects, $AA_5$ can be leucine and $AA_6$ can be glycine. In some aspects, $AA_5$ can be valine and $AA_6$ can be glycine. In some aspects, $AA_5$ can be phenylalanine and $AA_6$ can be glycine. In some aspects, $AA_5$ can be glycine and $AA_6$ can be glycine. In some aspects, Z can be —NH-$AA_3$-$AA_4$-$AA_5$-$AA_6$-C(O)-Q-X—Y—C(O)—W. In some aspects, $AA_5$ can be leucine and each of $AA_3$, $AA_4$, or $AA_6$ can be glycine. In some aspects, $AA_5$ can be valine and each of $AA_3$, $AA_4$, or $AA_6$ can be glycine. In some aspects, $AA_5$ can be phenylalanine and each of $AA_3$, $AA_4$, or $AA_6$ can be glycine. In some aspects, $AA_3$ can be glycine, $AA_4$ can be phenylalanine, $AA_5$ can be leucine and $AA_6$ can be glycine. In some aspects, each of $AA_3$, $AA_4$, $AA_5$ and $AA_6$ can be glycine.

In some aspects, -Q-X—Y can be

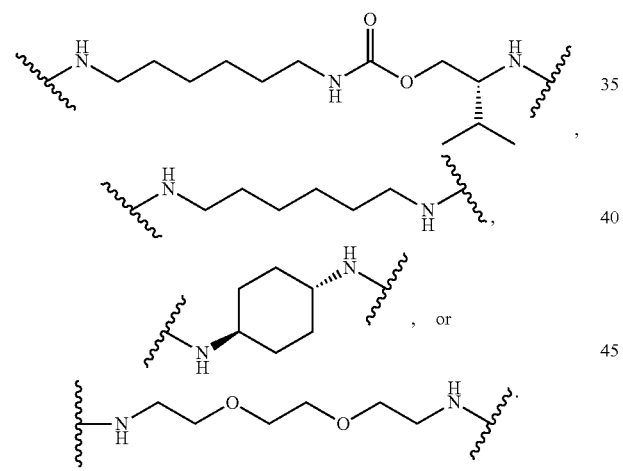

In some aspects, wherein W can be

In some aspects, the ratio of x to y can be in the range of about 30:1 to about 3:1. In some aspects, the ratio of x to y can be about 11:1.

In some aspects of the preceding methods, combinations and uses, the at least one MetAP2 inhibitor can have the Formula

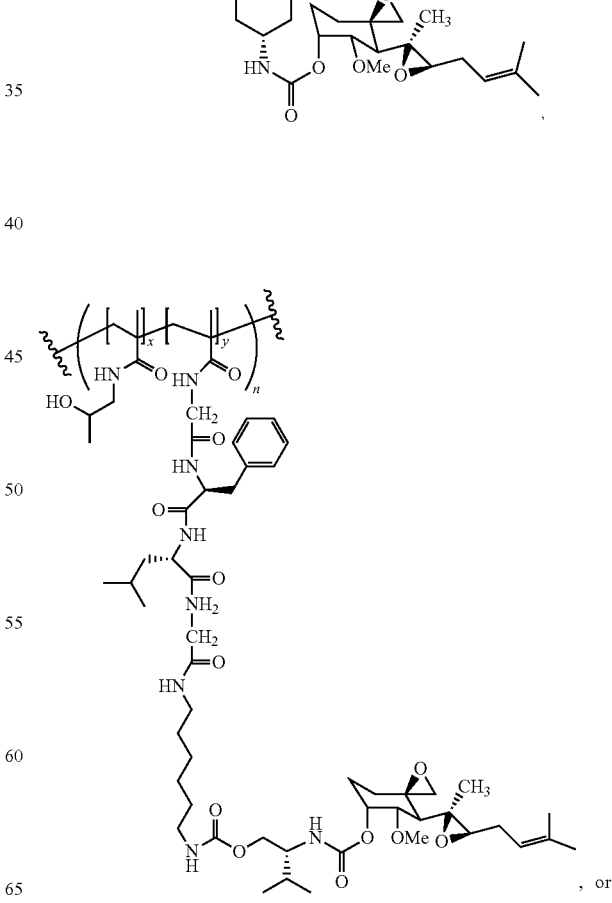

-continued

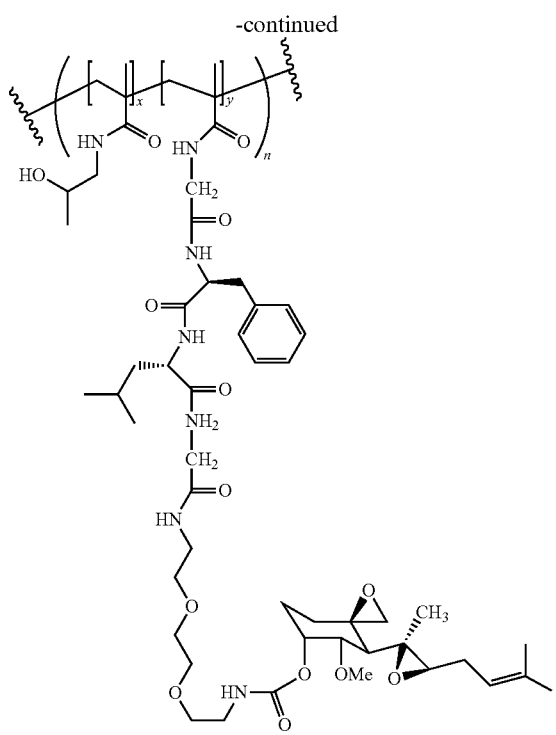

In some aspects of the preceding methods, combinations and uses, the at least one MetAP2 inhibitor can be represented by Z-Q-X—Y—C(O)—W wherein, independently for each occurrence, Z is —H, —$H_2N$-$AA_3$-$AA_4$-$AA_5$-$AA_6$-C(O)— or Z is $H_2N$-$AA_5$-$AA_6$-C(O); $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is alanine, asparagine, citrulline, glutamine, glycine, leucine, methionine, phenylalanine, serine, threonine, tryptophan, tyrosine, valine or $H_2N(CH_2)_mCO_2H$, wherein m is 2, 3, 4 or 5; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

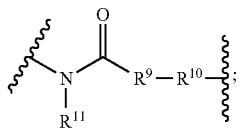

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety; p is 0 to 20; q is 2 or 3; and r is 1, 2, 3, 4, 5, or 6.

In some aspects, Z can be —NH-$AA_5$-$AA_6$-C(O)-Q-X—Y—C(O)—W, $AA_5$ can be leucine and $AA_6$ can be glycine. In some aspects, Z can be —NH-$AA_5$-$AA_6$-C(O)-Q-X—Y—C(O)—W, $AA_5$ can be valine and $AA_6$ can be glycine. In some aspects, Z can be —NH-$AA_5$-$AA_6$-C(O)-Q-X—Y—C(O)—W, $AA_5$ can be phenylalanine and $AA_6$ can be glycine. In some aspects, Z can be —NH-$AA_5$-$AA_6$-C(O)-Q-X—Y—C(O)—W, $AA_5$ can be glycine and $AA_6$ can be glycine. In some aspects, Z can be —NH-$AA_3$-$AA_4$-$AA_5$-$AA_6$-C(O)-Q-X—Y—C(O)—W, $AA_5$ can be leucine and each of $AA_3$, $AA_4$, or $AA_6$ can be glycine. In some aspects, Z can be —NH-$AA_3$-$AA_4$-$AA_5$-$AA_6$-C(O)-Q-X—Y—C(O)—W, $AA_5$ can be valine and each of $AA_3$, $AA_4$, or $AA_6$ can be glycine. In some aspects, Z can be —NH-$AA_3$-$AA_4$-$AA_5$-$AA_6$-C(O)-Q-X—Y—C(O)—W, $AA_5$ can be phenylalanine and each of $AA_3$, $AA_4$, or $AA_6$ can be glycine. In some aspects, Z can be —NH-$AA_3$-$AA_4$-$AA_5$-$AA_6$-C(O)-Q-X—Y—C(O)—W, $AA_5$ can be glycine, $AA_4$ can be phenylalanine, $AA_5$ can be leucine and $AA_6$ can be glycine. In some aspects, Z can be —NH-$AA_3$-$AA_4$-$AA_5$-$AA_6$-C(O)-Q-X—Y—C(O)—W, and each of $AA_3$, $AA_4$, $AA_5$ and $AA_6$ can be glycine. In some aspects, -Q-X—Y can be

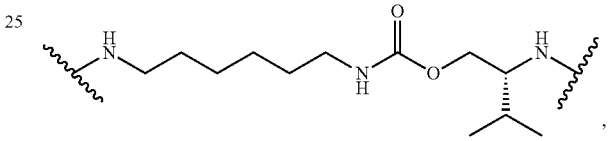

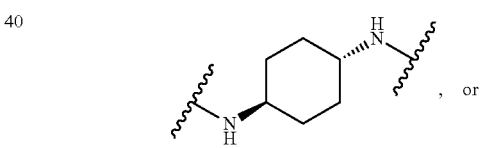

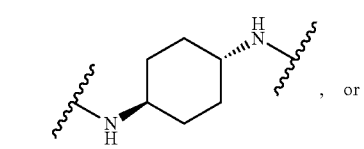

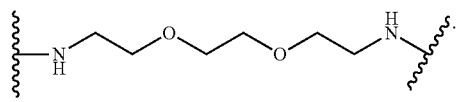

In some aspects, W can be

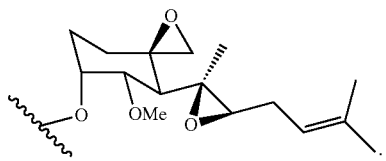

In some aspects, the at least one MetAP2 inhibitor can be selected from the group consisting of

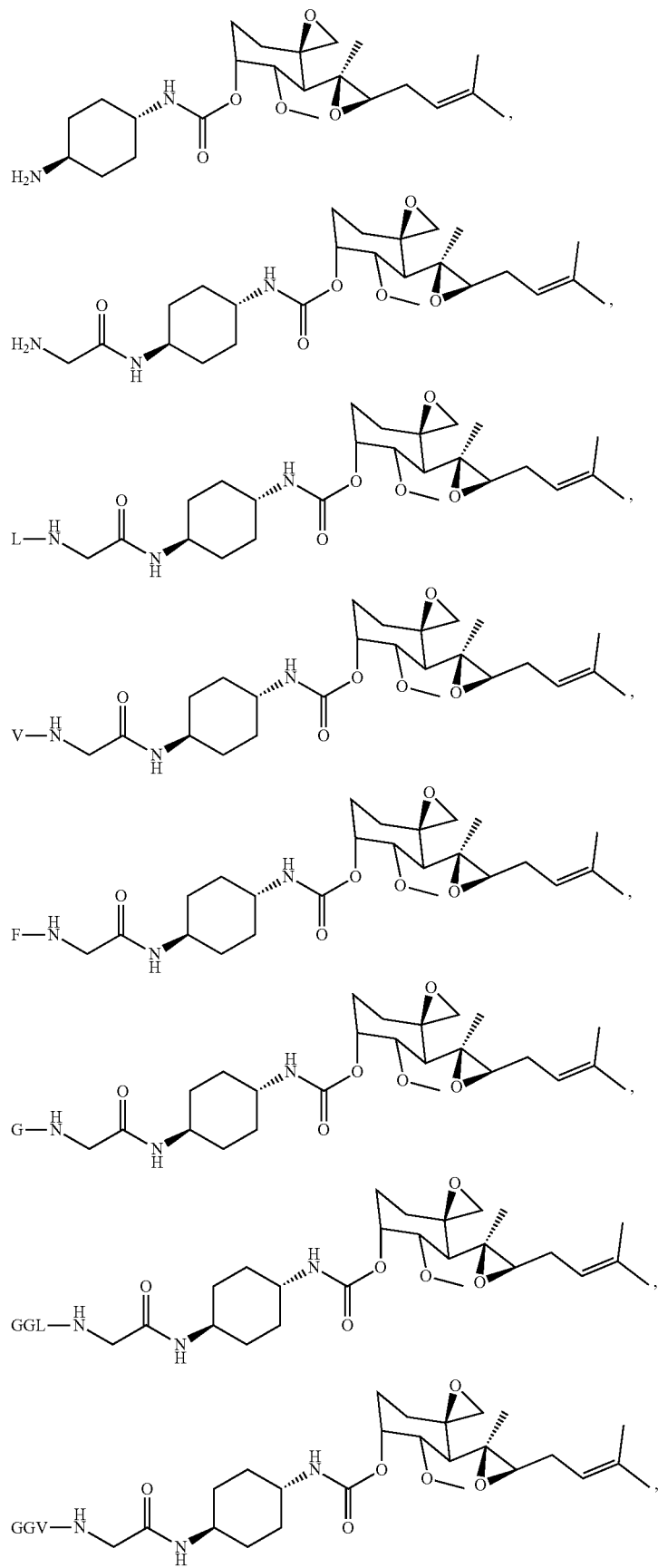

-continued
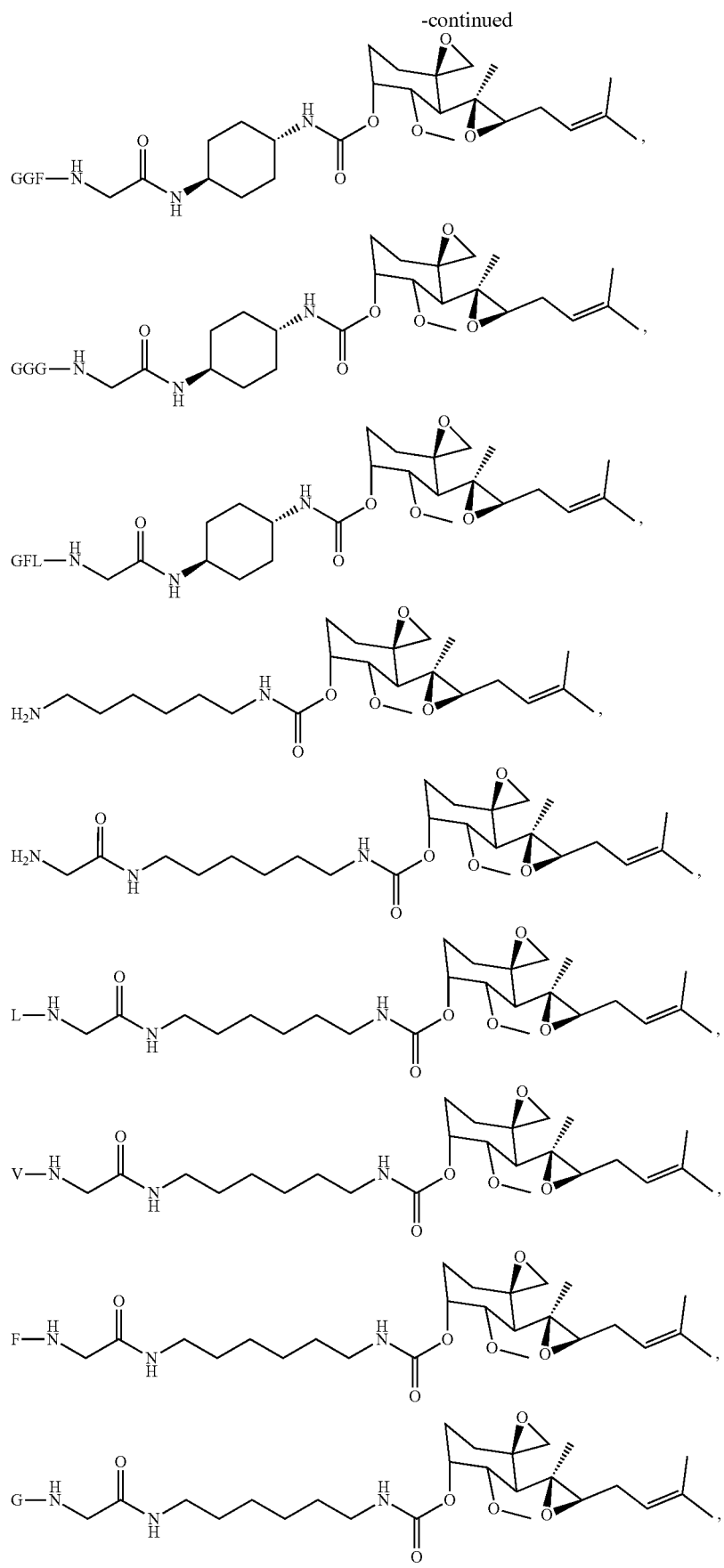

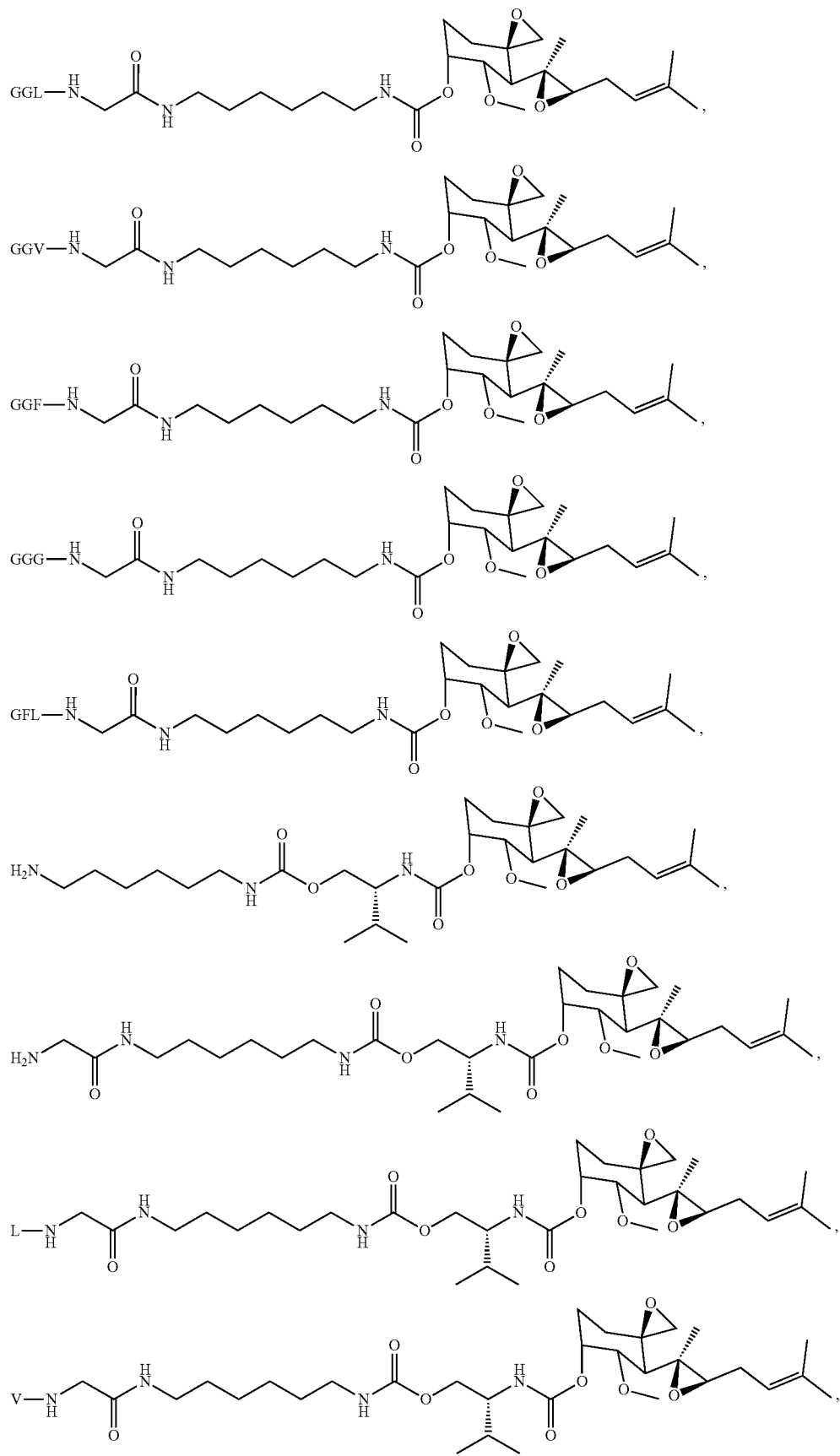

-continued
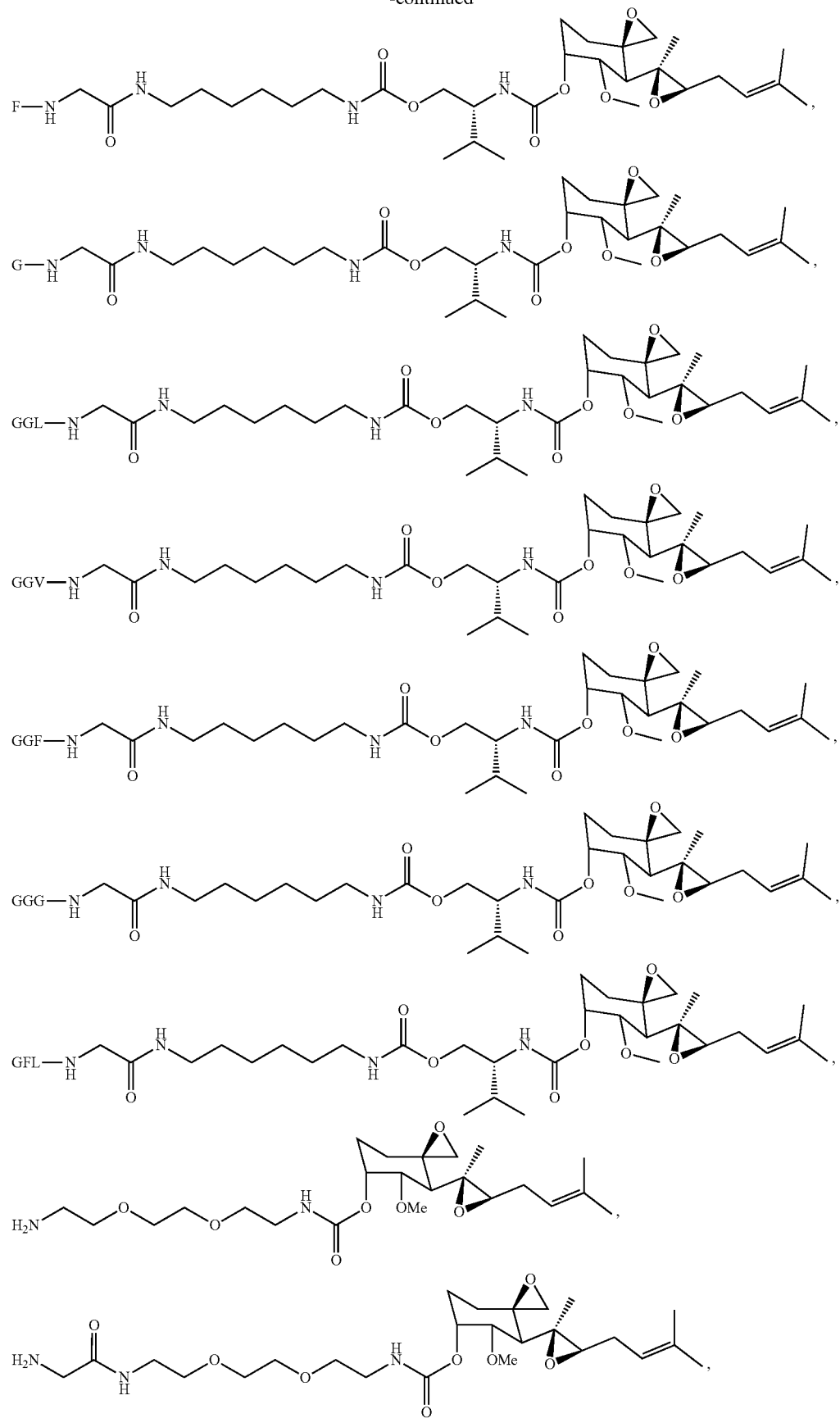

-continued
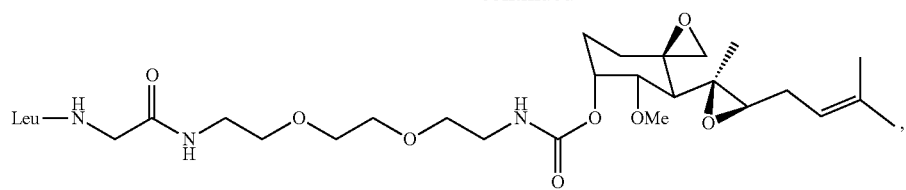
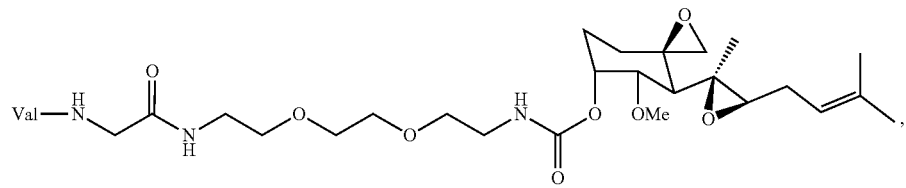
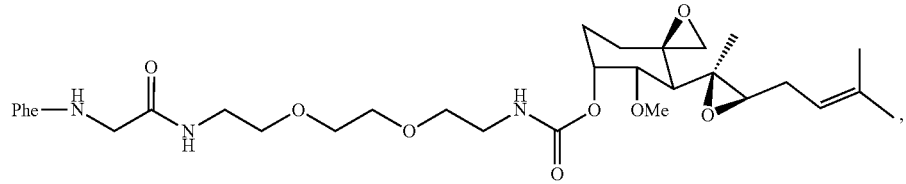
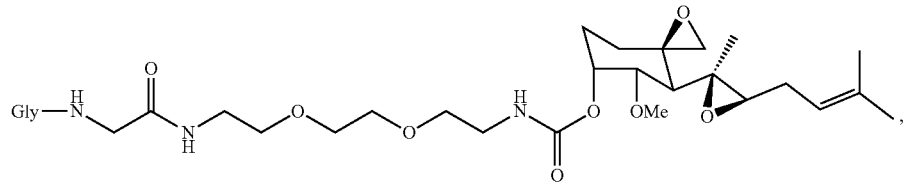
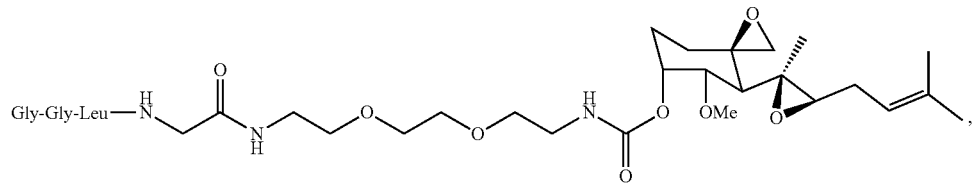
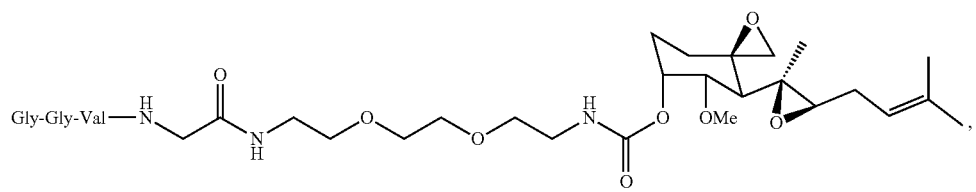
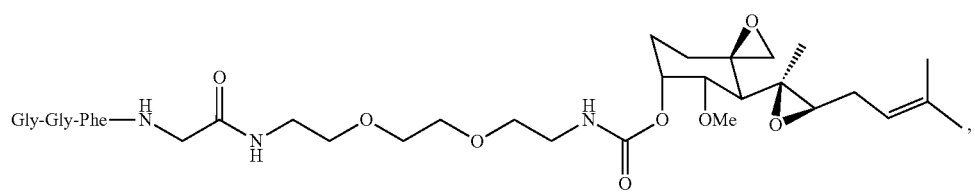
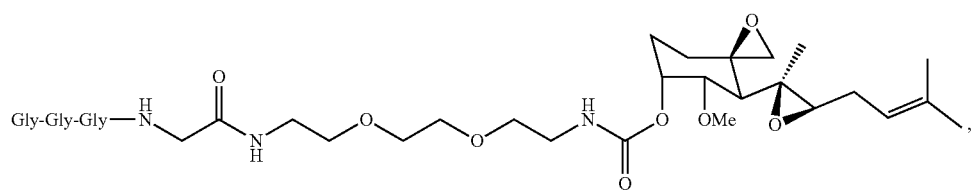
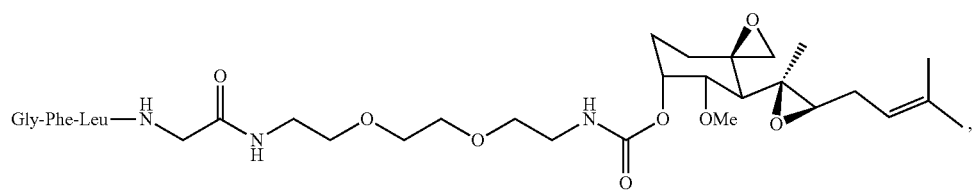

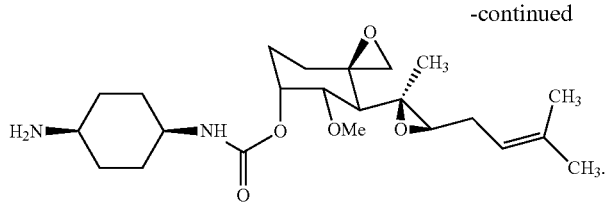

In some aspects of the preceding methods, combinations and uses, an at least one PI3K inhibitor can be Serabelisib (TAK-117), BYL-719 or any combination thereof. In some aspects of the preceding methods, combinations and uses, an AKT inhibitor can be AZD5363 (capavasertib).

In some aspects of the preceding methods, combinations and uses, a therapeutically effective amount or an effective amount of the at least one MetAP2 inhibitor can be from about 0.0001 mg/kg to about 5 mg/kg of body weight per day, or about 0.001 to about 0.005 mg/kg of body weight per day, or about 0.001 to about 0.1 mg/kg of body weight per day. In some aspects, the at least one MetAP2 inhibitor is administered from about 1 to about 5 times per week. In some aspects, the at least one MetAP2 inhibitor is administered in a q4d dosing schedule. In some aspects, the at least one MetAP2 inhibitor is administered in a q7d dosing schedule. In some aspects, the at least one MetAP2 inhibitor is administered on a q14d dosin schedule. In some aspects, the at least one MetAP2 inhibitor is administered once every three weeks. In some aspects, the at least one MetAP2 inhibitor is administered once a month. In some aspects of the preceding methods, combinations and uses, a subject is treated for at least about six months, or at least about one year, or at least two years, or at least three years. In some aspects of the preceding methods, combinations and uses, the at least one MetAP2 inhibitor can be administered parenterally or subcutaneously.

In some aspects of the preceding methods, combinations and uses, a therapeutically effective amount or an effective amount of the at least one compound of the present disclosure can be from about 0.0001 mg/kg to about 5 mg/kg of body weight per day, or about 0.001 to about 0.005 mg/kg of body weight per day, or about 0.001 to about 0.1 mg/kg of body weight per day. In some aspects, the at least one compound of the present disclosure is administered from about 1 to about 5 times per week. In some aspects, the at least one compound of the present disclosure is administered in a q4d dosing schedule. In some aspects, the at least one compound of the present disclosure is administered in a q7d dosing schedule. In some aspects, the at least one compound of the present disclosure is administered on a q14d dosin schedule. In some aspects, the at least one compound of the present disclosure is administered once every three weeks. In some aspects, the at least one compound of the present disclosure is administered once a month. In some aspects of the preceding methods, combinations and uses, a subject is treated for at least about six months, or at least about one year, or at least two years, or at least three years. In some aspects of the preceding methods, combinations and uses, the at least one compound of the present disclosure can be administered parenterally or subcutaneously.

In some aspects of the preceding methods, combinations and uses, cancer can be a metabolic hormone sensitive cancer, post-menopausal HR+/Her2− breast cancer, triple-negative breast cancer, prostate cancer, esophageal carcinoma, esophageal adenocarcinoma, tongue cancer, colorectal adenocarcinoma, gastro-intestinal stromal tumor (GIST), cervical cancer, endometrial cancer, ovarian cancer, pancreatic cancer, gall bladder cancer, cholangiocarcinoma, liver cancer, clear-cell renal cancer, melanoma, multiple myeloma, thyroid cancer, insulin-like growth factor sensitive lung cancer, or combinations thereof.

In some aspects of the preceding methods, combinations and uses, treating and/or ameliorating at least one symptom of metabolic dysfunction associated with a treatment can comprise decreasing insulin levels, decreasing hyperinsulinemia, decreasing hyperglycemia decreasing C-peptide levels, increasing adiponectin, decreasing leptin, decreasing fasting insulin, improving insulin resistance, reducing the leptin-to-adiponectin ratio, reducing glucose levels, lowering cholesterol, lowering triglycerides, or combinations thereof in a subject. In some aspects of the preceding methods, combinations and uses, treating and/or ameliorating at least one symptom of metabolic dysfunction associated with a treatment can comprise preventing hyperglycemia, preventing hyperinsulinemia and/or preventing increases in glucose levels that is/are induced by administration of the treatment.

In some aspects of the preceding methods, combinations and uses, "decreasing the level of" or "decreasing the amount of" can refer to a decrease of at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 99%.

In some aspects of the preceding methods, combinations and uses, a treatment, such as one that is associated with a metabolic dysfunction, can comprise administration of a phosphoinositide-3-kinase (PI3K) inhibitor, an AKT inhibitor, an mTOR inhibitor, a PI3K/AKT/mTOR pathway inhibitor dexamethasone, or a combination thereof.

In some aspects of the preceding methods, combinations and uses, a second agent or a second active agent can comprise a phosphoinositide-3-kinase (PI3K) inhibitor, an AKT inhibitor, an mTOR inhibitor, a PI3K/AKT/mTOR pathway inhibitor, dexamethasone, or a combination thereof.

PI3K inhibitors include, but are not limited to, Serabelisib (TAK-117), BYL-719 or any other PI3K inhibitor known in the art. AKT inhibitors include, but are not limited to AZD5363 (capavasertib), ipaseratib (GDC0068), and any other AKT inhibitor known in the art. MetAP2 inhibitors include, but are not limited to ZGN-1061, Beloranib and any other MetAP2 inhibitor known in the art. In some aspects, a MetAP2 inhibitor can be any conjugate or compound recited herein.

A PI3K/AKT/mTOR pathway inhibitor can include, but are not limited to (paclitaxel+sirolimus+tanespimycin), (paclitaxel+sirolimus+tanespimycin), A-443654, AB-610, ACP-2127, ADC-0008830, AE-116, AEZS-126, AEZS-127, afuresertib+trametinib, AL-58203, AL-58805, AL-58922, ALM-301, AP-185, AP-23675, AP-23841, apitolisib, ARQ-751, ASP-7486, AST-0669, AT-104, AT-13148, AUM-302, AZD-3147, AZD-8055, AZD-8154, BAY-1001931, BAY-1125976, BAY-1125976, BGT-226, bimiralisib, BN-107, BN-108, borussertib, buformin, BVD-723, capivasertib, CC-115, CC-2141, CC-2142, Certican ODT, CL-27, COTI-2, CT-365, dactolisib tosylate, DC-120, DHM-25, dihydroartemisinin, DS-3078, DS-7423, duvelisib, EM-101, everolimus, FP-208, FT-1518, FXY-1, galarmin, GDC-0349, gedatolisib, GM-6, GNE-317, GNE-555, GSK-690693, GT-0486, HD-148 series, HEC-68498, HM-032, HM-5016699, HMPL-518, ipatasertib, IPI-549, ISC-4, J-9, JRP-890, KIT-2014, KS-99, LD-101, lithium carbonate, LY-2503029, LY-2780301, M-2698, ME-344, miransertib mesylate, MK-2206, MKC-1, monepantel, NISC-6, nPT-mTOR, NSC-765844, NV-128, onatasertib, ONC-201, ONC-222, ONC-235, OSU-53, OT-043, OT-043, P-7170, P-7170, PBD-1226, perifosine, PF-04691502, pimasertib hydrochloride+voxtalisib, PKI-179, PQR-311, PQR-316, PQR-401, PQR-4XX, PQR-514, PQR-530, PQR-620, PWT-33597, PX-316, recilisib sodium, RES-529, ridaforolimus, RMC-5552, RP-6503, RV-1729, RX-0183, RX-0201, RX-0201N, RX-0301, RX-1792, RX-8243, samotolisib, sapanisertib, SB-2602, SCC-31, SF-1126, SF-2523, SN-202, SPR-965, SR-13668, STP-503, SX-MTR1, TAFA-93, TAM-01, TAM-03, TAS-117, TASP-0415914, TE-7105, temsirolimus, tenalisib, TOP-216, trametinib dimethyl sulfoxide+uprosertib, triciribine phosphate, UB-1201, uprosertib, VCC-405567, VCC-668662, vistusertib, VLI-27, voxtalisib, VS-5584, WX-008, WXFL-10030390, X-387, X-414, X-480, XL-388, XL-418, XP-105, Y-31, Zortress or any combination thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference in their entirety for all purposes. The references cited herein are not admitted to be prior art to the claimed disclosure. In the case of conflict, the present specification, including definitions, will control. In addition, the materials, methods and examples are illustrative only and are not intended to be limiting.

BRIEF DESCRIPTION OF THE DRAWINGS

FIG. 1A is a graph depicting change in E0771 mammary tumor volume over time in days in response to treatment of lean and obese mice with vehicle.

FIG. 9A depicts changes in leptin levels in ng/mL.

FIG. 9B depicts changes in leptin levels as a percent change compared to baseline.

FIG. 10A depicts changes in adiponectin levels in g/mL.

FIG. 10B depicts changes in adiponectin levels as a percent change compared to baseline.

FIG. 11A depicts changes in the leptin/adiponectin ratio in ng/μg.

FIG. 11B depicts changes in the leptin/adiponectin ratio as a percent change compared to baseline.

FIG. 12A is a graph depicting the pro-angiogenic marker VEGF-C levels in serum of cancer patients treated with compound 20 (noted in the Figure as Compound A) as part of the SDX-101 clinical trial. FIG. 12A depicts changes in VEGF-C levels in pg/mL.

FIG. 12B depicts changes in VEGF-C levels as a percent change compared to baseline.

FIG. 13A depicts changes in IGF-1 levels in ng/mL.

FIG. 13B depicts changes in IGF-1 levels as a percent change compared to baseline.

FIG. 14A depicts changes in bFGF/FGF2 levels in pg/mL.

FIG. 14B depicts changes in bFGF/FGF2 level as a percent change compared to baseline.

FIG. 15A shows the effect of compound 20 (noted in the Figure as Compound A) given to heavily pre-treated cancer patients on insulin levels, where baseline insulin is above 20 uU/ml in absolute values.

DETAILED DESCRIPTION OF THE INVENTION

Figure 1B:
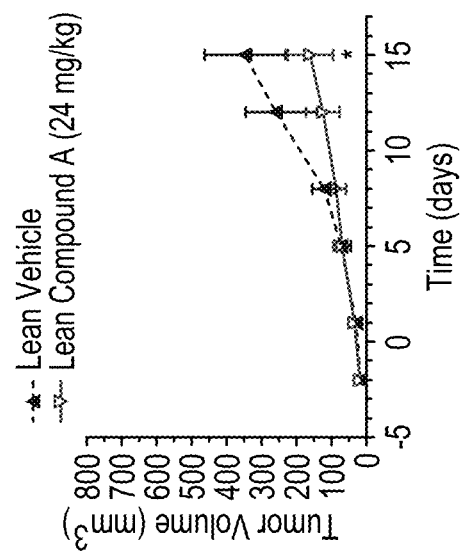
FIG. 1B is a graph depicting change in E0771 mammary tumor volume over time in days in response to treatment of lean mice with vehicle or compound 20 (noted in the Figure as Compound A).

The present disclosure provides methods of inducing or causing beneficial changes in a variety of cells, tissues and/or proteins that otherwise impede the clinical activity of a variety of cancer treatments. In certain aspects, the subject is overweight, obese or has metabolic dysfunction as a pre-existing condition or induced by some second agent.

The present disclosure provides methods of blunting or preventing the negative, systemic effects of certain cancer treatments on a patient's metabolic system. For example, certain cancer therapies induce hyperglycemia and subsequent hyperinsulinemia, which may attenuate their efficacy. A MetAP2 inhibitor of the present disclosure can blunt or prevent the negative metabolic effects of these cancer therapies and therefore improve oncologic treatment outcomes in a subject in need thereof comprising administering at least one compound of the present disclosure, or a pharmaceutically acceptable salt, prodrug, metabolite, analog or derivative thereof, in a therapeutically effective amount on a reasonable schedule to the subject to treat or ameliorate these underlying disease modifiers and improve treatment outcomes.

The present disclosure also provides methods of altering the tumor microenvironment in a subject in need thereof comprising administering at least one compound of the present disclosure, or a pharmaceutically acceptable salt, prodrug, metabolite, analog or derivative thereof, in a therapeutically effective amount on a reasonable schedule to the subject to enhance the effect of a co-administered therapy to treat or ameliorate these diseases and conditions.

The present disclosure also provides methods of reducing certain pro-angiogenic factors associated with obesity or cancer. Here, it is shown for the first time that MetAP2 inhibitors may also inhibit angiogenesis via systemic reductions in pro-angiogenic factors VEGF-C, bFGF and IGF-1.

Methods of Use

The present disclosure provides methods of treating, or ameliorating at least one symptom of, a proliferation disorder in a subject in need thereof comprising administering at least one MetAP2 inhibitor in a therapeutically effective amount to the subject, wherein the expression of at least one of IL-10, arginase-1, myeloid-derived suppressor cells (MDSC), regulatory T cells leptin, PD-1, PD-L1, CTLA-4, VEGF-C, IGF-1, and bFGF in a tumor, a tumor microenvironment, in plasma, or any combination thereof is reduced in a subject having cancer. In a preferred aspect, the proliferation disorder is cancer. The cancer can be HR+/Her2− breast cancer, triple negative breast cancer, Her2+ breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The subject may also be overweight or obese. The subject may have metabolic dysfunction, including any of the following; excessive visceral adiposity, elevated leptin levels, depressed adiponectin levels, high leptin-to-adiponectin ratio, elevated fasting insulin levels, elevated fasting insulin levels accompanied by chronic inflammation, hyperglycemia, elevated HbA1c, or combinations thereof. Preferably, the metabolic dysfunction is low adiponectin, elevated leptin, elevated fasting insulin, or combinations thereof. The methods of the present disclosure can also include treating or ameliorating at least one symptom of the metabolic dysfunction in addition to treating or ameliorating at least one symptom of the proliferation disorder.

The present disclosure provides methods of treating or ameliorating at least one symptom of metabolic dysfunction associated with cancer treatment in a subject comprising administering at least one MetAP2 inhibitor in a therapeutically effective amount. The cancer can be HR+/Her2− breast cancer, triple negative breast cancer, Her2+ breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, or multiple myeloma. The subject may also be overweight or obese. The metabolic dysfunction can include excessive visceral adiposity, elevated leptin levels, depressed adiponectin levels, high leptin-to-adiponectin ratio, elevated fasting insulin levels, elevated fasting insulin levels accompanied by chronic inflammation, hyperglycemia, elevated HbA1c, or combinations thereof. Preferably, the metabolic dysfunction is low adiponectin, elevated leptin, elevated fasting insulin, hyperglycemia, or combinations thereof. The methods of the present disclosure can also include treating, or ameliorating at least one symptom of the metabolic dysfunction in addition to treating or ameliorating at least one symptom of the proliferation disorder.

The present disclosure provides methods of reducing the expression of IL-10 in a tumor or in the systemic circulation (i.e., blood, plasma or serum) in a subject having cancer comprising administering at least one MetAP2 inhibitor in a therapeutically effective amount to the subject with metabolic dysfunction, wherein the expression of IL-10 in a tumor or plasma is reduced in a subject having cancer.

The present disclosure provides methods of reducing the expression of arginase-1 in a tumor, the tumor microenvironment or in the systemic circulation (i.e., blood, plasma or serum) in a subject having a cancer comprising administering at least one MetAP2 inhibitor in a therapeutically effective amount to the subject with metabolic dysfunction, wherein the expression of arginase-1 in a tumor or plasma is reduced in a subject having cancer.

The present disclosure provides methods of reducing the expression of myeloid-derived suppressor cells in a tumor or in the systemic circulation (i.e., blood) in a subject having a cancer comprising administering at least one MetAP2 inhibitor in a therapeutically effective amount to the subject with metabolic dysfunction, wherein the expression of myeloid-derived suppressor cells in a tumor, the tumor microenvironment or plasma is reduced in a subject having cancer.

The present disclosure provides methods of reducing the expression of regulatory T cells in a tumor or in the systemic circulation (i.e., blood) in a subject having a cancer comprising administering at least one MetAP2 inhibitor in a therapeutically effective amount to the subject with metabolic dysfunction, wherein the expression of regulatory T cells in a tumor, the tumor microenvironment or plasma is reduced in a subject having cancer.

The present disclosure provides methods of reducing the expression of leptin in a tumor or plasma in a subject having a cancer comprising administering at least one MetAP2 inhibitor in a therapeutically effective amount to the subject, wherein the expression of leptin in a tumor, the tumor microenvironment or plasma is reduced in a subject having cancer.

The present disclosure provides methods of reducing the expression of a growth factor in a tumor or in the systemic circulation (i.e., blood, plasma or serum) in a subject having a cancer comprising administering at least one MetAP2 inhibitor in a therapeutically effective amount to the subject with metabolic dysfunction, wherein the expression of the growth factor in a tumor, the tumor microenvironment or plasma is reduced in a subject having cancer. The growth factor can be VEGF-C, IGF-1, bFGF, or a combination thereof.

The present disclosure provides methods of treating or ameliorating at least one symptom of cancer in a subject in need thereof comprising administering at least one fumagillin analog or derivative or a reversible MetAP2 inhibitor in a therapeutically effective amount to the subject, wherein the expression of at least one of IL-10, arginase-1, myeloid-derived suppressor cells (MDSC), regulatory T cells leptin, insulin, VEGF-C, IGF-1, or bFGF in a tumor, the tumor microenvironment or in plasma is reduced and/or the level of the hormone adiponectin is increased in a subject having cancer.

The present disclosure provides methods of treating or ameliorating at least one symptom of metabolic dysfunction associated with cancer treatment in a subject having cancer comprising administering at least one fumagillin analog or derivative or conjugate in a therapeutically effective amount to the subject to treat or ameliorate at least one symptom of metabolic dysfunction associated with cancer treatment in a subject.

The present disclosure provides methods of reducing the expression of IL-10 in a tumor or plasma in a subject having cancer comprising administering at least one fumagillin analog or derivative in a therapeutically effective amount to the subject, wherein the expression of IL-10 in a tumor, the tumor microenvironment or plasma is reduced in a subject having cancer.

The present disclosure provides methods of reducing the expression of arginase-1 in a tumor or plasma in a subject having cancer comprising administering at least one fumagillin analog or derivative in a therapeutically effective amount to the subject, wherein the expression of arginase-1 in a tumor, the tumor microenvironment or plasma is reduced in a subject having cancer.

The present disclosure provides methods of reducing the expression of myeloid-derived suppressor cells in a tumor or plasma in a subject having cancer comprising administering at least one fumagillin analog or derivative in a therapeutically effective amount to the subject, wherein the expression of myeloid-derived suppressor cells in a tumor, the tumor microenvironment or plasma is reduced in a subject having cancer.

The present disclosure provides methods of reducing the expression of regulatory T cells in a tumor or plasma in a subject having cancer comprising administering at least one fumagillin analog or derivative in a therapeutically effective amount to the subject, wherein the expression of regulatory T cells in a tumor or plasma or the tumor microenvironment is reduced in a subject having cancer. The present disclosure provides methods of reducing the expression of leptin in a tumor or plasma in a subject having a cancer comprising administering at least one fumagillin analog or derivative in a therapeutically effective amount to the subject, wherein the expression of leptin in a tumor, the tumor microenvironment or plasma is reduced in a subject having cancer.

The present disclosure provides methods of reducing the expression of a growth factor in a tumor or plasma in a subject having a cancer comprising administering at least one fumagillin analog or derivative in a therapeutically effective amount to the subject, wherein the expression of the growth factor in a tumor, the tumor microenvironment or plasma is reduced in a subject having cancer. The growth factor can be VEGF-C, IGF-1, bFGF, or a combination thereof.

The present disclosure provides methods of treating or ameliorating at least one symptom of cancer in a subject in need thereof comprising administering at least one compound of the present disclosure in a therapeutically effective amount to the subject, wherein the expression of at least one of IL-10, arginase-1, myeloid-derived suppressor cells (MDSC), regulatory T cells leptin, insulin, VEGF-C, IGF-1, or bFGF in a tumor, the tumor microenvironment or plasma is reduced in a subject having cancer.

The present disclosure provides methods of treating, or ameliorating at least one symptom of metabolic dysfunction associated with cancer treatment in a subject having a cancer comprising administering at least one compound of the present disclosure in a therapeutically effective amount to the subject to treat or ameliorate at least one symptom of metabolic dysfunction associated with cancer treatment in a subject having cancer.

The present disclosure provides methods of reducing the expression of IL-10 in a tumor or plasma in a subject having a cancer comprising administering at least one compound of the present disclosure in a therapeutically effective amount to the subject, wherein the expression of IL-10 in a tumor, the tumor microenvironment or plasma is reduced in a subject metabolic dysfunction having cancer.

The present disclosure provides methods of reducing the expression of arginase-1 in a tumor or plasma in a subject having a cancer comprising administering at least one compound of the present disclosure in a therapeutically effective amount to the subject, wherein the expression of arginase-1 in a tumor, the tumor microenvironment or plasma is reduced in a subject having cancer.

The present disclosure provides methods of reducing the expression of myeloid-derived suppressor cells in a tumor or plasma in a subject having a cancer comprising administering at least one compound of the present disclosure in a therapeutically effective amount to the subject, wherein the expression of myeloid-derived suppressor cells in a tumor, the tumor microenvironment or plasma is reduced in a subject having cancer.

The present disclosure provides methods of reducing the expression of regulatory T cells in a tumor or plasma in a subject having a cancer comprising administering at least one compound of the present disclosure in a therapeutically effective amount to the subject, wherein the expression of regulatory T cells in a tumor, the tumor microenvironment or plasma is reduced in a subject having cancer.

The present disclosure provides methods of reducing the expression of a growth factor in a tumor or plasma in a subject having a cancer comprising administering at least one compound of the present disclosure in a therapeutically effective amount to the subject, wherein the expression of the growth factor in a tumor, the tumor microenvironment or plasma is reduced in a subject having cancer. The growth factor can be VEGF-C, IGF-1, bFGF, or a combination thereof.

Obesity has been identified as a risk factor for breast cancer and excess visceral adipose tissue is associated with a worse response to chemotherapy and reduced progression and/or disease-free survival (Schaffler, A., et al. (2007) Nat Clin Pract Endocrinol Metab 3:345-54; Vona-Davis, L. Rose, D P. (2007) Endocr Relat Cancer 14:189-206). Adipose tissue-derived factors (e.g. leptin, adiponectin, aromatase, IL-6) have been proposed as possible mediators of the obesity-breast cancer link, and recent data draw attention specifically to the adipokines leptin and adiponectin (Cleary, M P., et al. (2009) Front Biosci (School Ed) 1:329-57; Cleary, M P., et al. (2010) Vet Pathol 47:202-13). The molecular basis for underlying the role of leptin, adiponectin and other hormones, such as insulin and insulin-like growth factors have recently been described. Circulating adiponectin levels are inversely correlated with body mass index (BMI); in contrast, serum leptin positively correlates with BMI (Ryan, A S., et al. (2003) Diabetes Care 26:2383-8; Wauters, M., et al. (2000) Eur J Endocrinol 143:293-311). In obese individuals, especially in those with high visceral fat content, adiponectin levels are depressed (Brochu-Gaudreau K, et al. Endocrine 2010, 37(1): 11-32). Adiponectin is found in human serum at concentrations of 2-20 µg/ml (Grossmann, M E., et al. (2008) Br J Cancer 98:370-9). The mechanism underlying adiponectin signaling and cancer prevention is thought to involve the activation of intracellular signals AMPK and inhibition of growth and survival pathways (Brochu-Gaudreau K, et al. Endocrine 2010, 37(1): 11-32, Pfeiler G et al., Maturitas 2009, 63(3):253-256). Further, adiponectin may exert its biological activity indirectly, through selective sequestration of different growth factors (e.g., basic fibroblast growth factor, platelet-derived growth factor BB, heparin-binding epidermal growth factor) and inhibition of their normal receptor binding. These interactions involve specific oligomeric forms of adiponectin. Barb, D., Williams, C J., Neuwirth, A K., Mantzoros, C S. (2007) Am J Clin Nutr 86:s858-66. Wang et al. (2005) J Biol Chem 280:18341-7).

Several epidemiological studies found an inverse relation between adiponectin levels and breast cancer risk (Barb, et al. (2007) Am J Clin Nutr 86:s858-66; Miyoshi, et al. (2003) Clin Cancer Res 9:5699-704. Mantzoros, et al. (2004) J Clin Endocrinol Metab 89:1102-7; Chen, D C., et al. (2006) Cancer Lett 237:109-14). In breast cancer patients, the adiponectin levels and the adiponectin-to-leptin ratio tend to be reduced relative to that found in lean women (Cleary M P., et al., (2009) Front Biosci (Schol Ed) 1:329-57; Cleary, M P., et al. (2006) Cancer Lett 237:109-14). Breast cancer patients with low adiponectin levels are reported to have more aggressive tumors and higher frequency of lymph node metastasis (Schaffler, A., et al. (2007) Nat Clin Pract Endocrinol Metab 3:345-54; Hou, W K., et al. (2007) Chin Med J (Engl) 120:1592-6).

In one aspect, the present disclosure provides methods of utilizing at least one MetAP2 inhibitor, at least one fumagillin analog or derivative and/or at least one compound of the present disclosure to treat specific tumor types that are exacerbated by metabolic dysfunction, including HR+/Her2− breast cancer, triple negative breast cancer, Her2+ breast cancer, invasive breast carcinoma, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or acute myeloid lukemia. In preferred aspects, the present methods disclose subcutaneous administration of a MetAP2 inhibitor in cancer patients with pre-existing or treatment induced metabolic dysfunction. The metabolic dysfunction can include excessive visceral adiposity, elevated leptin levels, depressed adiponectin levels, high leptin-to-adiponectin ratio, elevated fasting insulin levels, elevated fasting insulin levels accompanied by chronic inflammation, hyperglycemia, elevated HbA1c or combinations thereof. The present methods can restore the patient to a more metabolically neutral and stable state and slow or reverse the progression of the patient's cancer.

Described herein are methods to improve the underlying metabolic dysfunction in patients with metabolically-sensitive tumors. The methods of treating the tumors include increasing the levels of adiponectin, lowering the levels of leptin, improving (decreasing) the leptin-to-adiponectin ratio, lowering the levels of insulin, lowering the fasting glucose level, or combinations thereof. Subcutaneous administration of the MetAP2 inhibitors described herein have demonstrated the ability to improve these levels and ratios in cancer patients, and thus, can be used for the treatment of metabolically sensitive tumors which can benefit from an adiponectin upregulation along with improved leptin and insulin sensitivity. Accordingly, in certain aspects, the MetAP2 inhibitors described herein can treat cancers including hormone-receptor positive (HR+) breast cancer, triple negative breast cancer, Her2+ breast cancer, castration resistant prostate cancer, esophageal adenocarcinoma, colorectal adenocarcinoma, cervical cancer, endometrial cancer, ovarian cancer, pancreatic adenocarcinoma, gall bladder, hepatocellular carcinoma, clear-cell renal cancer, melanoma, multiple myeloma, or combinations thereof. The aforementioned cancers can be related to, at least in part, to adiponectin deficiency and/or adiponectin resistance.

The present disclosure also provides methods of treating cancer in a subject in need thereof, said method comprising the steps of (i) identifying the patient as having hormone-receptor positive (HR+) breast cancer, triple negative breast cancer, Her2+ breast cancer, castration resistant prostate cancer, esophageal adenocarcinoma, colorectal adenocarcinoma, cervical, cancer endometrial cancer, ovarian cancer, pancreatic adenocarcinoma, gall bladder cancer, hepatocellular carcinoma, clear-cell renal cancer, melanoma, multiple myeloma, acute myeloid lukemia; (ii) determining whether the cancer patient has metabolic dysfunction, and (iii) if the subject is identified as having one of the cancers in step (i) and metabolic dysfunction in step (ii), administering a therapeutically effective amount of at least one MetAP2 inhibitor, at least one fumagillin analog or derivative, or at least one compound of the present disclosure. Preferably, the subject is administered a compound of the present disclosure. Preferably, the compound is administered subcutaneously. Metabolic dysfunction can include excessive visceral adiposity, elevated leptin levels, depressed adiponectin levels, high leptin-to-adiponectin ratio, elevated fasting insulin levels, elevated fasting insulin levels accompanied by chronic inflammation, hyperglycemia, elevated HbA1c or combinations thereof. Preferably, the metabolic dysfunction is low adiponectin, elevated leptin, elevated fasting insulin, hyperglycemia, or combinations thereof. The methods of the present disclosure can also include treating or ameliorating at least one symptom of the metabolic dysfunction in addition to treating the cancer.

In another aspect, the present disclosure provides a method of determining whether a tumor is metabolically sensitive and comprising: (1) identifying the tumor type as being one from the list of known metabolically-sensitive tumors (memingioma, thyroid, adenocarcinoma esophageal, liver, gallbladder, GIST, pancreatic, kidney, CRC, prostate, multiple myeloma, breast, ovarian, cervical, endometrial) (2) measuring the level of fasting insulin and glucose to determine the HOMA score (insulin sensitivity level) for the patient, (3) comparing the HOMA score to that of lean patients, and (4) determining that, if the level of the HOMA score is larger than the metabolically normal level, the cancer is susceptible to treatment with at least one MetAP2 inhibitor, at least one fumagillin analog or derivative, or at least one compound of the present disclosure.

In another aspect, the present disclosure provides a method of co-administering a MetAP2 inhibitor with a treatment that induces metabolic dysfunction. The treatment can be a cancer treatment. The treatment can be an AKT inhibitor, a PI3K inhibitor, an mTOR inhibitor, a PI3K/AKT/mTOR pathway inhibitor or any combination thereof.

As used herein, a "subject in need thereof" is a subject having a cell proliferative disorder, or a subject having an increased risk of developing a cell proliferative disorder relative to the population at large. A subject in need thereof can have a precancerous condition, such as hyperplasia. Preferably, a subject in need thereof has cancer or metastasis from a primary cancerous mass or hemaologic cancer. Preferably, the subject having a cell proliferative disorder also has pre-exciting or treatment-induced metabolic dysfunction.

A "subject" includes a mammal. The mammal can be e.g., any mammal, e.g., a human, primate, mouse, rat, dog, cat, cow, horse, goat, rabbit, camel, sheep or a pig. Preferably, the mammal is a human. The term "subject" and "patient" are used interchangeably herein.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the disclosure encompass a variety of conditions wherein cell division is deregulated. Exemplary cell proliferative disorders include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, B cell lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer or metastasis from a primary cancerous mass. A cell proliferative disorder includes a non-cancer condition or disorder. Preferably, the methods provided herein are used to treat or alleviate a symptom of cancer. The term "cancer" includes solid tumors, as well as hematologic tumors and/or malignancies or metastasis from a primary cancerous mass or hematologic origin. A "pre-cancer cell" or "precancerous cell" is a cell manifesting a cell proliferative disorder that is a precancer or a precancerous condition. A "cancer cell" or "cancerous cell" is a cell manifesting a cell proliferative disorder that is a cancer. As used herein the term "metastasis", "metastatic cancer" or "metastatic lesion" refers to the development of secondary malignant growth at a distance from a primary site of cancer. Any reproducible means of measurement may be used to identify cancer cells or precancerous cells. Cancer cells or precancerous cells can be identified by histological typing or grading of a tissue sample (e.g., a biopsy sample) or by evidence of DNA mutations. Cancer cells or precancerous cells can be identified through the use of appropriate molecular markers.

Exemplary cancers include, but are not limited to, adrenocortical carcinoma, AIDS-related cancers, AIDS-related lymphoma, B cell lymphomas, anal cancer, anorectal cancer, cancer of the anal canal, anal squamous cell carcinoma, angiosarcoma, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, head and neck squamous cell carcinoma, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, T-cell lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, lung squamous cell carcinoma, AIDS-related lymphoma, non-Hodgkin lymphoma, primary central nervous system lymphoma, B-cell lymphomas, primary effusion lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, pancreatic endocrine tumor, paranasal sinus and nasal cavity cancer, parathyroid cancer, cholangiocarcinoma, penile cancer, pharyngeal cancer, pheochromocytoma, pineoblastoma and supratentorial primitive neuroectodermal tumors, pituitary tumor, pituitary adenoma, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, B cell lymphomas, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present disclosure can be used to treat a cancer selected from the group consisting of a hematologic cancer of the present disclosure or a hematologic cell proliferative disorder of the present disclosure. A hematologic cancer of the present disclosure can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1 (mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter of the present disclosure is in direct contact with a cell, or is close enough to induce a desired biological effect in a cell.

In addition to treating or alleviating at least one symptom of one or more proliferation disorders, the compounds of the present disclosure can also treat or alleviate a variety of related disorders.

In particular, addition to treating or alleviating at least one symptom of one or more proliferation disorders, the compounds of the present disclosure can also treat or alleviate at least one metabolic dysfunction selected from the group consisting of excessive visceral adiposity, elevated leptin levels, depressed adiponectin levels, high leptin-to-adiponectin ratio, elevated fasting insulin levels, elevated fasting insulin levels accompanied by chronic inflammation, hyperglycemia, elevated HbA1c, or combinations thereof. Preferably, the metabolic dysfunction that is treated or ameliorated is low adiponectin, elevated leptin, elevated fasting insulin, hyperglycemia or combinations thereof.

In addition to treating or alleviating at least one symptom of one or more proliferation disorders, the compounds of the present disclosure can also treat or alleviate at least one symptom of obesity or treatment-induced metabolic dysfunction.

In addition to treating or alleviating at least one symptom of one or more proliferation disorders, the compounds of the present disclosure can also decrease body weight. In certain aspects, the subject is overweight or obese. In certain aspects, the subject is in need of reducing excess adipose tissue. Preferably, the adipose tissue being reduced is visceral adipose tissue or adipose tissue in close proximity to the tumor or metastases.

Obesity and being overweight refer to an excess of fat in a subject in proportion to lean body mass. Excess fat accumulation is associated with an increase in size (hypertrophy or steatosis) as well as number (hyperplasia) of adipose tissue cells. Obesity can be due to any cause, whether genetic (e.g. Prader-Willi Syndrome) or environmental. Obesity is variously measured in terms of absolute weight, weight:height ratio, degree of excess body fat, distribution of visceral or subcutaneous fat. A common measure of body fat is Body Mass Index (BMI). The BMI refers to the ratio of body weight (expressed in kilograms) to the square of height (expressed in meters). Body mass index can be accurately calculated using the formulas: SI units: BMI=weight (kg)/(height$^2$ (m$^2$), or US units: BMI= (weight (lb)*703)/(height$^2$ (in$^2$).

As described herein, "overweight" refers to a condition whereby an otherwise healthy adult that has a BMI of 25 kg/m$^2$ to 29.9 kg/m$^2$. As described herein, "obese" or "obesity" refers to a condition whereby an otherwise healthy adult that has a BMI of 30 kg/m² or greater. Obesity has several subcategories. An adult that has a BMI of 35 kg/m² or greater is referred to as "severely obese" or "severe obesity". An adult that has a BMI of ≥40-44.9 kg/m² or and adult that has a BMI of 35 kg/m² or greater and at least one obesity-related health condition is referred to as "morbidly obese" or "morbid obesity". An adult that has a BMI of 45 kg/m² or greater is referred to as "super obese" or "super obesity". For children, the definitions of overweight and obese take into account age and gender effects on body fat.

Different countries can define obesity and overweight with different BMI. The term "obesity" is meant to encompass definitions in all countries. For example, the increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25.0 kg/m². Ethnic South and Central Americans tend to be categorized more closely to Asians than Europeans or North Americans.

BMI does not account for the fact that excess adipose tissue can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass can involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA). DEXA allows body composition, particularly total body fat and/or regional fat mass, to be determined non-invasively. MRI can also be used to determine composition non-invasively.

In another instance, the present invention may alleviate symptoms of metabolic dysfunction induced by a second or other treatment. In a preferred embodiment, the other agent is a PI3K, AKT or mTOR inhibitor.

In another instance, the subject can be pre-treated with a compound of the instant invention, by 1 hour, 4 hours, 1 day, about 1 week, about 2 weeks, about 3 weeks, about 4 weeks, about 6 weeks, about 8 weeks.

In addition to treating or alleviating at least one symptom of one or more proliferation disorders, the compounds of the present disclosure can also decrease adipocytes or adipose tissue. Decreasing adipocytes means decreasing the number or decreasing the size (fat content) of the adipocytes. In certain aspects, the compounds of the present disclosure shrink the adipocytes in the subject. The adipose tissue can be white adipose tissue or brown adipose tissue.

In addition to treating or alleviating at least one symptom of one or more proliferation disorders, the compounds of the present disclosure can also decrease waist circumference. Waist circumference is assessed by using a tape measure placed around the abdomen 1 cm above the iliac crest. The subjects of the present disclosure can have a decrease in waist circumference from about 1 inch to about 20 inches (e.g., 1, 2, 3, 4, 5, 6, 7, 8, 9, 10, 11, 12, 13, 14, 15, 16, 17, 18, 19 or 20 inches).

In addition to treating or alleviating at least one symptom of one or more proliferation disorders, the compounds of the present disclosure can also decrease body fat and provide substantial maintenance of muscle mass in said patient. In certain aspects, upon administration, fat oxidation is enhanced in a patient as compared to a patient on a restricted food intake diet alone. Such a patient can retain substantially more muscle mass as compared to body fat reduction in a patient using an energy restricted diet alone.

In addition to treating or alleviating at least one symptom of one or more proliferation disorders, the compounds of the present disclosure can also lower insulin levels, leptin levels or both in the subject. In certain aspects, the subject is overweight or obese or has elevated fasting insulin and/or leptin. In certain aspects, the subject is in need of reducing excess adipose tissue.

In addition to treating or alleviating at least one symptom of one or more proliferation disorders, the compounds of the present disclosure can also improve surgical outcome comprising administering, prior to surgery, at least one compound of the present disclosure in a therapeutically effective amount to the subject to improve surgical outcome. In certain aspects, administration reduces liver and/or abdominal fat in said patient and improves surgical outcome. In certain aspects, the surgery is non-acute surgery. Such surgeries can include bariatric surgery, cardiovascular surgery, abdominal surgery, or orthopedic surgery.

As used herein, "monotherapy" refers to the administration of a single active or therapeutic compound of the present disclosure to a subject in need thereof. For example, administering a cancer monotherapy with one of the compounds of the present disclosure, or a pharmaceutically acceptable salt, prodrug, metabolite, analog or derivative thereof, to a subject in need of treatment of cancer. Monotherapy can be contrasted with combination therapy, in which a combination of multiple active compounds is administered, as described below. In one aspect, monotherapy with a compound of the present disclosure, or a pharmaceutically acceptable salt, prodrug, metabolite, polymorph or solvate thereof, is more effective than combination therapy in inducing a desired biological effect.

As used herein, "combination therapy" or "co-therapy" includes the administration of at least two compounds of the present disclosure, or pharmaceutically acceptable salts, prodrugs, metabolites, polymorphs or solvates thereof, as part of a specific treatment regimen intended to provide the beneficial effect from the co-action of these at least two compounds of the present disclosure. The beneficial effect of the combination includes, but is not limited to, pharmacokinetic or pharmacodynamic co-action resulting from the combination of these at least two compounds of the present disclosure. Administration of these at least two compounds of the present disclosure in combination typically is carried out over a defined time period (usually minutes, hours, days or weeks depending upon the combination selected). "Combination therapy" can be, but generally is not, intended to encompass the administration of two or more of these compounds of the present disclosure as part of separate monotherapy regimens that incidentally and arbitrarily result in the combinations of the present disclosure.

"Combination therapy" also embraces the administration of the compounds of the present disclosure in further combination with a second active agent and/or non-drug therapy (e.g., exercise, diet, surgery or radiation treatment). Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks. The second active agent can be conjugated to a polymer.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous manner as used herein is administration of at least two therapeutic agents within 2 hours of each other. Substantially simultaneous administration can be accomplished, for example, by administering to the subject a single composition having a fixed ratio of each therapeutic agent or in separate capsules for each of the therapeutic agents. Sequential manner as used herein is administration of one of the at least two therapeutic agents more than two hours after the other of the at least two therapeutic agents. Preferably, for sequential administration, one of the at least two therapeutic agents is administered at least 12 hours, at least 24 hours, at least 48 hours, at least 96 hours, at least one week, at least after two weeks, at least after 4 weeks, or at least after 8 weeks after administration of the other therapeutic agent. Sequential or substantially simultaneous administration of each therapeutic agent can be affected by any appropriate route including, but not limited to, oral routes, intravenous routes, subcutaneous routes, intramuscular routes, and direct absorption through mucous membrane tissues. The therapeutic agents can be administered by the same route or by different routes. For example, a first therapeutic agent of the combination selected can be administered by subcutaneous injection while the other therapeutic agents of the combination can be administered orally or introvenously. Alternatively, for example, all therapeutic agents can be administered orally or all therapeutic agents can be administered by subcutaneous injection. The sequence in which the therapeutic agents are administered is not narrowly critical for some agents.

In a preferred aspect, the second active agent is a chemotherapeutic or targeted agent. The additional chemotherapeutic or targeted agent (also referred to as an anti-neoplastic agent or anti-proliferative agent) can include, in a preferred embodiment 5FU or its oral version capecitabine, or agents from the PI3K, AKT, mTOR drug classes.

In some aspects, the second active agent is a compound that induces metabolic dysfunction. In some aspects, the second active agent is a PI3K inhibitor, an AKT inhibitor, an mTOR inhibitor or a PI3K/AKT/mTOR pathway inhibitor.

In some aspects, the second active agent is alpelisib/BYL-719, AZD5363 (capavasertib), everolimus or any combination thereof.

In some aspects, BYL-719 can be administered to the subject orally (per os, PO). In some aspects, BYL-719 can be administered once daily. In some aspects, BYL-719 can be administered in an amount of 150 mg per day. In some aspects, BYL-719 can be administered in an amount of 200 mg per day. In some aspects, BYL-719 can be administered at 250 mg per day. In some aspects, BYL-719 can be administered in an amount of 300 mg per day.

The present disclosure provides a method for treating, or ameliorating at least one symptom of, cancer in a subject in need thereof comprising administering at least one therapeutically effective amount of at least one MetAP2 inhibitor in combination with at least one therapeutically effective amount of at least one PI3K inhibitor.

In some aspects of the methods of the present disclosure, an at least one MetAP2 inhibitor can be ZGN-1061. ZGN-1061 has the following structure:

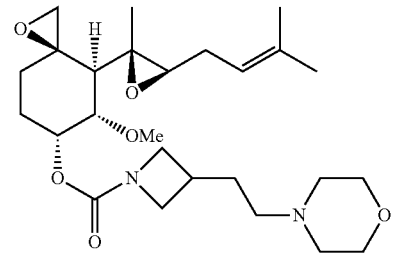 [SMILES: CO[C@@H]1[C@H](OC(=O)N2CC(CCN3CCOCC3)C2)CC[C@]2(CO2)[C@H]1[C@@]1(C)O[C@@H]1CC=C(C)C]

In some aspects of the methods of the present disclosure, an at least one MetAP2 inhibitor can be Beloranib. Beloranib has the following structure:

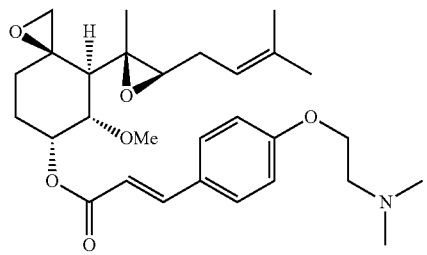 [SMILES: CO[C@@H]1[C@H](OC(=O)/C=C/c2ccc(OCCN(C)C)cc2)CC[C@]2(CO2)[C@H]1[C@@]1(C)O[C@@H]1CC=C(C)C]

In some aspects of the methods of the present disclosure, an at least one PI3K inhibitor can be Serabelisib (TAK-117). Serabelisib (TAK-117) has the following structure:

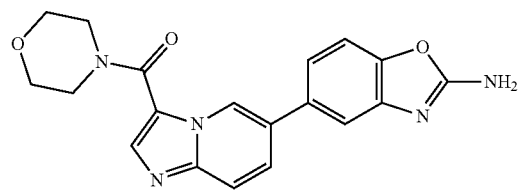 [SMILES: Nc1nc2cc(-c3ccc4ncc(C(=O)N5CCOCC5)n4c3)ccc2o1]

In some aspects of the methods of the present disclosure, an at least one PI3K inhibitor can be BYL-719. BYL-719 has the following structure:

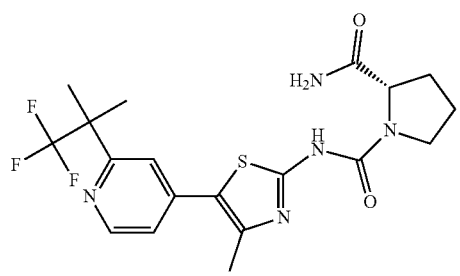 [SMILES: Cc1nc(NC(=O)N2CCC[C@H]2C(N)=O)sc1-c1ccnc(C(C)(C)C(F)(F)F)c1]
In some aspects of the disclosure, a MetAP2 inhibitors can include, but are not limited to A832234, JNJ4929821, Triazolopyrimidine, A357300, LAF389, indazole, triazole fumagalone, ZGN-1061, CKD-732, XMT-1191, TNP-470, PPI-2458 or any combination therefore.
In some aspects of the disclosure, a MetAP2 inhibitor can have any of the following structures:
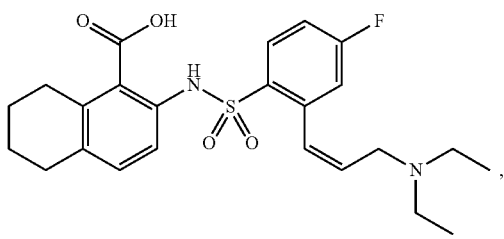
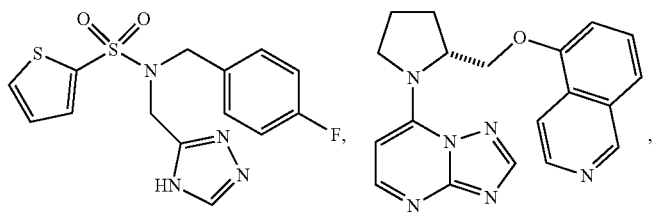
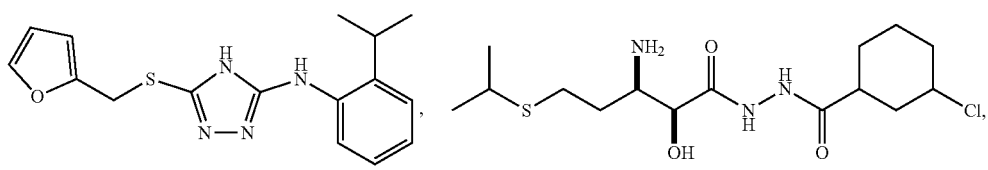
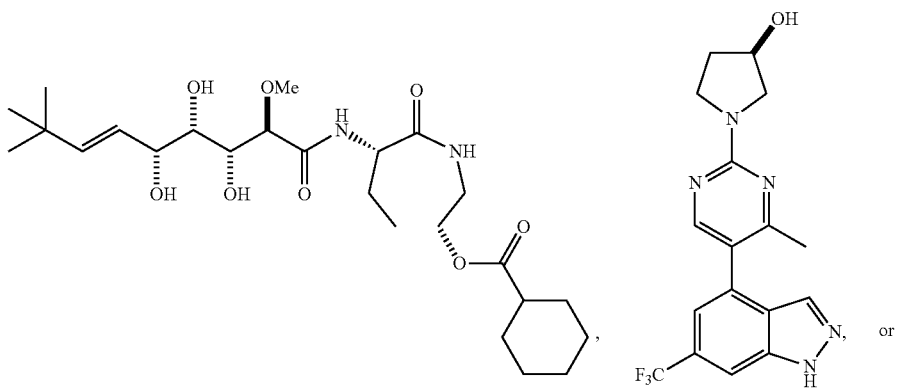

-continued

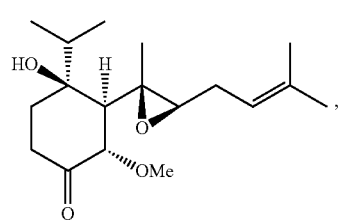

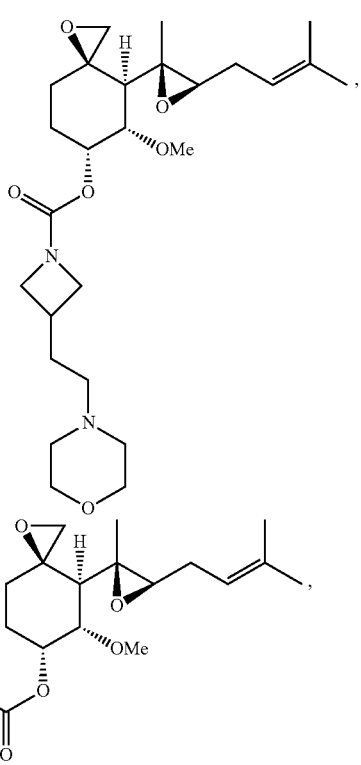

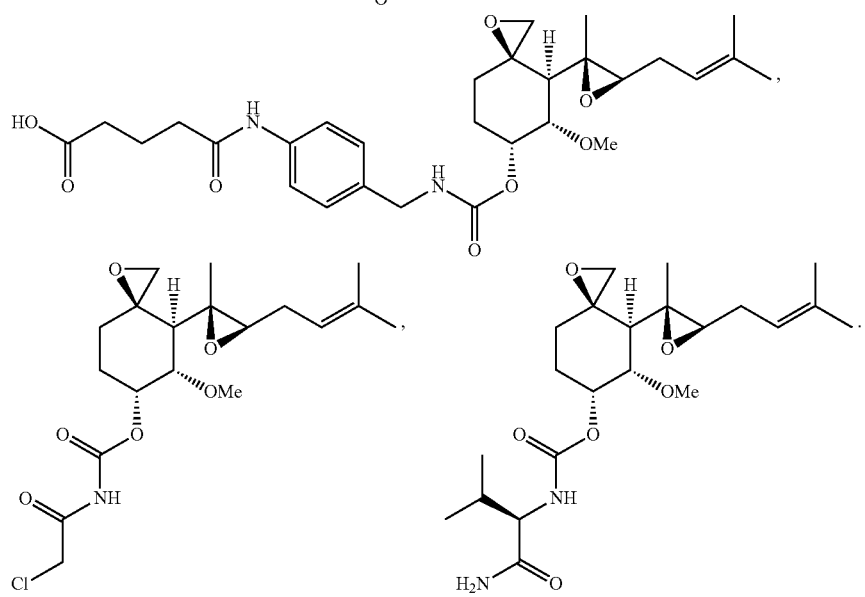

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. In these situations, delaying the recurrence of the cancer, slowing the progression of the cancer, prolonging the life expectancy of the subject and/or reducing pain and/or improving quality of life, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, chronic or acute discomfort, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. Signs are defined as things that can be seen by a doctor, nurse, or other health care professional.

Cancer is a group of diseases that may cause almost any sign or symptom. The signs and symptoms will depend on where the cancer is, the size of the cancer, the stage of the cancer, and how much it affects the nearby organs or structures. If a cancer spreads (metastasizes), then signs or symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms that may be difficult to detect.

Sometimes cancers start in places where it does not cause any symptoms until the cancer has grown quite large or progressed to an advanced stage. Pancreatic cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or unwanted weight loss. This may be because cancer cells induce a systemic pro-inflammatory state, or use up much of the body's energy supply or release substances that change the body's metabolism (e.g, the hyper-metabolic condition known as cachexia), or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin, some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant disclosure.

Treating cancer can result in a slowing of its growth or a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average progression or survival time of a population of treated subjects in comparison to a population receiving carrier alone. Preferably, the average progression or survival time is increased by more than 30 days; more preferably, by more than 60 days; more preferably, by more than 90 days; and most preferably, by more than 120 days. An increase in average progression or survival time of a population may be measured by any reproducible means. An increase in average progression or survival time of a population may be measured, for example, by calculating for a population the average length of progression or survival following initiation of treatment with an active compound. An increase in average progression or survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average progression or survival time of a population of treated subjects in comparison to a population receiving monotherapy with a drug that is not a compound of the present disclosure, or a pharmaceutically acceptable salt, prodrug, metabolite, analog or derivative thereof. Preferably, the average progression or survival time is increased by more than 30 days; more preferably, by more than 60 days; more preferably, by more than 90 days; and most preferably, by more than 120 days. An increase in average progression or survival time of a population may be measured by any reproducible means. An increase in average progression or survival time of a population may be measured, for example, by calculating for a population the average length of progression or survival following initiation of treatment with an active compound. An increase in average progression or survival time of a population may also be measured, for example, by calculating for a population the average length of progression or survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to the rate prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth, sometimes referred to as progression-free survival. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation.

Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present disclosure, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells.

Contacting a cell with a compound of the present disclosure, or a pharmaceutically acceptable salt, prodrug, metabolite, polymorph or solvate thereof, can induce or activate cell death selectively in cancer cells. Administering to a subject in need thereof a compound of the present disclosure, or a pharmaceutically acceptable salt, prodrug, metabolite, polymorph or solvate thereof, can induce or activate cell death (apoptosis) selectively in cancer cells. Contacting a cell with a compound of the present disclosure, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present disclosure, or a pharmaceutically acceptable salt, prodrug, metabolite, polymorph or solvate thereof, induces cell death selectively in one or more cells affected by a cell proliferative disorder.

The present disclosure relates to a method of treating or preventing cancer by administering a compound of the present disclosure, or a pharmaceutically acceptable salt, prodrug, metabolite, polymorph or solvate thereof, to a subject in need thereof, where administration of the compound of the present disclosure, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

A "therapeutically effective amount" of a compound, with respect to use in treatment, refers to an amount of a compound in a preparation which, when administered as part of a desired dosage regimen (to a mammal, preferably a human) alleviates a symptom, ameliorates a condition, or slows or prevents the onset of disease conditions according to clinically acceptable standards for the disorder or condition to be treated or the cosmetic purpose, e.g., at a reasonable benefit/risk ratio applicable to any medical treatment. A "therapeutically effective amount" is synonymous with "efficacious dose".

As used herein, an "effective dosage" or "effective amount" of drug, compound, or pharmaceutical composition is an amount sufficient to effect beneficial or desired clinical results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing intensity, duration, or frequency of attack of the disease, and decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For example, an effective amount of a compound of the present disclosure for treating a proliferation disorder is an amount sufficient to treat or ameliorate one or more symptoms associated with the proliferation disorder. An "effective amount" is an amount sufficient to result in one or more of the following (which can also correspond to various aspects of the disclosure): reducing tumor size, reducing tumor volume, reducing tumor number, decrease in metastatic lesions, increase in survival time, decrease in mortality rate, decrease in tumor growth rate, decrease in tumor regrowth, reduction in proportion of proliferating cells, or increasing the quality of life of those suffering from a proliferation disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. In providing a subject with one or more of the compounds described herein, the dosage of administered compound(s) will vary depending upon such factors as the subject's age, weight, height, sex, general medical condition, previous medical history, disease progression, route of administration, formulation and the like.

In another aspect, provided herein are effective dosages of a compound of the present disclosure. For example, provided here are methods that include administering doses of a compound of the present disclosure that are effective for tumor reduction. For example, contemplated dosage of a compound of the present disclosure in the methods described herein may include administering a dose independent of body weight of about 200 mg/day, about 80 mg/day, about 40 mg/day, about 20 mg/day, about 10 mg/day, about 5 mg/day, about 3 mg/day, about 2 mg/day, about 1 mg/day, about 0.5 mg/day, about 0.2 mg/day, about 0.05 mg/day, about 0.01 mg/day, or about 0.001 mg/day.

An effective amount of the drug for amelioration of metabolic dysfunction, improvements in tumor biomarkers, and/or tumor reduction in a patient may also be dosed based on body weight or surface area and be about 0.0001 mg/kg to about 5 mg/kg of body weight per day. For example, a contemplated dosage may be from about 0.001 to 5 mg/kg of body weight per day, about 0.001 mg/kg to 2 mg/kg of body weight per day, about 0.001 mg/kg to 0.1 mg/kg of body weight per day, about 0.001 to about 0.010 mg/kg of body weight a day or about 0.007 mg/kg of body weight a day in single, divided, or continuous doses. These doses may be adjusted for the patient's weight in kg, body surface area in $m^2$, and age in years. For example, a contemplated dosage may be about 1 mg/m$^2$ to about 100 mg/m$^2$, about 5 mg/m$^2$ to about 25 mg/m$^2$, about 5 mg/m$^2$ to about 100 mg/m$^2$, about 5 mg/m$^2$ to about 15 mg/m$^2$, or about 5 mg/m$^2$ to about 10 mg/m$^2$.

An effective amount of a pharmaceutical agent is that which provides an objectively identifiable improvement in a biomarker or in the tumor as noted by the clinician or other qualified observer. For example, delay of progression or regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Administration of a compound of the present disclosure in accordance with the method in the present disclosure can be continuous or intermittent, depending, for example, upon the recipient's physiological condition, whether the purpose of the administration is therapeutic or prophylactic, and other factors known to skilled practitioners. The administration of a compound of the present disclosure may be essentially continuous over a preselected period of time or may be in a series of spaced doses.

For repeated administrations over several hours or longer, depending on the condition, the treatment is sustained until a desired suppression of disease symptoms occurs or until sufficient therapeutic levels are achieved. For example, dosing from one to five times a week is contemplated. Other dosing regimens include a regimen of every three to four days, or less frequently. In certain aspects, a compound of the present disclosure is administered about every fourth day, about every seventh day, about ever tenth day or about every fourteenth day. In some aspects, a compound of the present disclosure is administered about once per week, once every two weeks, or about 1 to 4 times per month depending on the duration of the response to drug administration. Intermittent dosing regimen with staggered dosages spaced by 2 days up to 7 days or even 14 days may be used. In some aspects, treatment may start with a daily dosing and later change to weekly even monthly dosing. The progress of this therapy is easily monitored by conventional techniques and assays, or by measuring standard clinical chemistries.

Frequency of administration may be determined and adjusted over the course of therapy. For example, frequency of administration may be determined or adjusted based on the type and severity of the disease to be treated, whether the agent is administered for preventive or therapeutic purposes, previous therapy, the patient's clinical history and response to the agent, and the discretion of the attending physician. Typically, the clinician will administer a compound of the present disclosure until a dosage is reached that achieves the desired result.

Treatment can be continued for as long or as short a period as desired. A suitable treatment period can be, for example, at least about one week, at least about four weeks, at least about one month, at least about six months, at least about 1 year, at least about 2 years, or indefinitely. A treatment period, either monotherapy or in combination with another agent, can terminate when a desired result, for example tumor reduction target, is achieved. For example, when loss of about 5% tumor size, about 10% tumor size, about 20% tumor size, about 30% tumor size or more has been achieved. A treatment regimen can include a corrective phase, during which a compound of the present disclosure is administered in dose, or dosing frequency, sufficient to provide reduction of tumor size, delay in tumor growth, or reduction in rate of tumor growth is administered, followed by a maintenance phase, during which a lower compound dose, or decreased dosing frequency, sufficient to prevent or delay tumor regrowth is administered.

Compounds and Pharmaceutical Compositions of the Present Disclosure

In certain aspects, modifications to the active moiety are accomplished by using a linker having a structure such that upon cleavage, a fragment of the linker remains attached to the active moiety. That fragment may change any of the molecular weight, hydrophobicity, polar surface area, or charge of the active moiety, thereby producing a modified active moiety having reduced efflux from a target cell compared to the unmodified active moiety. For example, coupling MetAP2 inhibitory active moieties via the linkers described herein provide conjugates in which upon cleavage of the linker, produce an active moiety having a fragment of the linker attached thereto (modified active moiety). The modified active moieties described herein may have reduced efflux from a cell compared to the unmodified active moieties, resulting in modified active moieties with superior efficacy to the parent small molecules and superior efficacy to the parent small molecules and superior pharmacokinetic profiles.

The present disclosure provides conjugates with linkers having the structure:

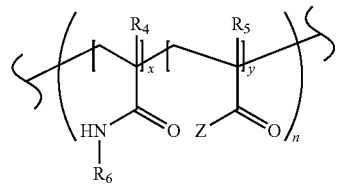

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)_mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

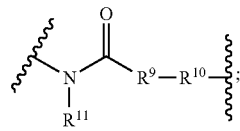

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; and r is 1, 2, 3, 4, 5, or 6. In some aspects, n is in the range of about 1 to about 90; about 1 to about 80; about 1 to about 70; about 1 to about 60; about 1 to about 55; or about 1 to about 50.

In certain aspects, $R_4$ is $C_1$-$C_6$ alkyl. In certain aspects, $R_4$ is methyl. In certain aspects, $R_5$ is $C_1$-$C_6$ alkyl. In certain aspects, $R_5$ is methyl. In certain aspects, $R_6$ is 2-hydroxyethyl, 2-hydroxypropyl or 3-hydroxypropyl. In certain aspects, $R_6$ is 2-hydroxypropyl.

In certain aspects, the compound has a molecular weight of greater than about 100 kDa. In certain aspects, the compound has a molecular weight of less than about 100 kDa. In other aspects, the molecular weight is less than about 95 kDa. In other aspects, the molecular weight is less than about 90 kDa. In other aspects, the molecular weight is less than about 80 kDa. In other aspects, the molecular weight is less than about 70 kDa. In other aspects, the molecular weight is less than about 65 kDa. In other aspects, the molecular weight is less than about 60 kDa. In other aspects, the molecular weight is less than about 45 kDa. In other aspects, the molecular weight is less than about 35 kDa.

In certain aspects, the ratio of x to y is in the range of about 100:1 to about 1:1. In certain aspects, the ratio of x to y is in the range of about 30:1 to about 3:1. In other aspects, the ratio of x to y is in the range of about 19:2 to about 7:2. In certain aspects, the ratio of x to y is in the range of about 9:1 to about 4:1. In certain aspects, the ratio of x to y is about 11:1. In certain aspects, the ratio of x to y is about 9:1. In certain aspects, the ratio of x to y is about 4:1. In certain aspects, the ratio of x to y is about 12:1. For example, in certain aspects, the ratio of x:y is about 3:1; the ratio of x:y is about 4:1; the ratio of x:y is about 5:1; the ratio of x:y is about 6:1; the ratio of x:y is about 7:1; the ratio of x:y is about 8:1; the ratio of x:y is about 9:1; the ratio of x:y is about 10:1; the ratio of x:y is about 11:1; the ratio of x:y is about 12:1; the ratio of x:y is about 13:1; the ratio of x:y is about 14:1; the ratio of x:y is about 15:1; the ratio of x:y is about 16:1; the ratio of x:y is about 17:1; the ratio of x:y is about 18:1; the ratio of x:y is about 19:1; the ratio of x:y is about 20:1; the ratio of x:y is about 21:1; the ratio of x:y is about 22:1; the ratio of x:y is about 23:1; the ratio of x:y is about 24:1; the ratio of x:y is about 25:1; the ratio of x:y is about 26:1; the ratio of x:y is about 27:1; the ratio of x:y is about 28:1; the ratio of x:y is about 29:1; or the ratio of x:y is about 30:1.

In certain aspects, Z is —NH-$AA_1$-$AA_2$-$AA_3$-$AA_4$-$AA_5$-$AA_6$-C(O)-L. In certain aspects, L is methoxy, ethoxy, pentafluorophenyloxy, phenyloxy, acetoxy, fluoride, chloride, methoxycarbonyloxy; ethoxycarbonyloxy, phenyloxycarbonyloxy, 4-nitrophenyloxy, trifluoromethoxy, pentafluoroethoxy, or trifluoroethoxy. In certain aspects, L is 4-nitrophenyloxy.

In certain aspects, Z is-NH-$AA_1$-$AA_2$-$AA_3$-$AA_4$-$AA_5$-$AA_6$-C(O)-Q-X—Y—C(O)—W. In certain aspects, $AA_1$ is glycine. In certain aspects, $AA_2$ is glycine. In certain aspects, $AA_3$ is glycine. In certain aspects, $AA_4$ is glycine or phenylalanine. In certain aspects, $AA_5$ is leucine, phenylalanine, valine or tyrosine. In certain aspects, $AA_6$ is asparagine, citrulline, glutamine, glycine, leucine, methionine, threonine or tyrosine. In certain aspects, $AA_5$-$AA_6$ is Leu-Cit, Leu-Gln, Leu-Gly, Leu-Leu, Leu-Met, Leu-Thr, Phe-Cit, Phe-Gln, Phe-Leu, Phe-Met, Phe-Thr, Val-Asn, Val-Cit, Val-Gln, Val-Leu, Val-Met, Val-Thr, Tyr-Cit, Tyr-Leu, or Tyr-Met. In certain aspects, $AA_1$, $AA_3$ and $AA_5$ are glycine, valine, tyrosine, tryptophan, phenylalanine, methionine, leucine, isoleucine, or asparagine. In certain aspects, $AA_2$, $AA_4$ and $AA_6$ are glycine, asparagine, citrulline, glutamine, glycine, leucine, methionine, phenylalanine, threonine or tyrosine. In certain aspects, $AA_2$ is a bond; and $AA_3$ is a bond. In certain aspects, $AA_1$ is glycine; $AA_4$ is phenylalanine; $AA_5$ is leucine; and $AA_6$ is glycine.

In certain aspects, W is

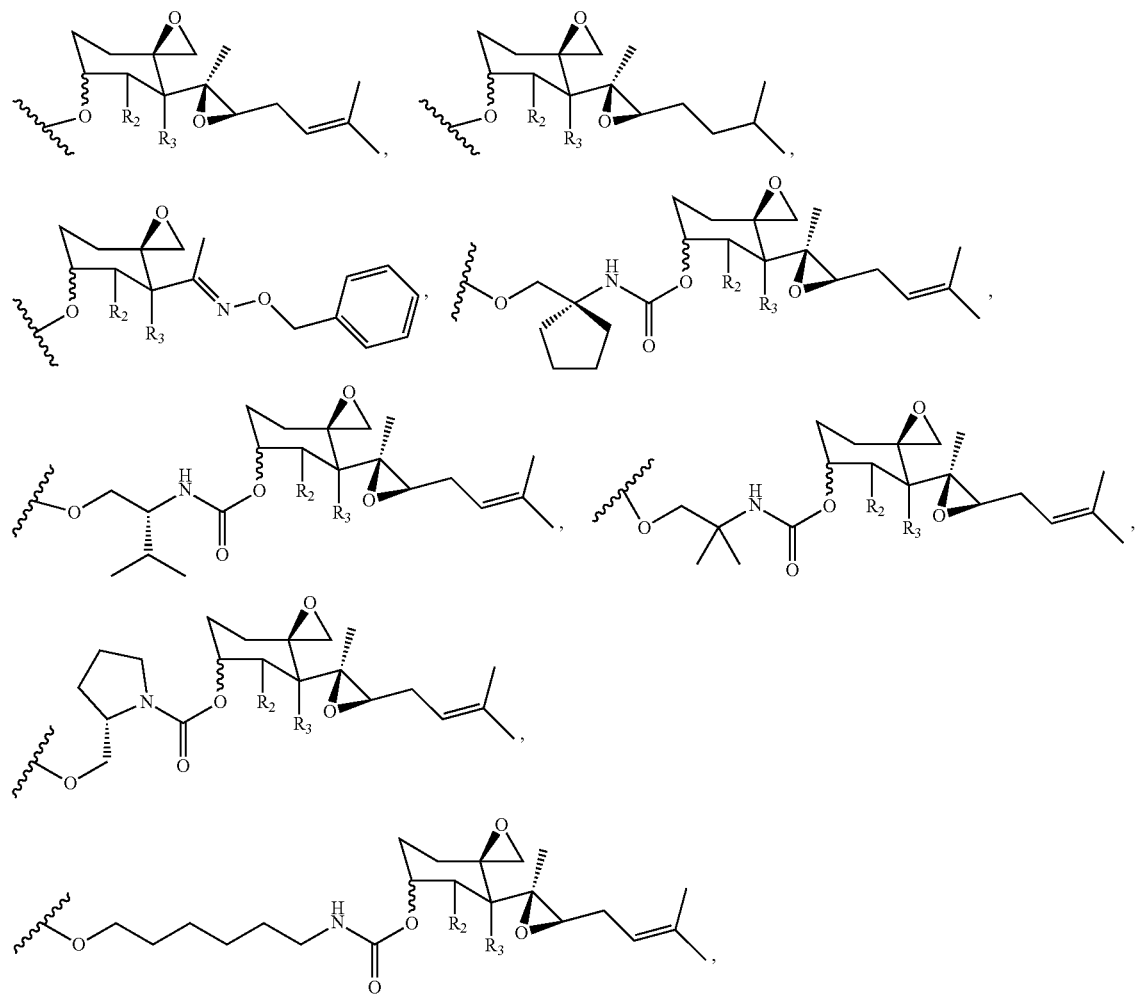

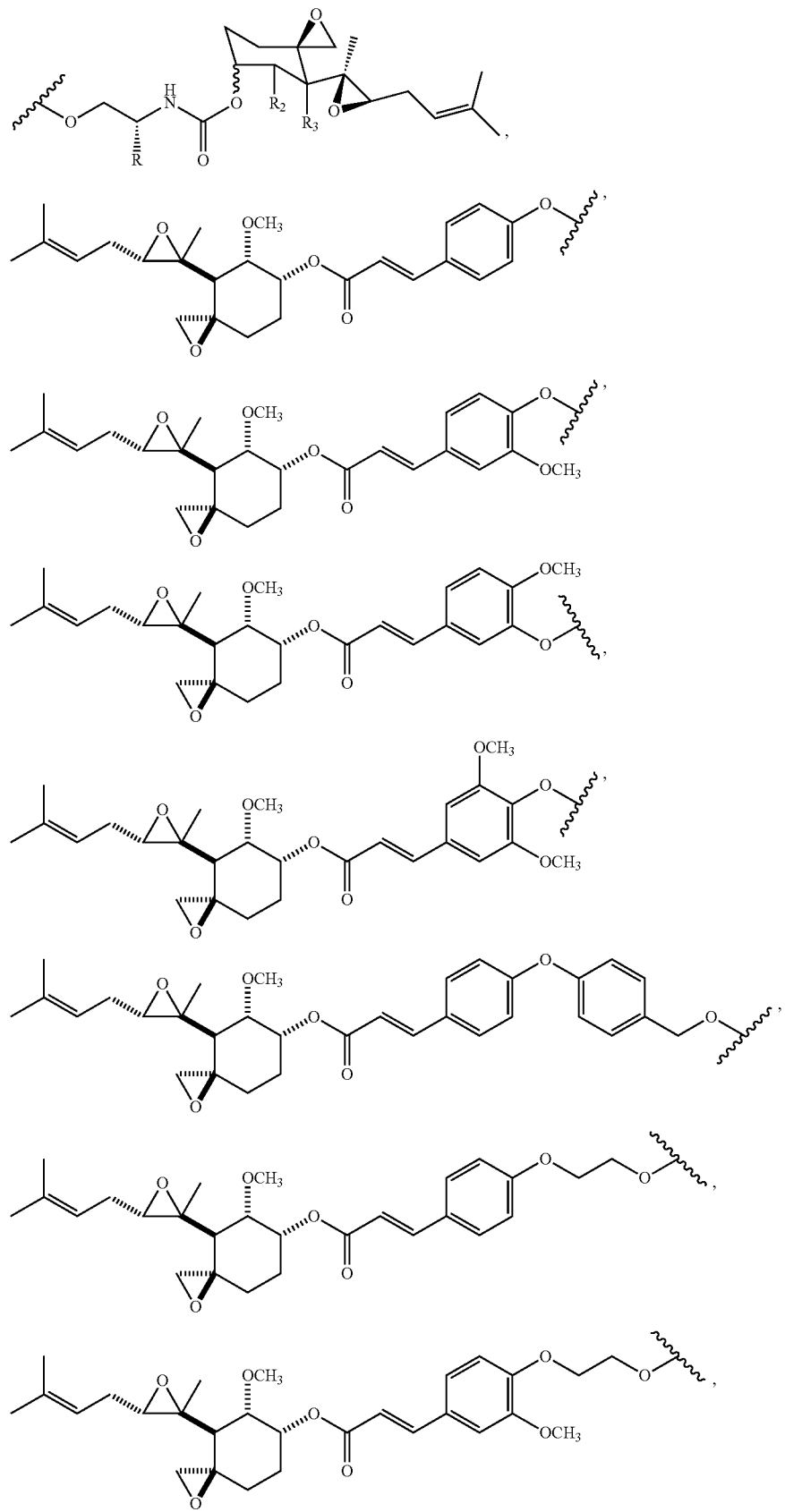

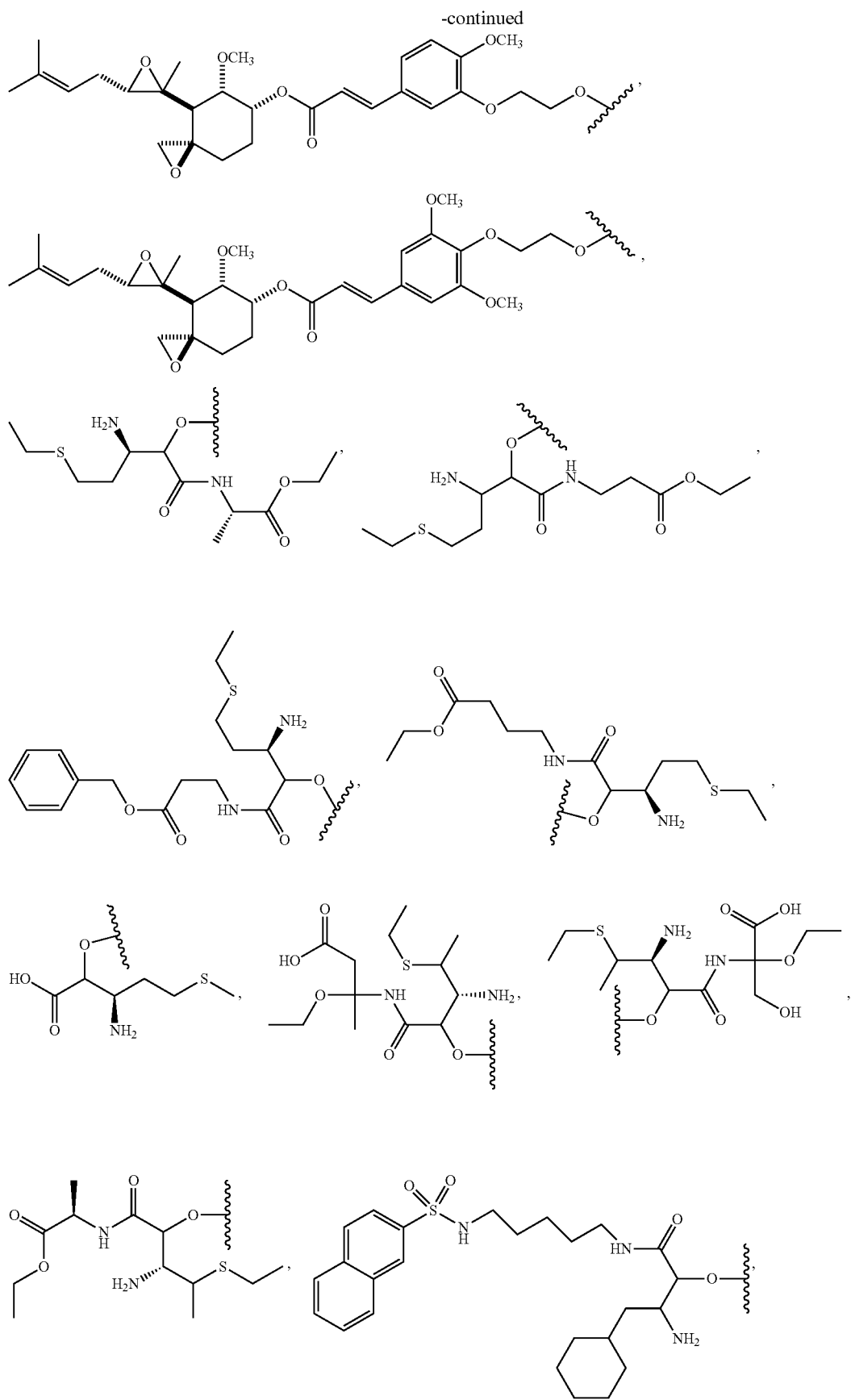

-continued
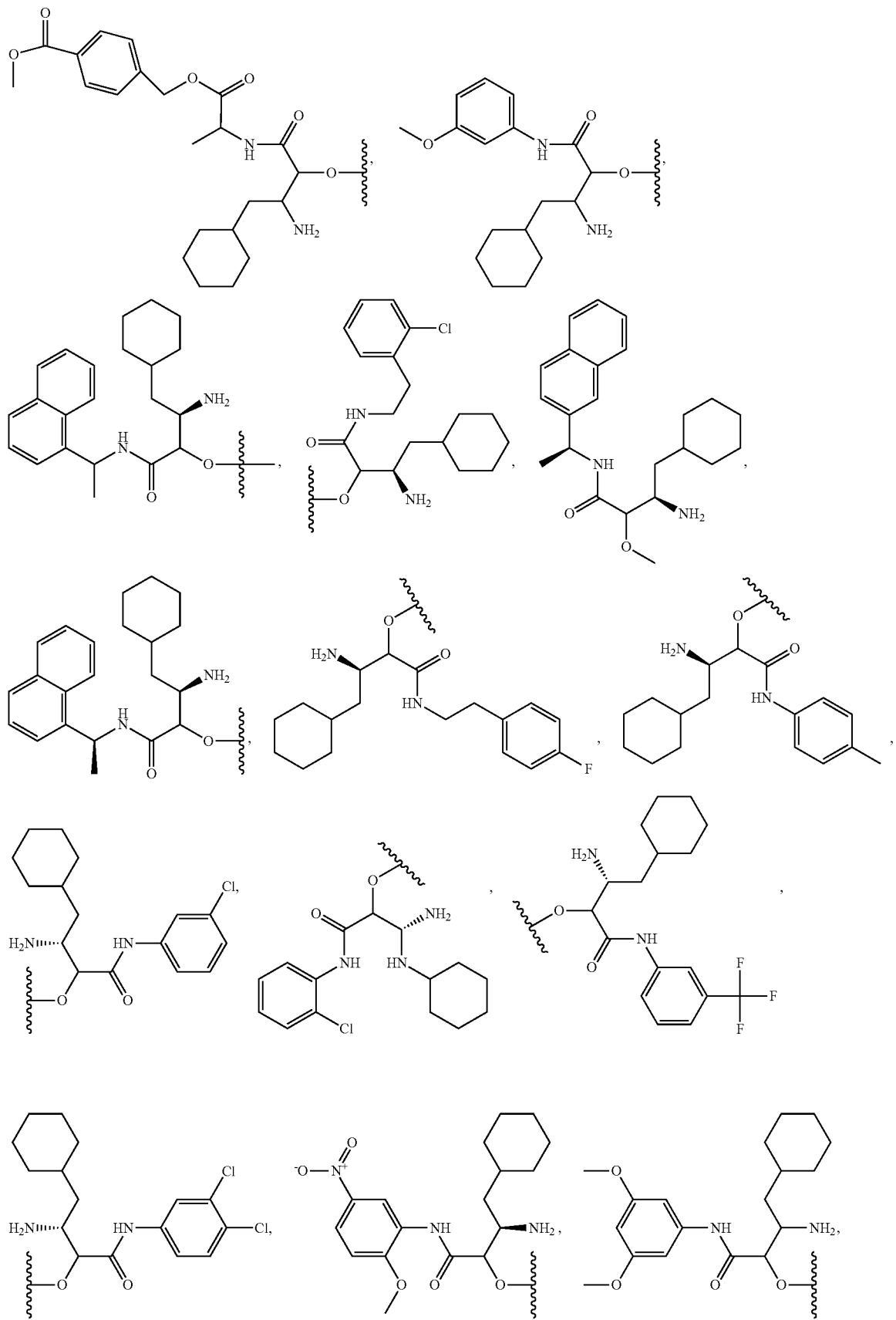

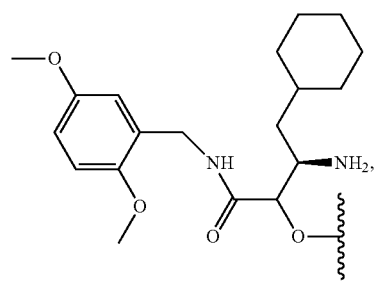
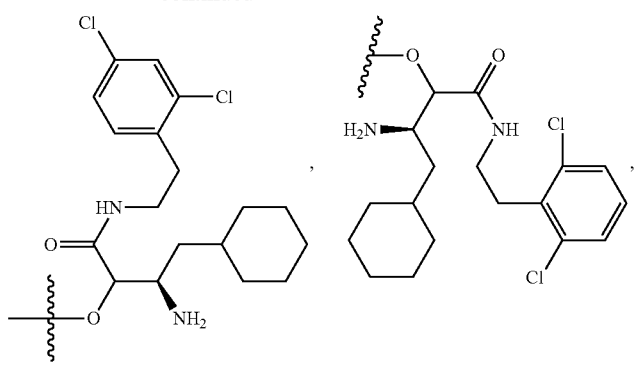
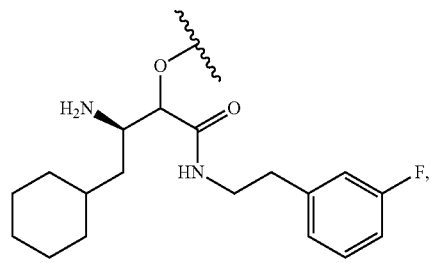
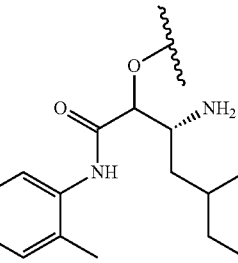
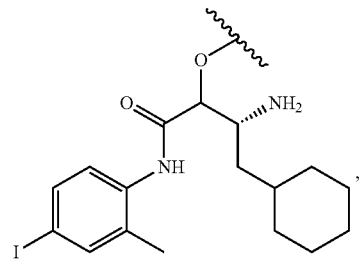
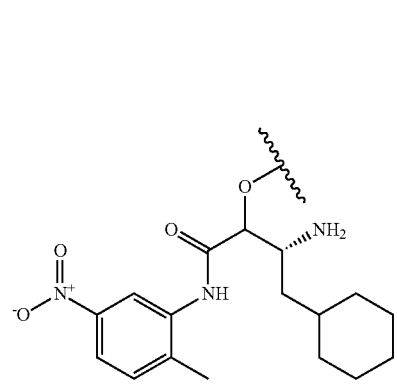
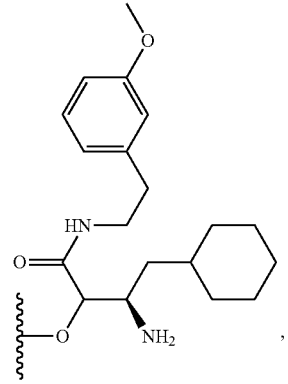
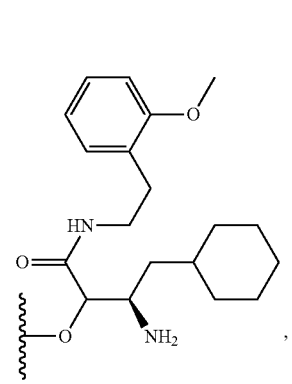
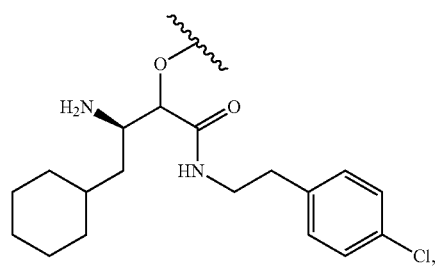
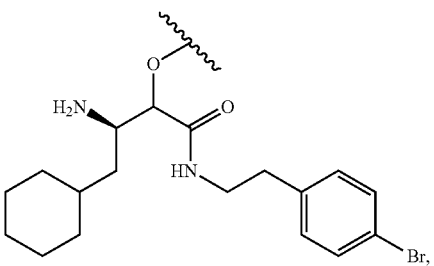
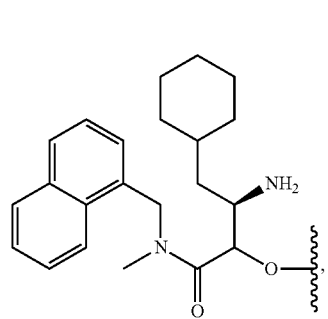
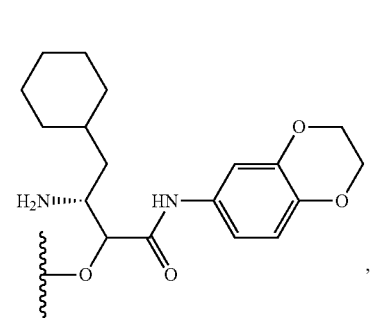
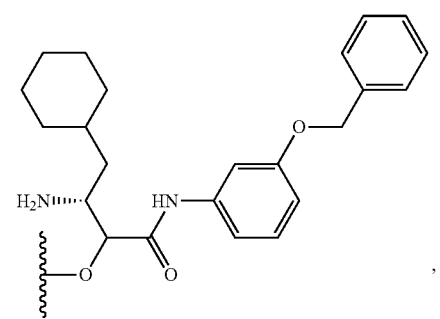

81
-continued
82
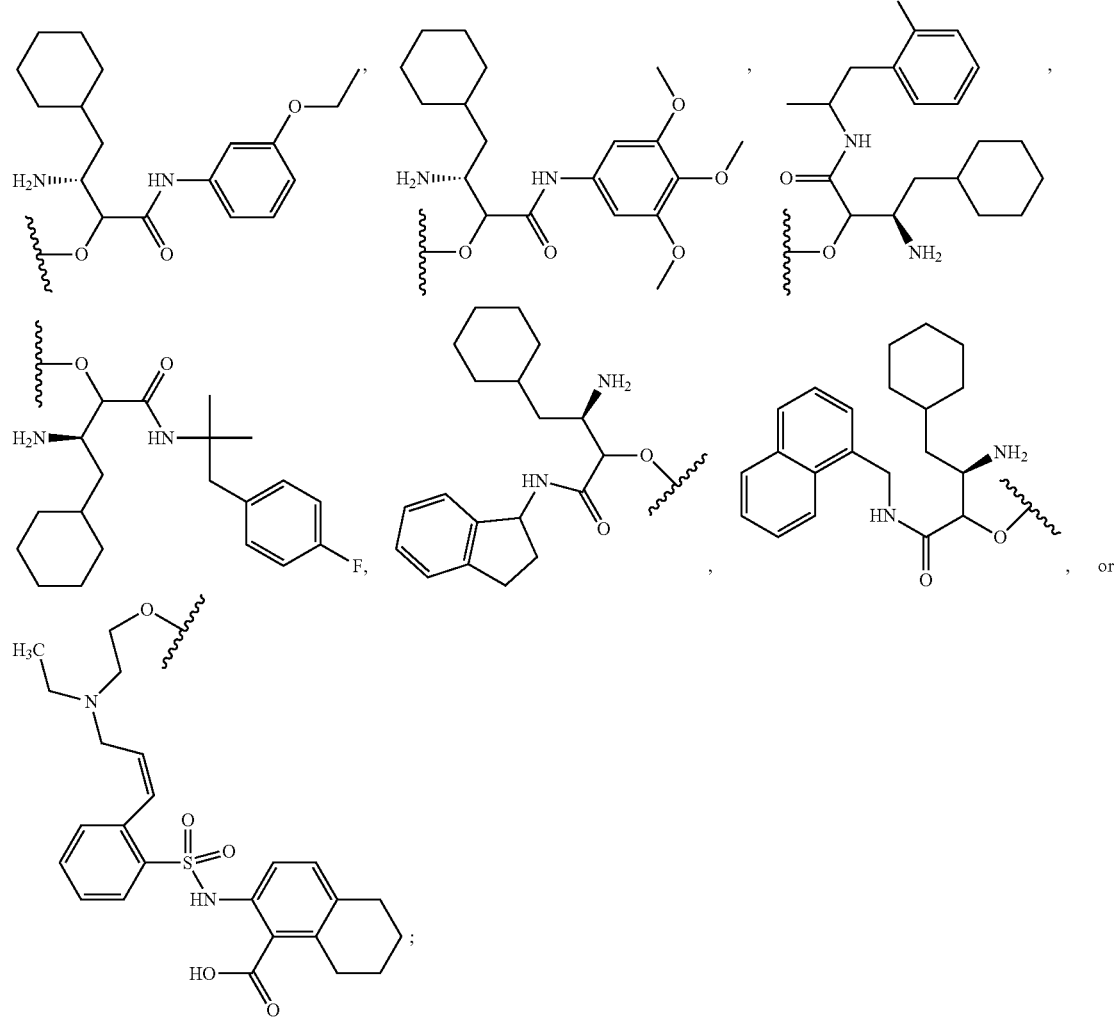
wherein R₂ is —OH or methoxy; and R₃ is H, —OH or methoxy.
In certain aspects, W is
-continued
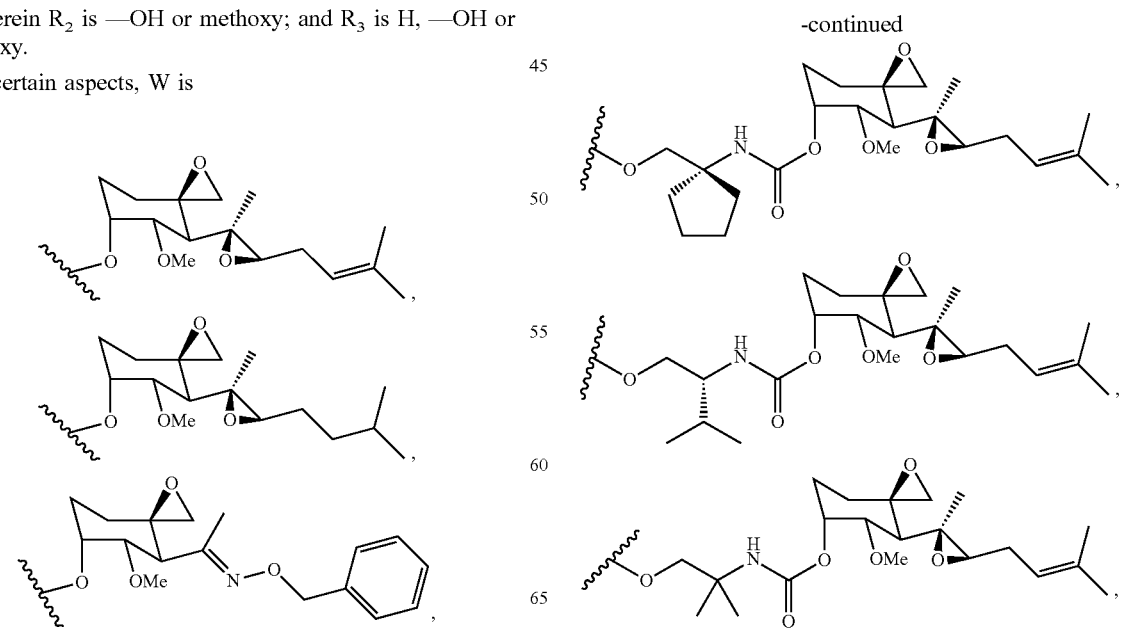

-continued
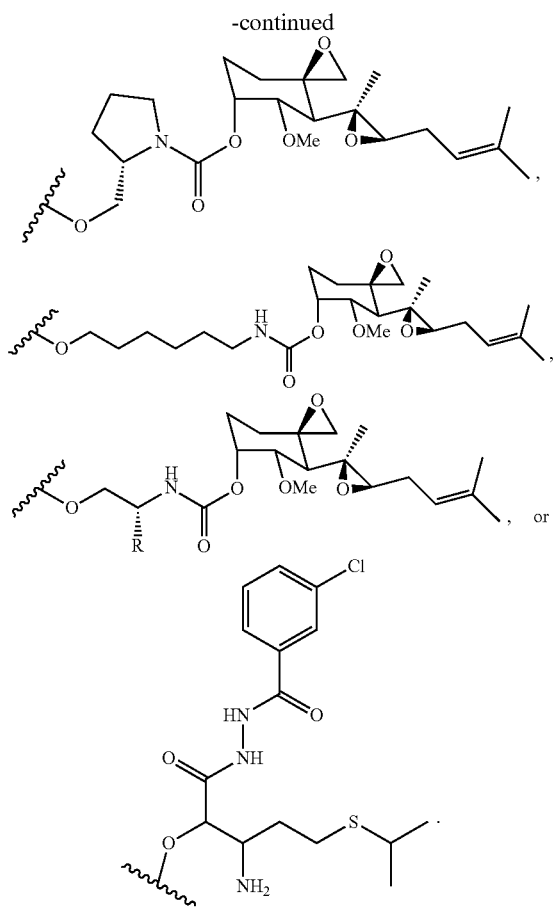
In certain aspects, W is
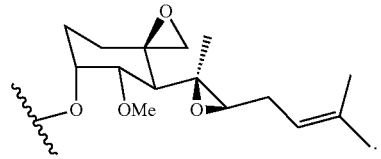
In certain aspects, Q is NR. In other aspects, Q is S.
In certain aspects, J is NR. In other aspects, J is $((CH_2)_q Q)_r$. In other aspects, J is $C_5$-$C_8$ cycloalkyl. In certain aspects, J is aryl.
In certain aspects, Y is NR. In other aspects, Y is S.
In certain aspects, -Q-X—Y— is
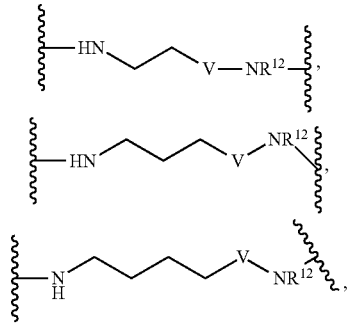
-continued
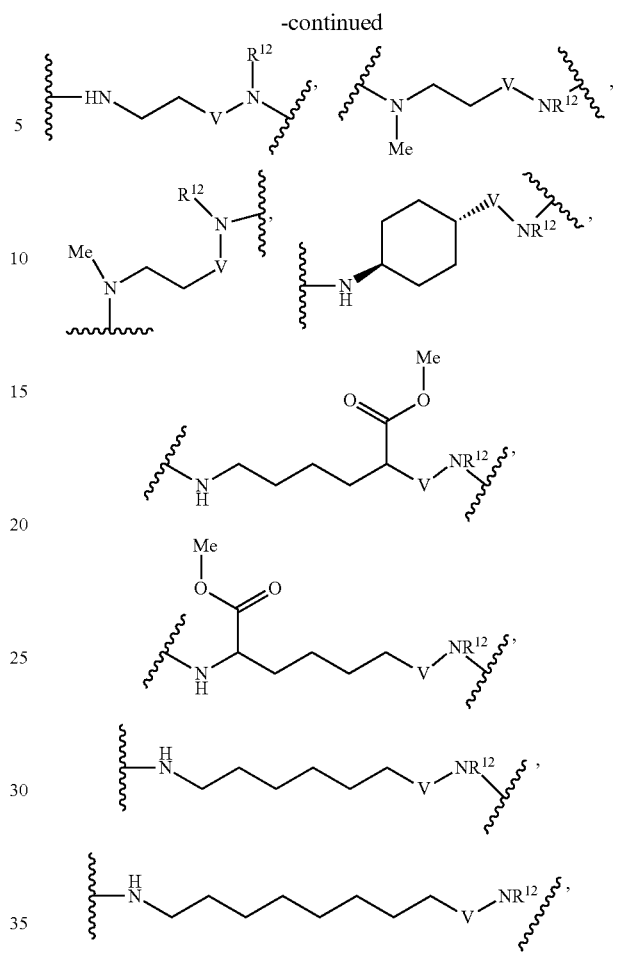

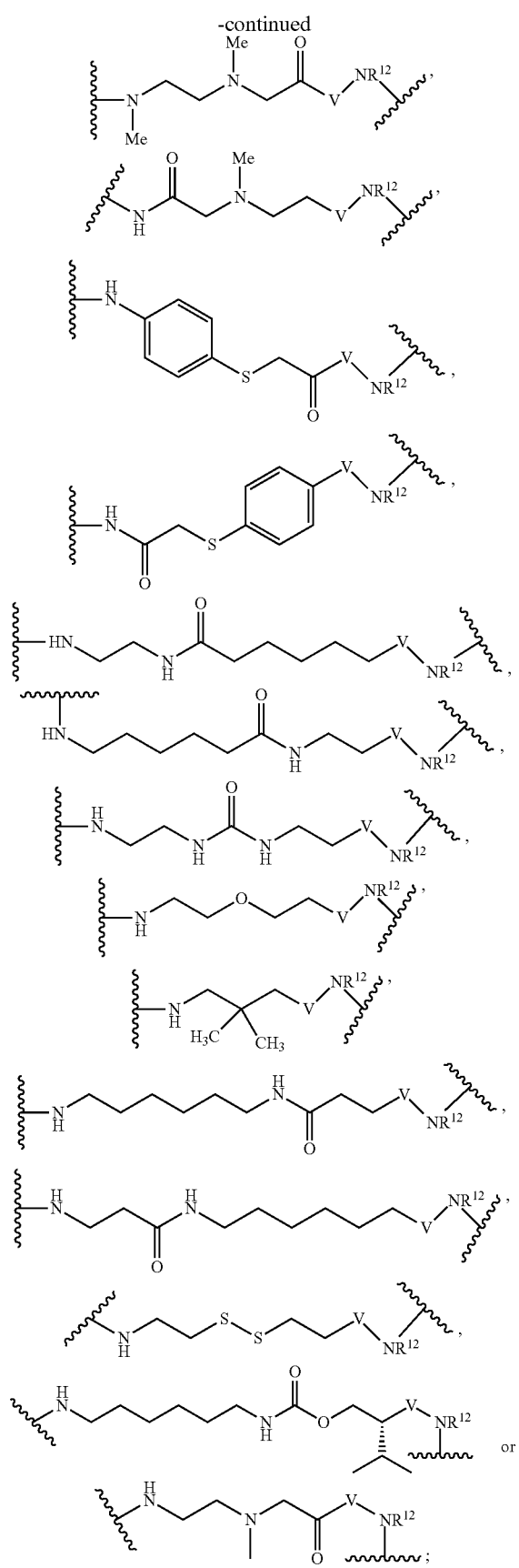
V is:
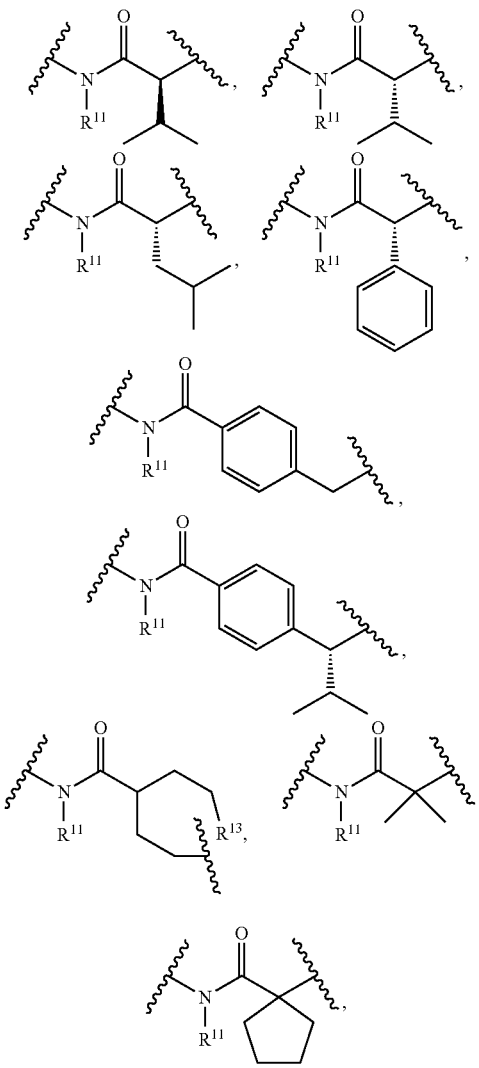
or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.
In certain aspects, -Q-X—Y— is
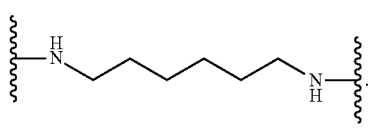 [SMILES: *NCCCCCCN*]
In certain aspects, -Q-X—Y— is
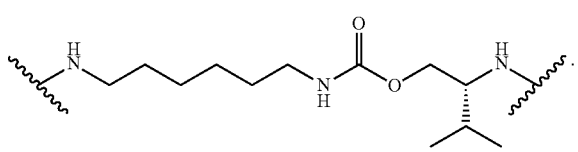 [SMILES: *NCCCCCCNC(=O)OC[C@H](N*)C(C)C]

In certain aspects, -Q-X—Y— is

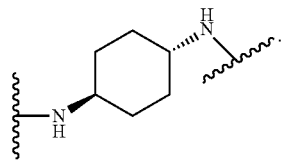 [SMILES: *N[C@H]1CC[C@H](N*)CC1]

In certain aspects, -QXY is

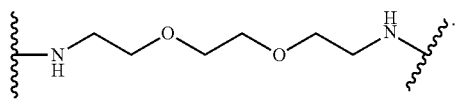 [SMILES: *NCCOCCOCCN*]

In certain aspects, -Q-X—Y— is

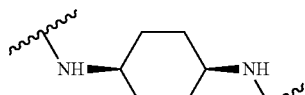

In certain aspects, -Q-X—Y— is

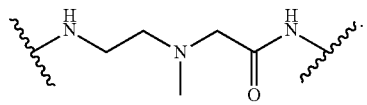 [SMILES: *NCCN(C)CC(=O)N*]

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine: $AA_5$ is leucine; $AA_6$ is glycine; -Q-X—Y— is

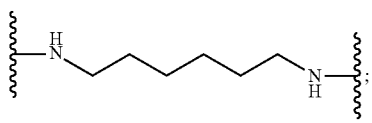 [SMILES: *NCCCCCCN*]

and W is

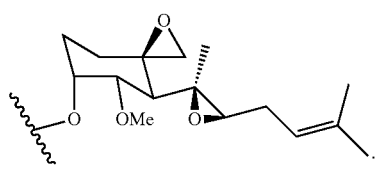

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

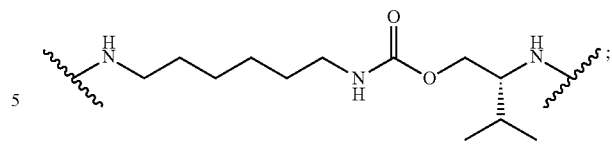

and W is

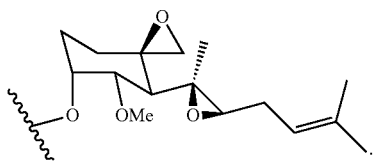

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

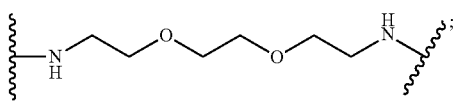 [SMILES: *NCCOCCOCCN*]

and W is

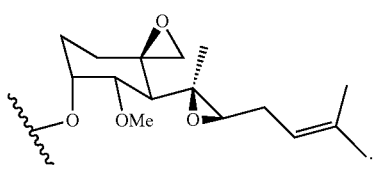

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

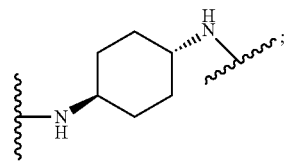 [SMILES: *N[C@H]1CC[C@H](N*)CC1]

and W is

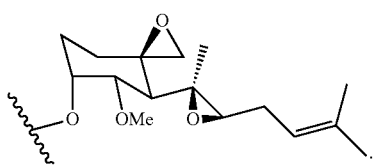

In certain aspects, -Q-X—Y— is a self-immolating linker that releases the MetAP2 inhibitor in the form of a carbamate derivative, as shown in the scheme below:

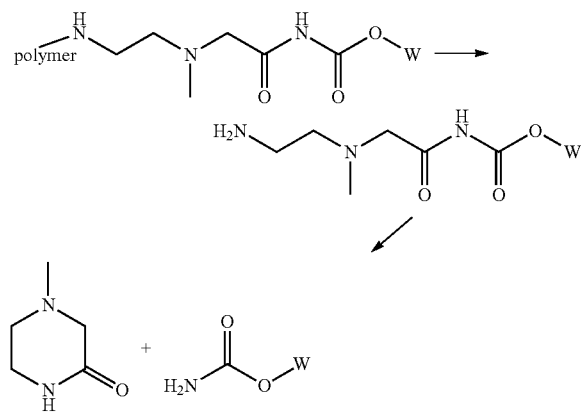

Another aspect of the present disclosure provides conjugates with linkers having the structure: Z-Q-X—Y—C(O)—W; wherein, independently for each occurrence, Z is $H_2N$-$AA_2$-$AA_3$-$AA_4$-$AA_5$-$AA_6$-C(O)— or H; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, alanine, cysteine, glycine, isoleucine, leucine, methionine, phenylalanine, valine, tryptophan, or; $AA_6$ is alanine, asparagine, citrulline, glutamine, glycine, leucine, methionine, phenylalanine, serine, threonine, tryptophan, tyrosine, valine or $H_2N(CH_2)_mCO_2H$, wherein m is 2, 3, 4 or 5; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

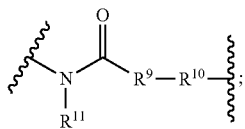

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety; p is 0 to 20; q is 2 or 3; and r is 1, 2, 3, 4, 5, or 6.

In certain aspects, Z is $H_2N$-$AA_5$-$AA_6$-C(O)—. In certain aspects, $AA_5$ is alanine, cysteine, glycine, isoleucine, leucine, methionine, phenylalanine, valine, tryptophan, or tyrosine and $AA_6$ is glycine. In certain aspects, $AA_5$ is leucine and $AA_6$ is glycine. In certain aspects, $AA_5$ is valine and $AA_6$ is glycine. In certain aspects, $AA_5$ is phenylalanine and $AA_6$ is glycine. In certain aspects, $AA_5$ is glycine and $AA_6$ is glycine. In certain aspects, $AA_5$ is not valine.

In other aspects, Z is $H_2N$-$AA_3$-$AA_4$-$AA_5$-$AA_6$-C(O)—. In certain aspects, $AA_5$ is alanine, cysteine, glycine, isoleucine, leucine, methionine, phenylalanine, valine, tryptophan, or tyrosine and each of $AA_3$, $AA_4$, or $AA_6$ is glycine. In certain aspects, $AA_5$ is leucine and each of $AA_3$, $AA_4$, or $AA_6$ is glycine. In certain aspects, $AA_5$ is valine and each of $AA_3$, $AA_4$, or $AA_6$ is glycine. In certain aspects, $AA_5$ is phenylalanine and each of $AA_3$, $AA_4$, or $AA_6$ is glycine. In certain aspects, $AA_3$ is glycine, $AA_4$ is phenylalanine, $AA_5$ is leucine and $AA_6$ is glycine. In certain aspects, each of $AA_3$, $AA_4$, $AA_5$ and $AA_6$ is glycine. In certain aspects, $AA_5$ is not valine.

In certain aspects, Z is H. In other aspects, Z is $H_2N$-$AA_6$-C(O)—. In certain aspects, $AA_6$ is glycine.

In certain aspects, Q is NR. In certain aspects, M is a bond. In certain aspects, J is a bond. In certain aspects, Y is NR.

In certain aspects, W is:

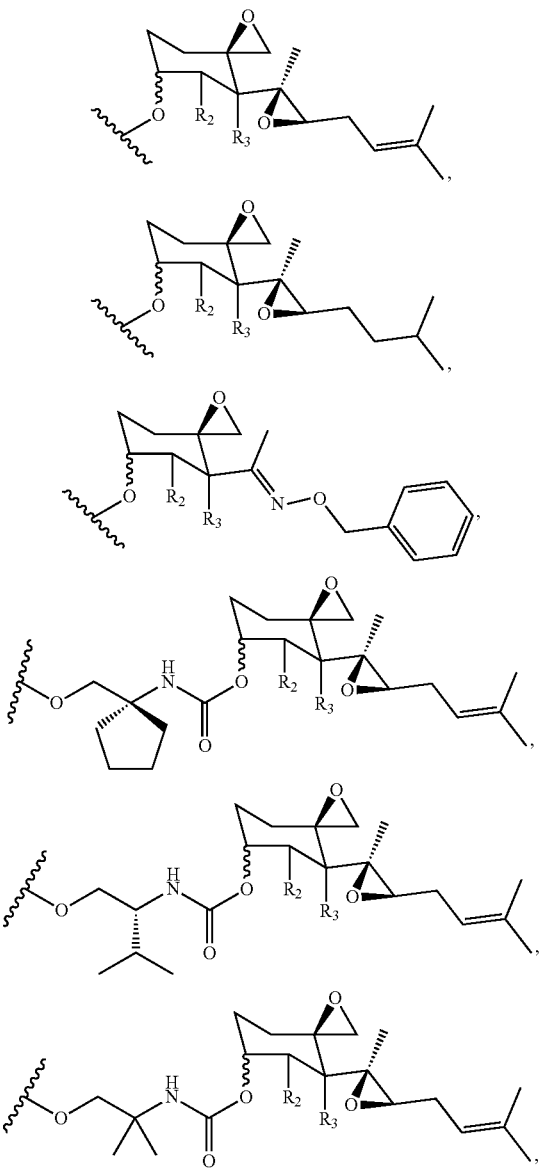

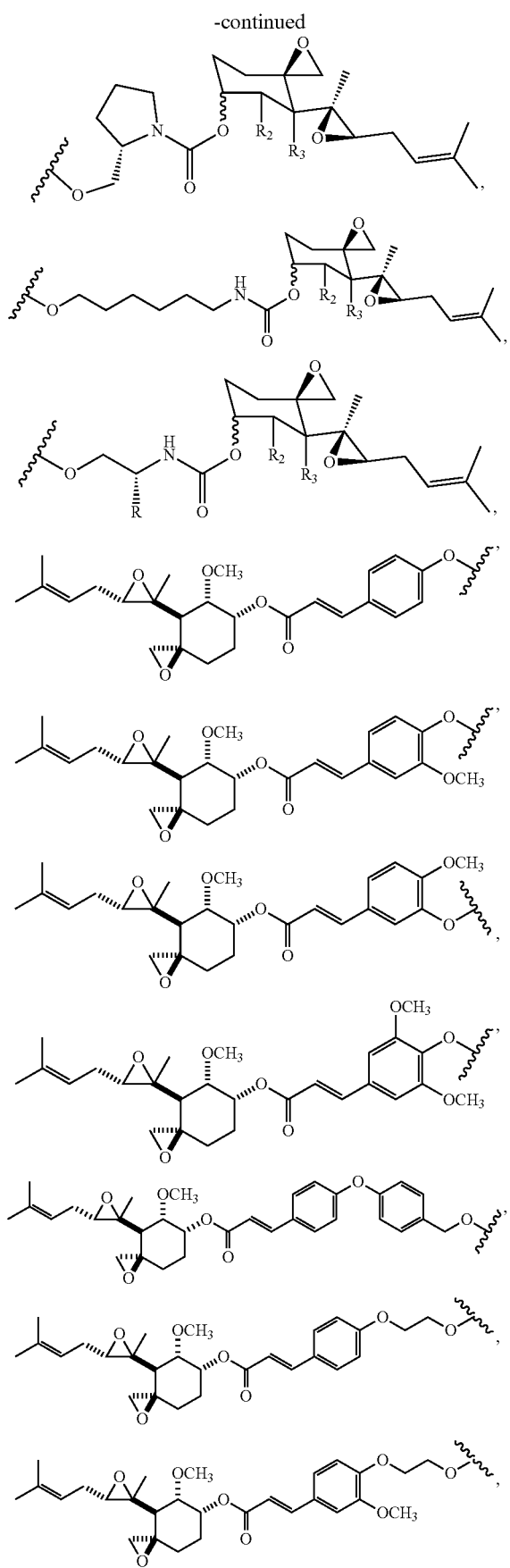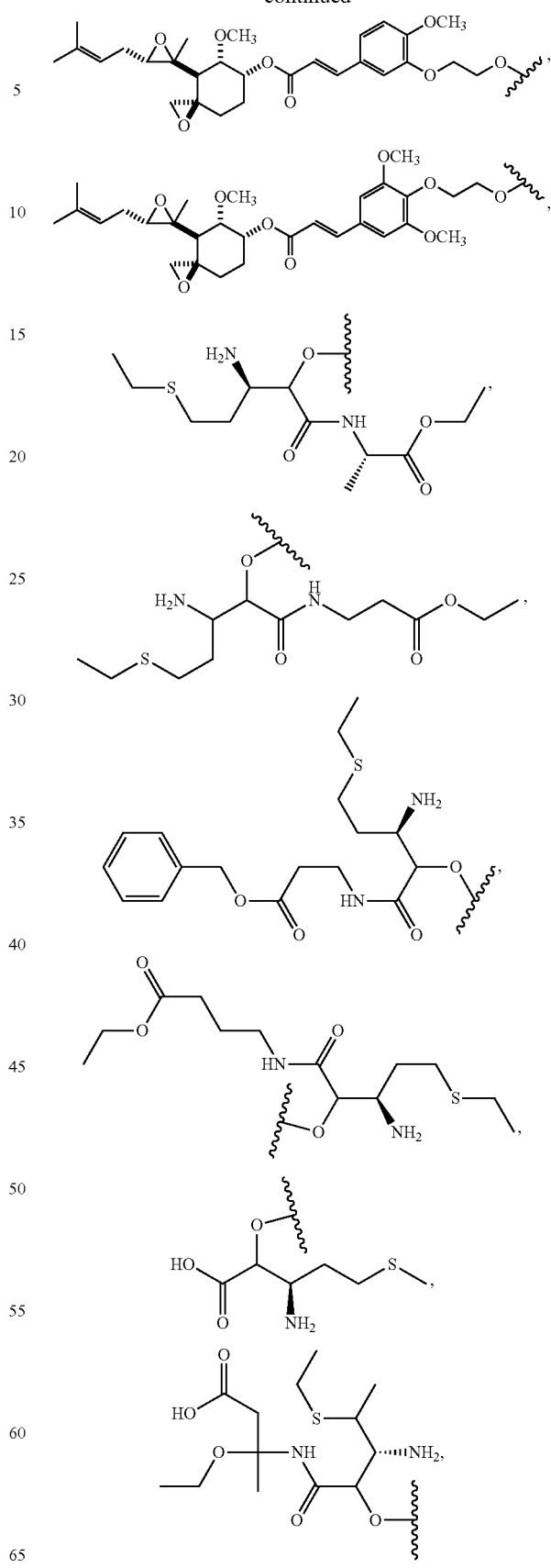

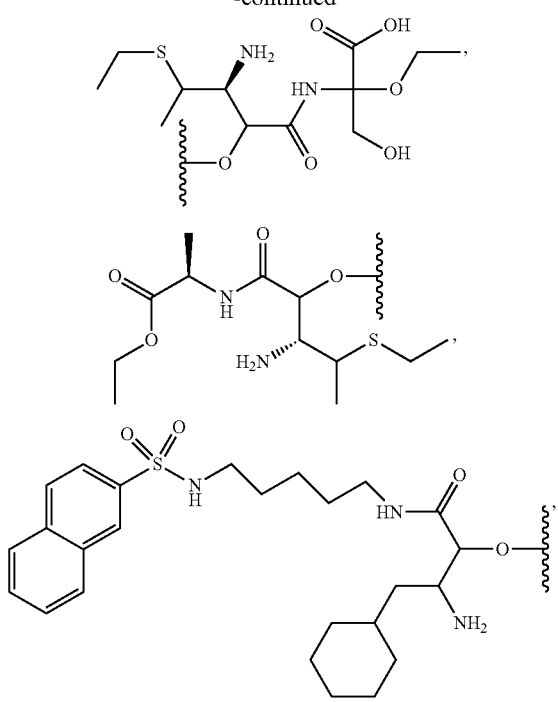
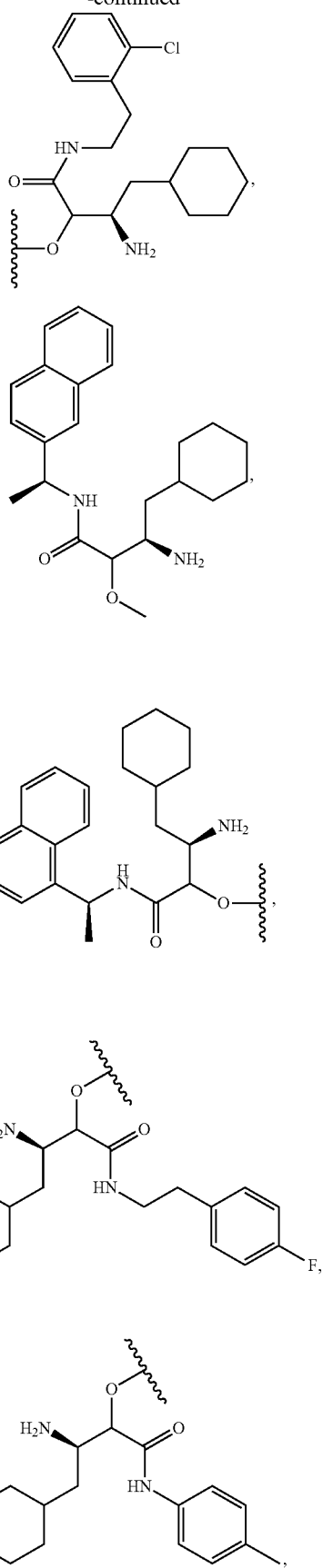

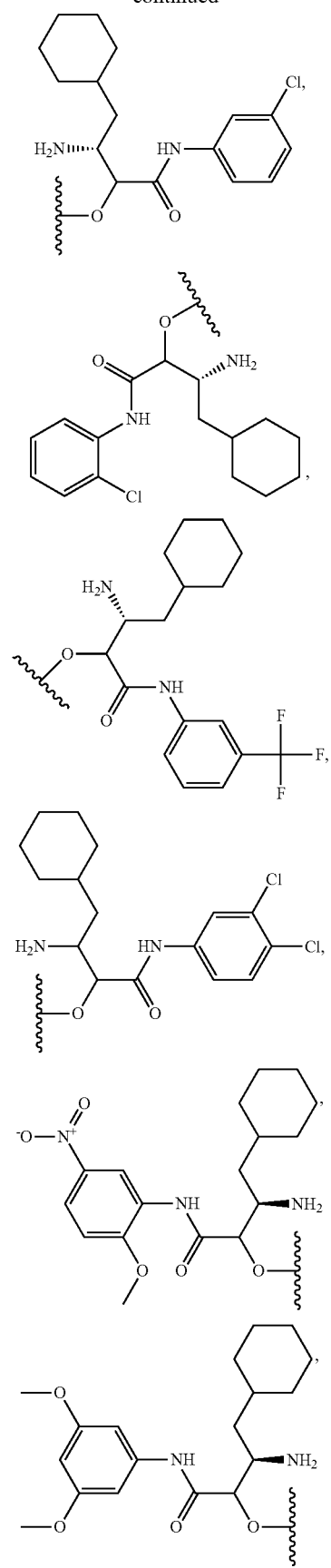
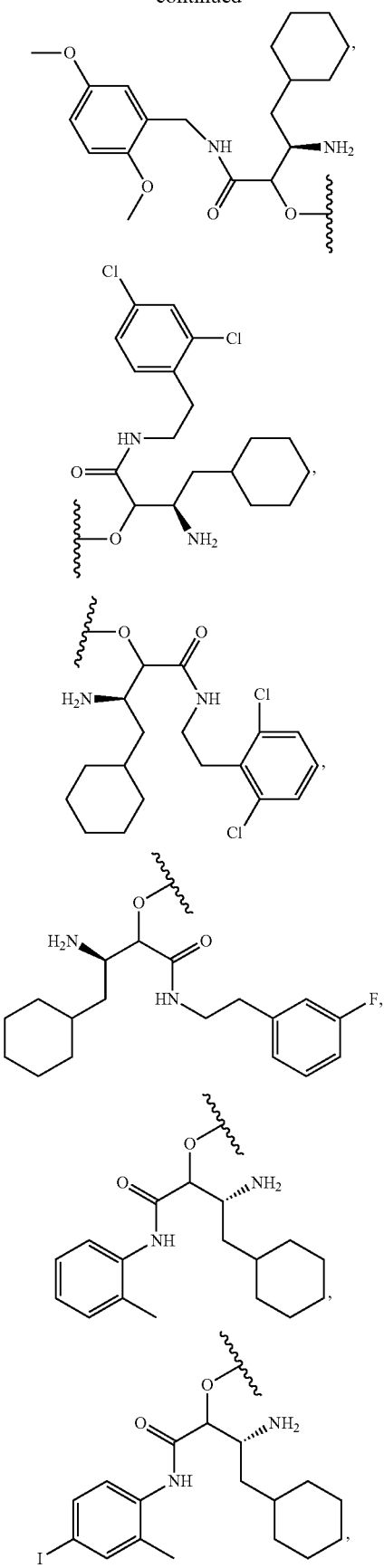

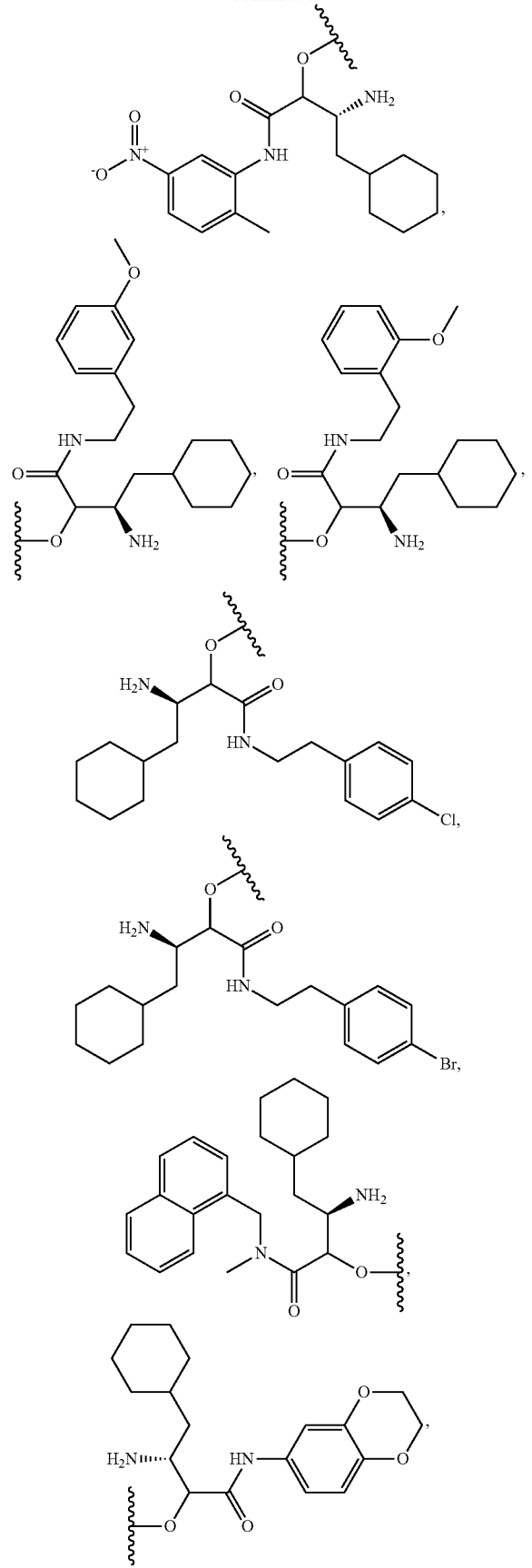
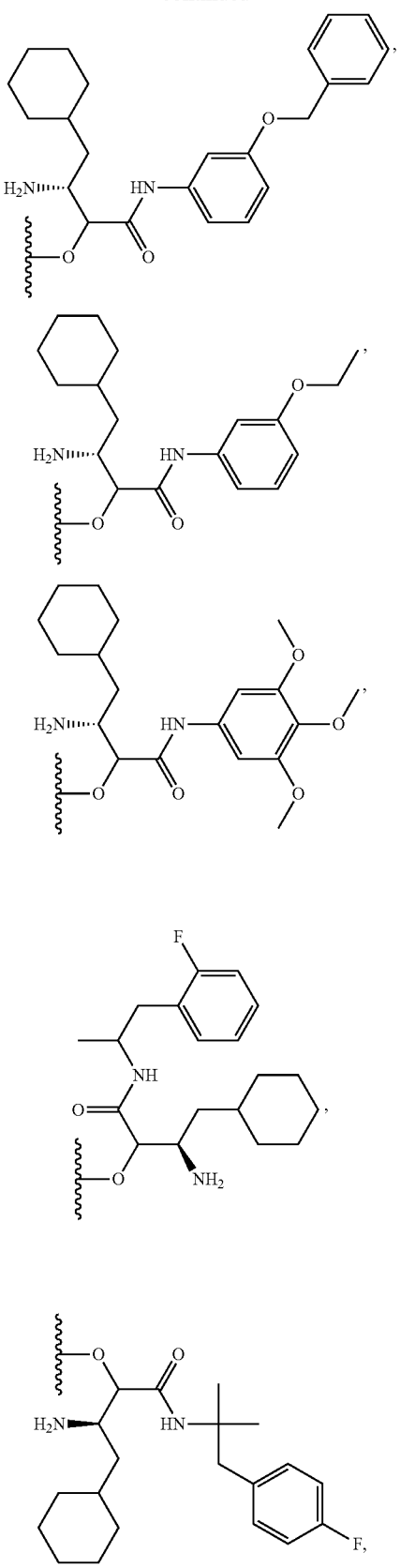

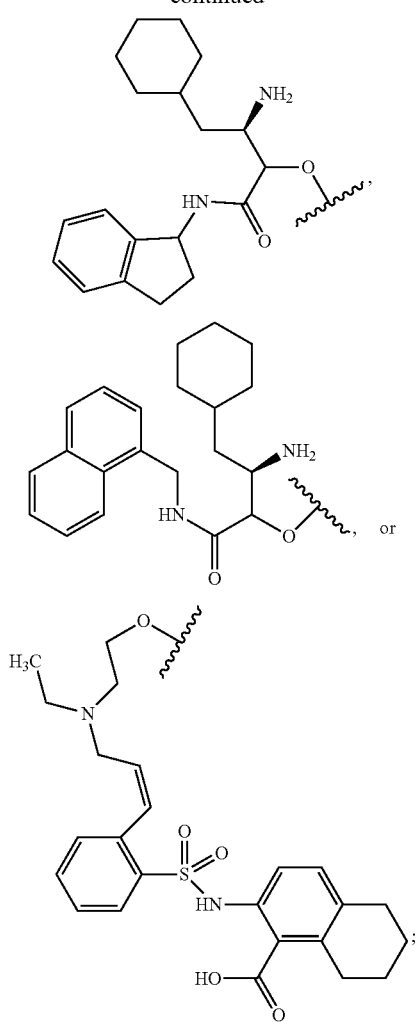
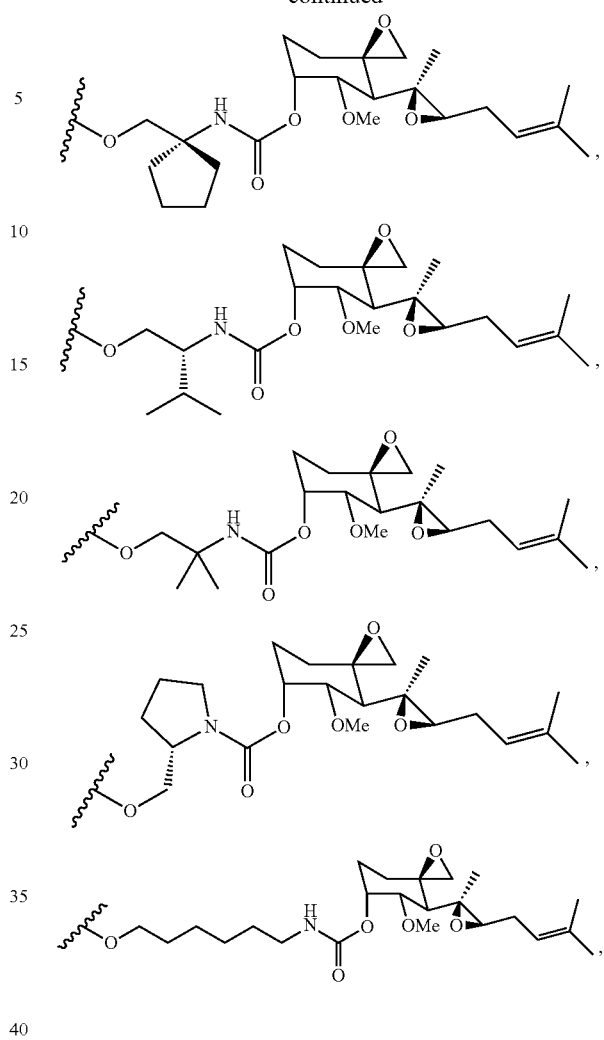
wherein R$_2$ is —OH or methoxy; and R$_3$ is H, —OH or methoxy.
In certain aspects, W is
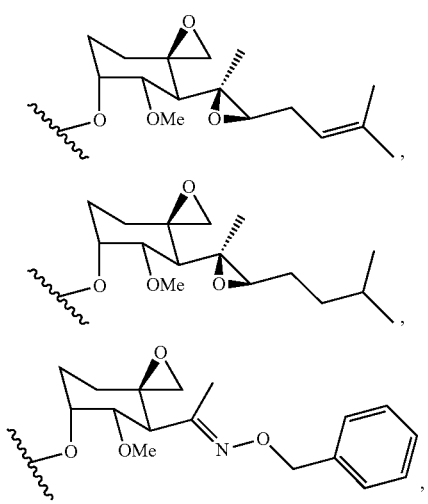
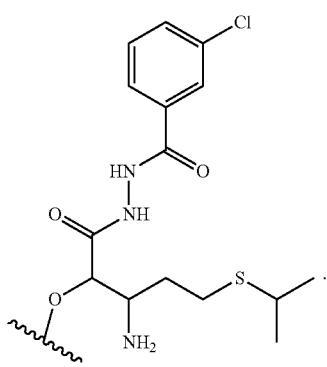

In certain aspects, W is
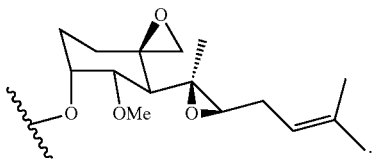
In certain aspects, -Q-X—Y— is
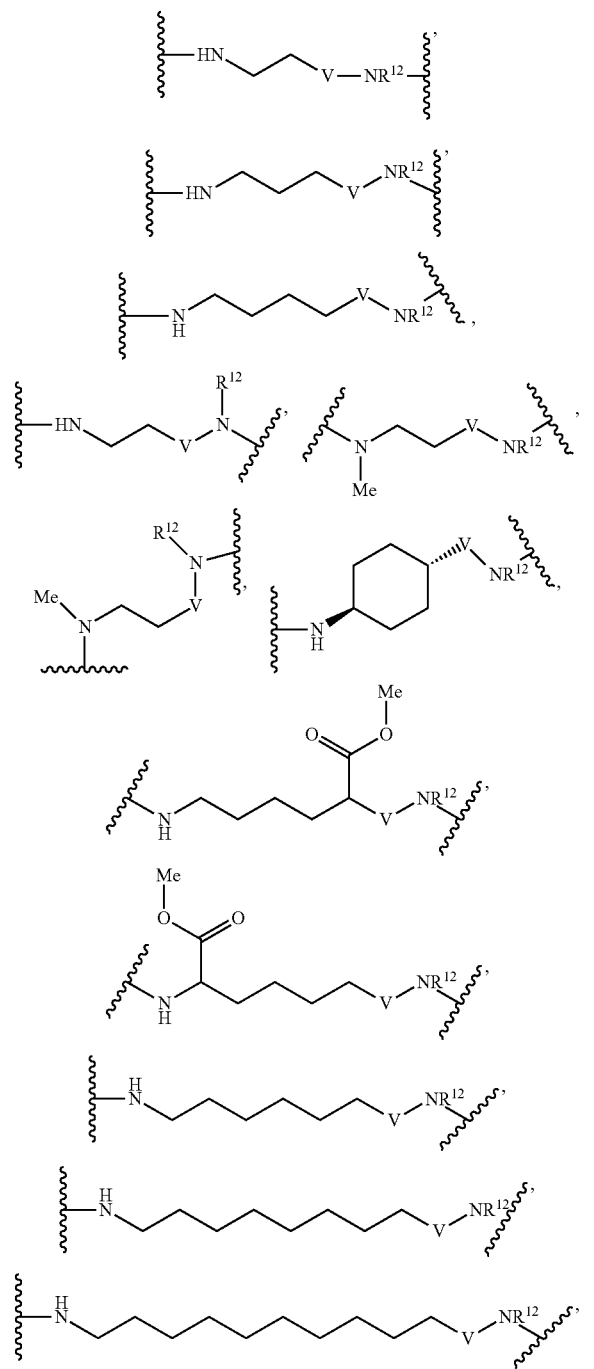
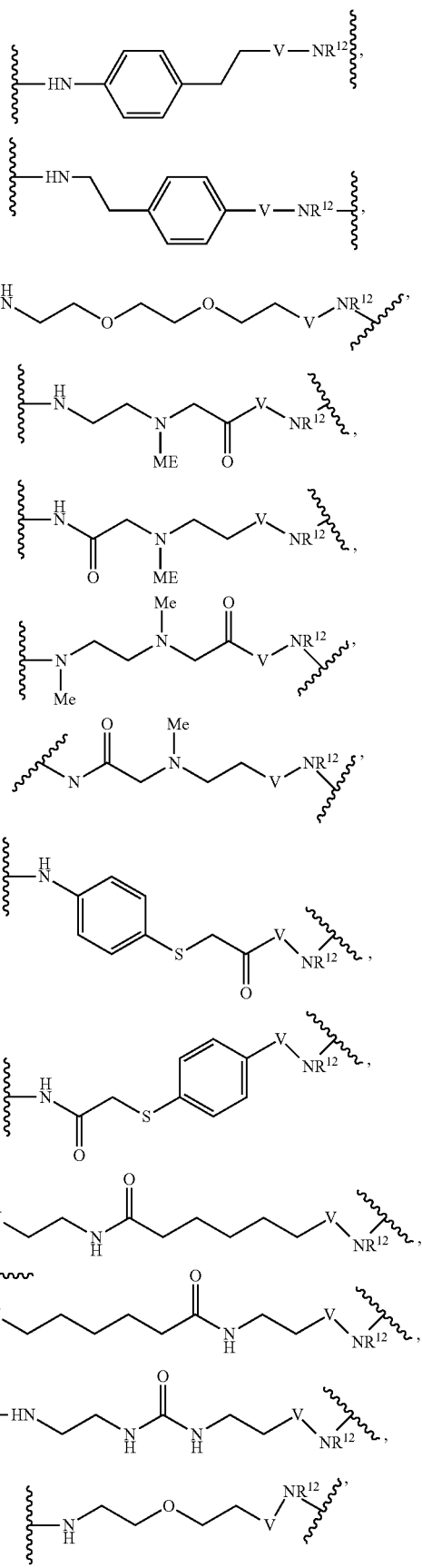

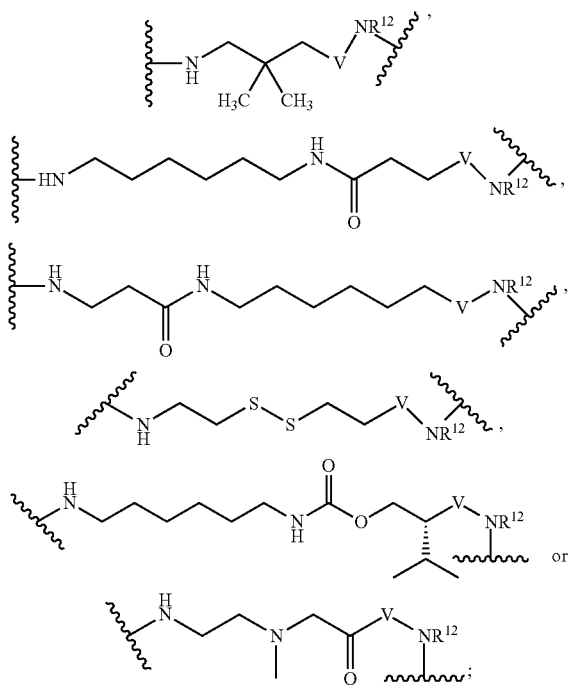

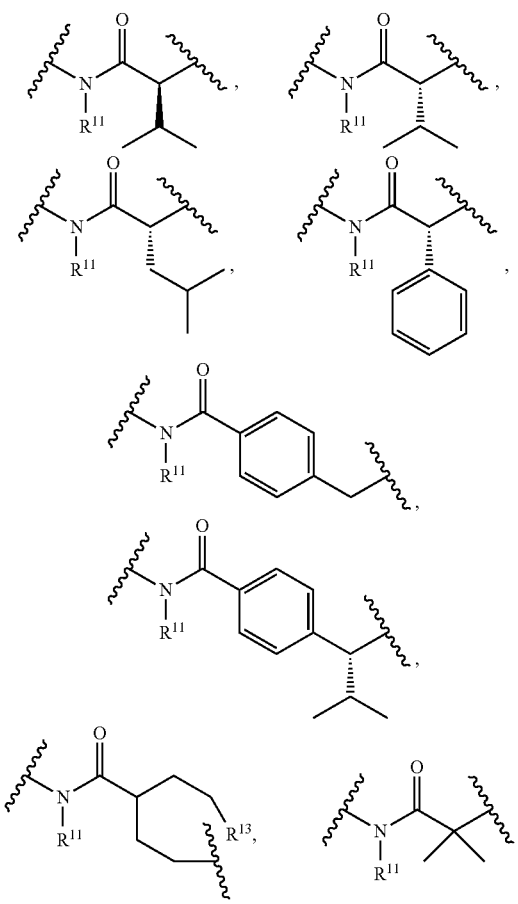

V is:

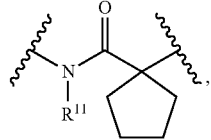

or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.

In certain aspects Z is $H_2N\text{-}AA_5\text{-}AA_6\text{-}C(O)\text{---}$; $AA_5$ is leucine and $AA_6$ is glycine; Q-X—Y is

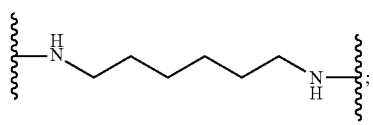

and W is

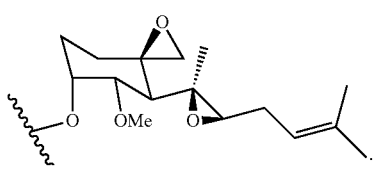

In certain aspects, Z is $H_2N\text{-}AA_5\text{-}AA_6\text{-}C(O)\text{---}$; $AA_5$ is valine and $AA_6$ is glycine; Q-X—Y is

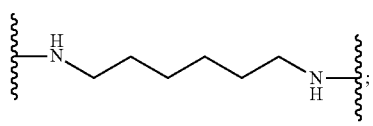 [SMILES: *NCCCCCCN*]

and W is

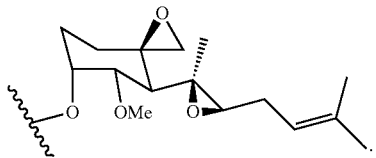

In certain aspects, Z is $H_2N\text{-}AA_5\text{-}AA_6\text{-}C(O)\text{---}$; $AA_5$ is phenylalanine and $AA_6$ is glycine; Q-X—Y is

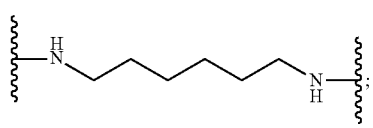

and W is

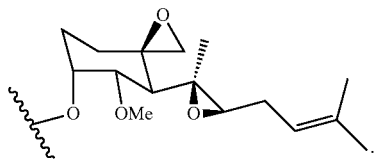

In certain aspects, Z is H₂N-AA₅-AA₆-C(O)—; AA₅ is glycine and AA₆ is glycine; Q-X—Y is

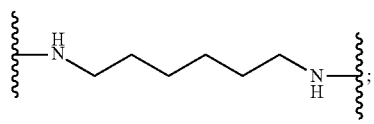

and W is

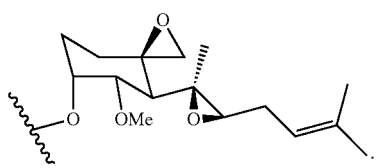

In certain aspects, Z is H₂N-AA₃-AA₄-AA₅-AA₆-C(O)—; AA₅ is leucine and each of AA₃, AA₄, or AA₆ is

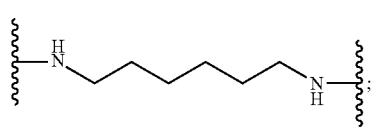

and W is

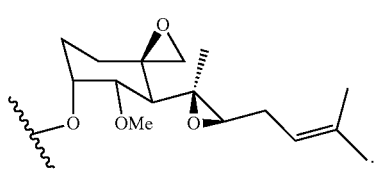

In certain aspects, Z is H₂N-AA₃-AA₄-AA₅-AA₆-C(O)—; AA₅ is valine and each of AA₃, AA₄, or AA₆ is glycine; Q-X—Y is

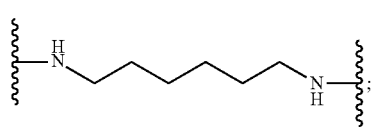

and W is

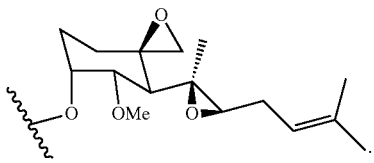

In certain aspects, Z is H₂N-AA₃-AA₄-AA₅-AA₆-C(O)—; AA₅ is phenylalanine and each of AA₃, AA₄, or AA₆ is glycine; Q-X—Y is

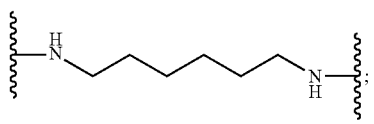

and W is

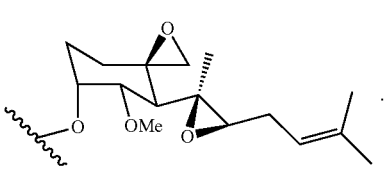

In certain aspects, Z is H₂N-AA₃-AA₄-AA₅-AA₆-C(O)—; AA₃ is glycine, AA₄ is phenylalanine, AA₅ is leucine and AA₆ is glycine; Q-X—Y is

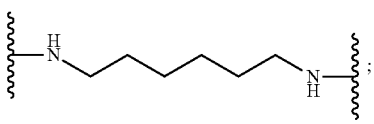 [SMILES: *NCCCCCCN*]

and W is

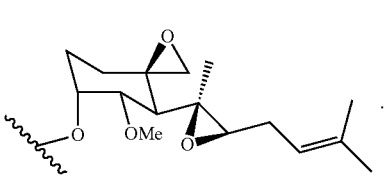

In certain aspects, Z is H₂N-AA₃-AA₄-AA₅-AA₆-C(O)—; each of AA₃, AA₄, AA₅ and AA₆ is glycine; Q-X—Y is

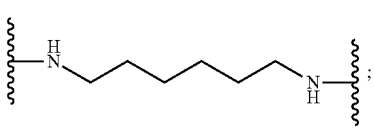 [SMILES: *NCCCCCCN*]

and W is

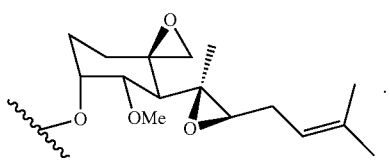

In certain aspects, Z is H₂N-AA₆-C(O)—; AA₆ is glycine; Q-X—Y is

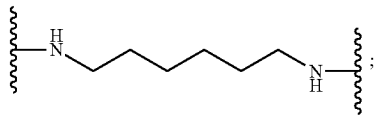 [SMILES: *NCCCCCCN*]

and W is

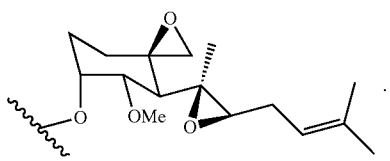

In certain aspects, Z is H; Q-X—Y is

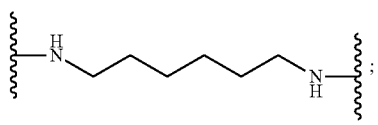 [SMILES: *NCCCCCCN*]

and W is

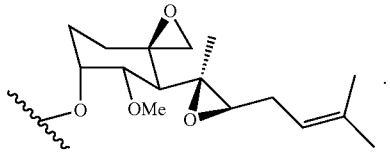

In certain aspects, Z is H₂N-AA₅-AA₆-C(O)—; AA₅ is leucine and AA₆ is glycine; Q-X—Y is

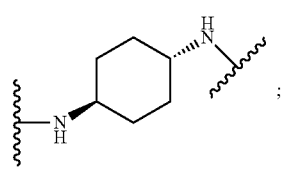 [SMILES: *N[C@H]1CC[C@H](N*)CC1]

and W is

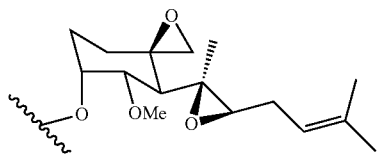

In certain aspects, Z is H₂N-AA₅-AA₆-C(O)—; AA₅ is valine and AA₆ is glycine; Q-X—Y is

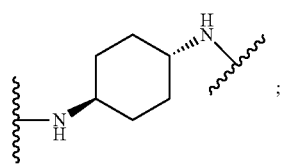 [SMILES: *N[C@H]1CC[C@H](N*)CC1]

and W is

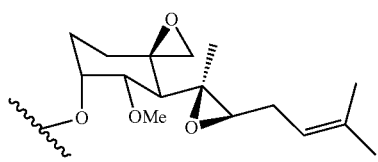

In certain aspects, Z is H₂N-AA₅-AA₆-C(O)—; AA₅ is phenylalanine and AA₆ is glycine; Q-X—Y is

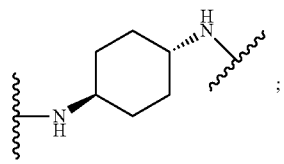 [SMILES: *N[C@H]1CC[C@H](N*)CC1]

and W is

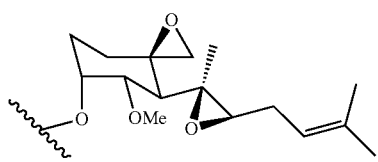

In certain aspects, Z is H₂N-AA₅-AA₆-C(O)—; AA₅ is glycine and AA₆ is glycine; Q-X—Y is

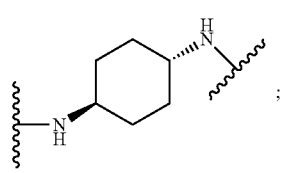 [SMILES: *N[C@H]1CC[C@H](N*)CC1]

and W is

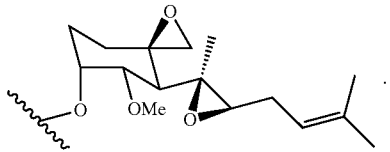

In certain aspects, Z is H$_2$N-AA$_3$-AA$_4$-AA$_5$-AA$_6$-C(O)—; AA$_5$ is leucine and each of AA$_3$, AA$_4$, or AA$_6$ is glycine; Q-X—Y is

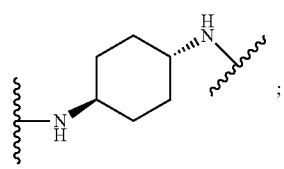 [SMILES: *N[C@H]1CC[C@H](N*)CC1]

and W is

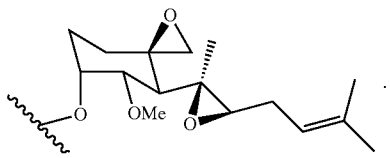

In certain aspects, Z is H$_2$N-AA$_3$-AA$_4$-AA$_5$-AA$_6$-C(O)—; AA$_5$ is valine and each of AA$_3$, AA$_4$, or AA$_6$ is glycine; Q-X—Y is

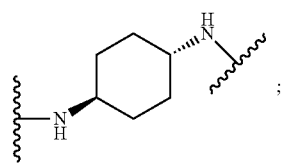 [SMILES: *N[C@H]1CC[C@H](N*)CC1]

and W is

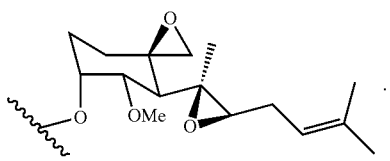

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

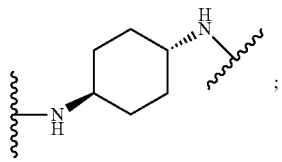 [SMILES: *N[C@H]1CC[C@H](N*)CC1]

and W is

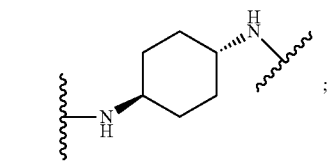 [SMILES: *N[C@H]1CC[C@H](N*)CC1]

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

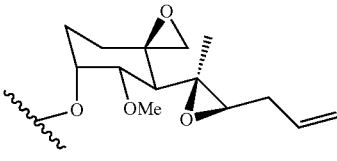

and W is

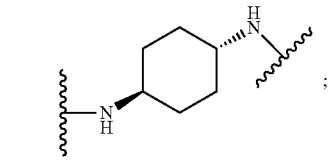 [SMILES: *N[C@H]1CC[C@H](N*)CC1]

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

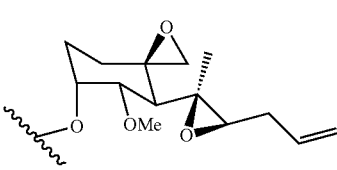

and W is

In certain aspects, Z is H$_2$N-AA$_6$-C(O)—; AA$_6$ is glycine; Q-X—Y is

111

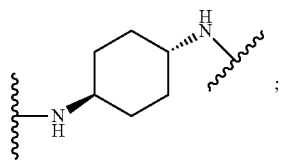 [SMILES: *N[C@H]1CC[C@H](N*)CC1]

and W is

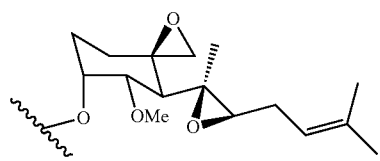

In certain aspects, Z is H; Q-X—Y is

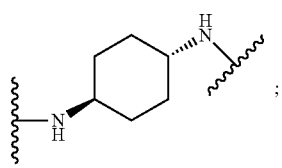 [SMILES: *N[C@H]1CC[C@H](N*)CC1]

and W is

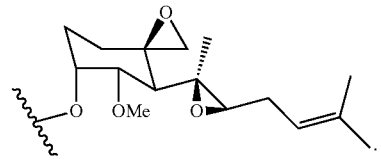

In certain aspects, Z is H₂N-AA₅-AA₆-C(O)—; AA₅ is leucine and AA₆ is glycine; Q-X—Y is

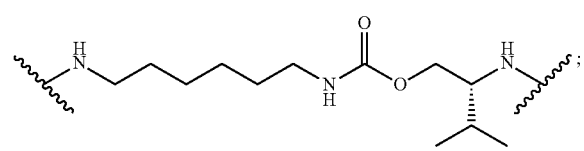 [SMILES: *NCCCCCCNC(=O)OC[C@H](N*)C(C)C]

and W is

112

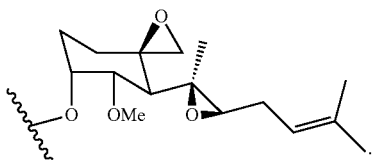

and W is

In certain aspects, Z is H₂N-AA₅-AA₆-C(O)—; AA₅ is phenylalanine and AA₆ is glycine; Q-X—Y is

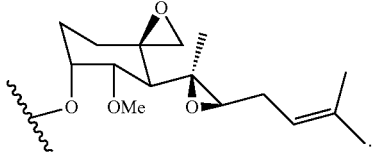

and W is

In certain aspects, Z is H₂N-AA₅-AA₆-C(O)—; AA₅ is glycine and AA₆ is glycine; Q-X—Y is

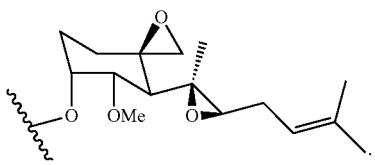

and W is

In certain aspects, Z is H₂N-AA₅-AA₆-C(O)—; AA₅ is valine and AA₆ is glycine; Q-X—Y is In certain aspects, Z is H₂N-AA₃-AA₄-AA₅-AA₆-C(O)—; AA₅ is leucine and each of AA₃, AA₄, or AA₆ is glycine; Q-X—Y is

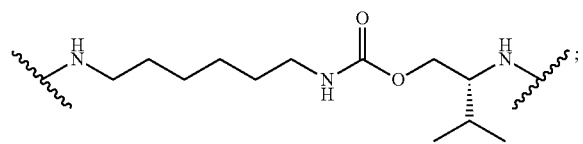 [SMILES: *NCCCCCCNC(=O)OC[C@H](N*)C(C)C]

and W is

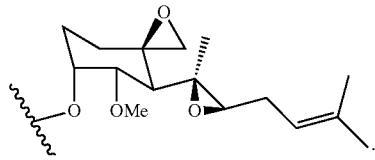

In certain aspects, Z is H$_2$N-AA$_3$-AA$_4$-AA$_5$-AA$_6$-C(O)—; AA$_5$ is valine and each of AA$_3$, AA$_4$, or AA$_6$ is glycine; Q-X—Y is

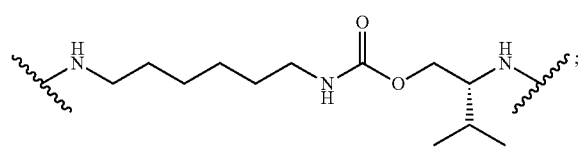 [SMILES: *NCCCCCCNC(=O)OC[C@H](N*)C(C)C]

and W is

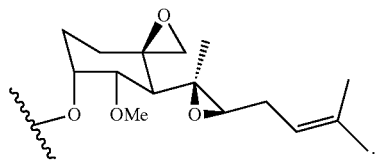

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

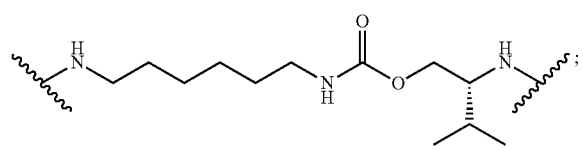 [SMILES: *NCCCCCCNC(=O)OC[C@H](N*)C(C)C]

and W is

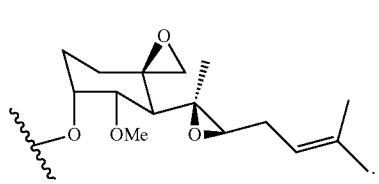

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

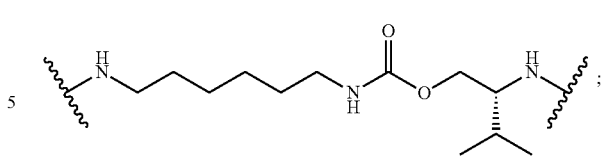

and W is

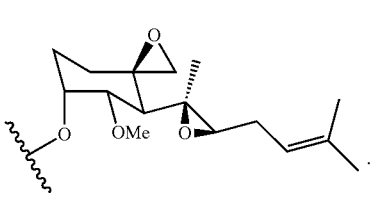

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

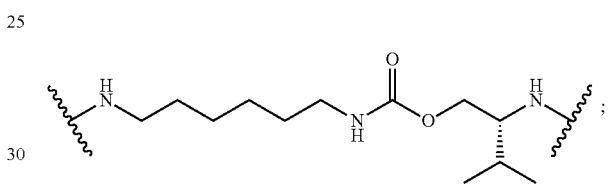

and W is

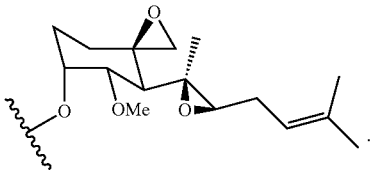

In certain aspects, Z is H$_2$N-AA$_6$-C(O)—; AA$_6$ is glycine; Q-X—Y is

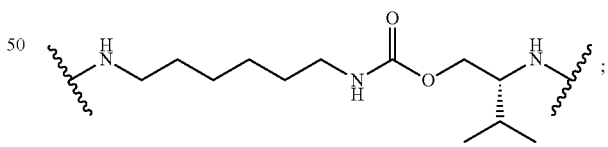

and W is

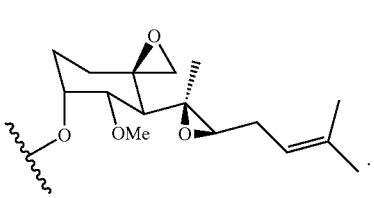

In certain aspects, Z is H; Q-X—Y is

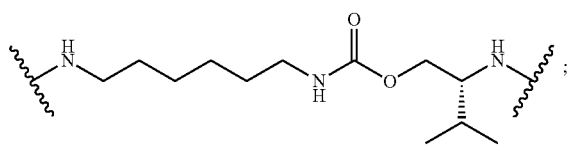 [SMILES: *NCCCCCCNC(=O)OC[C@H](N*)C(C)C]

and W is

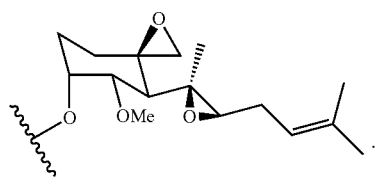

In certain aspects, Z is H₂N-AA₅-AA₆-C(O)—; AA₅ is leucine and AA₆ is glycine; Q-X—Y is

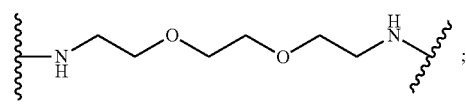

and W is

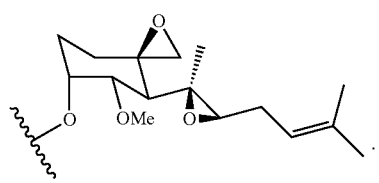

In certain aspects, Z is H₂N-AA₅-AA₆-C(O)—; AA₅ is valine and AA₆ is glycine; Q-X—Y is

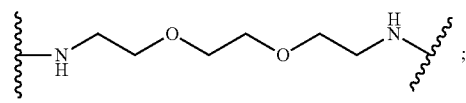

and W is

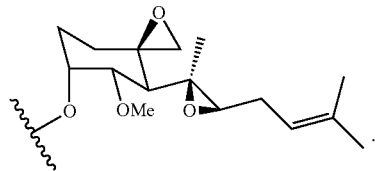

In certain aspects, Z is H₂N-AA₅-AA₆-C(O)—; AA₅ is phenylalanine and AA₆ is glycine; Q-X—Y is

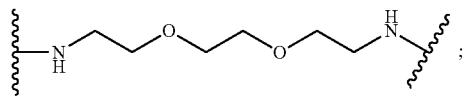

and W is

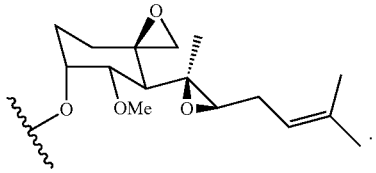

In certain aspects, Z is H₂N-AA₅-AA₆-C(O)—; AA₅ is glycine and AA₆ is glycine; Q-X—Y is

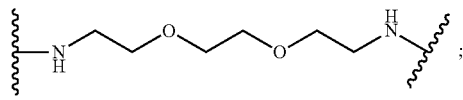 [SMILES: *NCCOCCOCCN*]

and W is

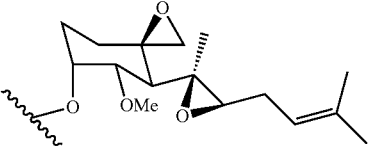

In certain aspects, Z is H₂N-AA₃-AA₄-AA₅-AA₆-C(O)—; AA₅ is leucine and each of AA₃, AA₄, or AA₆ is glycine; Q-X—Y is

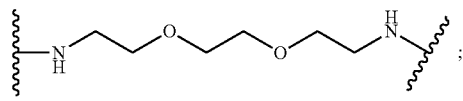 [SMILES: *NCCOCCOCCN*]

and W is

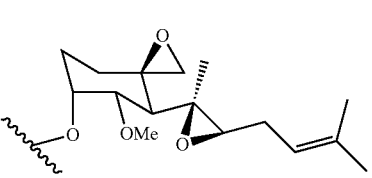

In certain aspects, Z is H₂N-AA₃-AA₄-AA₅-AA₆-C(O)—; AA₅ is valine and each of AA₃, AA₄, or AA₆ is glycine; Q-X—Y is

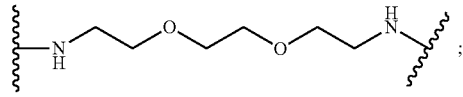 [SMILES: *NCCOCCOCCN*]

and W is

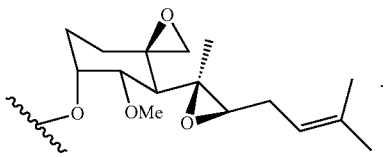

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

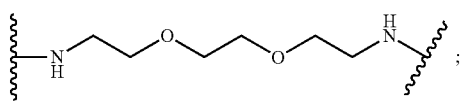 [SMILES: *NCCOCCOCCN*]

and W is

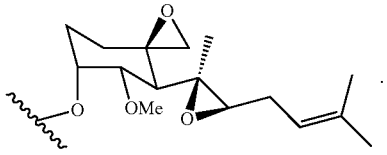

In certain aspects, Z is H$_2$N-AA$_3$-AA$_4$-AA$_5$-AA$_6$-C(O)—; AA$_3$ is glycine, AA$_4$ is Phenylalanine, AA$_5$ is leucine and AA$_6$ is glycine; Q-X—Y is

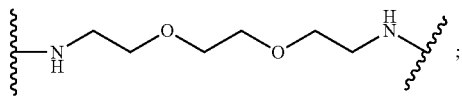 [SMILES: *NCCOCCOCCN*]

and W is

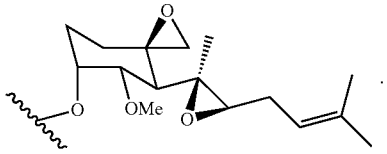

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

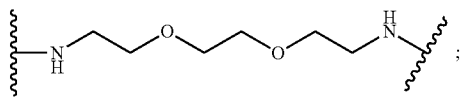 [SMILES: *NCCOCCOCCN*]

and W is

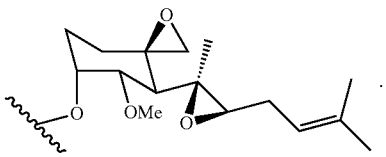

In certain aspects, Z is H$_2$N-AA$_6$-C(O)—; AA$_6$ is glycine; Q-X—Y is

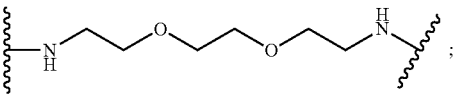 [SMILES: *NCCOCCOCCN*]

and W is

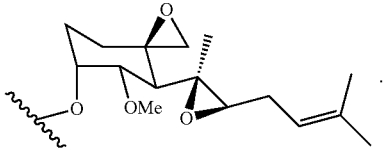

In certain aspects, Z is H; Q-X—Y is

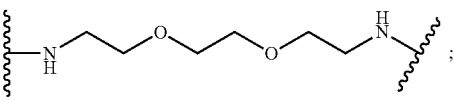 [SMILES: *NCCOCCOCCN*]

and W is

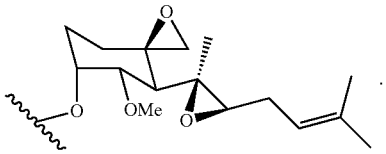

Other active moieties that may be modified to be used in conjugates of the disclosure include the following structures:

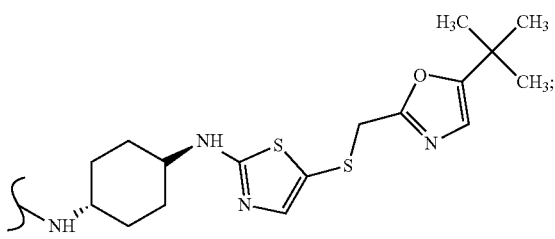

-continued

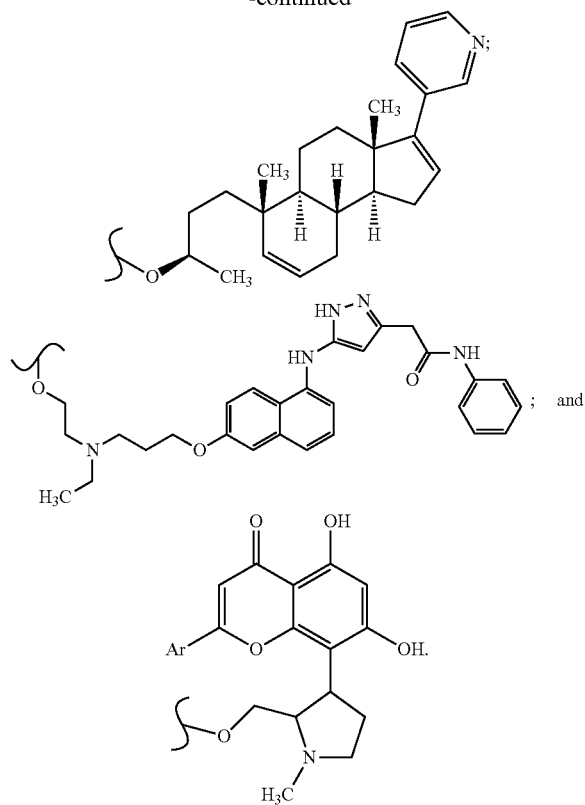

In certain aspects, the active moiety is an anti-tumor compound. In other aspects, the active moiety is a molecule that inhibits methionine aminopeptidase-2 (MetAP2), such as fumagillin, fumagillol, or an analog, derivative, salt or ester thereof. MetAP2 is a co-translational enzyme responsible for cleaving the initiator methionine off nascent polypeptides. It has several exclusive substrates that tend to be up-regulated under conditions of cellular stress, hypoxia and when cells are dividing. Fumagillin is a natural product derived from the biomass of the fungus *Aspergillus Fumigatus* Fresenius. Fumagillin and its analogs and derivatives are known to inhibit the aminopeptidase activity of MetAP2. Further exemplary MetAP2 inhibitors have been described in U.S. Pat. No. 6,242,494 to Craig et al, U.S. Pat. No. 6,063,812 to Hong et al., U.S. Pat. No. 6,887,863 to Craig et al., U.S. Pat. No. 7,030,262 to BaMaung et al., U.S. Pat. No. 7,491,718 to Comess et al., and patent application WO2017027684, each of which is incorporated by reference in its entirety. Additional exemplary MetAP2 inhibitors have been described in Wang et al. "Correlation of tumor growth suppression and methionine aminopeptidase-2 activity blockade using an orally active inhibitor," PNAS 105(6) 1838-1843 (2008); Lee at al. "Design, Synthesis, and Antiangiogenic Effects of a Series of Potent Novel Fumagillin Analogues," *Chem. Pharm. Bull.* 55(7) 1024-1029 (2007); Jeong et al. "Total synthesis and antiangiogenic activity of cyclopentane analogues of fumagillol," *Bioorganic and Medicinal Chemistry Letters* 15, 3580-3583 (2005); Arico-Muendel et al. "Carbamate Analogues of Fumagillin as Potent, Targeted Inhibitors of Methionine Aminopeptidase-2," *J. Med. Chem.* 52, 8047-8056 (2009); and International Publication No. WO 2010/003475 to Heinrich et al.

Fumagillin is a small molecule which has been used as an antimicrobial and antiprotozoal agent. Its physiochemical properties and method of production are well known (See U.S. Pat. No. 2,803,586 and Turner, J. R. et al., The Stereochemistry of Fumagillin, Proc. Natl. Acad. Sci. 48, 733-735 (1962)). The fermentation product, fumagillin, may be hydrolyzed to yield the alcohol fumagillol which in turn may be converted into various derivatives including carbamoylfumagillol, MW 325. The synthesis and preparation of carbamoylfumagillol and some small molecule derivatives are described in U.S. Pat. No. 5,166,172.

Fumagillin and related compounds are believed to exert their biological effects through the inhibition of MetAP2. This enzyme removes N-terminal methionine from nascent cellular proteins. (See Tucker, L. A., et al. "Ectopic Expression of Methionine Aminopeptidase-2 Causes Cell Transformation and Stimulates Proliferation", Oncogene 27, 3967 (2008).)

Carbamoylfumagillol and derivatives as well as other inhibitors of MetAP2 have shown therapeutic benefits in preclinical and clinical studies. These compounds inhibit cell proliferation and angiogenesis as described in U.S. Pat. No. 5,166,172. Fumagillin analogs or derivatives, such as CKD-732 and PPI-2458, are well studied in various systems as described in detail in Bernier et al., "Fumagillin class inhibitors of methionine aminopeptidase-2" *Drugs of the Future* 30(5): 497-508, 2005.

The anti-obesity effects of fumagillin and its analogs are well-known. Rupnick et al. "Adipose tissue mass can be regulated through the vasculature" PNAS 99, 10730-10735, 2002 describes weight loss in ob/ob mice with daily doses of TNP-470 ranging from 2.5 mg/kg to 10 mg/kg. Brakenhielm describes prevention of obesity at TNP-470 doses of 15 or 20 mg/kg every other day, "The Angiogenesis Inhibitor, TNP-470, Prevents Diet-Induced and Genetic Obesity in Mice" *Circulation Research* 94: 1579-1588, 2004. Kim, et al., in the "Assessment of the anti-obesity effects of the TNP-470 analog, CKD-732" J Molecular Endocrinology 38, 455-465, 2007 describe weight loss in C57BL/6J mice and SD rats at doses of 5 mg/kg/day. Lijnen et al. "Fumagillin reduces adipose tissue formation in murine models of nutritionally induced obesity" Hughes et al., (Obesity 12, 2241-2246, 2010) describes oral delivery of 1 mg/kg fumagillin daily resulting in weight loss in C57BL/6 mice.

One of these derivatives, chloroacetylcarbamoylfumagillol (TNP-470) has been extensively studied. (See H. Mann-Steinberg, et al., "TNP-470: The Resurrection of the First Synthetic Angiogenesis Inhibitor", Chapter 35 in Folkman and Figg, Angiogenesis: An Integrative Approach from Science to Medicine, Springer NY (2008).) TNP-470 has shown activity against many cancers including lung cancer, cervical cancer, ovarian cancer, breast cancer and colon cancer. Because of dose-limiting neurotoxicity, TNP-470 has been tested using multiple dosing regimens, but these attempts to limit its toxicity have been unsuccessful. Thus, TNP-470 has been found to be too toxic for human use. TNP-470 has a short half-life and requires extended intravenous administration for therapeutic use. A metabolite of TNP-470, carbamoylfumagillol has a half-life of 12 minutes in man. (See Herbst et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", *Journal of Clinical Oncology* 20(22) 4440-4447 (2002). In addition, fumagillin and its derivatives are hydrophobic and difficult to formulate.

Despite the known usefulness of fumagillin derivatives, they have not been used successfully as treatments because of the failure to overcome the problems of the low water solubility, short half-life values, and neurotoxic side-effects of these compounds. TNP-470 in combination with paclitaxel was determined to have an MTD of 60 mg/m2 dosed three times per week based on the previously observed dose limiting neuropsychiatric toxicities Herbst et al., "Safety and pharmacokinetic effects of TNP-470, an angiogenesis inhibitor, combined with paclitaxel in patients with solid tumors: evidence for activity in non-small-cell lung Cancer" Journal of Clinical Oncology 20, 4440-4447, 2002. Similarly Shin et al. "A Phase 1 pharmacokinetic and pharmacodynamics study of CKD-732, an antiangiogenic agent, in patients with refractory solid cancer" Investigational New Drugs 28, 650-658, 2010 reports that the MTD of CKD-732 was 15 mg/m2/day dosed on an every fourth day schedule due to confusion and insomnia. Accordingly, the compounds of the present disclosure are more potent, show reduced toxicity (less neurotoxic), improved water solubility, more stable, and/or have longer half-life (serum half-life) than presently known fumagillin derivatives.

The phrase "reduced toxicity" as used herein has its ordinary meaning as understood by persons of skill in the art. Merely by way of example, and by no means as a limitation on the meaning of the term, the administration of the fumagillin analog conjugate causes less side effects in open field tests with mice, as compared to the fumagillin analog alone.

The phrase "improved water solubility" has its ordinary meaning as understood by persons of skill in the art. Merely by way of example, and by no means as a limitation on the meaning of the term, the following description of the term is informative: an increased amount of a fumagillin analog will dissolve in water as a result of its covalent incorporation into a conjugate as compared to the amount of the unconjugated fumagillin analog that will dissolve in water alone.

The phrase "longer half-life" has its ordinary meaning as understood by persons of skill in the art. Merely by way of example, and by no means as a limitation on the meaning of the term, the following description of the term is informative: any appreciable increase in the length of time required to deactivate fumagillin conjugate either in vivo or in vitro as compared to the half-life of the fumagillin analog alone either in vivo or in vitro.

Without being bound by any theory, non-enzymatic actions of MetAP2 to suppress activity of extra-cellular signal regulated kinases 1 and 2 (ERK1/2) may be important as may be the binding of eukaryotic initiation factor, eIF, by MetAP2. Cellular responses to MetAP2 inhibition reflective of potential ERK-related processes may include suppression of sterol regulatory element binding protein (SREBP) activity, leading to reduced lipid and cholesterol biosynthesis. Interestingly, changes in the expression patterns of hepatic and adipose tissue genes after prolonged (approximately 9 months) fumagillin exposure suggest that MetAP2 inhibition also may alter the relative abundance of factors involved in inflammation, consistent with reduced ERK-dependent cellular processes. The putative mechanism of MetAP2 inhibition leading to mobilization of adipose depot and catabolism of free fatty acids as energy source by the body is supported by changes in plasma Q-hydroxybutyrate, adiponectin, leptin, and FGF21 observed in previous studies (Hughes et al., Obesity (2013) 21, 9, 1782-1788). Elevation in the levels of key catabolic hormones adiponectin and FGF21, coupled with the appearance of ketone bodies (O-hydroxybutyrate), suggest MetAP2 inhibition with the conjugated or modified fumagillin, fumagillol, or an analog, derivative, salt or ester thereof compounds of the present disclosure stimulates energy expenditure, fat utilization and lipid excretion. The reduction in leptin observed in previous studies and the studies provided herein is also consistent with a decrease in total adipose tissue and negative energy balance. It is also possible that the conjugated or modified fumagillin, fumagillol, or an analog, derivative, salt or ester thereof compounds of the present disclosure form a covalent bond with MetAP2, thereby irreversibly inhibiting and silencing existing enzyme until a newly produced pool of MetAP2 is generated in target tissues (e.g., liver and adipose tissue).

In certain aspects, the conjugated or modified fumagillin, fumagillol, or an analog, derivative, salt or ester thereof compounds of the present disclosure, for example have the following formula as shown in Table 1:

TABLE 1

| Compound No. | Chemical Structure |
| --- | --- |
| 5 | 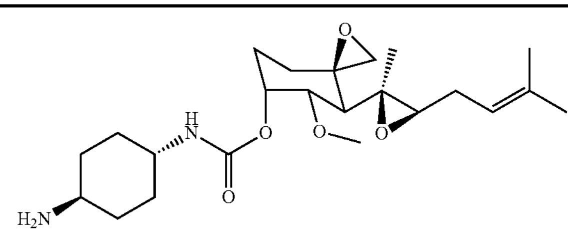 |
| 6 | 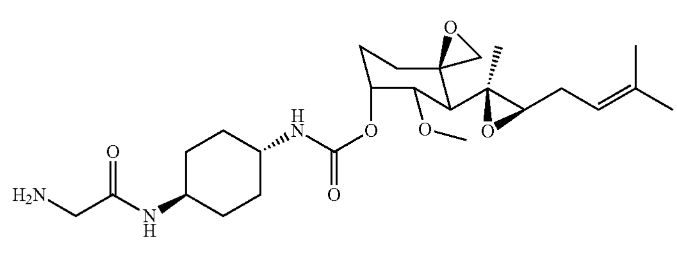 |

TABLE 1-continued
| Compound No. | Chemical Structure |
|---|---|
| 7 | 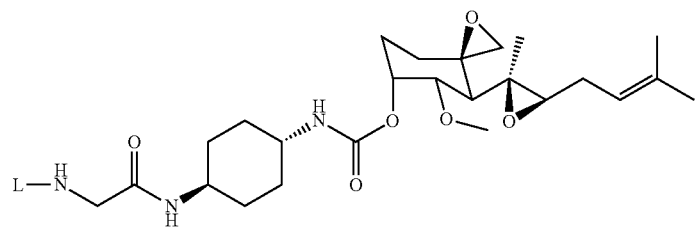 |
| 8 | 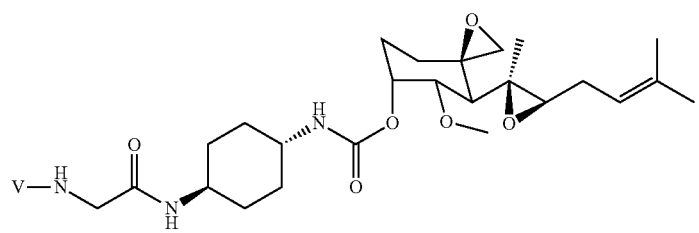 |
| 9 | 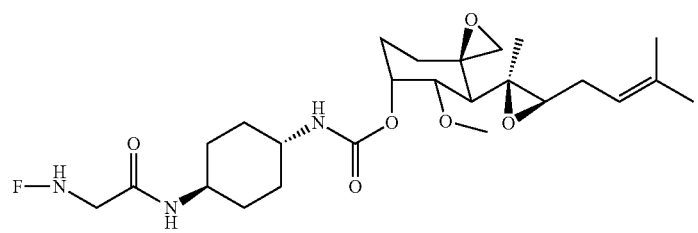 |
| 10 | 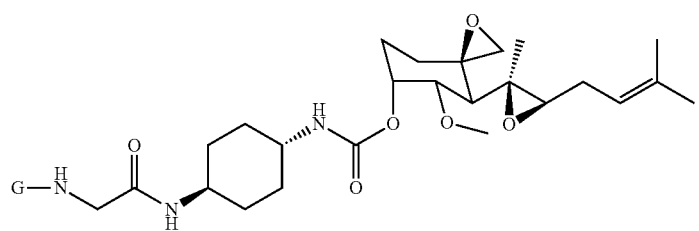 |
| 11 | 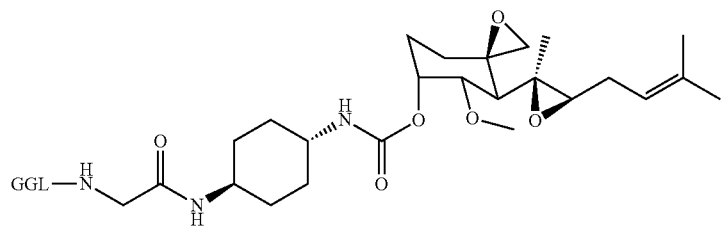 |
| 12 | 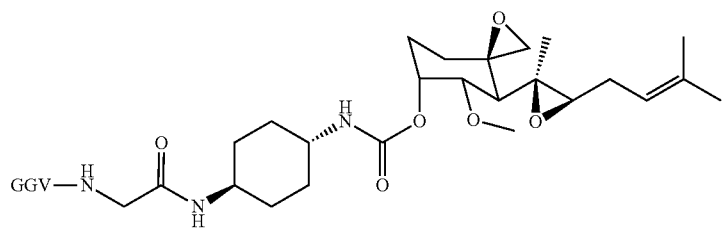 |

TABLE 1-continued

| Compound No. | Chemical Structure |
|---|---|
| 13 | GGF—NH—...—NH—C(O)—cyclohexyl—NH—C(O)O—[fumagillol core] |
| 14 | GGG—NH—...—NH—C(O)—cyclohexyl—NH—C(O)O—[fumagillol core] |
| 15 | GFL—NH—...—NH—C(O)—cyclohexyl—NH—C(O)O—[fumagillol core] |
| 16 | Polymer—GGL—NH—...—NH—C(O)—cyclohexyl—NH—C(O)O—[fumagillol core] |
| 17 | Polymer—GGV—NH—...—NH—C(O)—cyclohexyl—NH—C(O)O—[fumagillol core] |
| 18 | Polymer—GGF—NH—...—NH—C(O)—cyclohexyl—NH—C(O)O—[fumagillol core] |

TABLE 1-continued
| Compound No. | Chemical Structure |
|---|---|
| 19 | 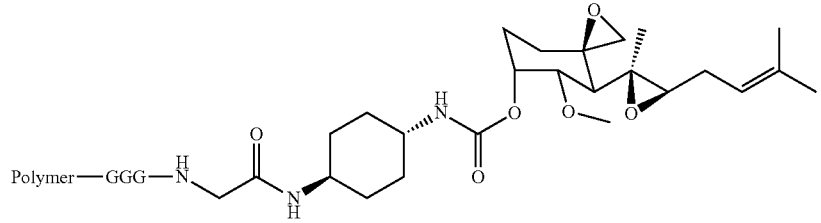 |
| 20 | 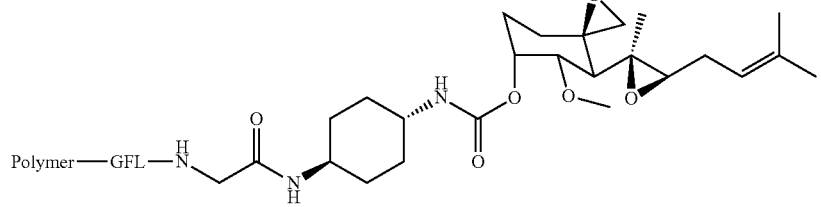 |
| 21 | 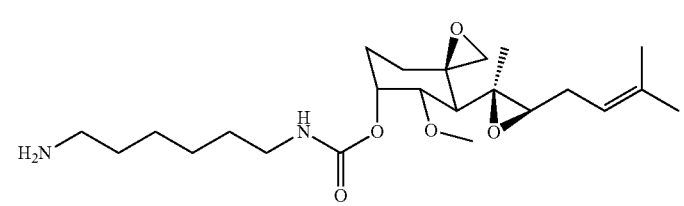 |
| 22 | 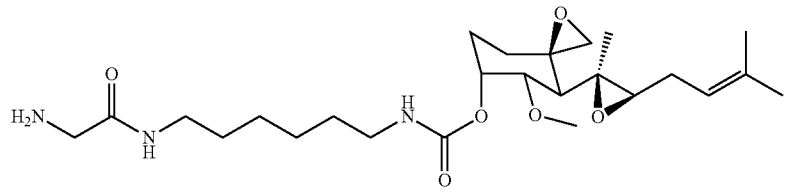 |
| 23 | 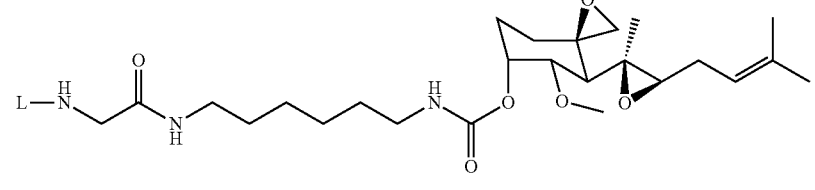 |
| 24 | 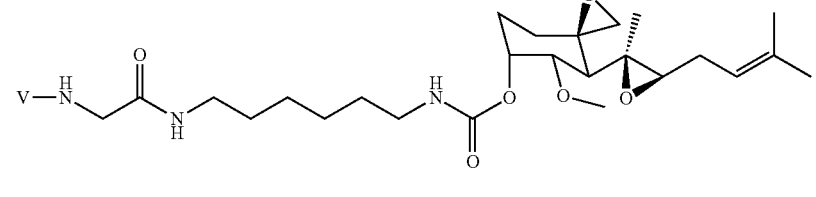 |
| 25 | 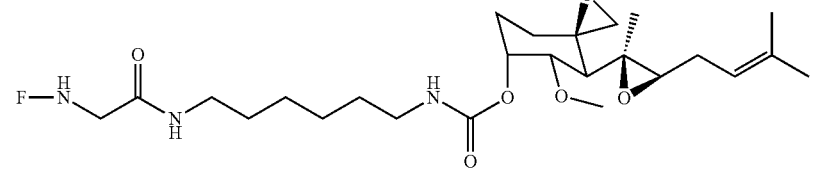 |

TABLE 1-continued

| Compound No. | Chemical Structure |
| --- | --- |
| 26 | G-NH-CH2-C(O)-NH-(CH2)6-NH-C(O)O-[drug] |
| 27 | GGL-NH-CH2-C(O)-NH-(CH2)6-NH-C(O)O-[drug] |
| 28 | GGV-NH-CH2-C(O)-NH-(CH2)6-NH-C(O)O-[drug] |
| 29 | GGF-NH-CH2-C(O)-NH-(CH2)6-NH-C(O)O-[drug] |
| 30 | GGG-NH-CH2-C(O)-NH-(CH2)6-NH-C(O)O-[drug] |
| 31 | GFL-NH-CH2-C(O)-NH-(CH2)6-NH-C(O)O-[drug] |
| 32 | Polymer-GGL-NH-CH2-C(O)-NH-(CH2)6-NH-C(O)O-[drug] |

TABLE 1-continued
| Compound No. | Chemical Structure |
|---|---|
| 33 | 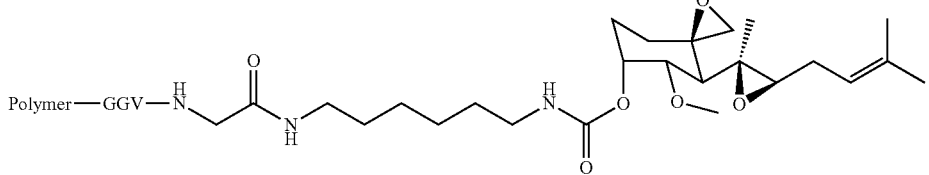 |
| 34 | 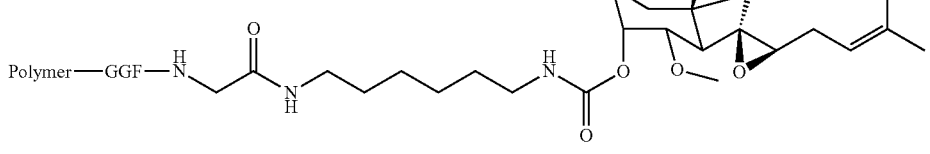 |
| 35 | 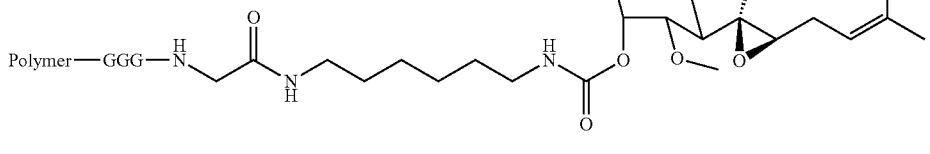 |
| 36 | 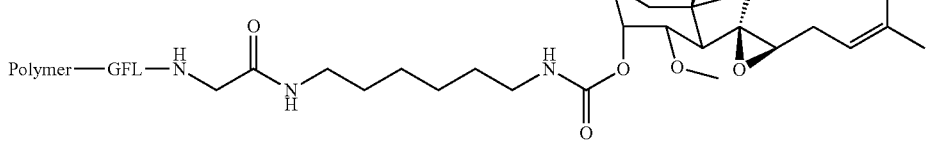 |
| 37 | 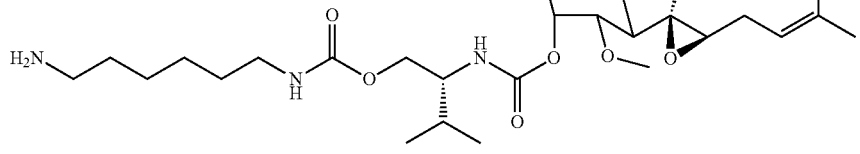 |
| 38 | 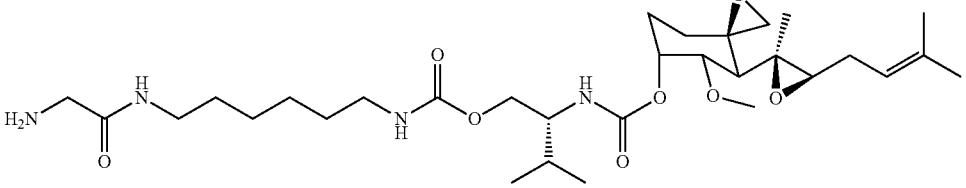 |
| 39 | 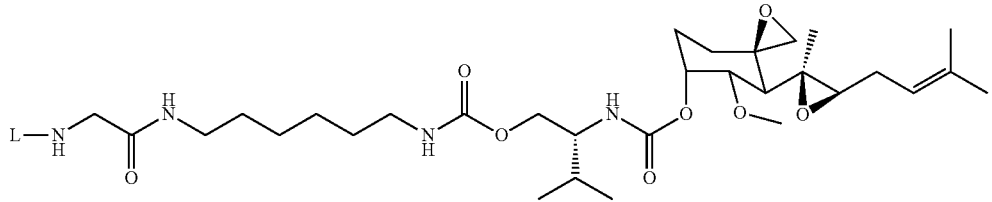 |

TABLE 1-continued
| Compound No. | Chemical Structure |
|---|---|
| 40 | 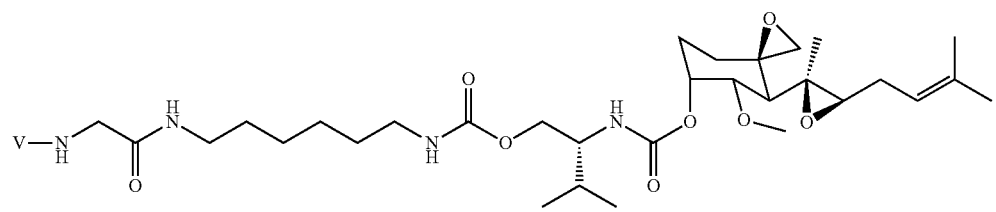 |
| 41 | 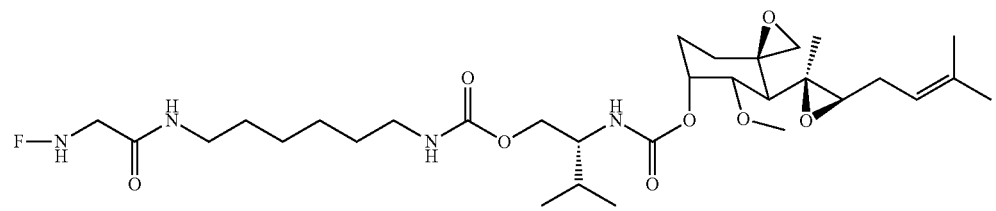 |
| 42 | 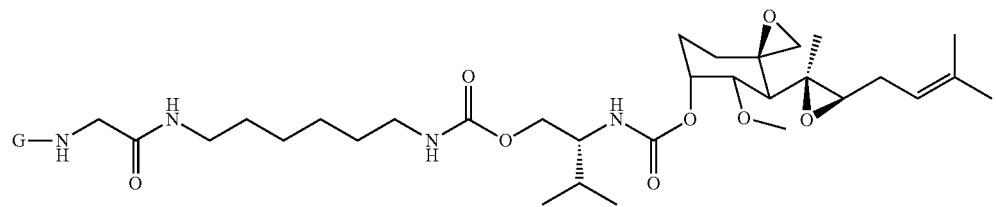 |
| 43 | 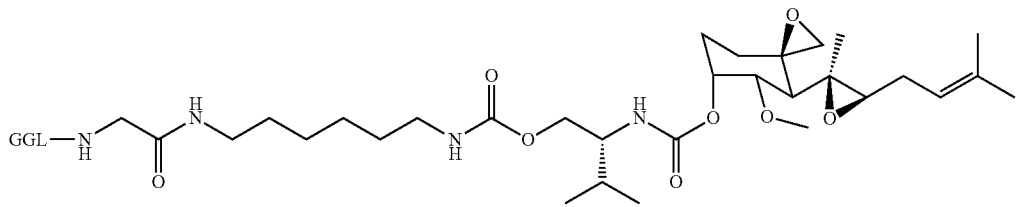 |
| 44 | 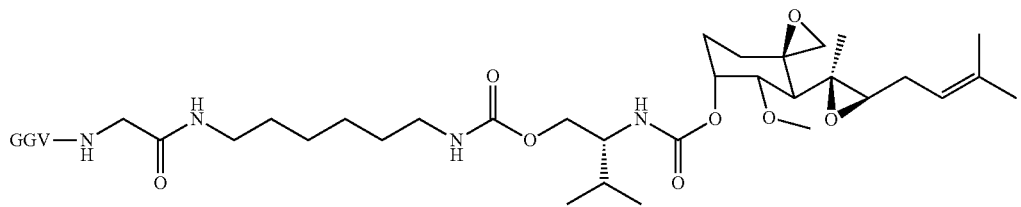 |
| 45 | 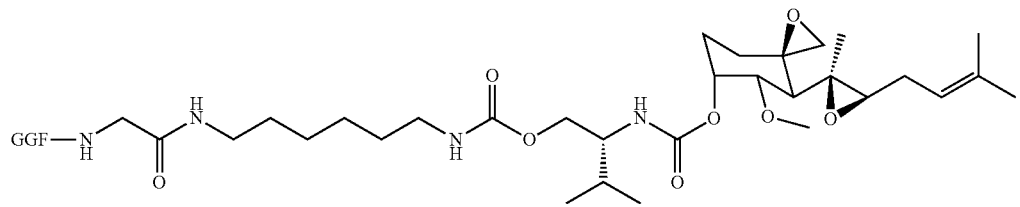 |
| 46 | 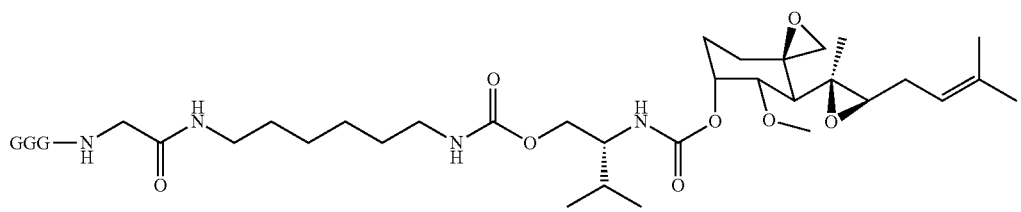 |

TABLE 1-continued
| Compound No. | Chemical Structure |
|---|---|
| 47 | 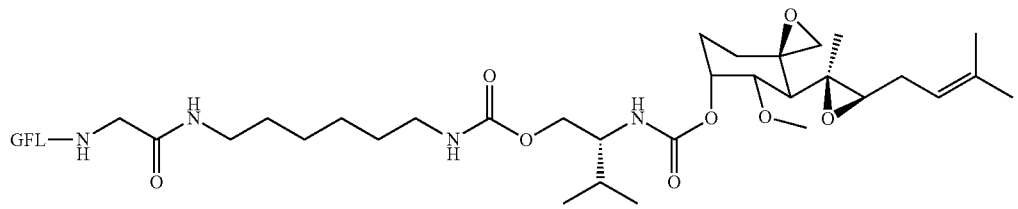 |
| 48 | 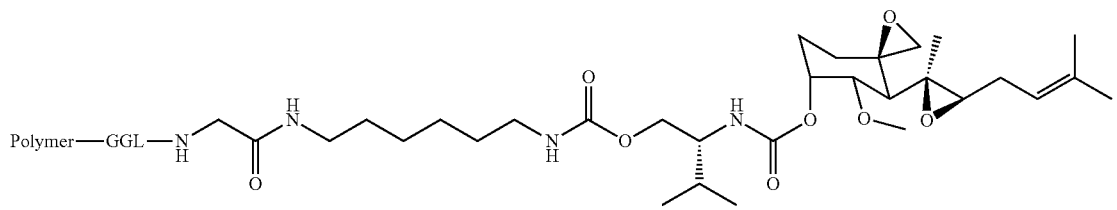 |
| 49 | 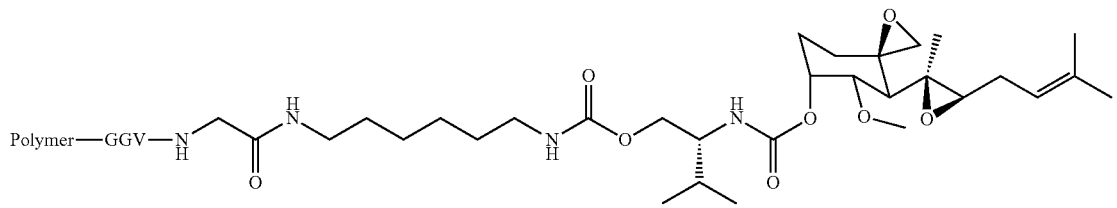 |
| 50 | 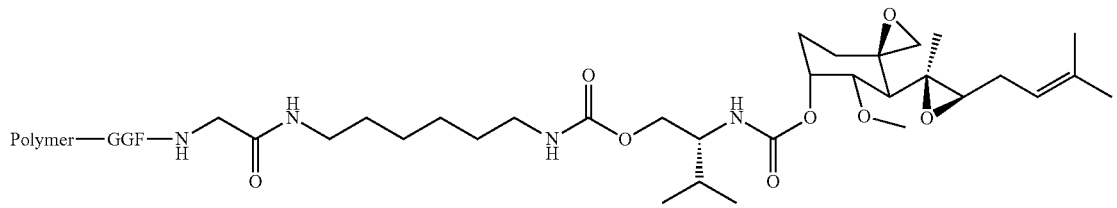 |
| 51 | 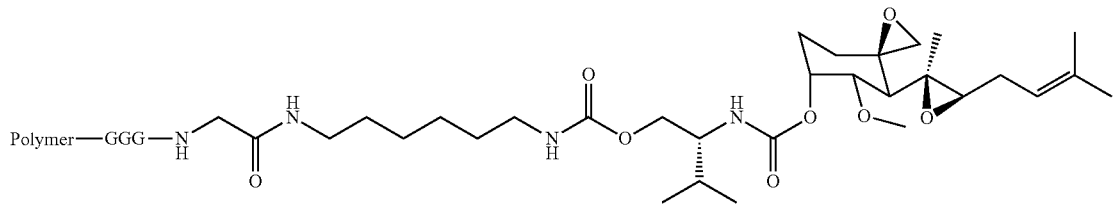 |
| 52 | 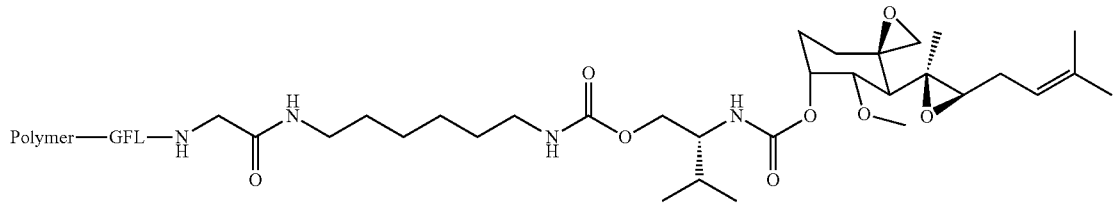 |
| 53 | 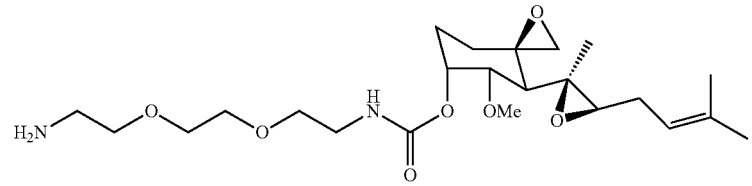 |

TABLE 1-continued
| Compound No. | Chemical Structure |
|---|---|
| 54 | 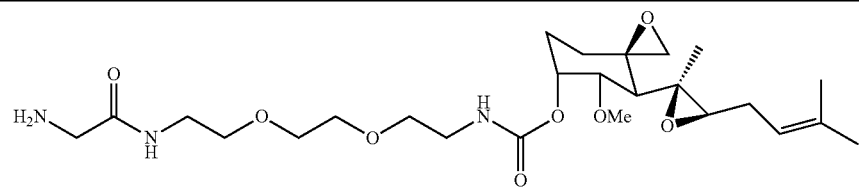 |
| 55 | 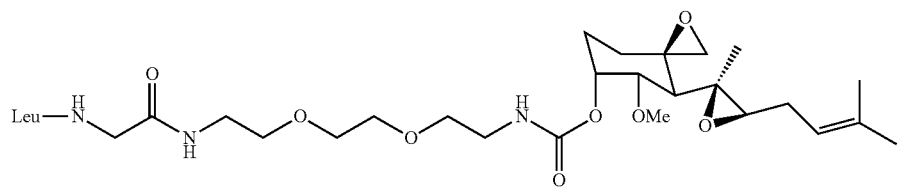 |
| 56 | 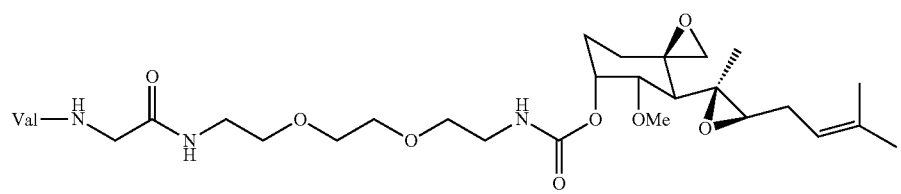 |
| 57 | 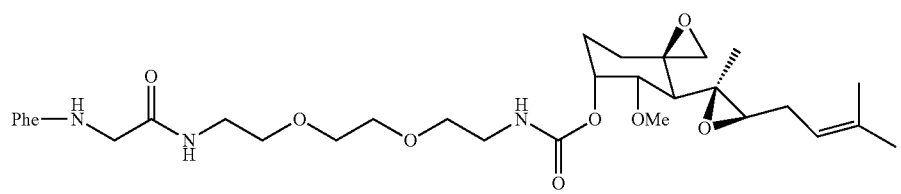 |
| 58 | 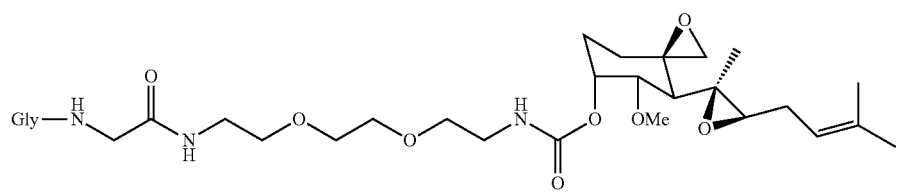 |
| 59 | 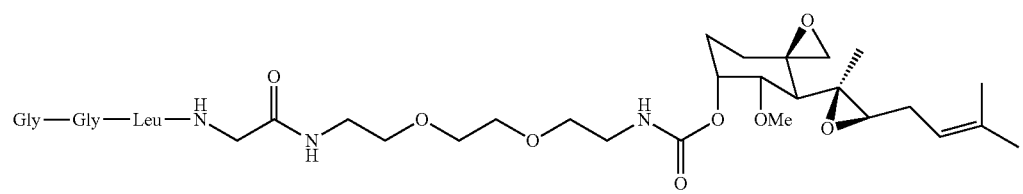 |
| 60 | 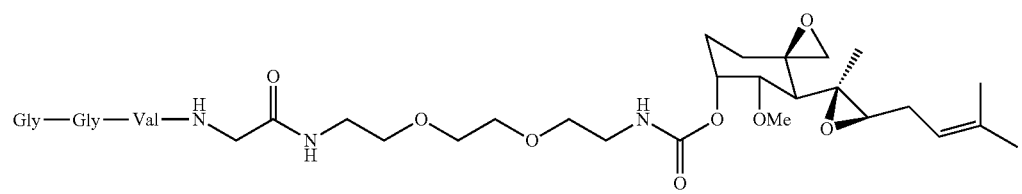 |
| 61 | 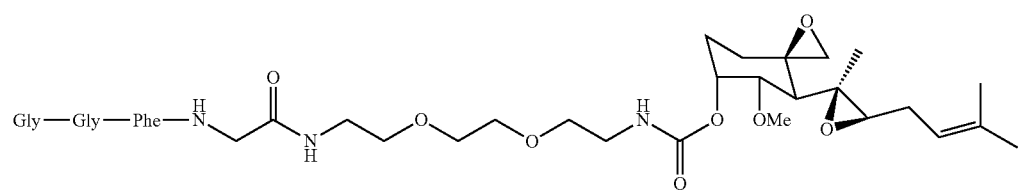 |

TABLE 1-continued

| Compound No. | Chemical Structure |
|---|---|
| 62 | Gly—Gly—Gly—NH—C(O)—CH2—NH—CH2CH2—O—CH2CH2—O—CH2CH2—NH—C(O)—O—[mutilin-OMe-epoxide-prenyl] |
| 63 | Gly—Phe—Leu—NH—C(O)—CH2—NH—CH2CH2—O—CH2CH2—O—CH2CH2—NH—C(O)—O—[mutilin-OMe-epoxide-prenyl] |
| 64 | Polymer—Gly—Gly—Leu—NH—C(O)—CH2—NH—CH2CH2—O—CH2CH2—O—CH2CH2—NH—C(O)—O—[mutilin-OMe-epoxide-prenyl] |
| 65 | Polymer—Gly—Gly—Val—NH—C(O)—CH2—NH—CH2CH2—O—CH2CH2—O—CH2CH2—NH—C(O)—O—[mutilin-OMe-epoxide-prenyl] |
| 66 | Polymer—Gly—Gly—Phe—NH—C(O)—CH2—NH—CH2CH2—O—CH2CH2—O—CH2CH2—NH—C(O)—O—[mutilin-OMe-epoxide-prenyl] |
| 67 | Polymer—Gly—Gly—Gly—NH—C(O)—CH2—NH—CH2CH2—O—CH2CH2—O—CH2CH2—NH—C(O)—O—[mutilin-OMe-epoxide-prenyl] |
| 68 | Polymer—Gly—Phe—Leu—NH—C(O)—CH2—NH—CH2CH2—O—CH2CH2—O—CH2CH2—NH—C(O)—O—[mutilin-OMe-epoxide-prenyl] |

TABLE 1-continued
| Compound No. | Chemical Structure |
|---|---|
| 69 | 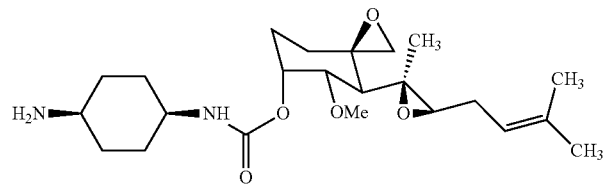 |
| 70 | 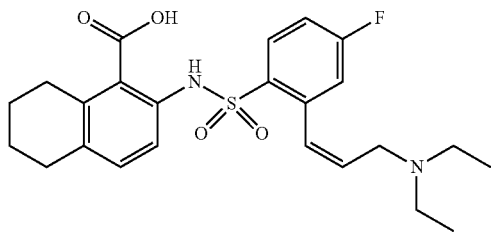 [SMILES: CCN(CC)C/C=C\c1cc(F)ccc1S(=O)(=O)Nc1ccc2c(c1C(=O)O)CCCC2] |
| 71 | 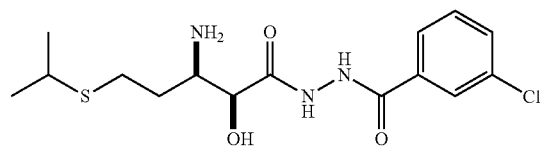 [SMILES: CC(C)SCC[C@@H](N)[C@H](O)C(=O)NNC(=O)c1cccc(Cl)c1] |
| 72 | 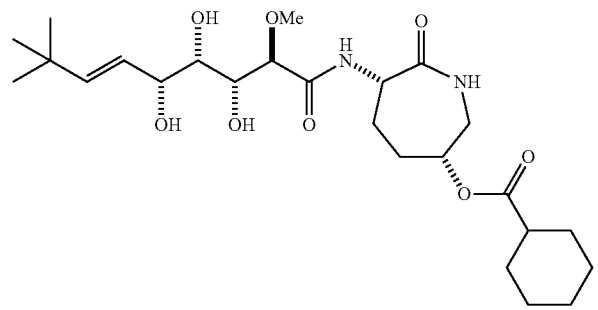 |
| 73 | 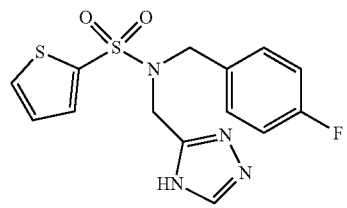 [SMILES: O=S(=O)(c1cccs1)N(Cc1ccc(F)cc1)Cc1nnc[nH]1] |
| 74 | 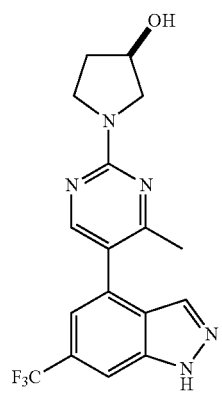 [SMILES: Cc1nc(N2CC[C@@H](O)C2)ncc1-c1cc(C(F)(F)F)cc2[nH]ncc12] |

TABLE 1-continued
| Compound No. | Chemical Structure |
|---|---|
| 75 | 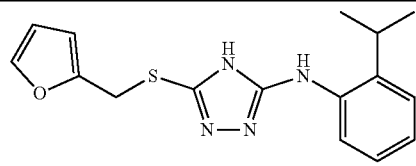 |
| 76 | 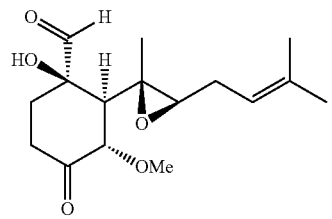 [SMILES: CO[C@@H]1C(=O)CC[C@](O)(C=O)[C@H]1[C@@]1(C)O[C@@H]1CC=C(C)C] |
| 77 | 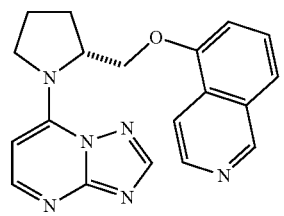 [SMILES: c1cc(OC[C@H]2CCCN2c2ccnc3ncnn23)c2ccncc2c1] |
| 78 | 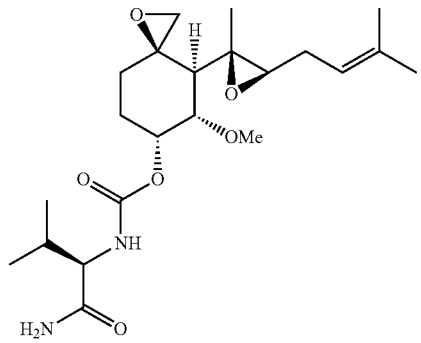 [SMILES: CO[C@@H]1[C@H](OC(=O)N[C@@H](C(N)=O)C(C)C)CC[C@]2(CO2)[C@H]1[C@@]1(C)O[C@@H]1CC=C(C)C] |
| 79 | 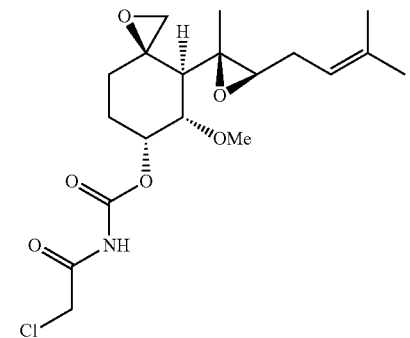 [SMILES: CO[C@@H]1[C@H](OC(=O)NC(=O)CCl)CC[C@]2(CO2)[C@H]1[C@@]1(C)O[C@@H]1CC=C(C)C] |
| 80 | 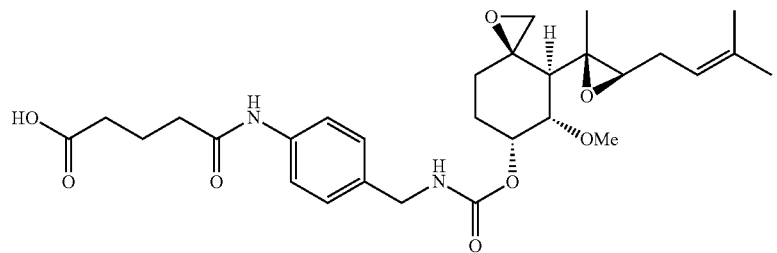 [SMILES: CO[C@@H]1[C@H](OC(=O)NCc2ccc(NC(=O)CCCC(=O)O)cc2)CC[C@]2(CO2)[C@H]1[C@@]1(C)O[C@@H]1CC=C(C)C] |

TABLE 1-continued
| Compound No. | Chemical Structure |
|---|---|
| 81 | 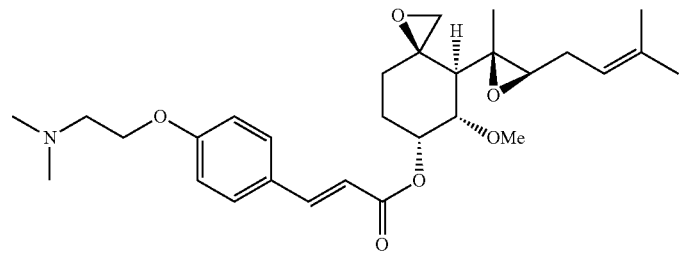 [SMILES: CO[C@@H]1[C@H](OC(=O)/C=C/c2ccc(OCCN(C)C)cc2)CC[C@]2(CO2)[C@H]1[C@@]1(C)O[C@@H]1CC=C(C)C] |
| 82 | 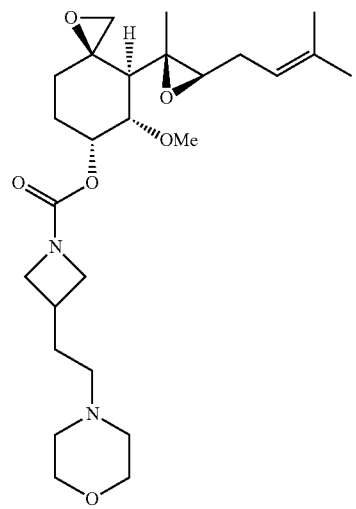 [SMILES: CO[C@@H]1[C@H](OC(=O)N2CC(CCN3CCOCC3)C2)CC[C@]2(CO2)[C@H]1[C@@]1(C)O[C@@H]1CC=C(C)C] |
| 83 | 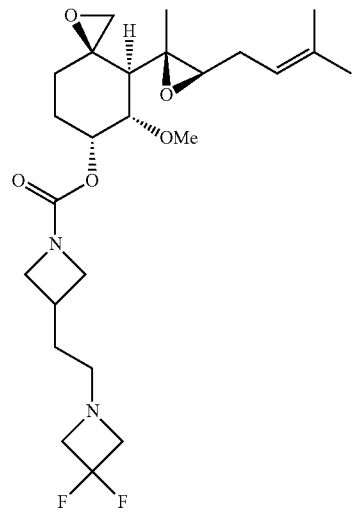 [SMILES: CO[C@@H]1[C@H](OC(=O)N2CC(CCN3CC(F)(F)C3)C2)CC[C@]2(CO2)[C@H]1[C@@]1(C)O[C@@H]1CC=C(C)C] |

| Compound No. | Chemical Structure |
|---|---|
| 84 | 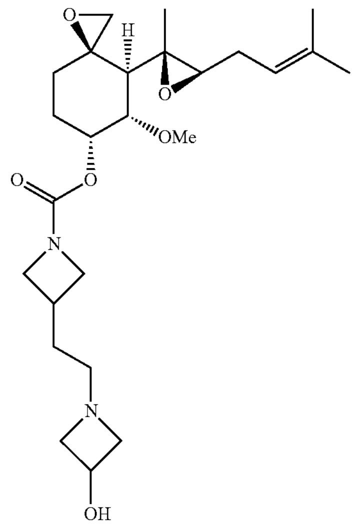 [SMILES: CO[C@@H]1[C@H](OC(=O)N2CC(CCN3CC(O)C3)C2)CC[C@]2(CO2)[C@H]1[C@@]1(C)O[C@@H]1CC=C(C)C] |
| 85 | 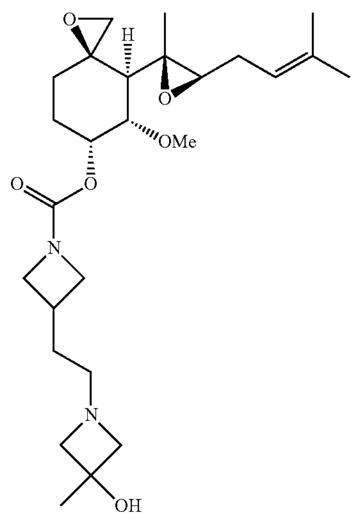 [SMILES: CO[C@@H]1[C@H](OC(=O)N2CC(CCN3CC(C)(O)C3)C2)CC[C@]2(CO2)[C@H]1[C@@]1(C)O[C@@H]1CC=C(C)C] |
| 86 | 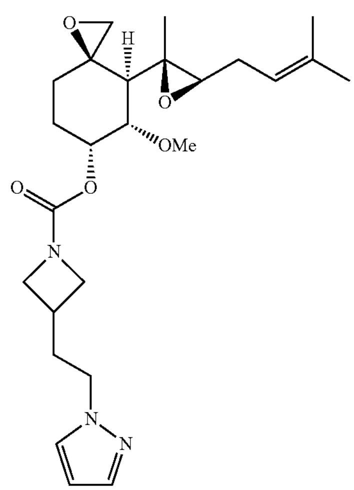 [SMILES: CO[C@@H]1[C@H](OC(=O)N2CC(CCn3cccn3)C2)CC[C@]2(CO2)[C@H]1[C@@]1(C)O[C@@H]1CC=C(C)C] |

TABLE 1-continued
| Compound No. | Chemical Structure |
|---|---|
| 87 | 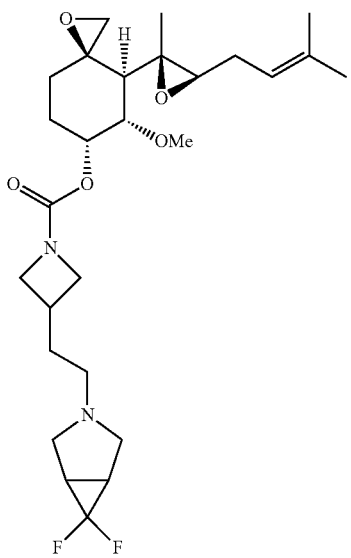 [SMILES: CO[C@@H]1[C@H](OC(=O)N2CC(CCN3CC4C(C3)C4(F)F)C2)CC[C@]2(CO2)[C@H]1[C@@]1(C)O[C@@H]1CC=C(C)C] |
| 88 | 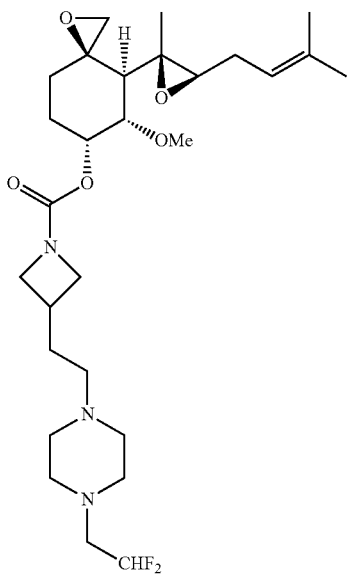 |

TABLE 1-continued
| Compound No. | Chemical Structure |
|---|---|
| 89 | 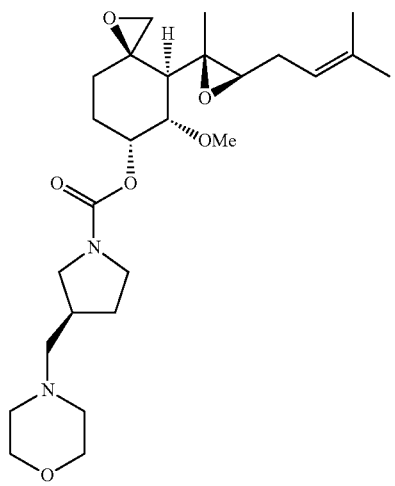 [SMILES: CO[C@@H]1[C@H](OC(=O)N2CC[C@@H](CN3CCOCC3)C2)CC[C@]2(CO2)[C@H]1[C@@]1(C)O[C@@H]1CC=C(C)C] |
| 90 | 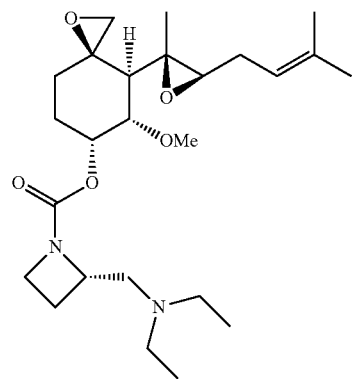 [SMILES: CCN(CC)C[C@@H]1CCN1C(=O)O[C@@H]1CC[C@]2(CO2)[C@@H]([C@@]2(C)O[C@@H]2CC=C(C)C)[C@@H]1OC] |
| 91 | 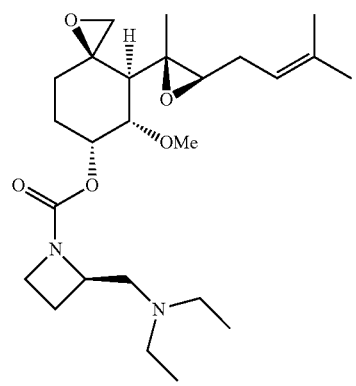 [SMILES: CCN(CC)C[C@H]1CCN1C(=O)O[C@@H]1CC[C@]2(CO2)[C@@H]([C@@]2(C)O[C@@H]2CC=C(C)C)[C@@H]1OC] |

TABLE 1-continued
| Compound No. | Chemical Structure |
|---|---|
| 92 | 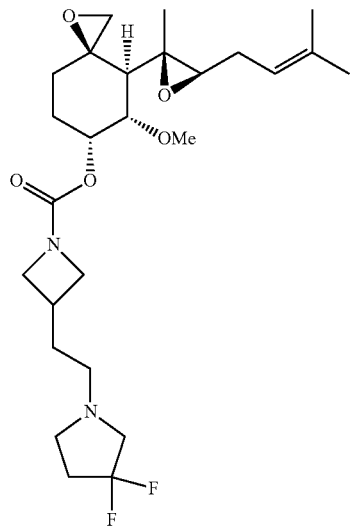 [SMILES: CO[C@@H]1[C@H](OC(=O)N2CC(CCN3CCC(F)(F)C3)C2)CC[C@]2(CO2)[C@H]1[C@@]1(C)O[C@@H]1CC=C(C)C] |
| 93 | 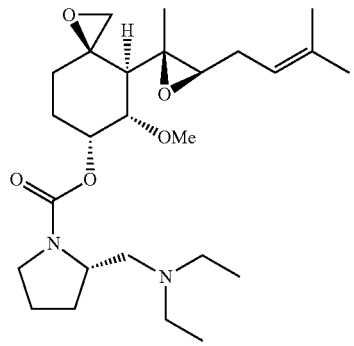 [SMILES: CCN(CC)C[C@@H]1CCCN1C(=O)O[C@@H]1CC[C@]2(CO2)[C@@H]([C@@]2(C)O[C@@H]2CC=C(C)C)[C@@H]1OC] |
| 94 | 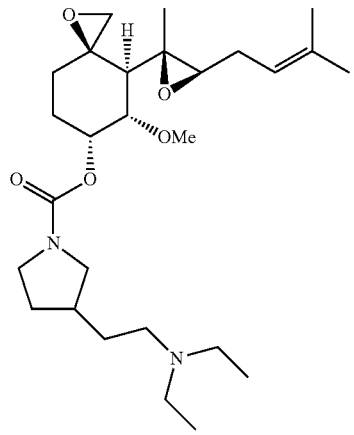 [SMILES: CCN(CC)CCC1CCN(C(=O)O[C@@H]2CC[C@]3(CO3)[C@@H]([C@@]3(C)O[C@@H]3CC=C(C)C)[C@@H]2OC)C1] |

TABLE 1-continued
| Compound No. | Chemical Structure |
|---|---|
| 95 | 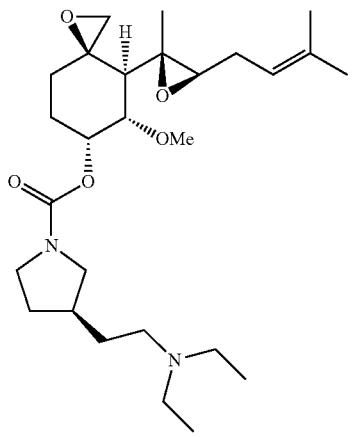 [SMILES: CCN(CC)CC[C@H]1CCN(C(=O)O[C@@H]2CC[C@]3(CO3)[C@@H]([C@@]3(C)O[C@@H]3CC=C(C)C)[C@@H]2OC)C1] |
| 96 | 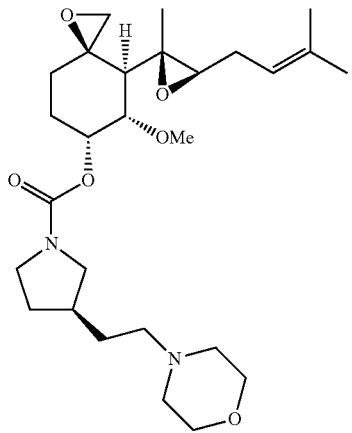 [SMILES: CO[C@@H]1[C@H](OC(=O)N2CC[C@H](CCN3CCOCC3)C2)CC[C@]2(CO2)[C@H]1[C@@]1(C)O[C@@H]1CC=C(C)C] |
| 97 | 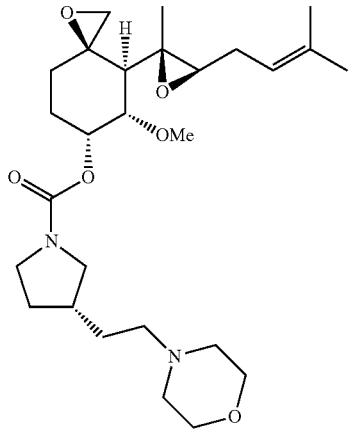 [SMILES: CO[C@@H]1[C@H](OC(=O)N2CC[C@@H](CCN3CCOCC3)C2)CC[C@]2(CO2)[C@H]1[C@@]1(C)O[C@@H]1CC=C(C)C] |

TABLE 1-continued
| Compound No. | Chemical Structure |
|---|---|
| 98 | 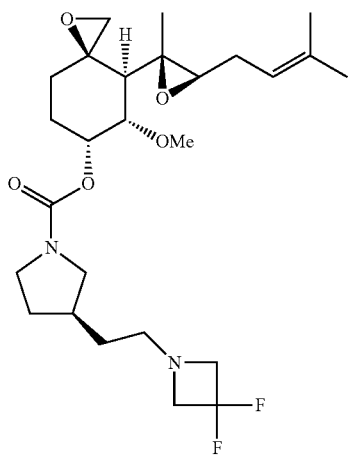 [SMILES: CO[C@@H]1[C@H](OC(=O)N2CC[C@H](CCN3CC(F)(F)C3)C2)CC[C@]2(CO2)[C@H]1[C@@]1(C)O[C@@H]1CC=C(C)C] |
| 99 | 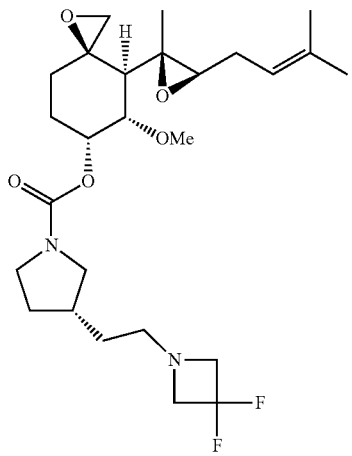 [SMILES: CO[C@@H]1[C@H](OC(=O)N2CC[C@@H](CCN3CC(F)(F)C3)C2)CC[C@]2(CO2)[C@H]1[C@@]1(C)O[C@@H]1CC=C(C)C] |
| 100 | 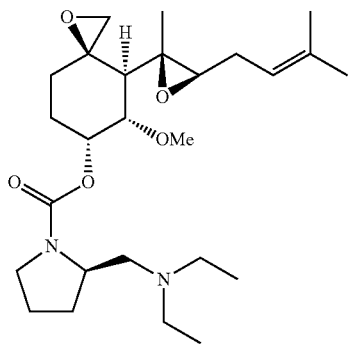 [SMILES: CCN(CC)C[C@H]1CCCN1C(=O)O[C@@H]1CC[C@]2(CO2)[C@@H]([C@@]2(C)O[C@@H]2CC=C(C)C)[C@@H]1OC] |

TABLE 1-continued
| Compound No. | Chemical Structure |
|---|---|
| 101 | 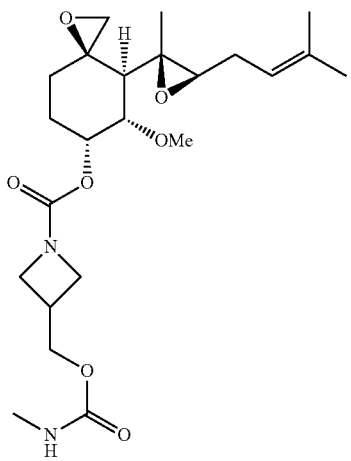 [SMILES: CNC(=O)OCC1CN(C(=O)O[C@@H]2CC[C@]3(CO3)[C@@H]([C@@]3(C)O[C@@H]3CC=C(C)C)[C@@H]2OC)C1] |
| 102 | 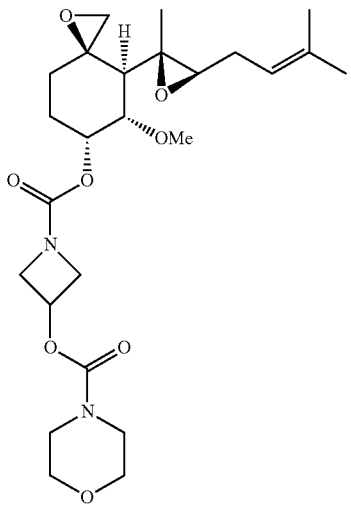 [SMILES: CO[C@@H]1[C@H](OC(=O)N2CC(OC(=O)N3CCOCC3)C2)CC[C@]2(CO2)[C@H]1[C@@]1(C)O[C@@H]1CC=C(C)C] |
| 103 | 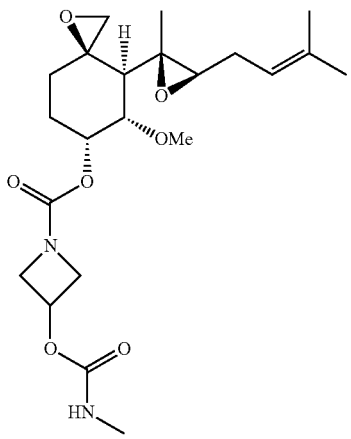 [SMILES: CNC(=O)OC1CN(C(=O)O[C@@H]2CC[C@]3(CO3)[C@@H]([C@@]3(C)O[C@@H]3CC=C(C)C)[C@@H]2OC)C1] |

TABLE 1-continued
| Compound No. | Chemical Structure |
|---|---|
| 104 | 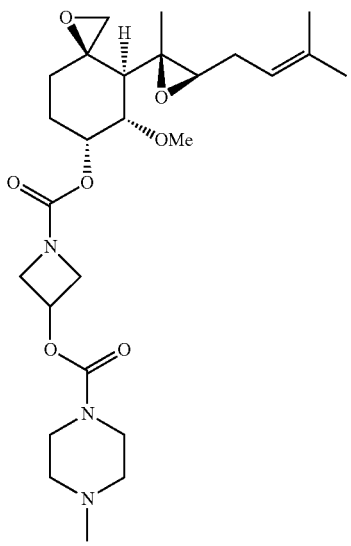 [SMILES: CO[C@@H]1[C@H](OC(=O)N2CC(OC(=O)N3CCN(C)CC3)C2)CC[C@]2(CO2)[C@H]1[C@@]1(C)O[C@@H]1CC=C(C)C] |
| 105 | 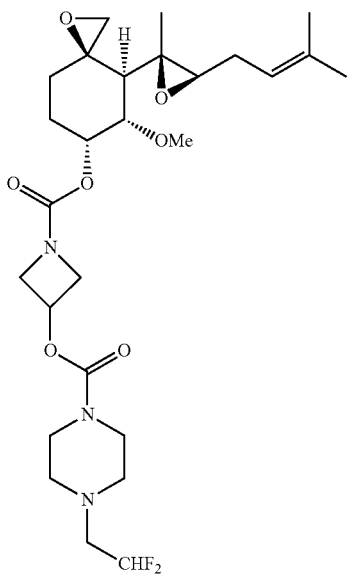 [SMILES: CO[C@@H]1[C@H](OC(=O)N2CC(OC(=O)N3CCN(CC(F)F)CC3)C2)CC[C@]2(CO2)[C@H]1[C@@]1(C)O[C@@H]1CC=C(C)C] |

TABLE 1-continued
| Compound No. | Chemical Structure |
|---|---|
| 106 | 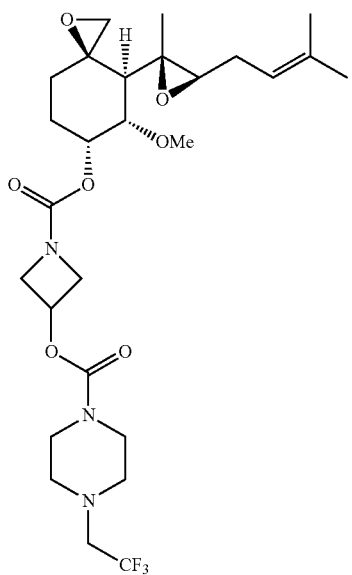 [SMILES: CO[C@@H]1[C@H](OC(=O)N2CC(OC(=O)N3CCN(CC(F)(F)F)CC3)C2)CC[C@]2(CO2)[C@H]1[C@@]1(C)O[C@@H]1CC=C(C)C] |
| 107 | 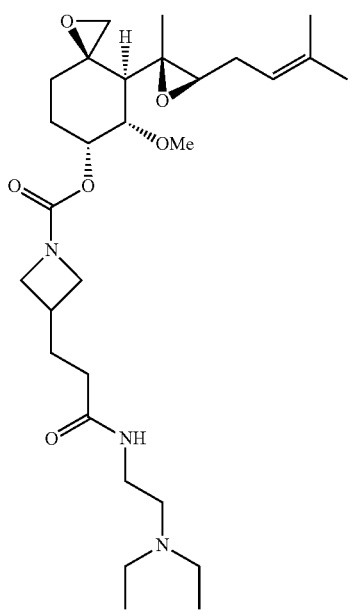 [SMILES: CCN(CC)CCNC(=O)CCC1CN(C(=O)O[C@@H]2CC[C@]3(CO3)[C@@H]([C@@]3(C)O[C@@H]3CC=C(C)C)[C@@H]2OC)C1] |

TABLE 1-continued
| Compound No. | Chemical Structure |
|---|---|
| 108 | 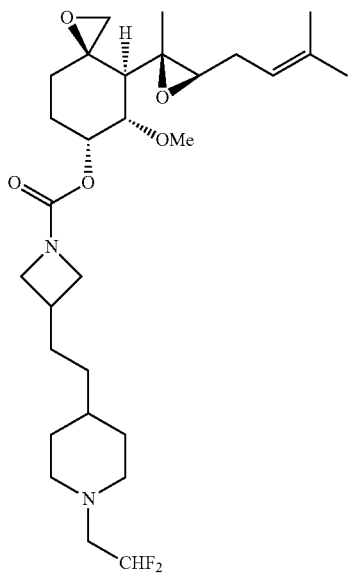 [SMILES: CO[C@@H]1[C@H](OC(=O)N2CC(CCC3CCN(CC(F)F)CC3)C2)CC[C@]2(CO2)[C@H]1[C@@]1(C)O[C@@H]1CC=C(C)C] |
| 109 | 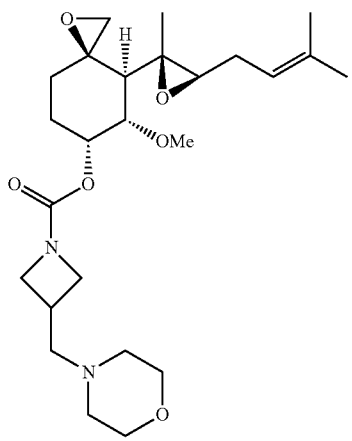 [SMILES: CO[C@@H]1[C@H](OC(=O)N2CC(CN3CCOCC3)C2)CC[C@]2(CO2)[C@H]1[C@@]1(C)O[C@@H]1CC=C(C)C] |
| 110 | 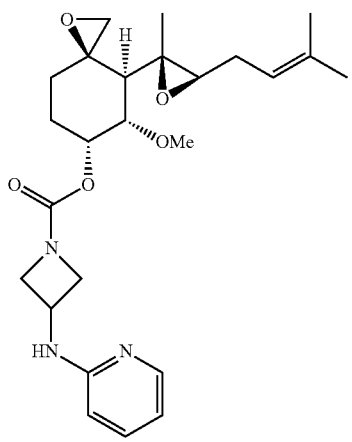 [SMILES: CO[C@@H]1[C@H](OC(=O)N2CC(Nc3ccccn3)C2)CC[C@]2(CO2)[C@H]1[C@@]1(C)O[C@@H]1CC=C(C)C] |

TABLE 1-continued
| Compound No. | Chemical Structure |
|---|---|
| 111 | 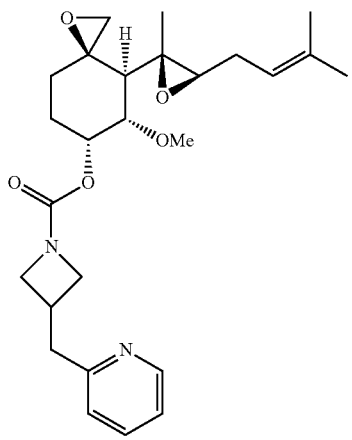 [SMILES: CO[C@@H]1[C@H](OC(=O)N2CC(Cc3ccccn3)C2)CC[C@]2(CO2)[C@H]1[C@@]1(C)O[C@@H]1CC=C(C)C] |
| 112 | 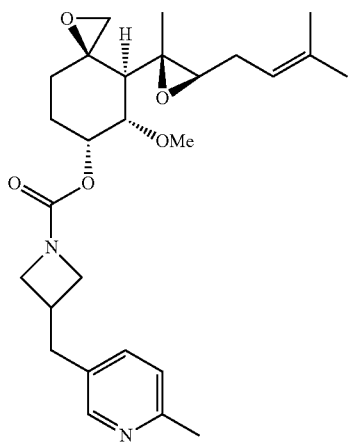 [SMILES: CO[C@@H]1[C@H](OC(=O)N2CC(Cc3ccc(C)nc3)C2)CC[C@]2(CO2)[C@H]1[C@@]1(C)O[C@@H]1CC=C(C)C] |
| 113 | 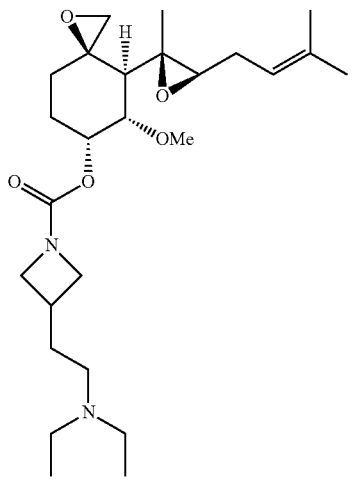 [SMILES: CCN(CC)CCC1CN(C(=O)O[C@@H]2CC[C@]3(CO3)[C@@H]([C@@]3(C)O[C@@H]3CC=C(C)C)[C@@H]2OC)C1] |

TABLE 1-continued
| Compound No. | Chemical Structure |
|---|---|
| 114 | 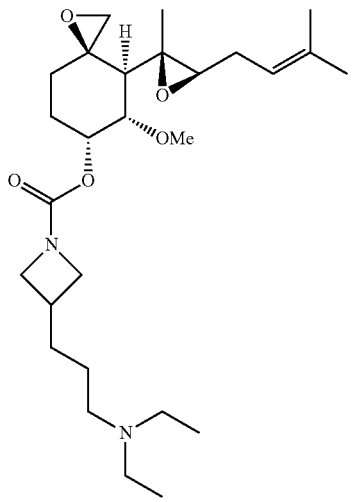 [SMILES: CCN(CC)CCCC1CN(C(=O)O[C@@H]2CC[C@]3(CO3)[C@@H]([C@@]3(C)O[C@@H]3CC=C(C)C)[C@@H]2OC)C1] |
| 115 | 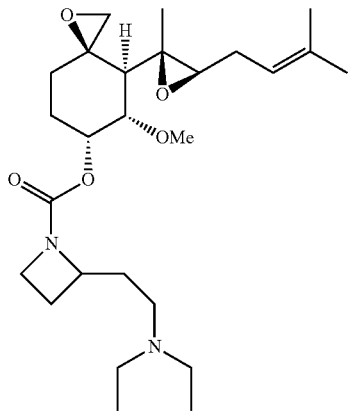 [SMILES: CCN(CC)CCC1CCN1C(=O)O[C@@H]1CC[C@]2(CO2)[C@@H]([C@@]2(C)O[C@@H]2CC=C(C)C)[C@@H]1OC] |
| 116 | 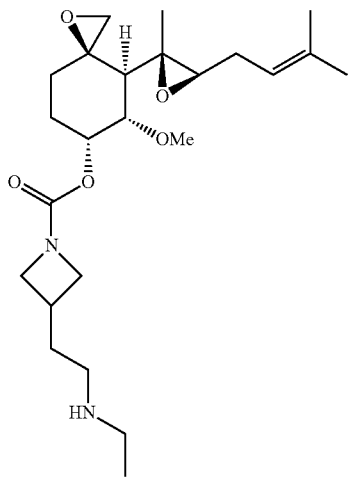 [SMILES: CCNCCC1CN(C(=O)O[C@@H]2CC[C@]3(CO3)[C@@H]([C@@]3(C)O[C@@H]3CC=C(C)C)[C@@H]2OC)C1] |

TABLE 1-continued
| Compound No. | Chemical Structure |
|---|---|
| 117 | 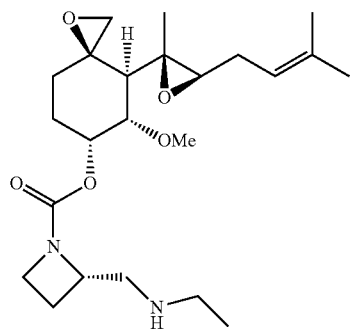 [SMILES: CCNC[C@@H]1CCN1C(=O)O[C@@H]1CC[C@]2(CO2)[C@@H]([C@@]2(C)O[C@@H]2CC=C(C)C)[C@@H]1OC] |
| 118 | 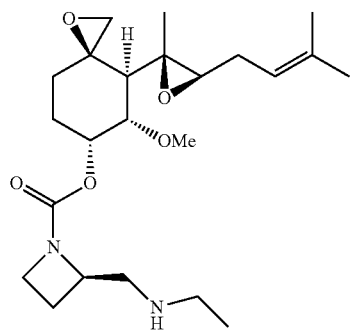 [SMILES: CCNC[C@H]1CCN1C(=O)O[C@@H]1CC[C@]2(CO2)[C@@H]([C@@]2(C)O[C@@H]2CC=C(C)C)[C@@H]1OC] |
| 119 | 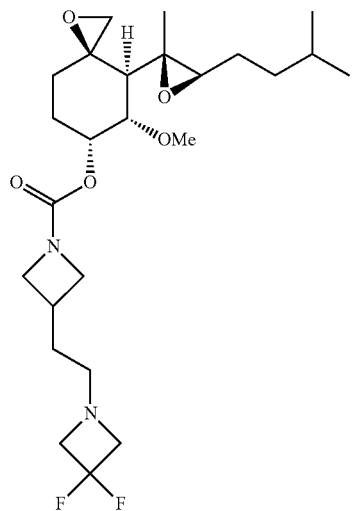 [SMILES: CO[C@@H]1[C@H](OC(=O)N2CC(CCN3CC(F)(F)C3)C2)CC[C@]2(CO2)[C@H]1[C@@]1(C)O[C@@H]1CCC(C)C] |

TABLE 1-continued
| Compound No. | Chemical Structure |
| --- | --- |
| 120 | 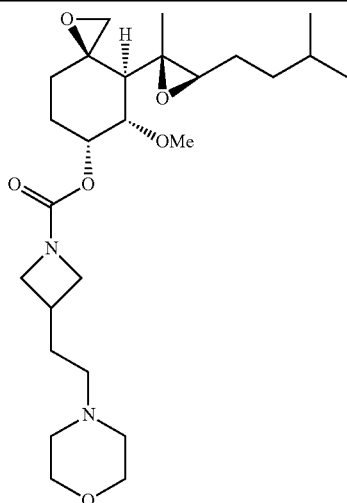 |
| 121 | 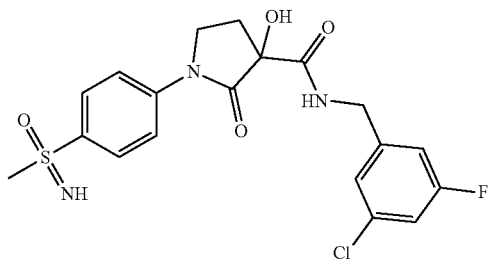 [SMILES: CS(=N)(=O)c1ccc(N2CCC(O)(C(=O)NCc3cc(F)cc(Cl)c3)C2=O)cc1] |
| 122 | 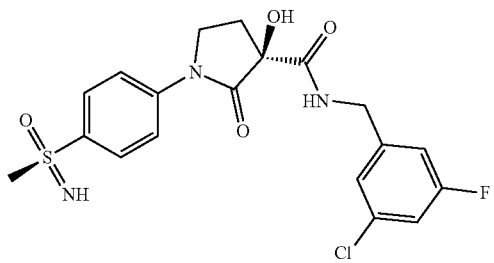 [SMILES: C[S@@](=N)(=O)c1ccc(N2CC[C@](O)(C(=O)NCc3cc(F)cc(Cl)c3)C2=O)cc1] |
| 123 | 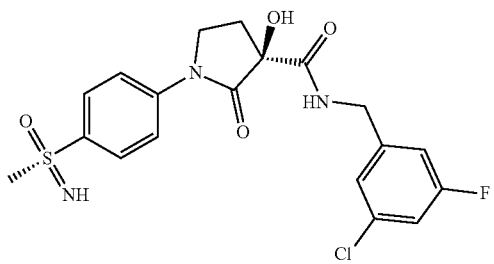 [SMILES: C[S@](=N)(=O)c1ccc(N2CC[C@](O)(C(=O)NCc3cc(F)cc(Cl)c3)C2=O)cc1] |
| 124 | 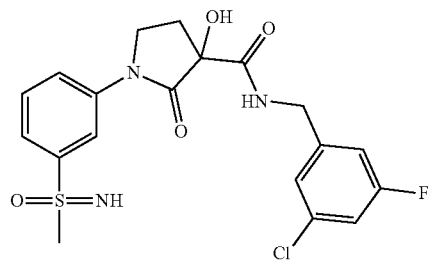 [SMILES: CS(=N)(=O)c1cccc(N2CCC(O)(C(=O)NCc3cc(F)cc(Cl)c3)C2=O)c1] |

TABLE 1-continued
| Compound No. | Chemical Structure |
|---|---|
| 125 | 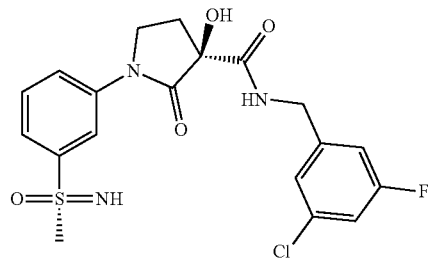 [SMILES: C[S@](=N)(=O)c1cccc(N2CC[C@](O)(C(=O)NCc3cc(F)cc(Cl)c3)C2=O)c1] |
| 126 | 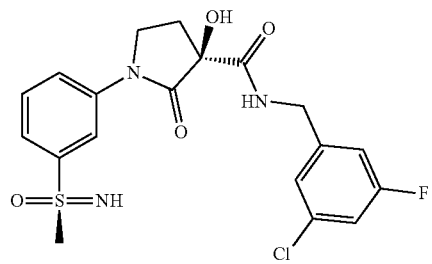 [SMILES: C[S@@](=N)(=O)c1cccc(N2CC[C@](O)(C(=O)NCc3cc(F)cc(Cl)c3)C2=O)c1] |
| 127 | 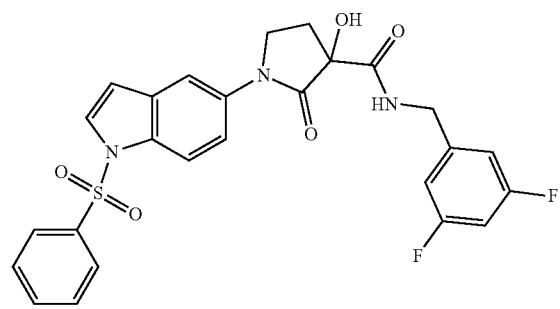 [SMILES: O=C(NCc1cc(F)cc(F)c1)C1(O)CCN(c2ccc3c(ccn3S(=O)(=O)c3ccccc3)c2)C1=O] |
| 128 | 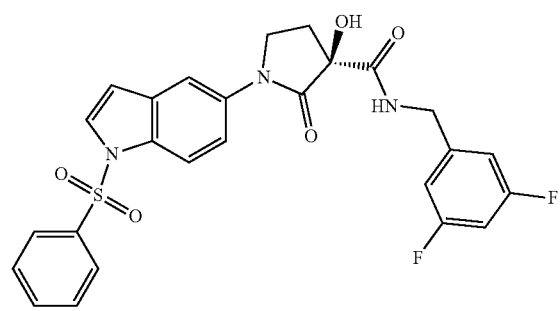 [SMILES: O=C(NCc1cc(F)cc(F)c1)[C@@]1(O)CCN(c2ccc3c(ccn3S(=O)(=O)c3ccccc3)c2)C1=O] |
| 129 | 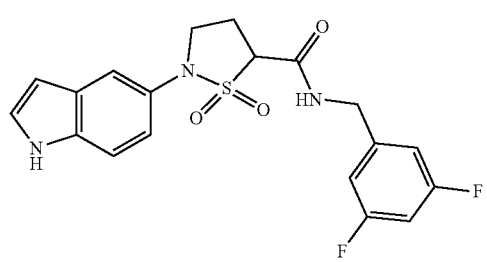 [SMILES: O=C(NCc1cc(F)cc(F)c1)C1CCN(c2ccc3[nH]ccc3c2)S1(=O)=O] |

TABLE 1-continued
| Compound No. | Chemical Structure |
|---|---|
| 130 | 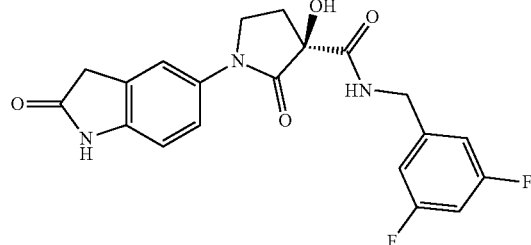 [SMILES: O=C1Cc2cc(N3CC[C@](O)(C(=O)NCc4cc(F)cc(F)c4)C3=O)ccc2N1] |
| 131 | 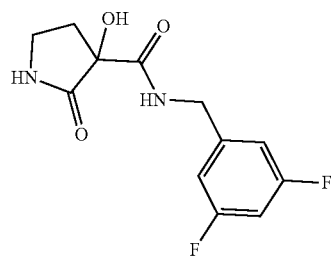 [SMILES: O=C1NCCC1(O)C(=O)NCc1cc(F)cc(F)c1] |
| 132 | 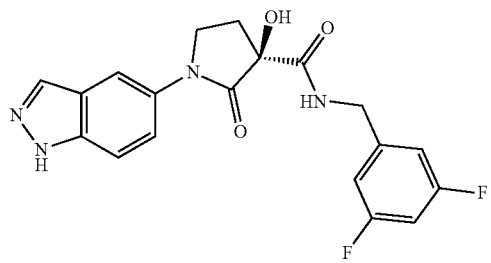 [SMILES: O=C(NCc1cc(F)cc(F)c1)[C@@]1(O)CCN(c2ccc3[nH]ncc3c2)C1=O] |
| 133 | 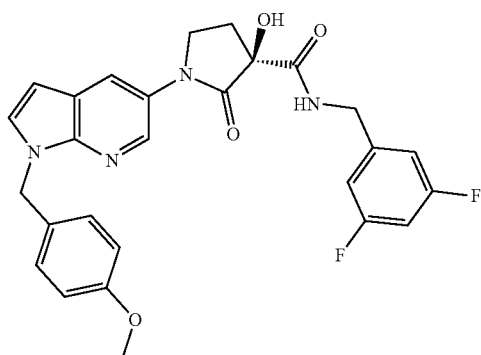 [SMILES: COc1ccc(Cn2ccc3cc(N4CC[C@](O)(C(=O)NCc5cc(F)cc(F)c5)C4=O)cnc32)cc1] |
| 134 | 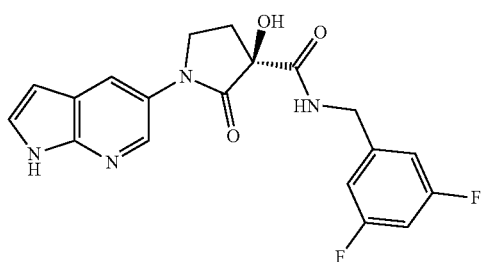 [SMILES: O=C(NCc1cc(F)cc(F)c1)[C@@]1(O)CCN(c2cnc3[nH]ccc3c2)C1=O] |

TABLE 1-continued
| Compound No. | Chemical Structure |
|---|---|
| 135 | 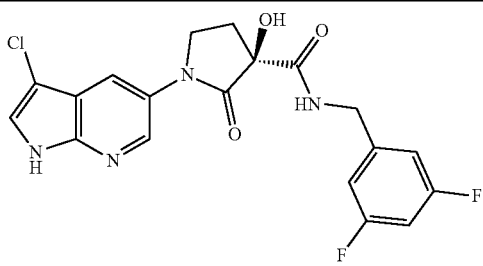 |
| 136 | 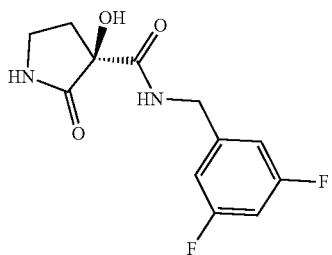 [SMILES: O=C1NCC[C@]1(O)C(=O)NCc1cc(F)cc(F)c1] |
| 137 | 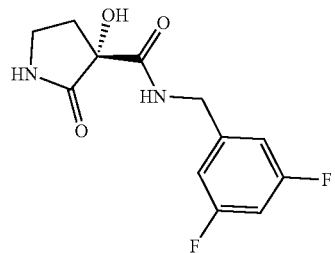 [SMILES: O=C1NCC[C@@]1(O)C(=O)NCc1cc(F)cc(F)c1] |
| 138 | 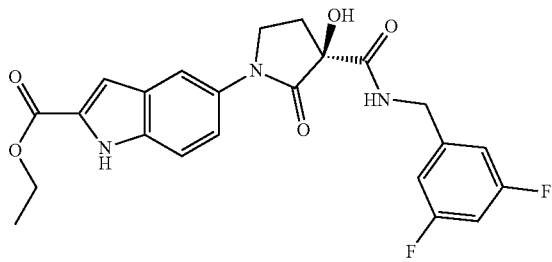 [SMILES: CCOC(=O)c1cc2cc(N3CC[C@](O)(C(=O)NCc4cc(F)cc(F)c4)C3=O)ccc2[nH]1] |
* wherein Polymer has the structure of:
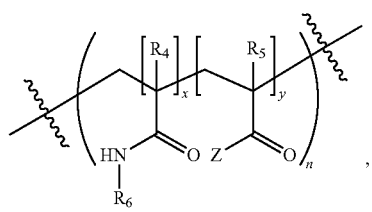
and preferably the structure of:
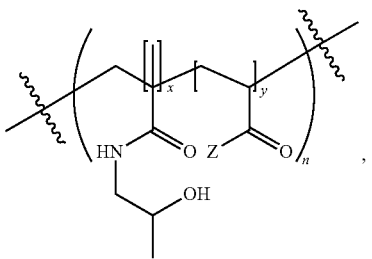

181
In some aspects, the compound is:
(Compound 1)
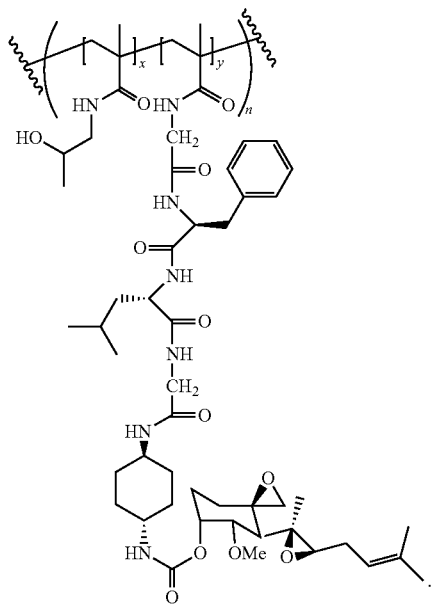
In some aspects, the compound is:
(Compound 2)
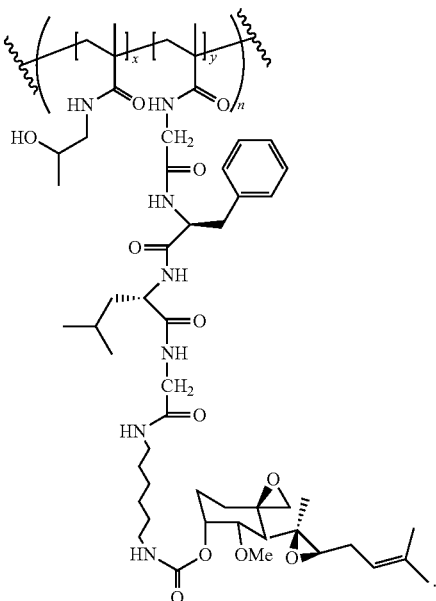
182
In some aspects, the compound is:
(Compound 3)
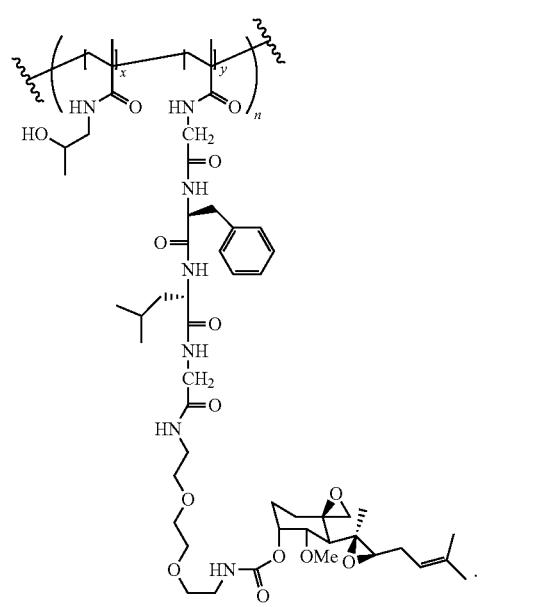
In some aspects, the compound is:
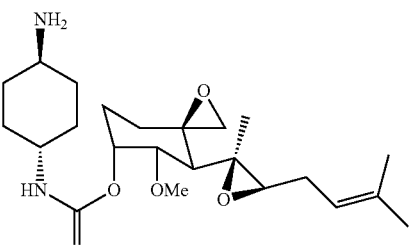
In some aspects, the compound is:
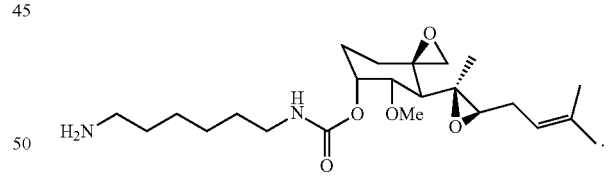
In some aspects, the compound is:
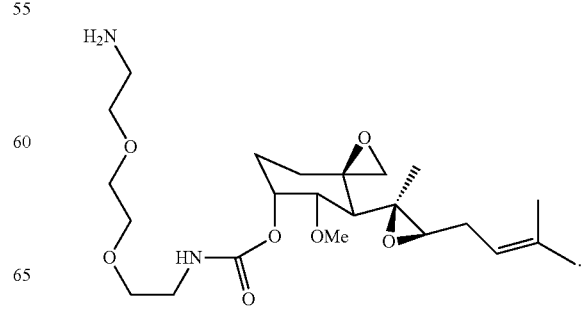

In one or more aspects, a compound for use in the present disclosure can be selected from cis-(3aRS,9bRS)-7-(benzenesulfonylamino)-1,3a,4,9b-tetrahydro-2H-furo[2,3-c]chromene-6-carboxylic acid; cis-(3 aRS,9bRS)-7-[2-(3-diethylaminopropyl)-4-fluorobenzenesulfonyl-amino]-1,3a,4,9b-tetrahydro-2H-furo[2,3-c]chromene-6-carboxylic acid; cis-(3 aRS,9bRS)-7-[2-(3-{pyrrolidin-1-yl}propyl)-4-fluorobenzenesulfonylamino]-1,3a,4,9b-tetrahydro-2H-furo[2,3-c]chromene-6-carboxylic acid; cis-(3aRS,9bRS)-7-[2-((Z)-3-diethyl aminoprop-1-enyl)-4-fluorobenzenesulfonylamino]-1,3a,4,9b-tetrahydro-2H-furo[2,3-c]chromene-6-carboxylic acid; cis-(3aR,9bR)-7-[2-((Z)-3-diethylaminoprop-1-enyl)-4-fluoro-benzenesulfonylamino]-1,3a,4,9b-tetrahydro-2H-furo[2,3-c]chromene-6-carboxylic acid; cis-(3aS,9bS)-7-[2-((Z)-3-diethylaminoprop-1-enyl)-4-fluorobenzenesulfonylamino]-1,3a,4,9b-tetrahydro-2H-furo[2,3-c]chromene-6-carboxylic acid; 7-[2-((Z)-3-diethylaminoprop-1-enyl)-4-fluorobenzenesulfonylamino]-1,2-dihydrofuro[2,3-c]quinoline-6-carboxylic acid formate salt; 7-(benzenesulfonylamino))-1,2-dihydrofuro[2,3-c]quinoline-6-carboxylic acid formate salt; cis-(3aRS,9bRS)-7-[2-((Z)-3-diethylaminoprop-1-enyl)-4-fluorobenzenesulfonylamino]-1,2,3a,4,5,9b-hexahydrofuro[2,3-c]quinoline-6-carboxylic acid; (1aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aR,7bS)-5-[2-((Z)-3-diethylaminoprop-1-enyl)-4-fluorobenzenesulfonylamino]-1,1a,2,7b-tetrahydrocyclopropa[c]chromene-4-carboxylic acid; (1 aS,7bR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aRS,7bSR)-5-[2-((Z)-3-diethylaminoprop-1-enyl)-4-fluorobenzenesulfonylamino]-7b-methyl-1,1a,2,7b-tetrahydrocyclopropa[c]chromene-4-carboxylic acid; (1aRS,7bSR)-5-[2-((E)-3-diethylaminoprop-1-enyl)-4-fluorobenzenesulfonylamino]-7b-methyl-1,1a,2,7b-tetrahydrocyclopropa[c]chromene-4-carboxylic acid; cis-(3aRS,9bRS)-7-[2-(4-dimethylaminobutylamino)-benzenesulfonylamino]-1,3a,4,9b-tetrahydro-2H-furo[2,3-c]chromene-6-carboxylic acid; (1aR,7bS)-5-[2-(3-diethylaminopropyl)-4-fluorobenzenesulfonyl-amino]-1,1a,2,7b-tetrahydrocyclopropa[c]chromene-4-carboxylic acid; (1aRS,7bSR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aR,7bS)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1 aS,7bR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aRS,7bSR)-5-[2((Z)-3-ethylaminoprop-1-enyl)-4-fluorobenzenesulfonylamino]-1,1a,2,7b-tetrahydrocyclopropa-[c]chromene-4-carboxylic acid; (1aR,7bS)-5-[2((Z)-3-ethylaminoprop-1-enyl)-4-fluorobenzenesulfonylamino]-1,1a,2,7b-tetrahydrocyclopropa[c]chromene-4-carboxylic acid; (1aS,7bR)-5-[2((Z)-3-ethylaminoprop-1-enyl)-4-fluorobenzene-sulfonylamino]-1,1a,2,7b-tetrahydro-cyclopropa[c]chromene-4-carboxylic acid; (1aRS,7bSR)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid; (1aR,7bS)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid; (1 aS,7bR)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid; (1aRS,7bSR)-5-[2-(3-dimethylaminopropylamino)-benzenesulfonylamino]-1,1a,2,7b-tetrahydrocyclopropa[c]chromene-4-carboxylic acid; (1 aR,7bS)-5-[2-(3-dimethylaminopropylamino)benzenesulfonylamino]-1,1a,2,7b-tetrahydrocyclopropa[c]chromene-4-carboxylic acid; (1aS,7bR)-5-[2-(3-dimethylaminopropyl-amino)benzenesulfonylamino]-1,1a,2,7b-tetrahydrocyclopropa[c]chromene-4-carboxylic acid; (1aRS,7bSR)-5-[2-(4-dimethylaminobutylamino)benzenesulfonylamino]-1,1a,2,7b-tetrahydrocyclopropa[c]chromene-4-carboxylic acid; (1aR,7bS)-5-[2-(4-dimethyl-amino-butylamino)benzenesulfonylamino]-1,1a,2,7b-tetrahydrocyclopropa[c]chromene-4-carboxylic acid; (1aS,7bR)-5-[2-(4-dimethylaminobutylamino]-1,1a,2,7b-tetrahydrocyclopropa[c]chromene-4-carboxylic acid; (1aRS,7bSR)-5-[2-(5-dimethylamino-pentylamino)benzene-sulfonylamino]-1,1a,2,7b-tetrahydrocyclopropa[c]chromene-4-carboxylic acid; (1aRS,7bSR)-5-{2[(Z)-3-(propan-2-yl)aminoprop-1-enyl]-4-fluorobenzenesulfonylamino}-1,1a,2,7b-tetrahydrocyclopropa[c]chromene-4-carboxylic acid; (1aRS,7bSR)-5-{2[(Z)-3-((S)-3-hydroxypyrrolidin-1-yl)aminoprop-1-enyl]-4-fluorobenzenesulfonylamino}-1,1a,2,7b-tetrahydrocyclopropa[c]chromene-4-carboxylic acid; (1aRS,7bSR)-5-{2[(Z)-3-((R)-3-hydroxypyrrolidin-1-yl)aminoprop-1-enyl]-4-fluorobenzene-sulfonylamino}-1,1a,2,7b-tetrahydro-cyclopropa[c]chromene-4-carboxylic acid; (1aRS,7bSR)-5-[2((Z)-4-diethylaminobut-1-enyl)-4-fluorobenzenesulfonyl-amino]-1,1a,2,7b-tetrahydrocyclopropa[c]chromene-4-carboxylic acid; (1aR,7bS)-5-[2((Z)-4-diethylaminobut-1-enyl)-4-fluorobenzenesulfonyl-amino]-1,1a,2,7b-tetrahydrocyclopropa[c]chromene-4-carboxylic acid; (1 aS,7bR)-5-[2((Z)-4-diethylaminobut-1-enyl)-4-fluorobenzenesulfonyl-amino]-1,1a,2,7b-tetrahydro-cyclopropa[c]chromene-4-carboxylic acid; (1aRS,7bSR)-5-{2-[2-(4-ethylpiperazin-1-yl)-ethyl]-4-fluorobenzenesulfonylamino}-1,1a,2,7b-tetrahydrocyclopropa[c]chromene-4-carboxylic acid; (1aRS,7bSR)-5-{2[(Z)-3-(azetidin-1-yl)prop-1-enyl]-4-fluorobenzene-sulfonylamino}-1,1a,2,7b-tetrahydro-cyclopropa[c]chromene-4-carboxylic acid; (1aRS,7bSR)-5-{2[(Z)-3-(3-hydroxy-azetidin-1-yl)prop-1-enyl]-4-fluorobenzenesulfonylamino}-1,1a,2,7b-tetrahydrocyclopropa-[c]chromene-4-carboxylic acid; (1aRS,7bSR)-5-{2[(Z)-3-(azetidin-1-yl)propyl]-4-fluorobenzenesulfonylamino}-1,1a,2,7b-tetrahydrocyclopropa[c]chromene-4-carboxylic acid; (1 aRS,7bSR)-5-[2((Z)-4-diethylaminobutyl)-4-fluorobenzenesulfonylamino]-1,1a,2,7b-tetrahydrocyclopropa[c]chromene-4-carboxylic acid; (1aRS,7bSR)-5-{2-[N-(4-dimethylaminobutyl)-N-methylamino]-benzenesulfonyl-amino}-1,1a,2,7b-tetrahydrocyclopropa-[c]chromene-4-carboxylic acid; (1aRS,7bSR)-5-{2-[((S)-1-ethylpyrrolidin-3-ylcarbamoyl)-methyl]-4-fluorobenzenesulfonyl-amino}-1,1a,2,7b-tetrahydrocyclopropa-[c]chromene-4-carboxylic acid; (1aRS,7bSR)-5-[2-(1-ethylazetidin-3-yl)-4-fluorobenzenesulfonylamino]-1,1a,2,7b-tetrahydro-cyclopropa[c]chromene-4-carboxylic acid; (1aRS,7bSR)-5-{2-[((R)-1-ethylpyrrolidin-3-ylcarbamoyl)methyl]-4-fluorobenzenesulfonyl-amino}-1,1a,2,7b-tetrahydro-cyclopropa[c]chromene-4-carboxylic acid; (1aRS,7bSR)-5-{2-[2-(pyrrolidin-1-yl)-ethyl]-4-fluorobenzenesulfonylamino}-1,1a,2,7b-tetrahydrocyclopropa[c]chromene-4-carboxylic acid; (1aRS,7bSR)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1 aS,7bR)-5-[2-((R)-

1-ethylpyrrolidin-3-ylmethyl)-4-fluorobenzenesulfonyl-amino]-1,1a,2,7b-tetrahydro-cyclopropa[c]chromene-4-carboxylic acid; (1aR,7bS)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1aRS,7bSR)-5-{2-[((S)-1-ethylpyrrolidin-2-yl)carbonyl-aminomethyl]-4-fluorobenzene-sulfonylamino}-1,1a,2,7b-tetrahydrocyclopropa[c]chromene-4-carboxylic acid; (1aRS,7bSR)-5-[2-(4-dimethylaminobutyrylamino)-4-fluorobenzenesulfonyl-amino]-1,1a,2,7b-tetrahydrocyclopropa-[c]chromene-4-carboxylic acid; (1aRS,7bSR)-5-[2-((S)-1-ethyl-pyrrolidin-3-ylmethyl)-4-fluorobenzenesulfonyl-amino]-1,1a,2,7b-tetrahydrocyclopropa[c]chromene-4-carboxylic acid; (1aRS,7bSR)-5-[2-(3-dimethylaminopropylcarbamoyl)benzene-sulfonylamino]-1,1a,2,7b-tetrahydrocyclopropa[c]chromene-4-carboxylic acid; (1aRS,7bSR)-5-(2-{[N—((S)-1-ethyl-pyrrolidin-3-yl)-N-methylcarbamoyl]methyl}-4-fluoro-benzenesulfo-nylamino)-1,1a,2,7b-tetrahydrocyclopropa-[c]chromene-4-carboxylic acid; (1aRS,7bSR)-5-(2-{[N—((R)-1-ethyl-pyrrolidin-3-yl)-N-methylcarbamoyl]methyl}-4-fluoro-benzenesulfonylamino)-1,1a,2,7b-tetrahydrocyclopropa-[c]chromene-4-carboxylic acid; (1aRS,7bSR)-5-{2-[2-((S)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-{2-[2-((R)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-[2-(3-N,N,-diethylaminopropylamino)benzene-sulfonylamino]-1,1a,2,7b-tetrahydrocyclopropa[c]chromene-4-carboxylic acid; (1aRS,7bSR)-5-(2-{[((R)-1-ethylpyrrolidine-2-yl)carbonyl-amino]methyl}-4-fluorobenzenesulfonylamino)-1,1a,2,7b-tetrahydrocyclopropa[c]chromene-4-carboxylic acid; (1aRS,7bSR)-5-{2-[(1-ethylazetidin-3-ylmethyl)amino]benzene-sulfonylamino}-1,1a,2,7b-tetrahydrocyclopropa[c]chromene-4-carboxylic acid; (1 aS,7bR)-5-[2-((Z)-3-diethylaminoprop-1-enyl)benzenesulfonylamino]-1,1a,2,7b-tetrahydrocyclopropa[c]chromene-4-carboxylic acid; (1aR,7bS)-5-[2-((Z)-3-diethylaminoprop-1-enyl)benzenesulfonylamino]-1,1a,2,7b-tetrahydrocyclopropa[c]chromene-4-carboxylic acid; (1aRS,7bSR)-5-(2-{N—[((R)-1-ethylpyrrolidine-2-yl)carbonyl]-N-methyl-aminomethyl}-4-fluorobenzenesulfonylamino)-1,1a,2,7b-tetrahydrocyclopropa[c]chromene-4-carboxylic acid; (1aRS,7bSR)-5-(2-{N—[((S)-1-ethylpyrrolidine-2-yl)carbonyl]-N-methylamino-methyl}-4-fluorobenzenesulfo-nylamino)-1,1a,2,7b-tetrahydrocyclopropa[c]chromene-4-carboxylic acid; (1aRS,7bSR)-5-[2-(4-dimethylaminobutylamino)-4-fluorobenzenesulfonyl-amino]-1,1a,2,7b-tetrahydrocyclopropa[c]chromene-4-carboxylic acid; (1aRS,7bSR)-5-{2-[((R)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-[2-(4-ethyl-2-oxopiperazin-1-ylmethyl)-4-fluorobenzenesulfonylamino]-1,1a,2,7b-tetrahydrocyclopropa[c]chromene-4-carboxylic acid; (1aRS,7bSR)-5-[2-(1-ethylpiperidin-4-ylmethyl)-4-fluoro-benzenesulfonylamino]-1,1a,2,7b-tetrahydrocyclopropa-[c]chromene-4-carboxylic acid; (1aRS,7bSR)-5-{2-[2-(1-ethylazetidin-3-yl)ethyl]-4-fluoro-benzenesulfonyl-amino}-1,1a,2,7b-tetrahydrocyclopropa[c]chromene-4-carboxylic acid; (1 aRS,7bSR)-5-{2-[((S)-1-azabicyclo[2.2.2]oct-3-yl)amino]benzenesulfonyl-amino}-1,1a,2,7b-tetrahydrocyclo-propa[c]chromene-4-carboxylic acid; (1aRS,7bSR)-5-{2-[((R)-1-azabicyclo-[2.2.2]oct-3-yl)amino]benzenesulfonyl-amino}-1,1a,2,7b-tetrahydrocyclopropa[c]chromene-4-carboxylic acid; (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylic acid; (1 aRS,7bSR)-5-{2-[2-((R)-1-ethylpyrrolidin-3-ylamino)ethyl]-4-fluoro-benzenesulfonylamino}-1,1a,2,7b-tetrahydrocyclopropa-[c]chromene-4-carboxylic acid; (1aRS,7bSR)-5-{2-[((R)-1-ethylpyrrolidin-3-yl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-yl)amino]-benzenesulfonylamino}-1,1a,2,7b-tetrahydrocyclopropa-[c]chromene-4-carboxylic acid; (1 aRS,7bSR)-5-(2-{[((R)-1-ethylpyrrolidine-3-carbonyl)amino]-methyl)}-4-fluoro-benzenesulfonylamino)-1,1a,2,7b-tetrahydro-cyclopropa[c]chromene-4-carboxylic acid; (1aRS,7bSR)-5-[2-((Z)-3-diethylamino-2-methylprop-1-enyl)-4-fluorobenzene-sulfonylamino]-1,1a,2,7b-tetrahydrocyclopropa[c]chromene-4-carboxylic acid; (1aRS,7bSR)-5-{2-[2-((R)-1-ethylpyrrolidin-3-yl)ethylamino]-benzenesulfonylamino}-1,1a,2,7b-tetrahydrocycyclopropa-[c]chromene-4-carboxylic acid; (1aRS,7bSR)-5-{2-[2-((S)-1-ethylpyrrolidin-3-yl)ethylamino]-benzenesulfonyl-amino}-1,1a,2,7b-tetrahydrocyclopropa-[c]chromene-4-carboxylic acid; (1aR,7bS)-5-[2-((S)-1-ethylpyrrolidin-3-yloxymethyl)-4-fluoro-benzenesulfonyl-amino]-1,1a,2,7b-tetrahydrocyclopropa-[c]chromene-4-carboxylic acid; (1aR,7bS)-5-[2-((R)-1-ethylpyrrolidin-3-yloxymethyl)-4-fluoro-benzenesulfonylamino]-1,1a,2,7b-tetrahydrocyclopropa-[c]chromene-4-carboxylic acid; (1aR,7bS)-5-[2-(1-ethylpiperidin-3-ylmethyl)-4-fluorobenzene-sulfonylamino]-1,1a,2,7b-tetrahydrocyclopropa[c]chromene-4-carboxylic acid; (1aR,7bS)-5-{2-[2-((R)-1-ethylpyrrolidin-2-yl)ethyl]-4-fluorobenzenesulfonyl-amino}-1,1a,2,7b-tetrahydrocyclopropa-[c]chromene-4-carboxylic acid; and pharmaceutically acceptable salts, stereoisomers, esters and prodrugs thereof.

In one or more aspects, the compound is selected from:

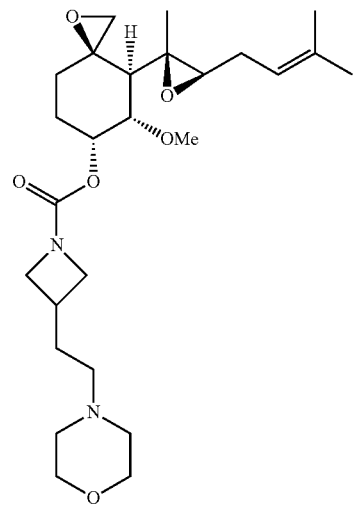

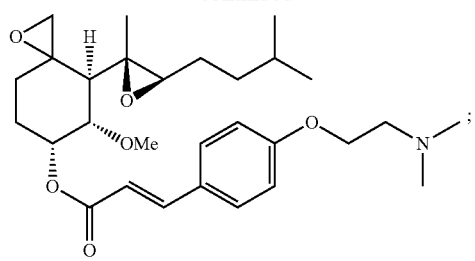
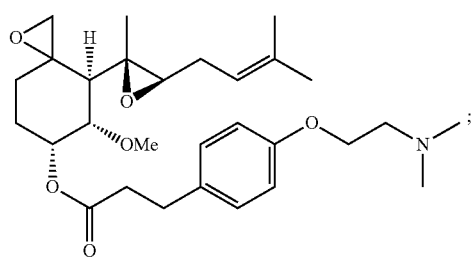
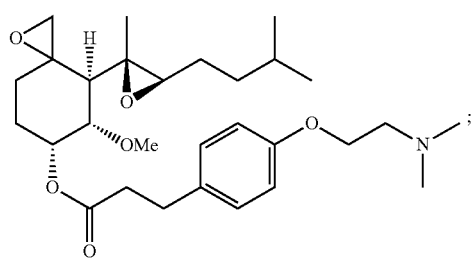
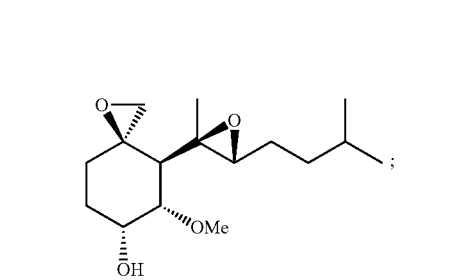
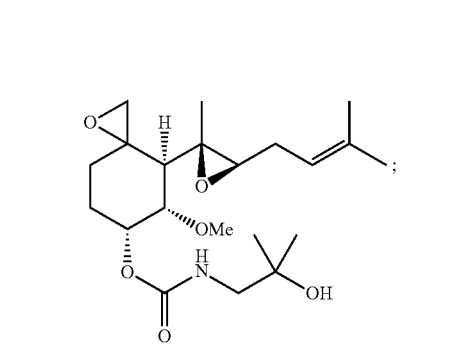
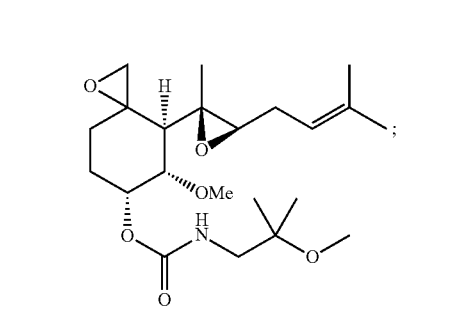
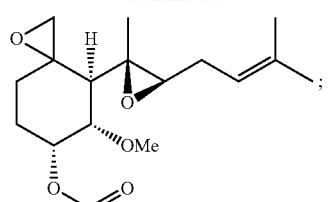
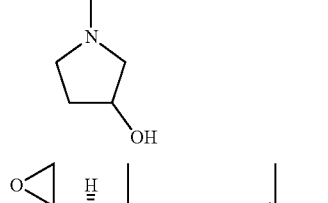
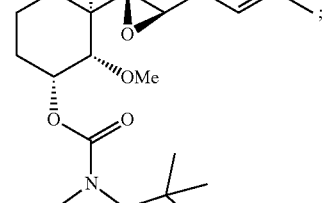
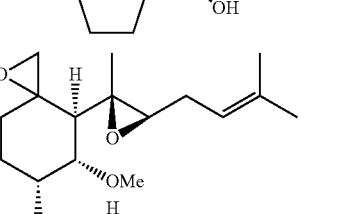
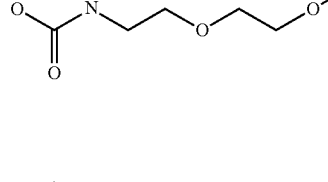
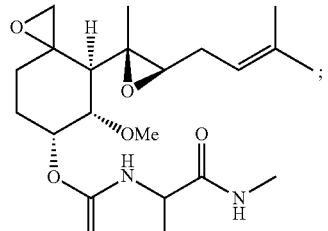
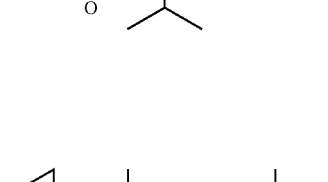
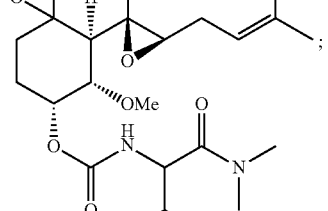

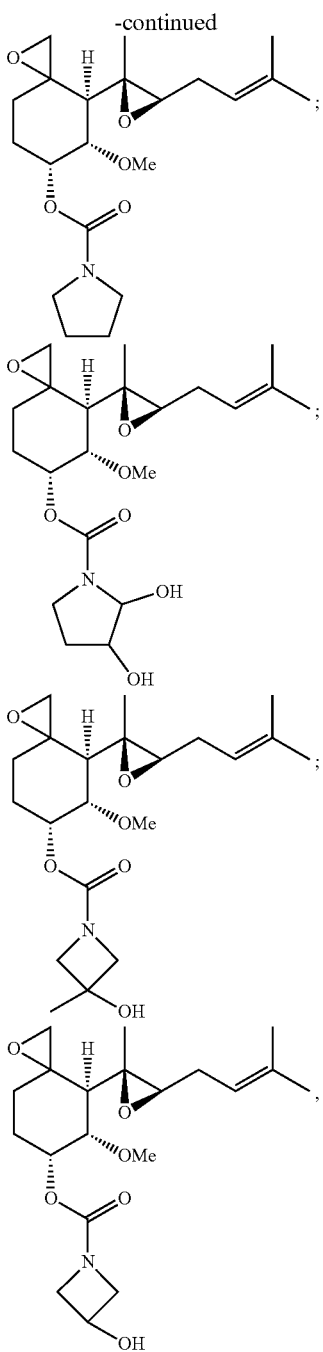

and pharmaceutically acceptable salts or stereoisomers thereof.

For purposes of this disclosure, the chemical elements are identified in accordance with the Periodic Table of the Elements, CAS version, Handbook of Chemistry and Physics, 67th Ed., 1986-87, inside cover.

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain aspects, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, certain cycloalkyls have from 3-10 carbon atoms in their ring structure, and may have 5, 6, or 7 carbons in the ring structure.

Unless the number of carbons is otherwise specified, "lower alkyl", as used herein, means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, certain alkyl groups are lower alkyls. In certain aspects, a substituent designated herein as alkyl is a lower alkyl.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having one or more triple bonds in the radical.

The terms "alkoxyl" or "alkoxy" as used herein refers to an alkyl group, as defined below, having an oxygen radical attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_1$, where m and R$_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, or the like.

The term "alkylthio" refers to an alkyl group, as defined above, having a sulfur radical attached thereto. In certain aspects, the "alkylthio" moiety is represented by one of —(S)-alkyl, —(S)-alkenyl, —(S)-alkynyl, and —(S)—(CH$_2$)$_m$—R$_1$, wherein m and R$_1$ are defined below. Representative alkylthio groups include methylthio, ethylthio, and the like.

As used herein, the term "nitro" means —NO$_2$; the term "halogen" designates F, Cl, Br or I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formulae:

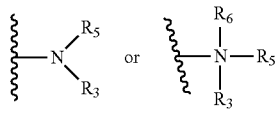

wherein R$_3$, R$_5$ and R$_6$ each independently represent a hydrogen, an alkyl, an alkenyl, —(CH$_2$)$_m$—R$_1$, or R$_3$ and R$_5$ taken together with the N atom to which they are attached complete a heterocycle having from 4 to 8 atoms in the ring structure; R$_1$ represents an alkenyl, aryl, cycloalkyl, a cycloalkenyl, a heterocyclyl or a polycyclyl; and m is zero or an integer in the range of 1 to 8. In certain aspects, only one of R$_3$ or R$_5$ can be a carbonyl, e.g., R$_3$, R$_5$ and the nitrogen together do not form an imide. In certain aspects, R$_3$ and R$_5$ (and optionally R$_6$) each independently represent a hydrogen, an alkyl, an alkenyl, or —(CH$_2$)$_m$—R$_1$. Thus, the term "alkylamine" as used herein means an amine group, as defined above, having a substituted or unsubstituted alkyl attached thereto, i.e., at least one of R$_3$ and R$_5$ is an alkyl group. In certain aspects, an amino group or an alkylamine is basic, meaning it has a pK$_a$≥7.00. The protonated forms of these functional groups have pK$_a$s relative to water above 7.00.

The term "carbonyl" (C(O)) is art-recognized and includes such moieties as can be represented by the general formula:

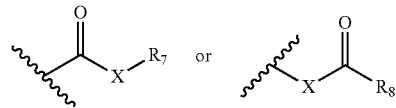

wherein X is a bond or represents an oxygen or a sulfur, and R$_7$ represents a hydrogen, an alkyl, an alkenyl, —(CH$_2$)$_m$—R$_1$ or a pharmaceutically acceptable salt, R$_8$ represents a hydrogen, an alkyl, an alkenyl or —(CH$_2$)$_m$—R$_1$, where m and R$_1$ are as defined above. Where X is an oxygen and R$_7$ or R$_8$ is not hydrogen, the formula represents an "ester". Where X is an oxygen, and R$_7$ is as defined above, the moiety is referred to herein as a carboxyl group, and particularly when R$_7$ is a hydrogen, the formula represents a "carboxylic acid". Where X is an oxygen, and R$_8$ is hydrogen, the formula represents a "formate". In general, where the oxygen atom of the above formula is replaced by sulfur, the formula represents a "thiocarbonyl" group. Where X is a sulfur and R$_7$ or R$_8$ is not hydrogen, the formula represents a "thioester" group. Where X is a sulfur and R$_7$ is hydrogen, the formula represents a "thiocarboxylic acid" group. Where X is a sulfur and R$_8$ is hydrogen, the formula represents a "thioformate" group. On the other hand, where X is a bond, and R$_7$ is not hydrogen, the above formula represents a "ketone" group. Where X is a bond, and R$_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

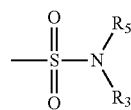

in which R$_3$ and R$_5$ are as defined above.

The term "sulfate" is art recognized and includes a moiety that can be represented by the general formula:

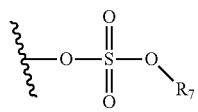

in which $R_7$ is as defined above.

The term "sulfamido" is art recognized and includes a moiety that can be represented by the general formula:

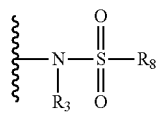

in which $R_2$ and $R_4$ are as defined above.

The term "sulfonate" is art-recognized and includes a moiety that can be represented by the general formula:

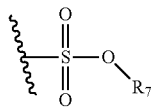

in which $R_7$ is an electron pair, hydrogen, alkyl, cycloalkyl, or aryl.

The terms "sulfoxido" or "sulfinyl", as used herein, refers to a moiety that can be represented by the general formula:

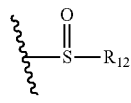

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The term "amino acid" is intended to embrace all compounds, whether natural or synthetic, which include both an amino functionality and an acid functionality, including amino acid analogs and derivatives. In certain aspects, the amino acids contemplated in the present disclosure are those naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list. The abbreviations are accepted in the peptide art and are recommended by the IUPAC-IUB commission in biochemical nomenclature.

By the term "amino acid residue" is meant an amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are $-CH_2CH_2SCH_3$ (the side chain of methionine), $-CH_2(CH_3)-CH_2CH_3$ (the side chain of isoleucine), $-CH_2CH(CH_3)_2$ (the side chain of leucine) or H-(the side chain of glycine). These side chains are pendant from the backbone C□ carbon.

The term "peptide," as used herein, refers to a sequence of amino acid residues linked together by peptide bonds or by modified peptide bonds. The term "peptide" is intended to encompass peptide analogs, peptide derivatives, peptidomimetics and peptide variants. The term "peptide" is understood to include peptides of any length. Peptide sequences set out herein are written according to the generally accepted convention whereby the N-terminal amino acid is on the left, and the C-terminal amino acid is on the right (e.g., $H_2N$-$AA_1$-$AA_2$-$AA_3$-$AA_4$-$AA_5$-$AA_6$-$CO_2H$).

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure. Any representation of a particular isomer is merely exemplary (e.g., the exemplification of a trans-isomer, also encompasses a cis-isomer).

If, for instance, a particular enantiomer of a compound of the present disclosure is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as H$_2$O.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The synthetic processes of the disclosure can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry. Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

In particular, the compounds of the present disclosure, and their synthesis, are further described in PCT Publication Nos. WO 2011/150022 and WO 2011/150088 and U.S. Pat. Nos. 9,173,956, 9,320,805, and 9,433,600. Each of these publications is incorporated by reference in their entireties for all purposes.

The present disclosure also provides pharmaceutical compositions comprising a compound of the present disclosure, or pharmaceutically acceptable salts, solvates, diastereomers, and polymorphs thereof, and a pharmaceutically acceptable carrier or excipient.

A "pharmaceutical composition" is a formulation containing the compounds of the present disclosure in a form suitable for administration to a subject. In one aspect, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one aspect, the active compound is mixed under sterile conditions with a pharmaceutically acceptable carrier, and with any preservatives, buffers or propellants that are required.

As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this disclosure. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions. In certain aspects, the pharmaceutical composition comprises DMSO.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (See, for example, Berge et al. (1977) "Pharmaceutical Salts", *J. Pharm. Sci.* 66:1-19)

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

As used herein, the term "metabolite" means a product of metabolism of the compound of present disclosure, or pharmaceutically acceptable salts, solvates, diastereomers, and polymorphs thereof, that exhibits a similar activity in vivo to the compound of present disclosure, or pharmaceutically acceptable salts, solvates, diastereomers, and polymorphs thereof.

As used herein, the term "prodrug" means the compound of present disclosure, or pharmaceutically acceptable salts, solvates, diastereomers, and polymorphs thereof covalently linked to one or more pro-moieties, such as an amino acid moiety or other water solubilizing moiety. The compound of present disclosure, or pharmaceutically acceptable salts, solvates, diastereomers, and polymorphs thereof may be released from the pro-moiety via hydrolytic, oxidative, and/or enzymatic release mechanisms. In an aspect, a prodrug composition of the present disclosure exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake. Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like, See Bundegaard, H., *Design of Prodrugs*, p 1-92, Elesevier, New York-Oxford (1985).

The compounds of the present disclosure, or pharmaceutically acceptable salts, esters, solvates, diastereomers, polymorphs, or pro-drugs thereof (or pharmaceutical compositions thereof) can be administered by any means known in the art. For example, the compounds or compositions of the present disclosure are administered orally, nasally, transdermally, topically, pulmonary, inhalationally, buccally, sublingually, intraperintoneally, subcutaneously, intramuscularly, intravenously, rectally, intrapleurally, intrathecally and parenterally. Administration can be systemic, e.g., intravenous administration, or localized. In certain aspects, the route of administration may be intravenous, intramuscular, subcutaneous, intradermal, intraperitoneal, intrathecal, intrapleural, intrauterine, rectal, vaginal, topical, and the like. In certain aspects, the compound is administered subcutaneously.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the disclosure can be administered to a subject in many of the well-known methods currently used for chemotherapeutic treatment. For example, for treatment of cancers, a compound of the disclosure may be injected directly into tumors, injected into the blood stream or body cavities, injected subcutaneously, or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

In one aspect, the compounds of the present disclosure, or pharmaceutically acceptable salts, esters, solvates, diastereomers, polymorphs, or pro-drugs thereof, are administered in a suitable dosage form or formulation prepared by combining a therapeutically effective amount (e.g., an efficacious level sufficient to achieve the desired therapeutic effect) of the compounds of the present disclosure, or pharmaceutically acceptable salts, esters, solvates, diastereomers, polymorphs, or pro-drugs thereof (as an active ingredient) with standard pharmaceutical carriers or diluents according to conventional procedures (i.e., by producing a pharmaceutical composition of the disclosure). These procedures may involve mixing, granulating, and compressing or dissolving the ingredients as appropriate to attain the desired preparation.

Parenteral dosage forms may be prepared by any means known in the art. For example, sterile injectable aqueous or oleaginous suspensions may be formulated according to the known art using suitable dispersing or wetting agents and suspending agents.

Oral dosage forms, such as capsules, tablets, pills, powders, and granules, may be prepared using any suitable process known to the art. For example, the compounds of the present disclosure may be mixed with enteric materials and compressed into tablets. Alternatively, formulations of the disclosure are incorporated into chewable tablets, crushable tablets, tablets that dissolve rapidly within the mouth, or mouth wash.

For pulmonary (e.g., intrabronchial) administration, the compounds of the present disclosure can be formulated with conventional excipients to prepare an inhalable composition in the form of a fine powder or atomizable liquid. For ocular administration, the compounds of the present disclosure can be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Commercially available nebulizers for liquid formulations, including jet nebulizers and ultrasonic nebulizers are useful for administration. Liquid formulations can be directly nebulized and lyophilized powder can be nebulized after reconstitution. Alternatively, the compounds of the present disclosure can be aerosolized using a fluorocarbon formulation and a metered dose inhaler, or inhaled as a lyophilized and milled powder.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for rectal or vaginal administration may be suppositories which can be prepared by mixing the compounds of the present disclosure with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, contemplated formulations can be administered by release from a lumen of an endoscope after the endoscope has been inserted into a rectum of a subject.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

Example 1: Effect of Compound 20 (Shown in the Figure as Compound A) on Obese and Lean Mice Female C57Bl/6 mice were surgically ovariectomized at six weeks of age (Jackson Lab) and following recovery were placed upon either a high-fat diet (HFD) or low-fat diet (LFD) until the average weight of mice on the HFD exceeded 40 grams. EO771 cells (50,000; from $CH_3$ Biosystems) were then injected into the fourth mammary gland and when tumors reached approximately 50 $mm^3$ treatment with SDX-7320 was initiated (s.c., Q4D, total of four doses). Mice were euthanized and terminal blood samples were obtained 15 days after intitaing dosing. Plasma was analyzed for leptin and total adiponectin by MSD. Adipose tissue depots were dissected and weighed. Tumors were dissected, weighed and a portion was placed in 10% buffered formalin for histology and another portion was placed in ice-cold tissue culture media for subsequent processing and analysis of leukocytes by flow cytometry.

Figure 1C:
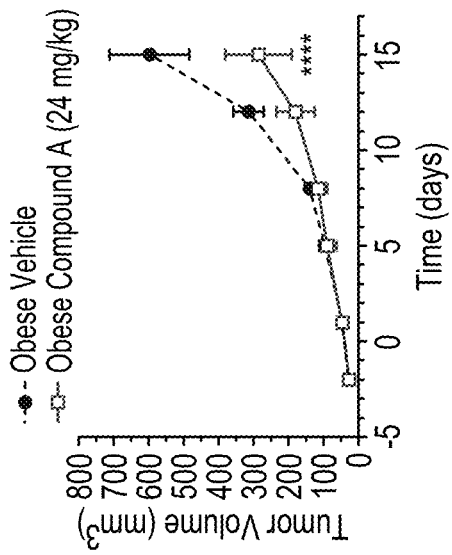
FIG. 1C is a is a graph depicting change in E0771 mammary tumor volume over time in days in response to treatment of obese mice with vehicle or compound 20 (noted in the Figure as Compound A).
Figure 2A:
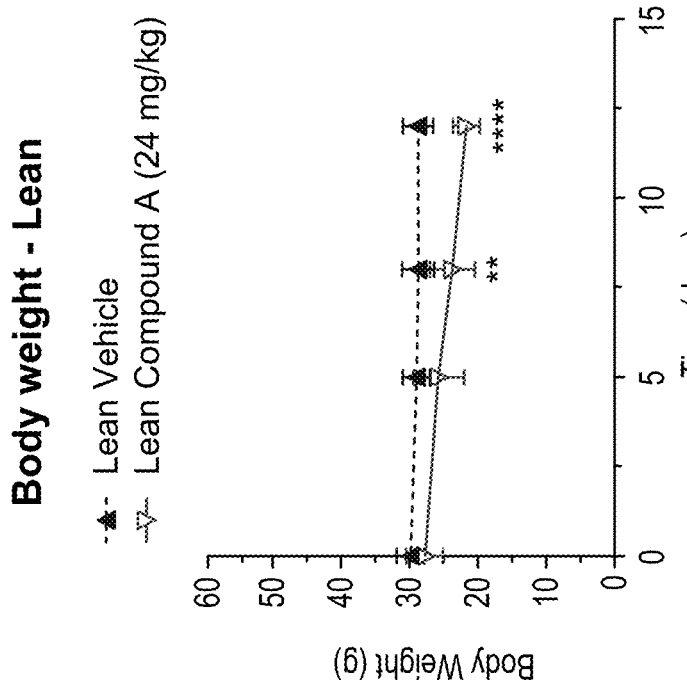
FIG. 2A is a graph depicting change in body weight over time in lean mice treated with vehicle or compound 20 (noted in the Figure as Compound A).
Figure 2B:
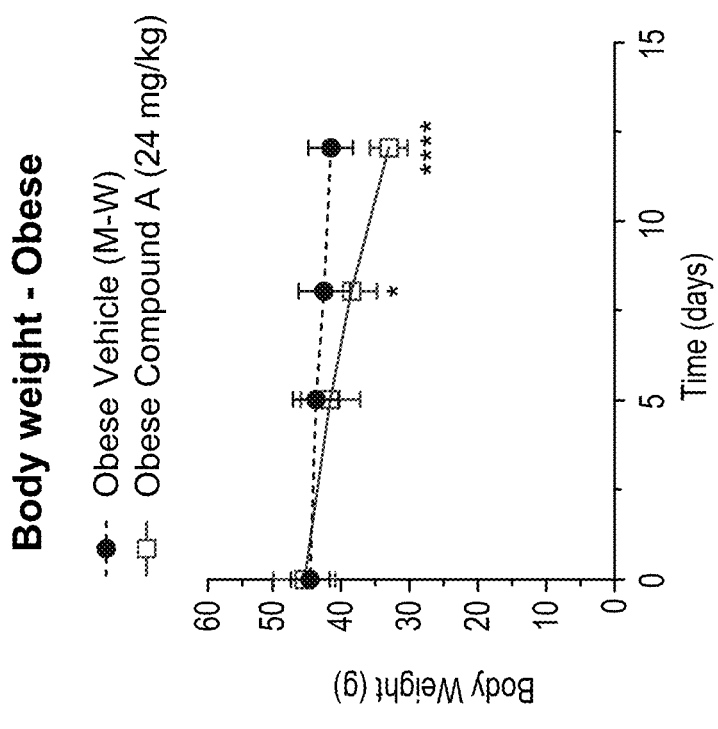
FIG. 2B is a graph depicting change in body weight over time in obese mice treated with vehicle or compound 20 (noted in Figure as Compound A).
Figure 3A:
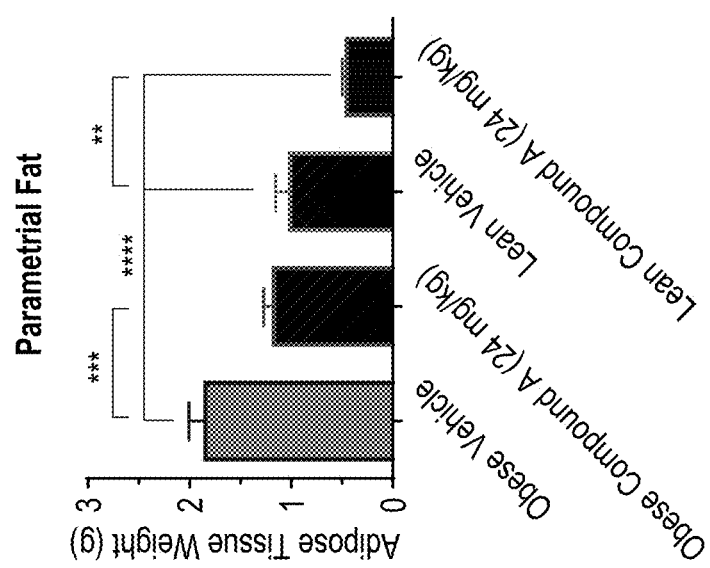
FIG. 3A is a graph depicting changes in adipose tissue mass in parametrial fat in lean and obese mice upon treatment with vehicle or compound 20 (noted in the Figure as Compound A).
Figure 3B:
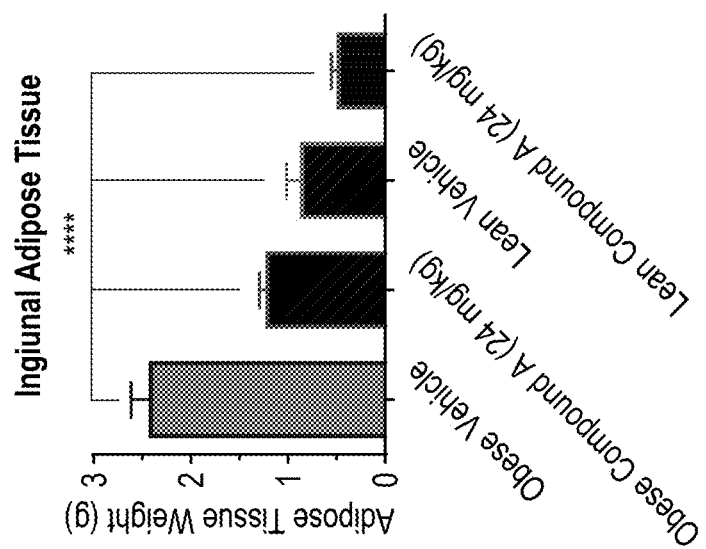
FIG. 3B is a graph depicting changes in adipose tissue mass in inguinal adipose tissue in lean and obese mice upon treatment with vehicle or compound 20 (noted in the Figure as Compound A).
Figure 3C:
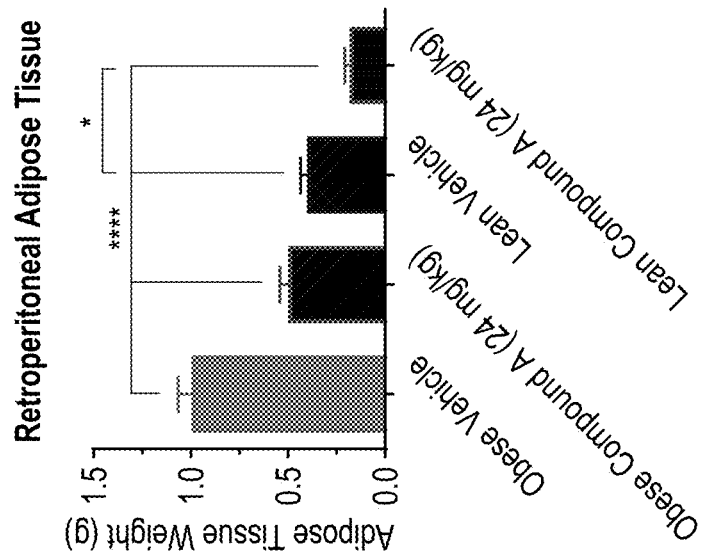
FIG. 3C is a graph depicting changes in adipose tissue mass in retroperitoneal adipose tissue in lean and obese mice upon treatment with vehicle or compound 20 (noted in the Figure as Compound A).

EO771 tumors grew at a faster rate in obese mice compare to age-matched lean mice (FIG. 1A). Compound A significantly attenuated tumor growth in both lean and obese mice (FIG. 1B, 1C). Compound A significantly decreased body weight of both lean and obese mice (FIG. 2), which was due (in part) to significant reductions in adipose tissue mass (FIG. 3).

Figure 4A:
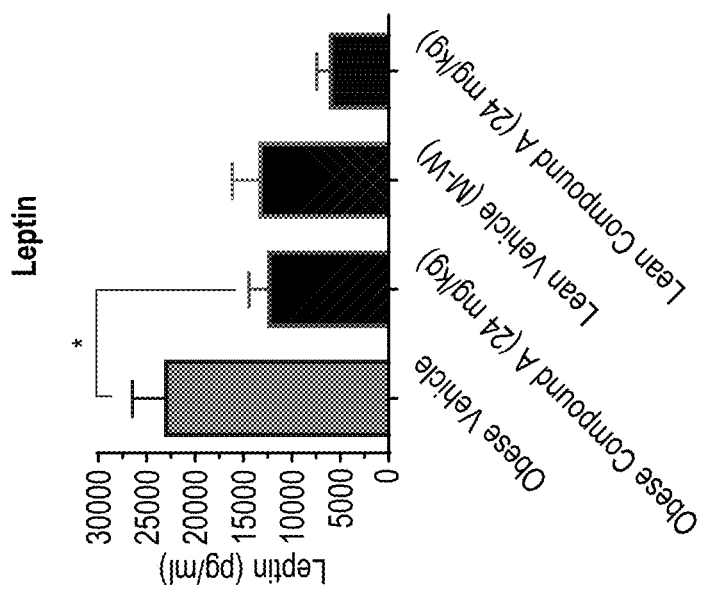
FIG. 4A is a graph depicting changes in the expression levels of leptin in lean and obese mice treated with vehicle or compound 20 (noted in the Figure as Compound A).
Figure 4B:
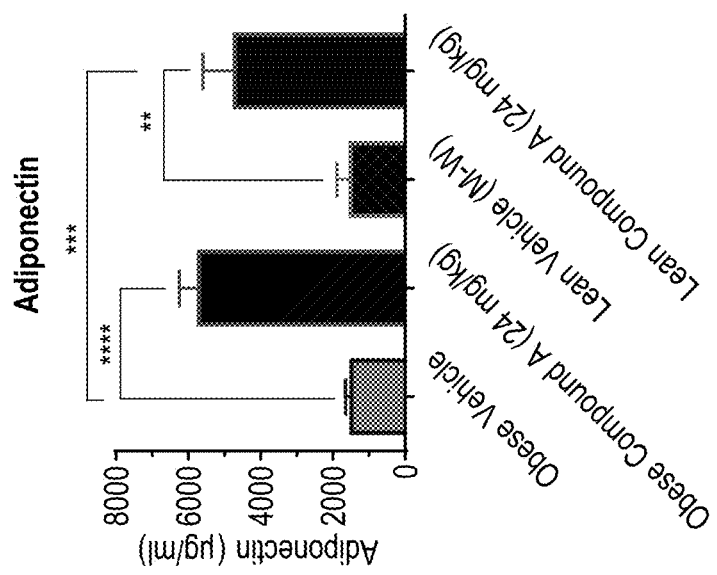
FIG. 4B is a graph depicting changes in the expression levels of adiponectin in lean and obese mice treated with vehicle or compound 20 (noted in the Figure as Compound A).
Figure 4C:
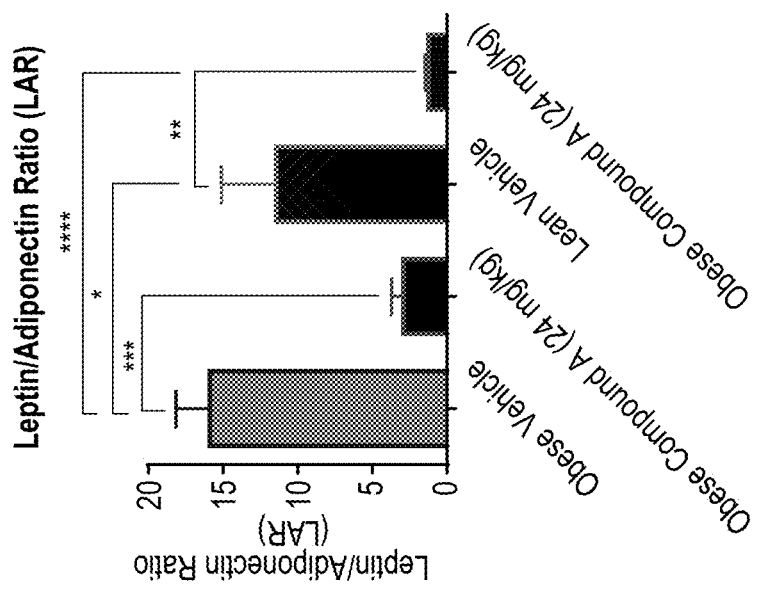
FIG. 4C is a graph depicting changes in the Leptin/Adiponectin Ratio (LAR) in lean and obese mice treated with vehicle or compound 20 (noted in the Figure as Compound A).

Example 2: Effect of Compound 20 (Shown in the Figure as Compound A) on Tumor and Serum Biomarkers in Lean and Obese Mice Leptin levels were significantly reduced in obese mice by Compound A (FIG. 4A) while adiponectin levels were significantly increased by Compound A in both lean and obese mice (FIG. 4B). The leptin/adiponectin ratio was significantly decreased by Compound A in both lean and obese mice (FIG. 4C).

Figure 5A:
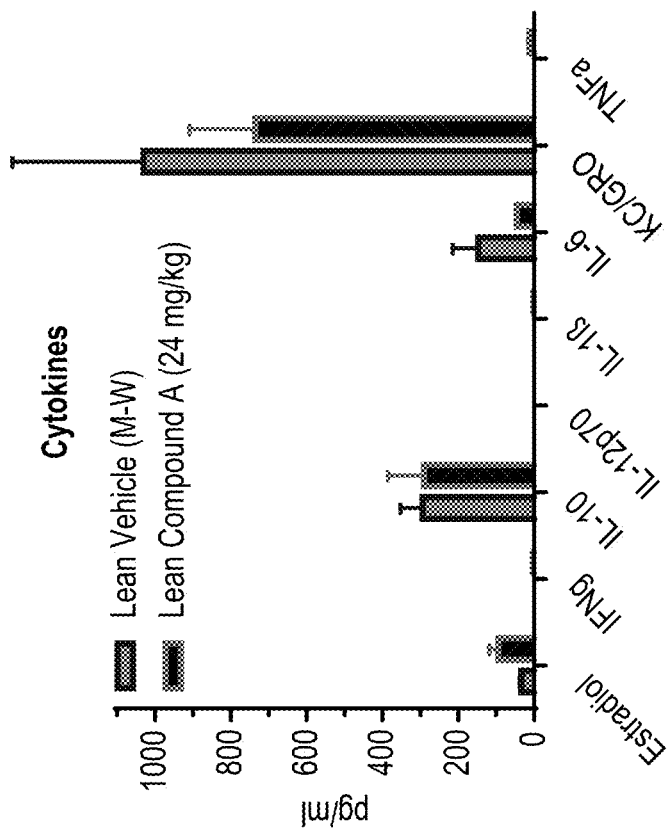
FIG. 5A is a graph depicting changes in the immunosuporessive cytokine IL10 levels in lean mice treated with compound 20 (noted in the Figure as Compound A).
Figure 5B:
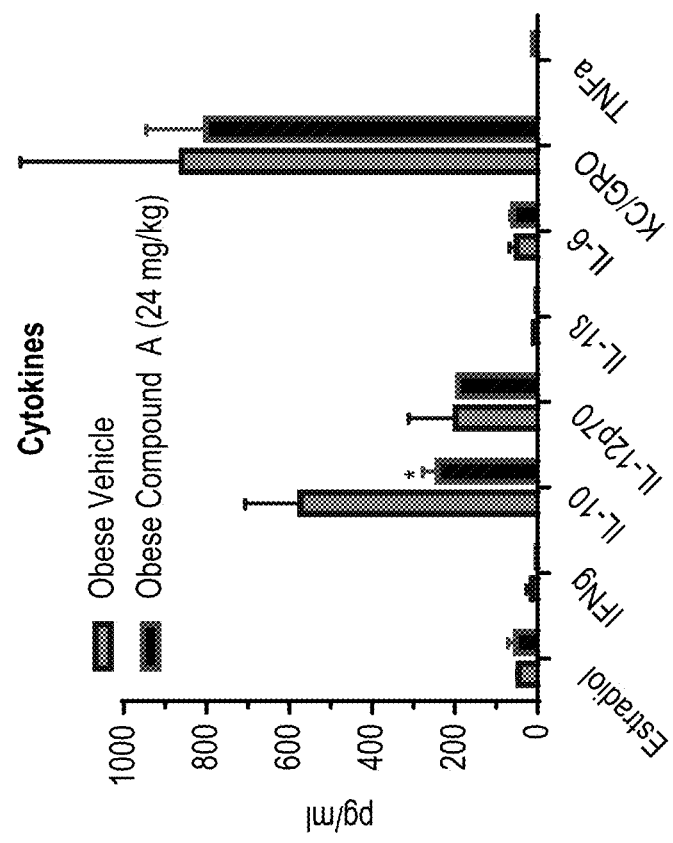
FIG. 5B is a graph depicting changes in the immunosuporessive cytokine IL10 levels obese mice treated with compound 20 (noted in the Figure as Compound A).

Compound A significantly reduced levels of the immunosuppressive cytokine, IL-10 in obese mice (FIG. 5B). Therefore the effects of Compound A to lower the levels of circulating IL-10 is expected to alter the tumor microenvironment in a manner that reduces the immunosuppressive state of the TME.

Figure 6A:
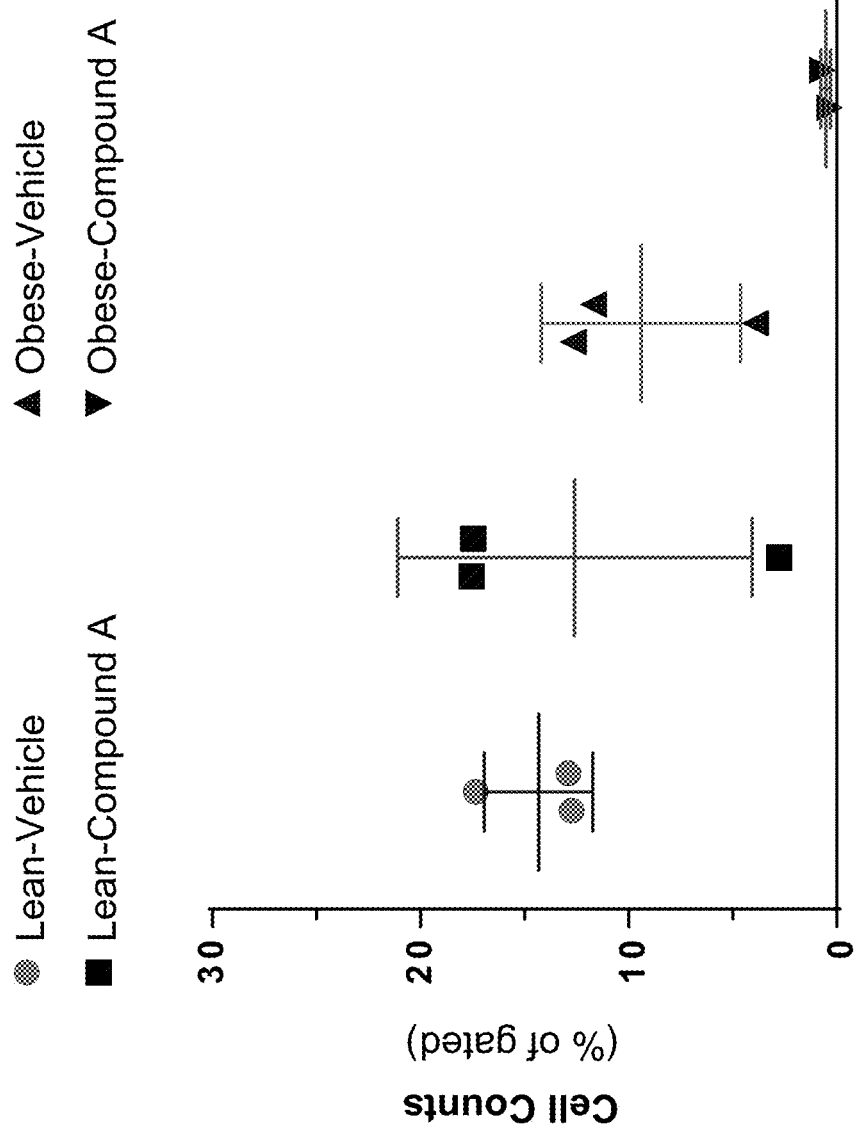
FIG. 6A is a plot and comparison graphs depicting changes in the tumor suppressor myeloid-derived suppressor cells (MSDCs) in tumor cells of lean and obese mice upon treatment with compound 20 (noted in the Figure as Compound A).
Figure 6B:
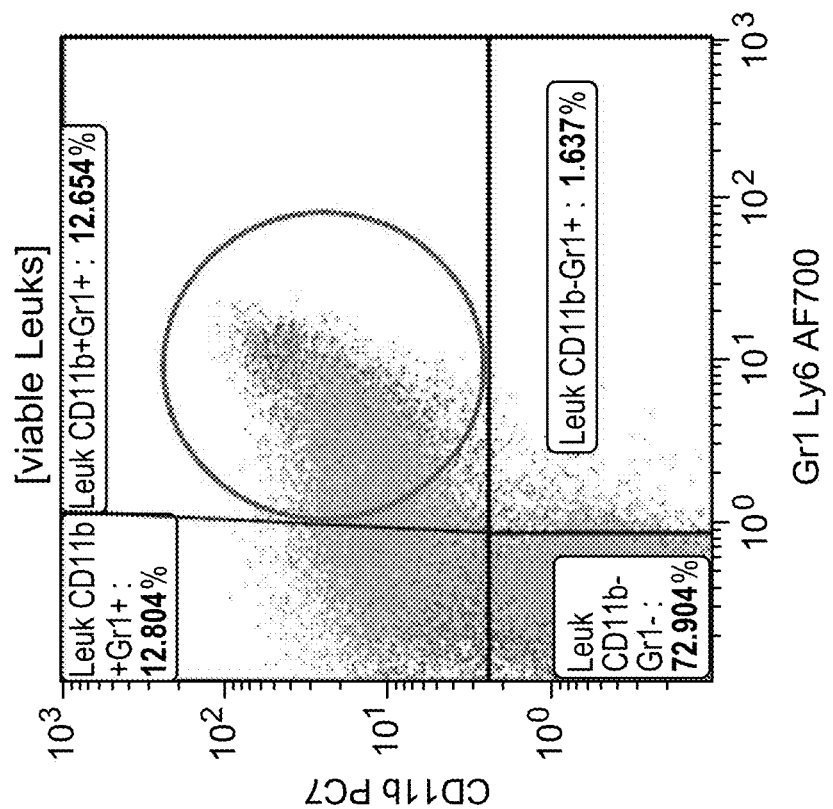
FIG. 6B is a plot and comparison graphs depicting changes in the tumor suppressor myeloid-derived suppressor cells (MSDCs) in tumor cells of lean and obese mice upon treatment with compound 20 (noted in the Figure as Compound A).
Figure 6C:
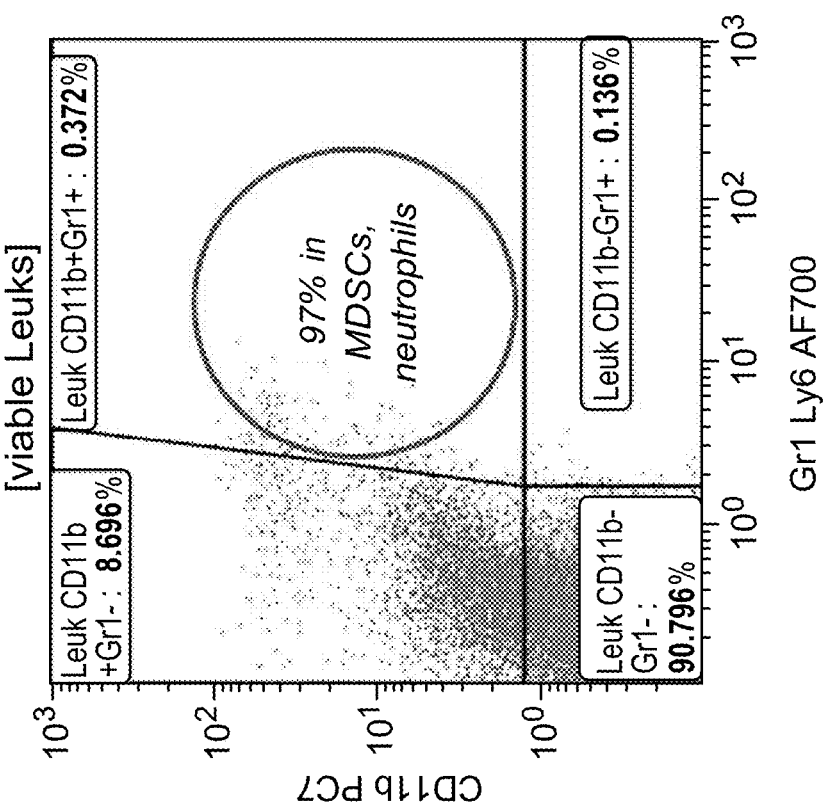
FIG. 6C is a plot and comparison graphs depicting changes in the tumor suppressor myeloid-derived suppressor cells (MSDCs) in tumor cells of lean and obese mice upon treatment with compound 20 (noted in the Figure as Compound A).

A subset of tumor samples from each group (n=3/group, except for samples from obese mice treated with Compound A which consisted of n=2 due to low cell viability in one of the samples) were processed for analysis of leukocyte content by flow cytometry. In particular, the intratumoral content of a population of immature myeloid-derived suppressor cells (MDSCs) was measured based on their elevated CD11b+/GR-1+ content. These cells are known to suppress T cell-mediated immunity and enable tumors to escape immune surveillance. While Compound A did not affect intratumoral MDSC content in lean mice, the tumor content of these cells in obese mice was decreased >90% after treatment with Compound A (FIG. 6).

Figure 7A:
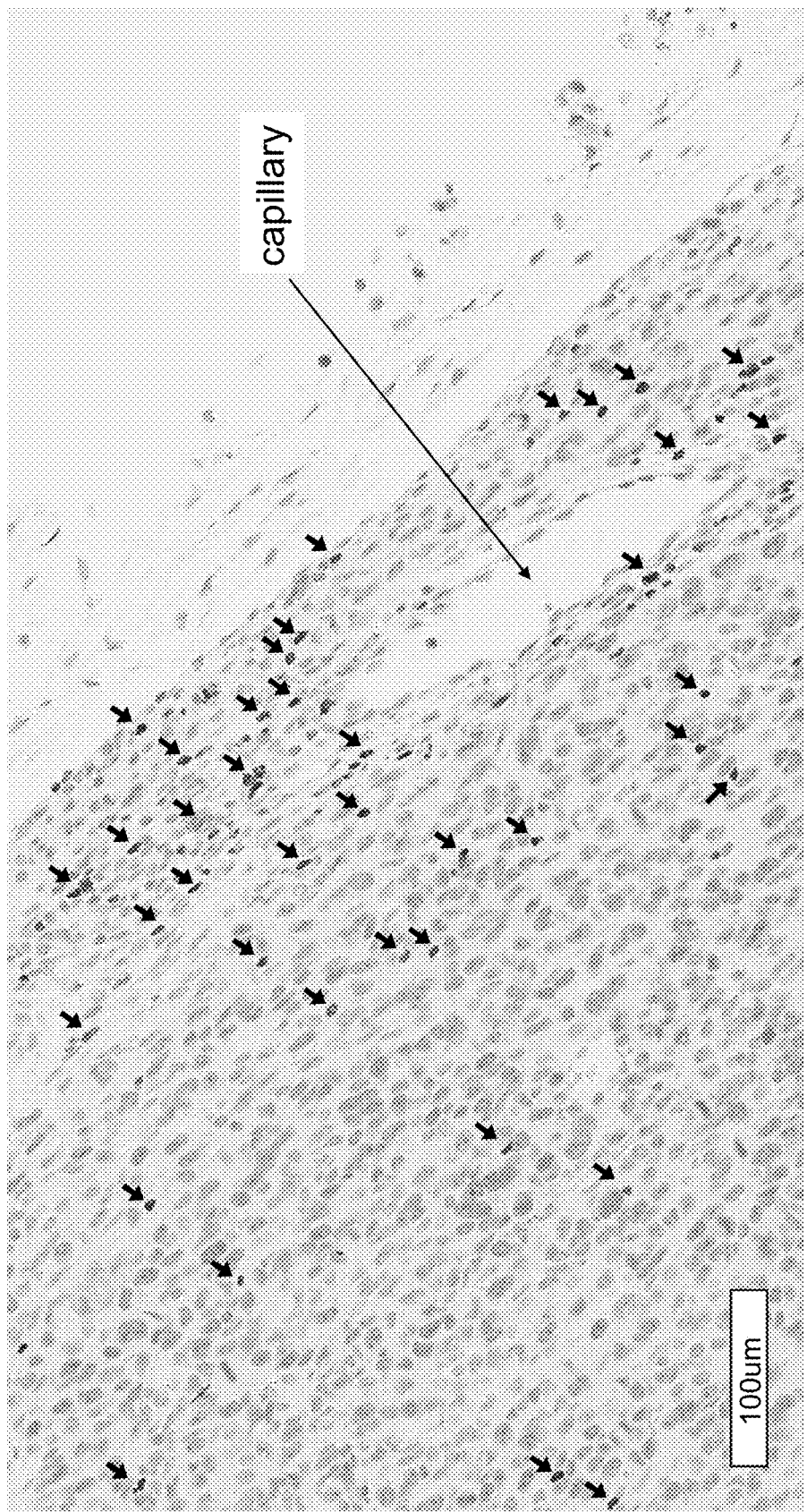
FIG. 7A is an image of an immunohistochemically-stained E0771 mammary gland tumor from an obese vehicle-treated mouse stained for the Treg marker FoxP3.
Figure 7B:
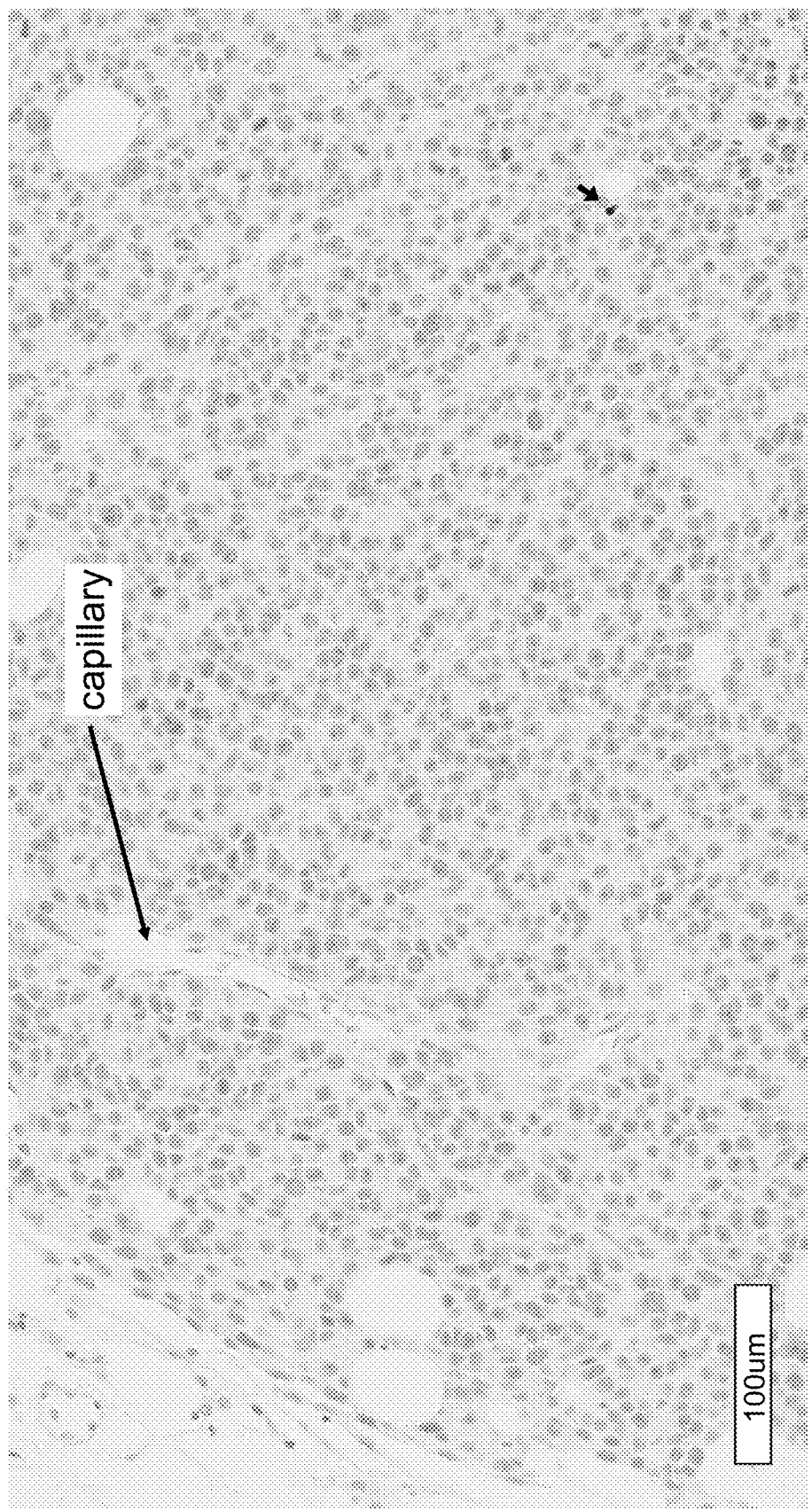
FIG. 7B is an image of an immunohistochemically-stained E0771 mammary gland tumor from an obese mouse treated with compound 5 (noted in the Figure as Compound A) stained for the Treg marker FoxP3.

E0771 mammary gland tumors were analysed by immunohistochemistry (IHC) for the nuclear antigen FoxP3, which is a marker of Tregs (Hori et al, 2003, *Science*. 299 (5609): 1057-61). The results of this analysis showed that tumors from vehicle-treated, obese mice had numerous FoxP3-positive cells within the tumor and surrounding capillaries (identified in FIG. 7A by arrowheads). In contrast, tumors from Compound A-treated mice exhibited reduced numbers of FoxP3-positive cells (indicated by arrowheads in FIG. 7B). This indicates that the tumor microenvironment (TME) was altered by Compound A, resulting in a less immune-suppressive TME due to the reduction in number of Tregs. Slides were counter-stained with hematoxylin to visualize cell nuclei.

Figure 8A:
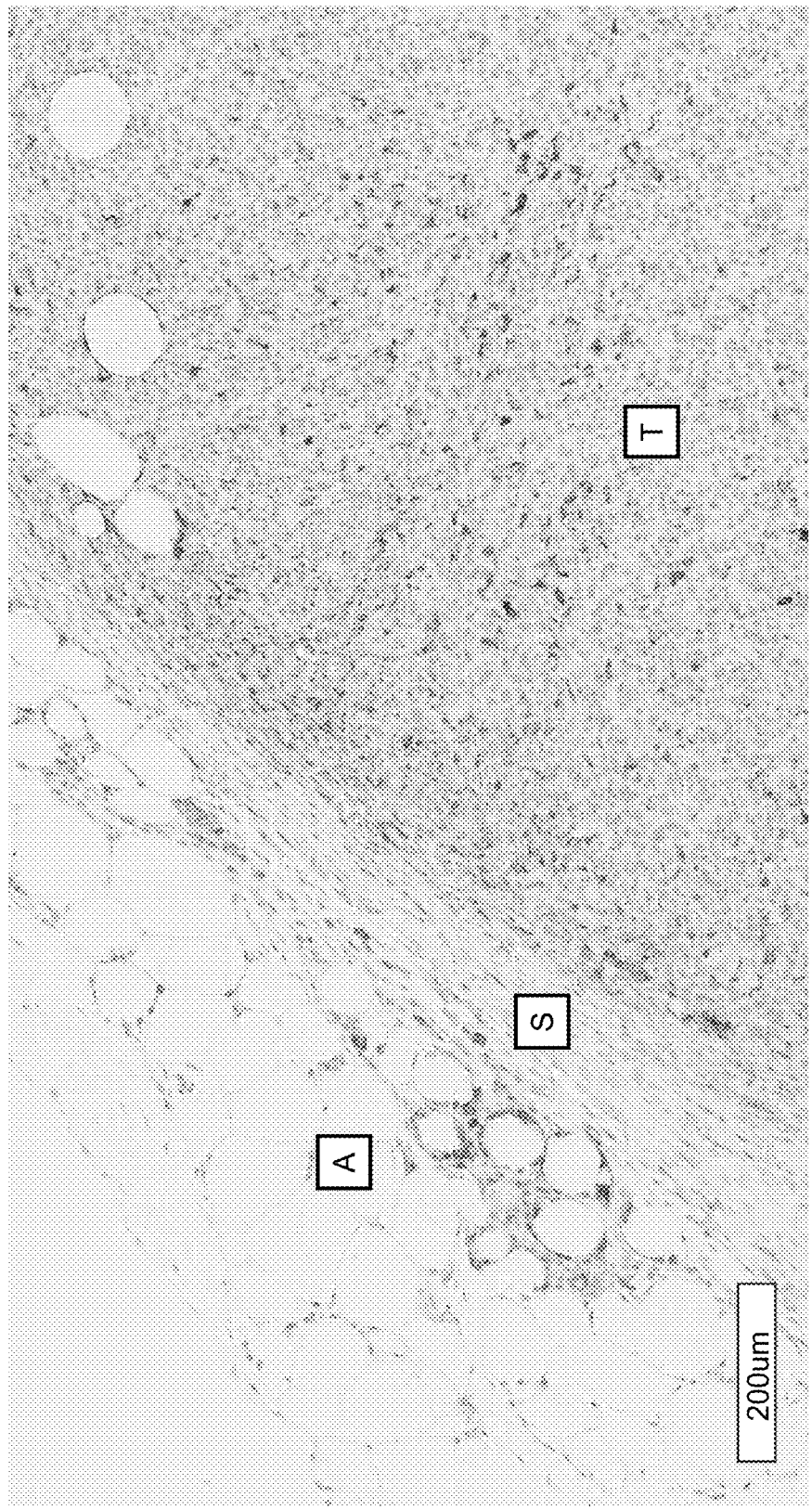
FIG. 8A is an image of an immunohistochemically-stained E0771 mammary gland tumor from an obese vehicle-treated mouse stained for the tumor-associated macrophage enzyme Arg-1.
Figure 8B:
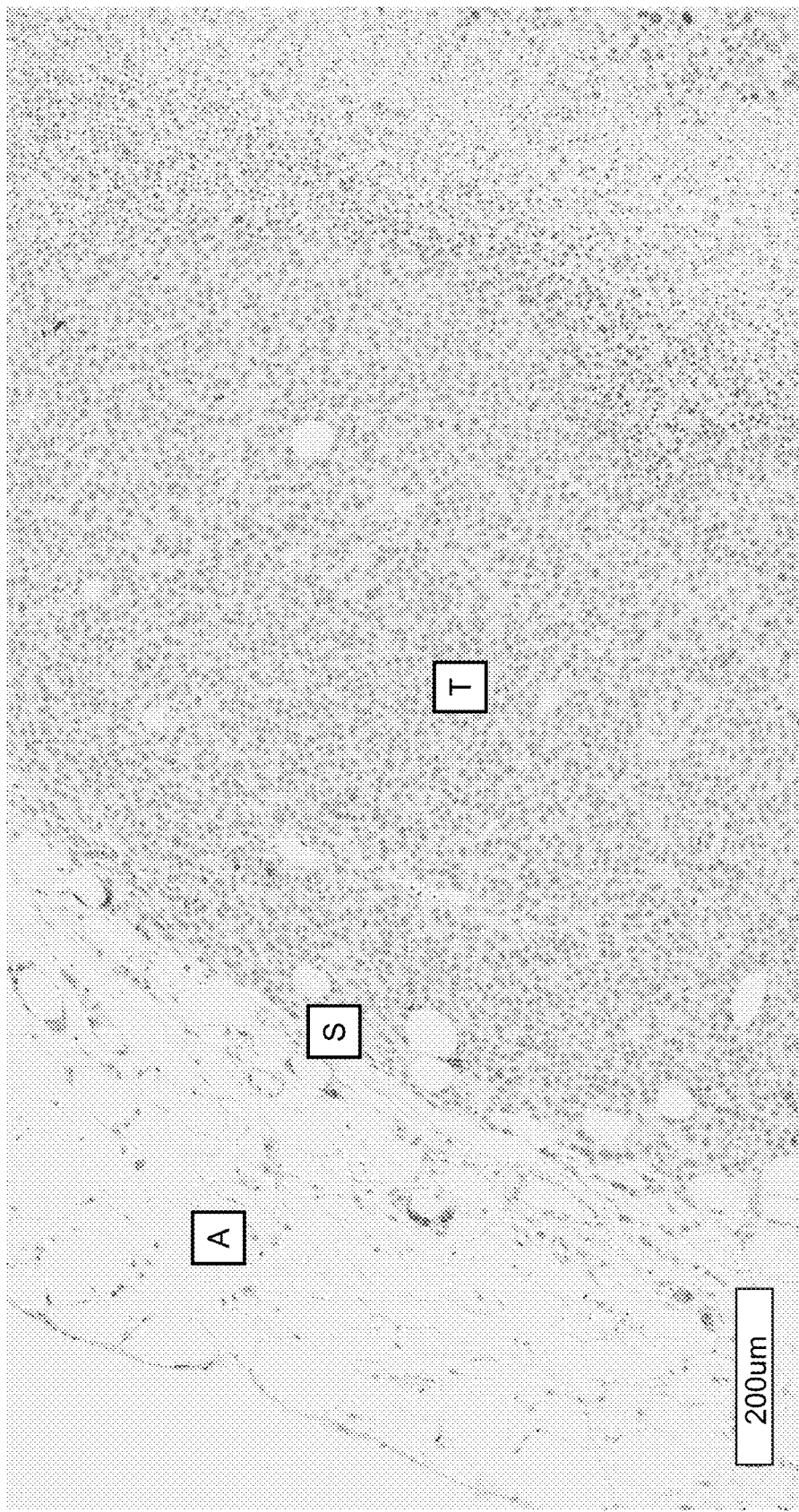
FIG. 8B is an image of an immunohistochemically-stained E0771 mammary gland tumor from an obese mouse treated with compound 20 (noted in the Figure as Compound A) stained for the tumor-associated macrophage enzyme Arg-1.

Additional IHC analysis of E0771 tumors from obese mice was conducted for the enzyme arginase-1 (Arg-1), which metabolizes arginine. Within tumors, elevated activity of Arg-1 reduces levels of extracellular arginine, and deprives cytotoxic T lymphocytes of an important energy source, which results in reduced tumororicidal activity (Popovic et al, J. Nutr. 137: 1681S-1686S, 2007). IHC results showed that tumors from obese mice had robust Arg-1 staining within certain areas of the tumor (T), tumor stroma (S) as well as surrounding tumor-associated adipocytes (A; FIG. 8A). In contrast, Arg-1 staining in tumors from obese mice treated with Compound A was reduced, especially within the tumor (T), while staining sometimes remained evident in the tumor stroma (S) and the surrounding adipose tissue (A; FIG. 8B).

Figure 9A:
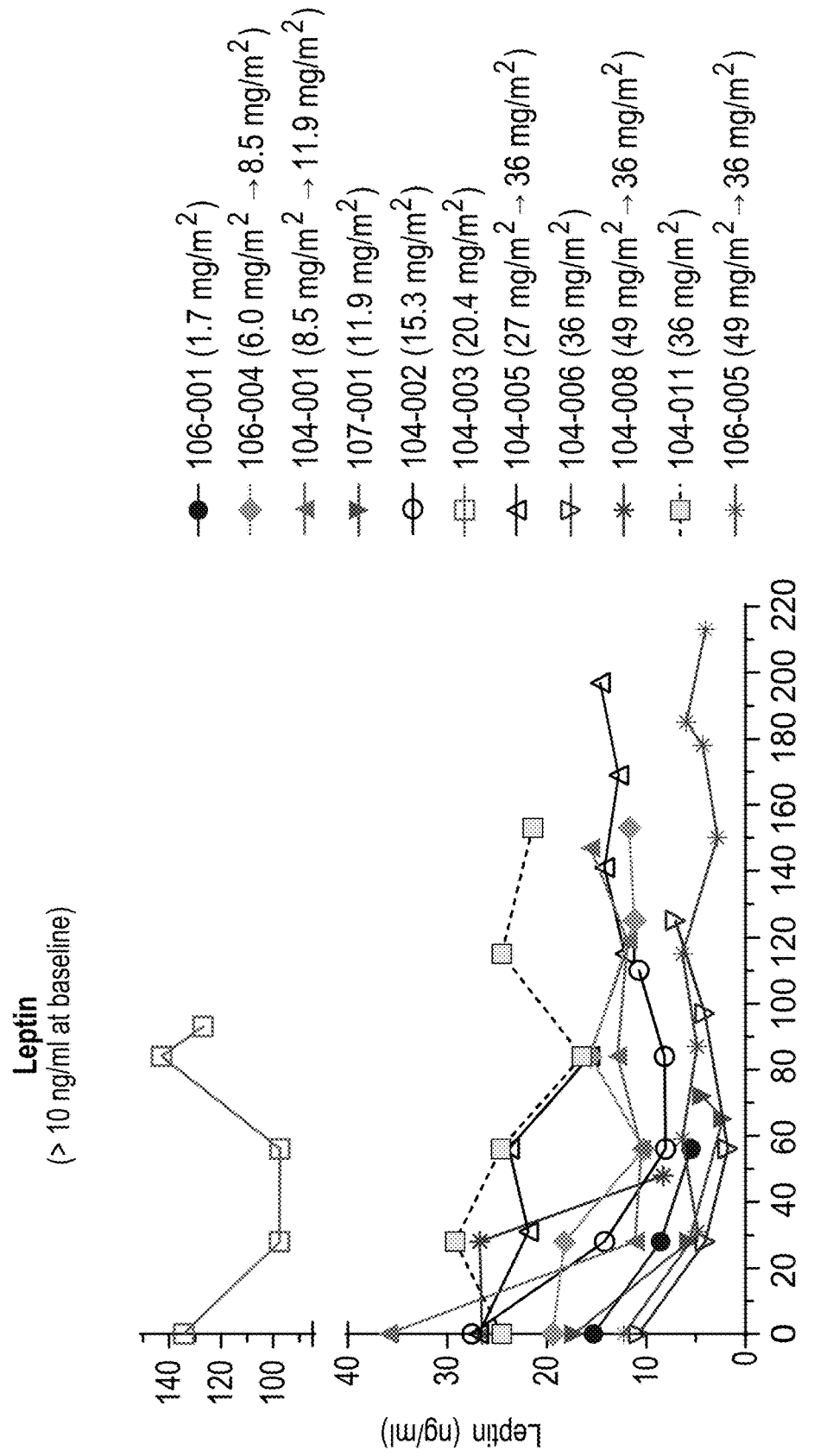
FIG. 9A is a graph depicting leptin levels in serum of cancer patients treated with compound 20 (noted in the Figure as Compound A) as part of the SDX-101 clinical trial.
Figure 9B:
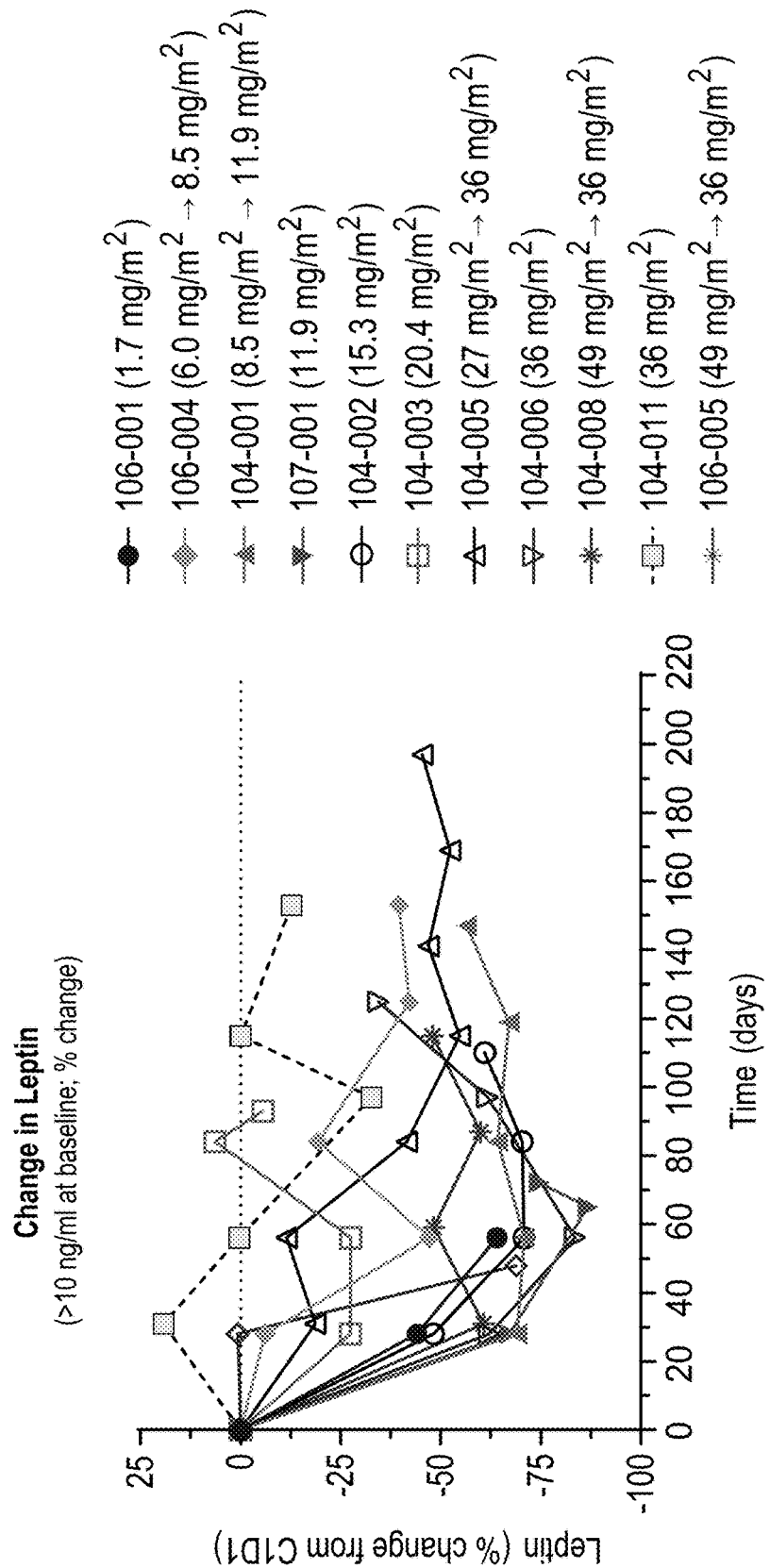
FIG. 9B is a graph depicting leptin levels in serum of cancer patients treated with compound 20 (noted in the Figure as Compound A) as part of the SDX-101 clinical trial.
Figure 10A:
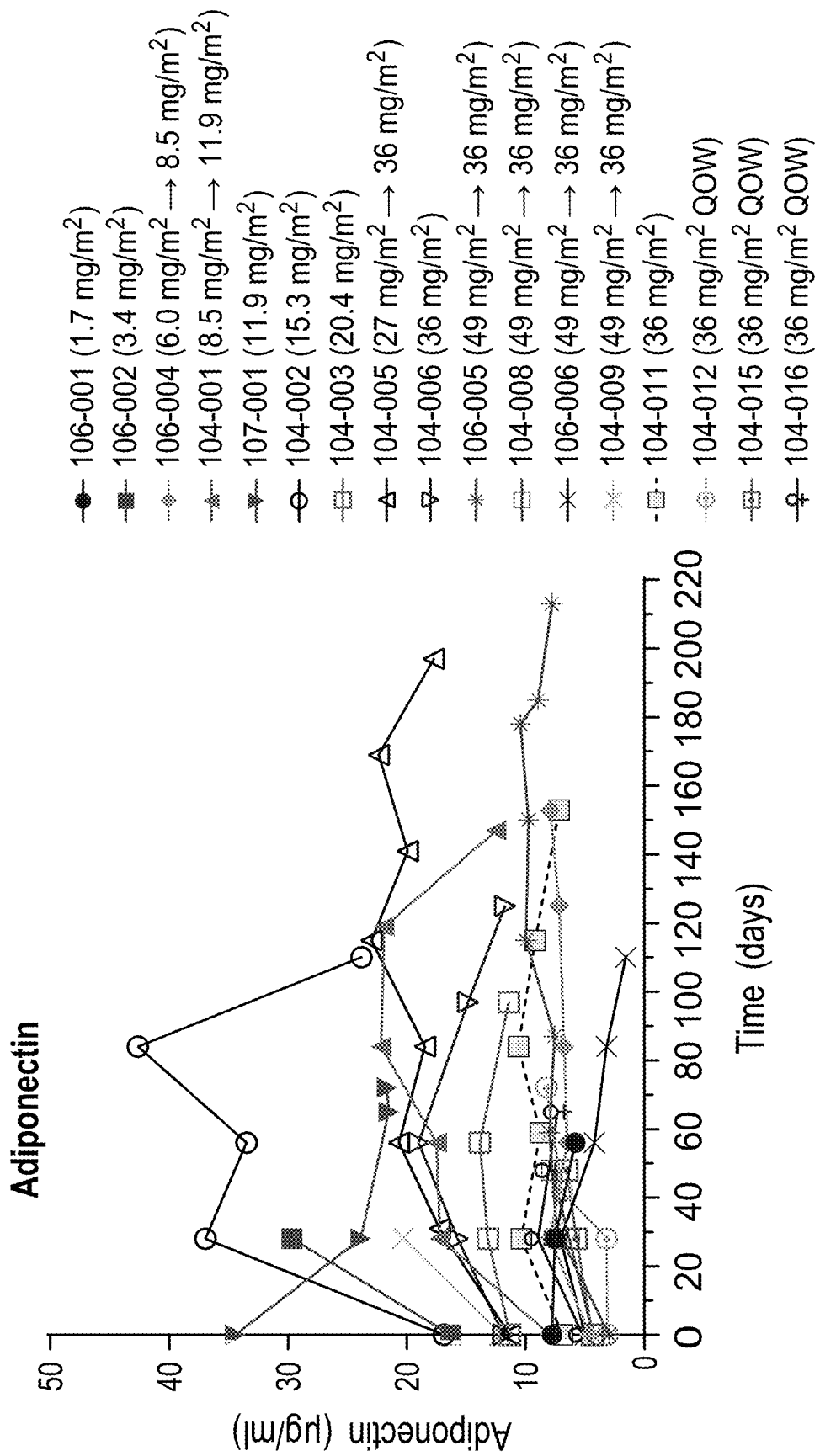
FIG. 10A is a graph depicting adiponectin levels in serum of cancer patients treated with compound 20 (noted in the Figure as Compound A) as part of the SDX-101 clinical trial.
Figure 10B:
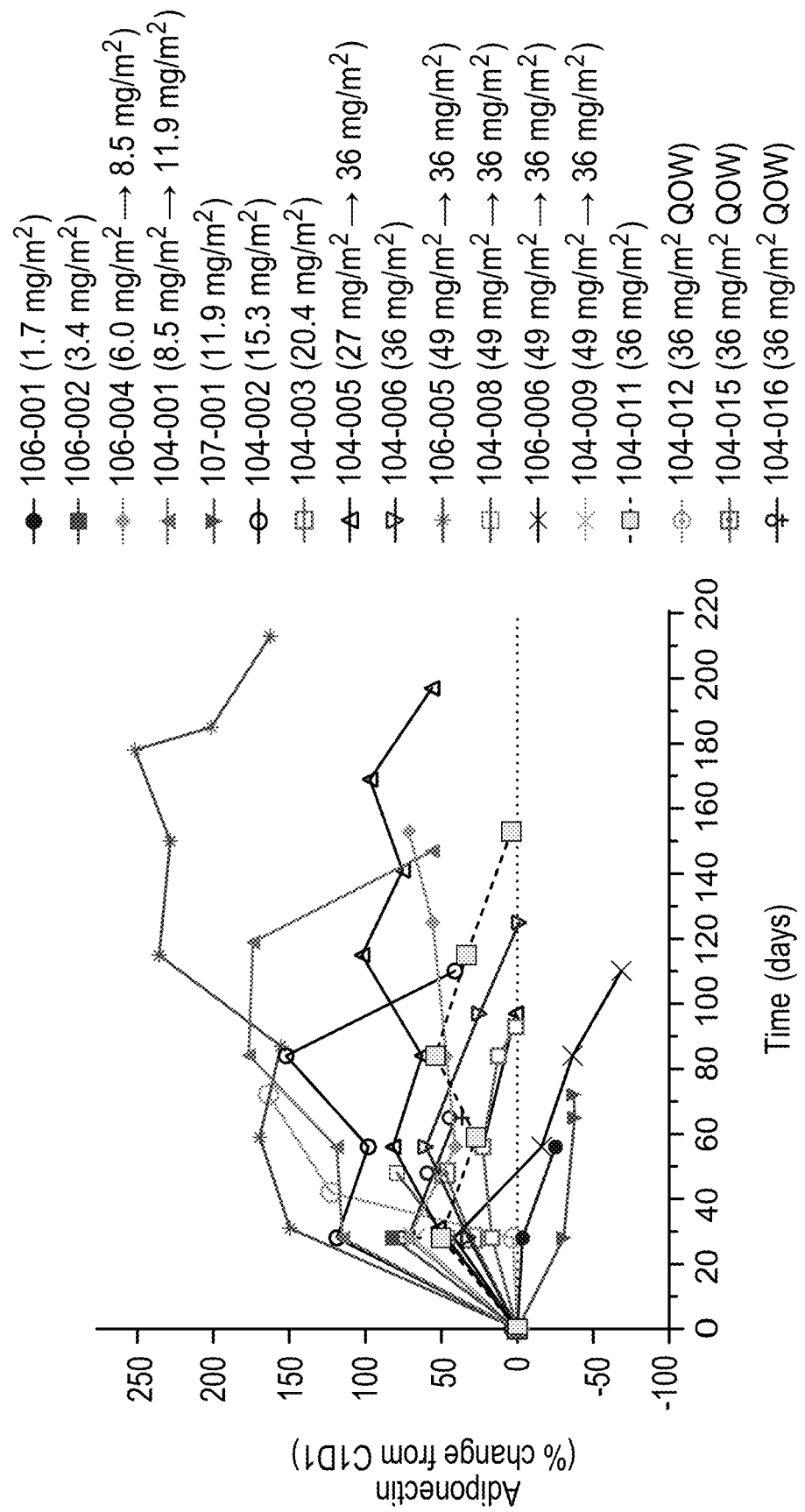
FIG. 10B is a graph depicting adiponectin levels in serum of cancer patients treated with compound 20 (noted in the Figure as Compound A) as part of the SDX-101 clinical trial.
Figure 11A:
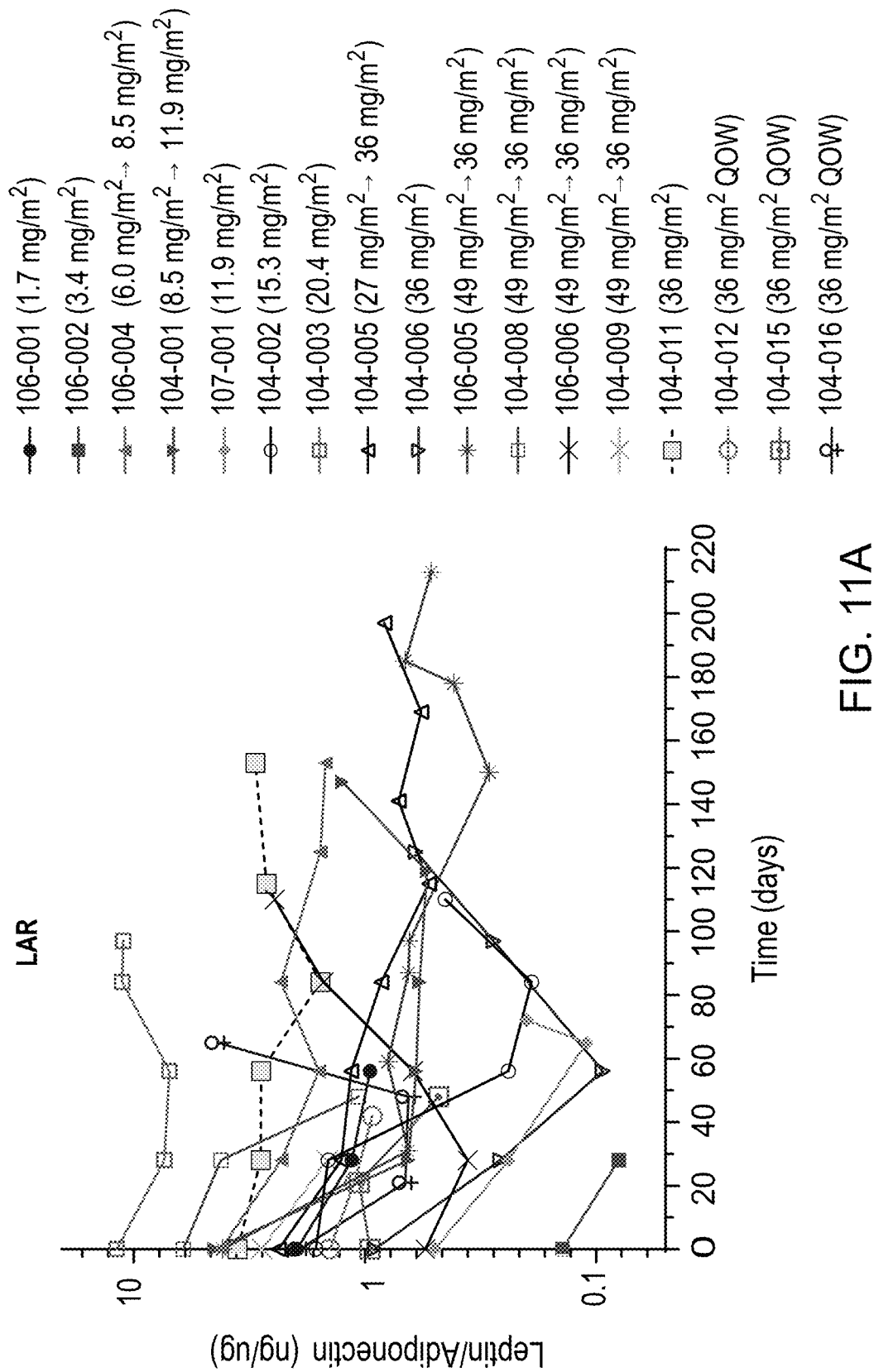
FIG. 11A is a graph depicting the leptin/adiponectin ratio in the serum of cancer patients treated with compound 20 (noted in the Figure as Compound A) as part of the SDX-101 clinical trial.
Figure 11B:
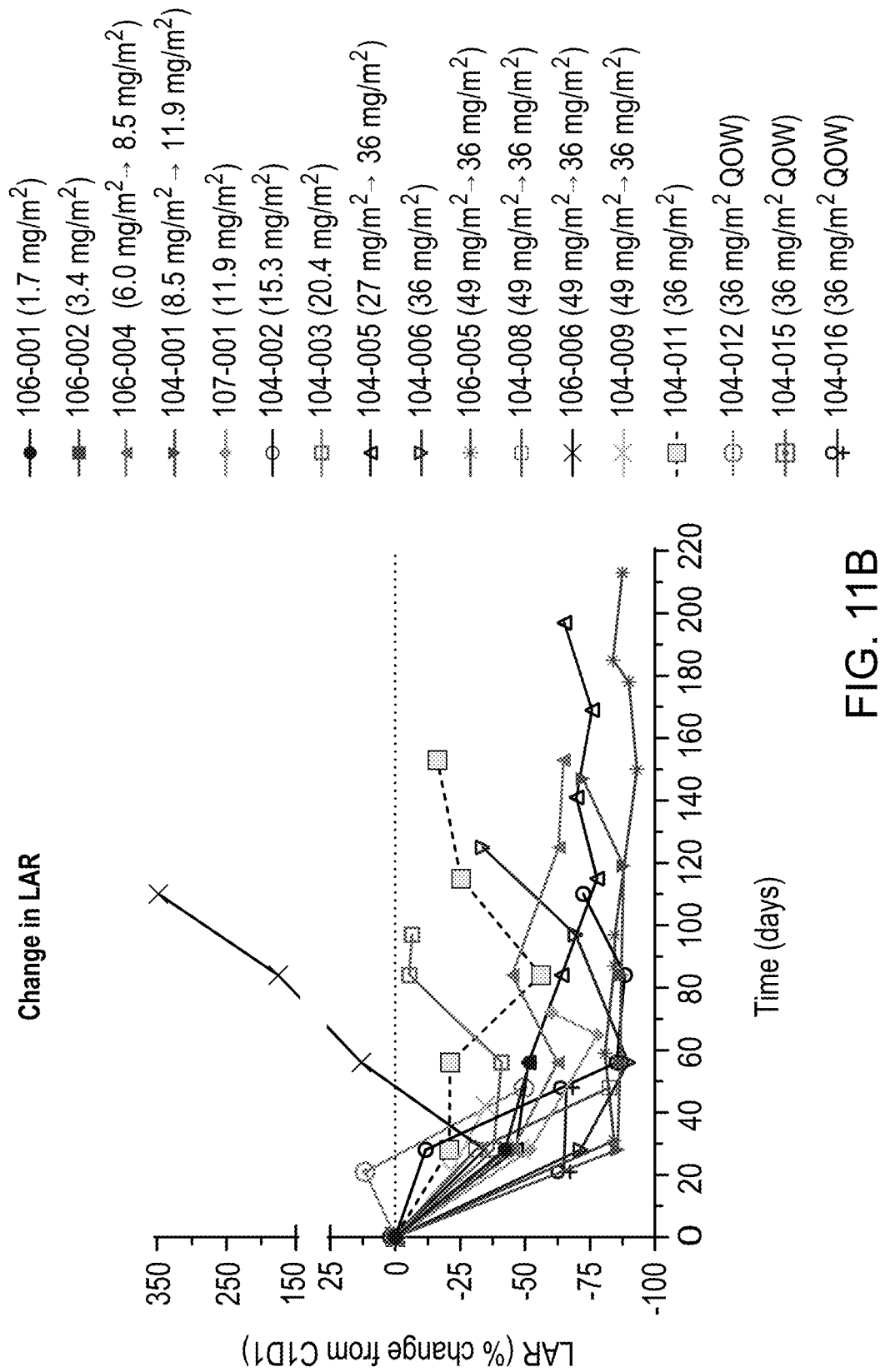
FIG. 11B is a graph depicting the leptin/adiponectin ratio in the serum of cancer patients treated with compound 20 (noted in the Figure as Compound A) as part of the SDX-101 clinical trial.
Figure 12B:
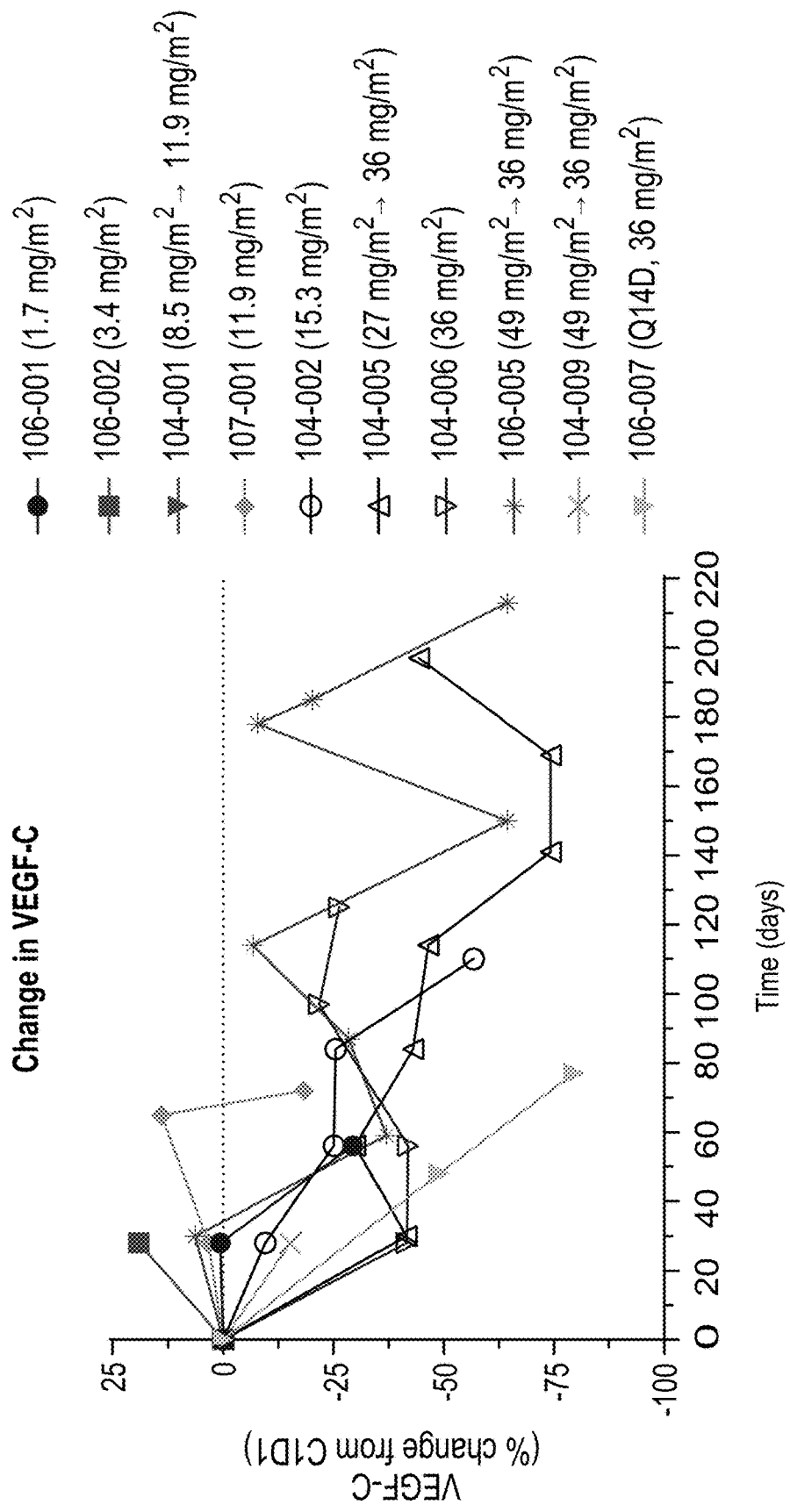
FIG. 12B is a graph depicting the pro-angiogenic marker VEGF-C levels in serum of cancer patients treated with compound 20 (noted in the Figure as Compound A) as part of the SDX-101 clinical trial.
Figure 15B:
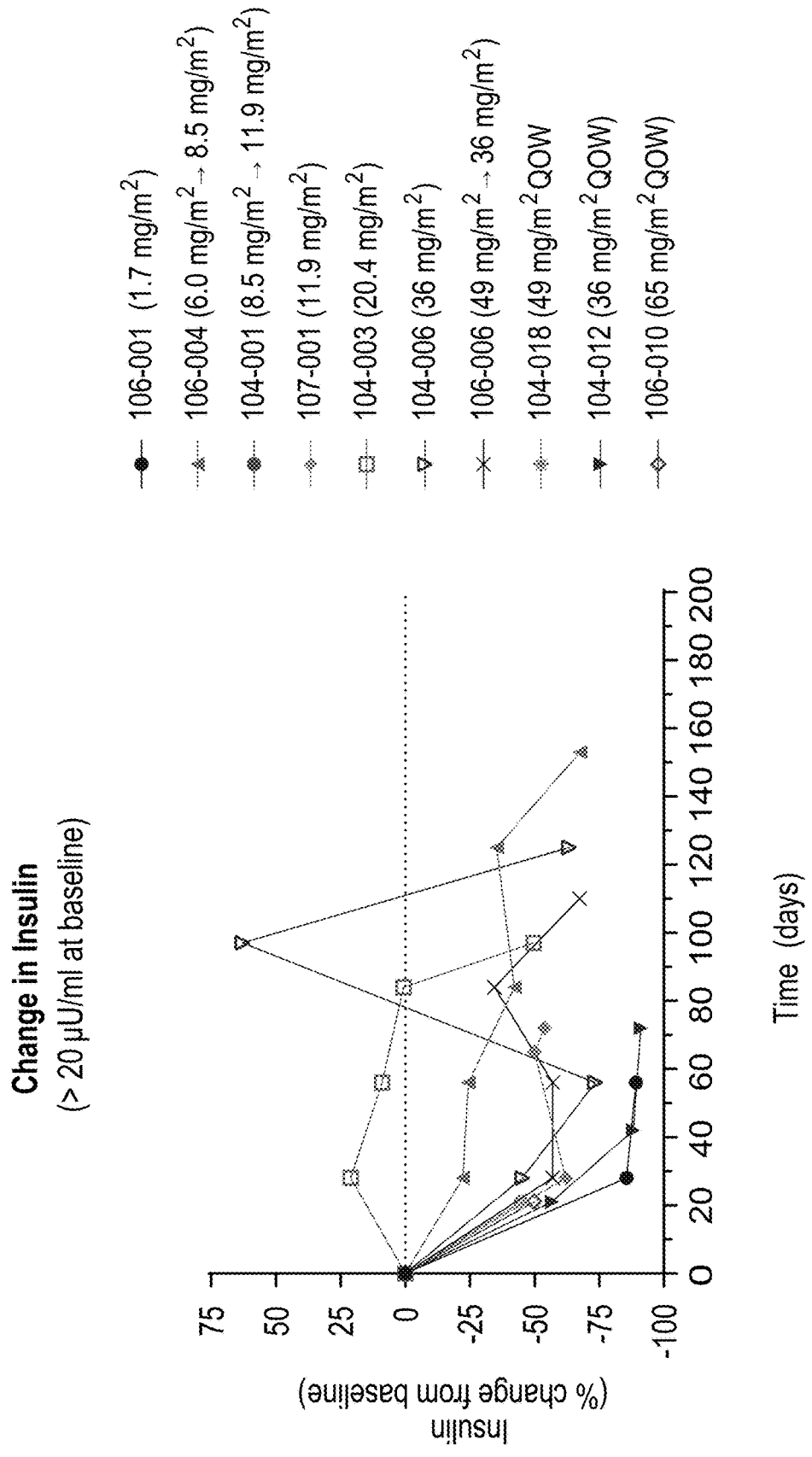
FIG. 15B shows the effect of compound 20 (noted in the Figure as Compound A) given to heavily pre-treated cancer patients on insulin levels, where baseline insulin is above 20 uU/ml in percent change.
Figure 19:
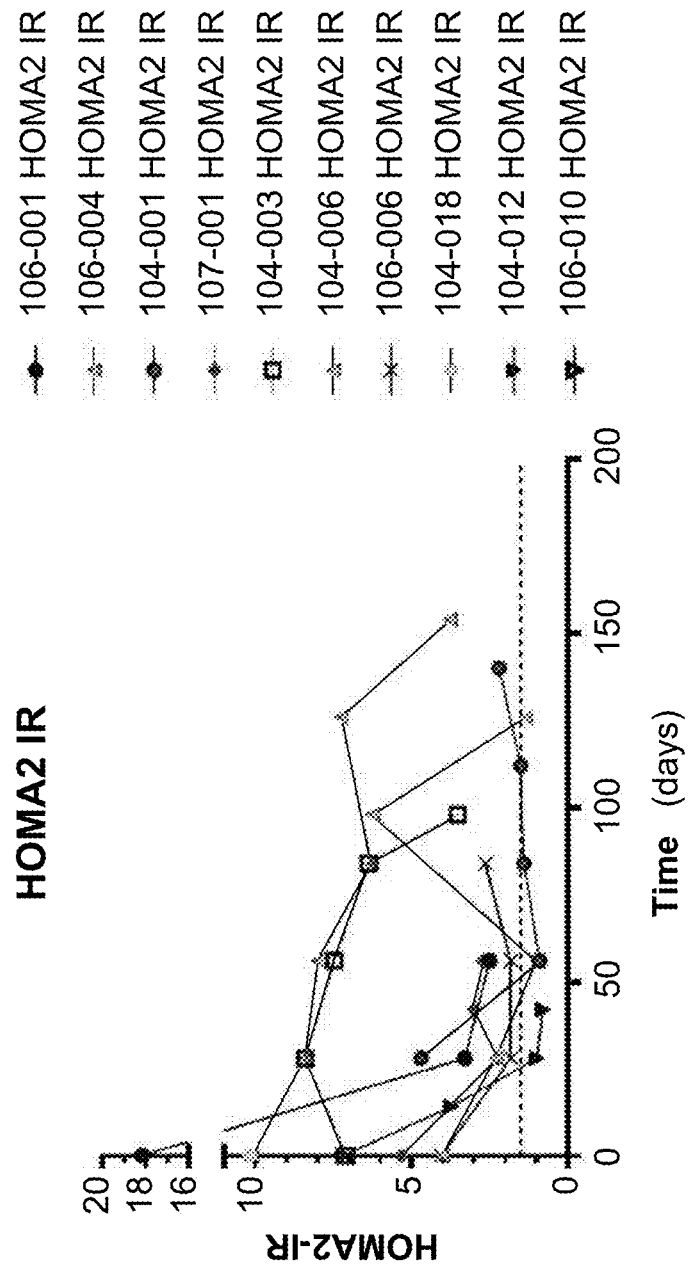
FIG. 19 shows the global improvements in insulin resistance in cancer patients treated with compound 20 as calculated using the HOMA2-IR Score method. The majority of these late-stage cancer patients did not have overt metabolic dysfunction demonstrating the surprising effect of insulin resistance improvements in cancer patients.

Example 3: Effect of Compound 20 (Shown in the Figure as Compound A) on Biomarker Expression in Human Cancer Patients The following exploratory biomarkers were measured in serum from late-stage cancer patients treated with Compound A as part of an ongoing clinical trial (SDX-0101) using standard immunologic assays. Compound A was dosed subcutaneously as a sterile solution in 5% mannitol/water once every seven days or once every fourteen days. The results showed that leptin levels in patients treated with Compound A generally declined (FIG. 9A) which is particularly apparent when the data are expressed as "% change from baseline" (FIG. 9B). Note that leptin data was stratified on baseline leptin (>10 ng/ml). Conversely the levels of another adipokine (eg, an adipose-tissue derived hormone) adiponectin generally increased after treatment with Compound A (FIG. 10A, B). The ratio of leptin to adiponectin (LAR) also generally declined after initiating treatment with Compound A (FIG. 11A, B). Insulin is another biomarker in cancer patients with or without metabolic dysfunction. Insulin was measured in heavily pre-treated cancer patients with Compound A, dosed subcutaneously once every seven days or once every fourteen days. The results showed that insulin levels in patients treated with Compound A generally declined (FIG. 15 A) with the percent change from baseline (for patients with insulin levels above 20 uU/ml) (FIG. 15B). Inulin alone, while a potent mitogen and known stimulator of tumor cells, does not necessarily speak to the effects of insulin resistance. Insulin resistance is recognized as a negative prognosticator for cancer patients (Duggan et al., J Clin Oncol (2010) 29:32-39). Here we show that patients whose baseline insulin was above 20 uU/ml had significant reductions in their insulin resistance scores (using the HOMA2 IR method) regardless of their obesity state (FIG. 19).

Figure 13A:
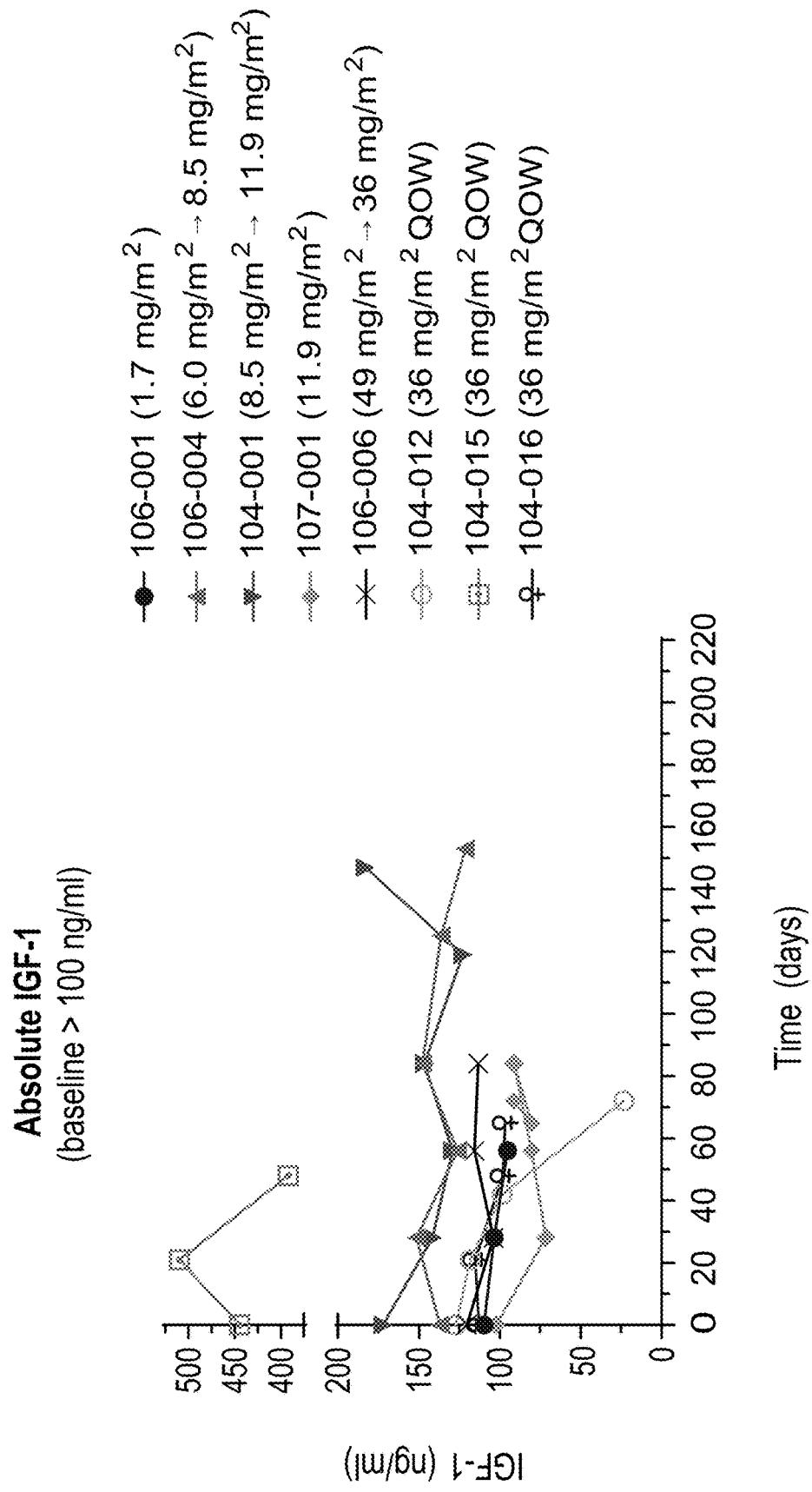
FIG. 13A is a graph depicting the pro-angiogenic and pro-tumor marker IGF-1 levels in serum of cancer patients treated with compound 20 (noted in the Figure as Compound A) as part of the SDX-101 clinical trial.
Figure 13B:
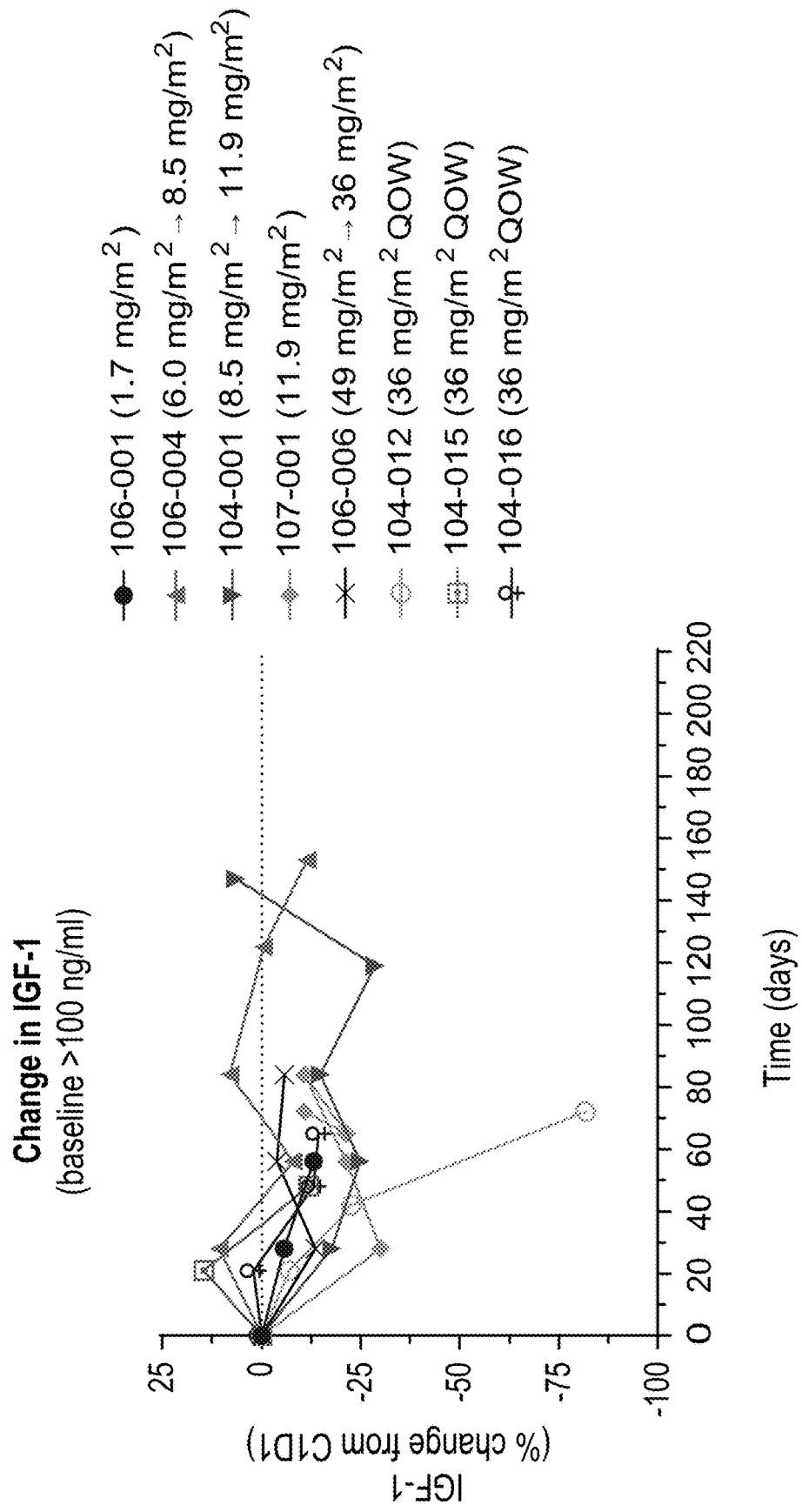
FIG. 13B is a graph depicting the pro-angiogenic and pro-tumor marker IGF-1 levels in serum of cancer patients treated with compound 20 (noted in the Figure as Compound A) as part of the SDX-101 clinical trial.
Figure 14A:
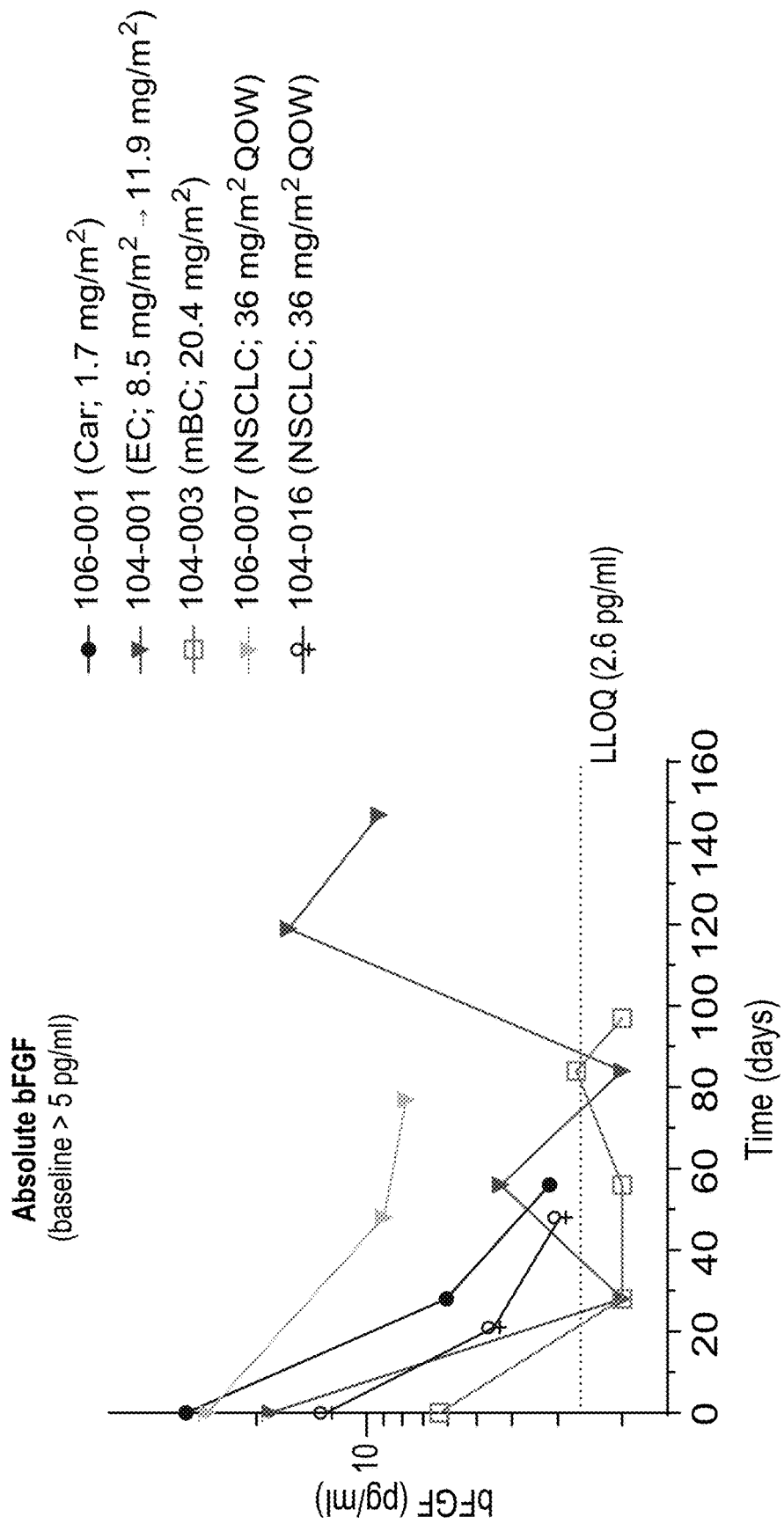
FIG. 14A is a graph depicting pro-angiogenic biomarker bFGF/FGF2 levels in serum of cancer patients treated with compound 20 (noted in the Figure as Compound A) as part of the SDX-101 clinical trial.
Figure 14B:
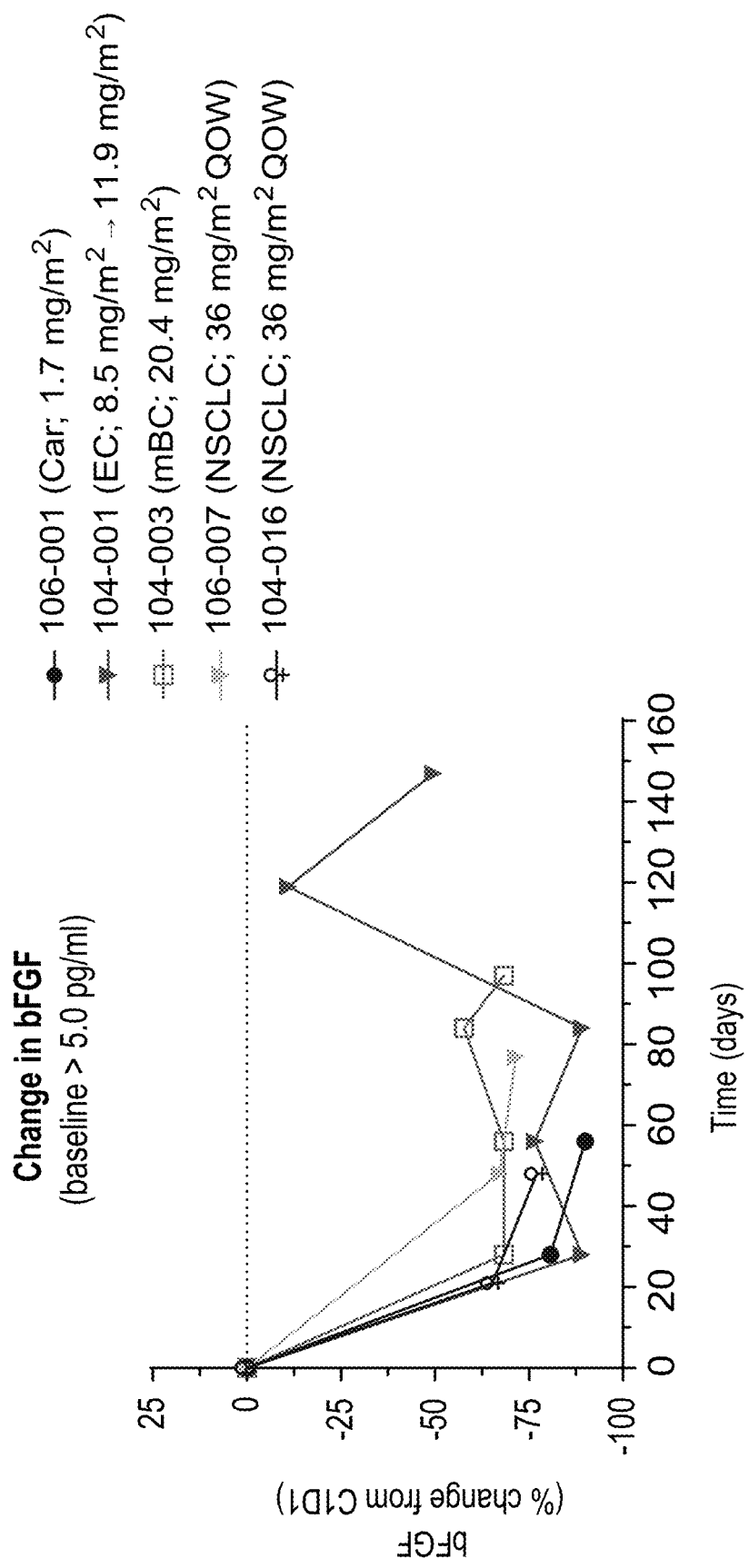
FIG. 14B is a graph depicting pro-angiogenic biomarker bFGF/FGF2 levels in serum of cancer patients treated with compound 20 (noted in the Figure as Compound A) as part of the SDX-101 clinical trial.

The angiogenic protein vascular endothelial growth factor C (VEGF-C) was measured in the serum of cancer patients before and after treatment with Compound A. For patients with baseline VEGF-C>200 pg/ml, the levels of VEGF-C generally declined after treatment with Compound A (FIG. 11A, B). In addition, the serum levels of another important cancer growth factor, insulin-like growth factor-1 (IGF-1) were analyzed and for patients with IGF-1>100 ng/ml at baseline, IGF-1 levels often declined after initiating treatment with Compound A (FIG. 13A, B). Serum levels of another pro-angiogeneic and growth-promoting hormone, bFGF/FGF2, were shown to decline after initiating treatment with Compound A, in particular in patients whose baseline levels were >5.0 pg/ml (FIG. 14A, B). Note that for serum samples whose bFGF/FGF2 levels were below the LLOQ for the assay (LLOQ=2.6 pg/ml), a value of 2.0 pg/ml was assigned to facilitate presentation of the data in FIG. 14B ("Change in bFGF").

Insulin is a potent tumor mitogen. In cancer patients it has been reported that elevated levels of insulin correlate with disease progression and mortality (Tsujimoto et al, Int. J. Cancer, 2017, 141, 102-111). FIG. 15 shows general reductions in cancer patients' insulin levels with baseline levels greater than 20 uU/ml. The cancer patients have a variety of tumors, were given a range of doses (1.7-65 mg/m$^2$) and dosing schedules (once weekly or once every two weeks) of Compound A. FIG. 19 shows the improvements in insulin sensitivity in these patients using the HOMA2-IR method of calculating insulin sensitivity.

Figure 16:
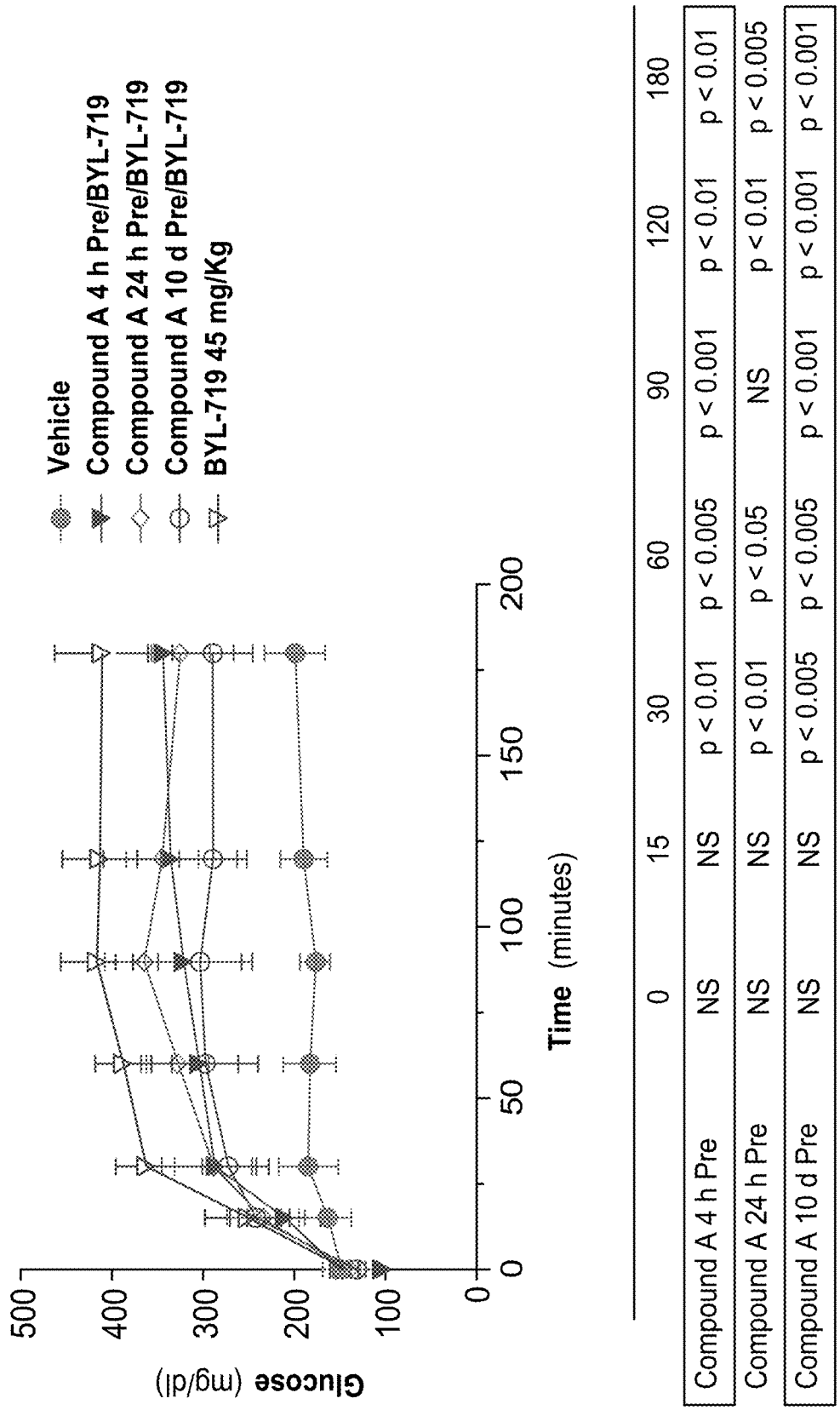
FIG. 16 shows the attenuation of glucose spikes in a mouse model of a PI3K inhibitor mediated hyperglycemia, where normal C57Bl/6 mice were dosed with the PI3K inhibitor to induce hyperclygemia, and were either pre-treated with compound 20 (noted in the Figure as Compound A) 10 days before on an every-four-day dosing regimen, or 24 hours before injection with the PI3K inhibitor, or 4 hours before injection with the PI3K inhibitor.
Figure 20:
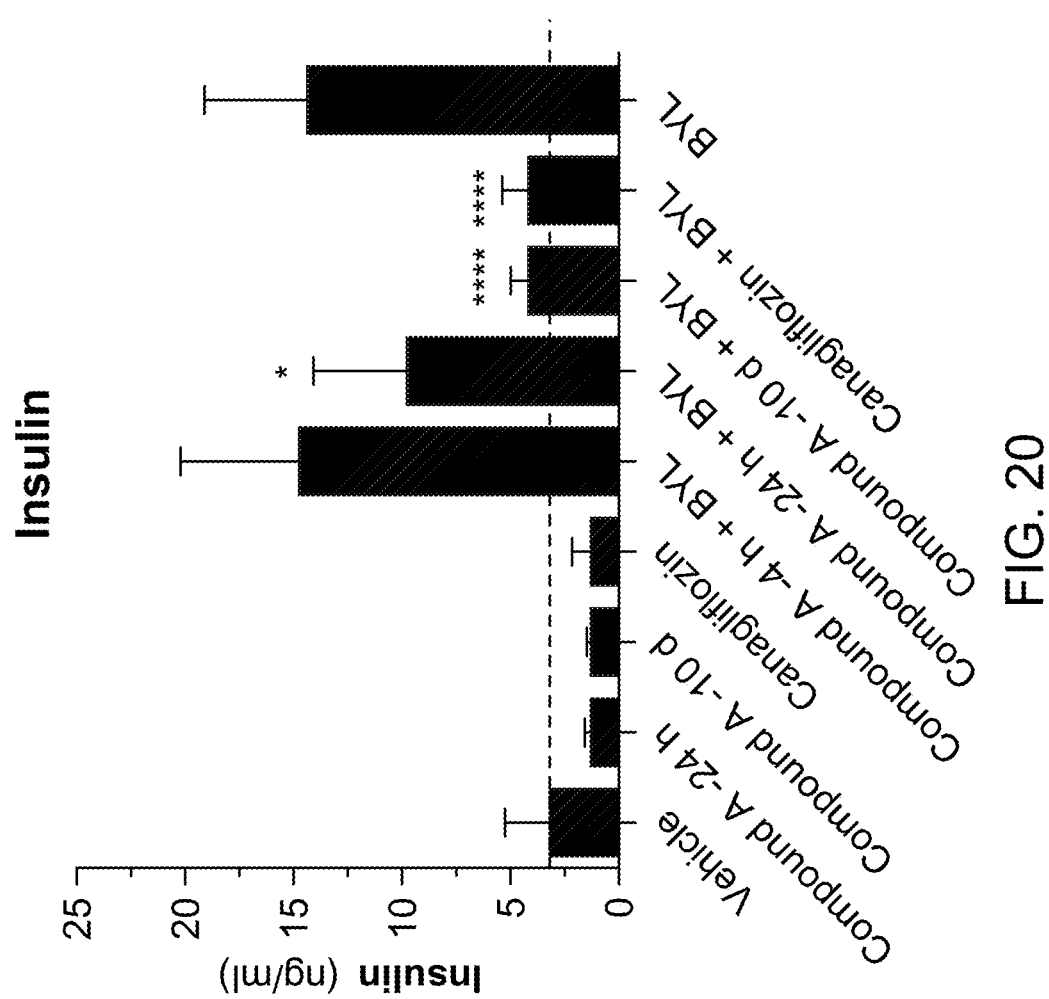
FIG. 20 shows the surprising time course lowering of insulin in metabolically normal mice that were treated with a drug from the PI3K class of therapeutics (BYL-719)– in combination with Compound 20 (shown as Compound A in the figure) and suffered hyperglycemia as a result of the PI3K treatment.
Figure 21:
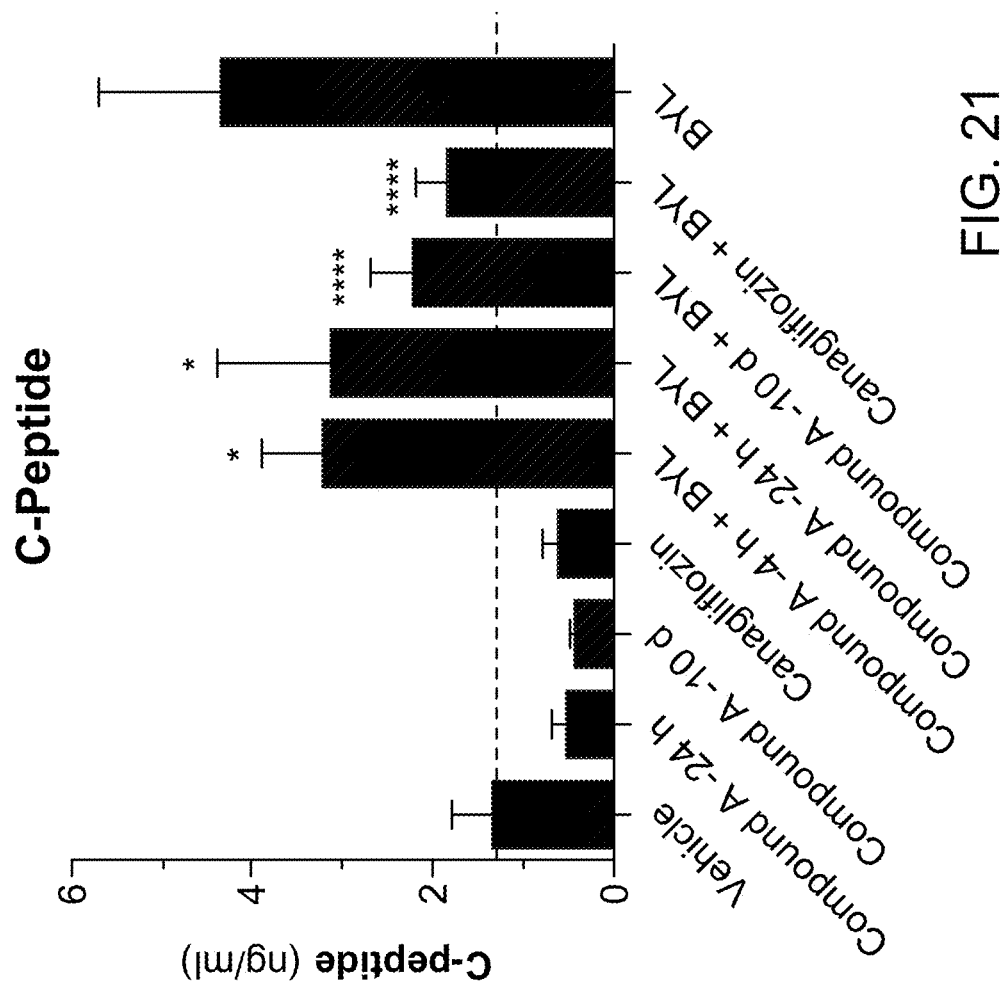
FIG. 21 shows the surprising time course lowering of C-peptide in metabolically normal mice that were treated with a drug from the PI3K drug class of therapies (BYL-719)– in combination with Compound 20 (shown as Compound A in the figure), and suffered hyperglycemia as a result of the PI3K treatment.

This has been highlighted more recently for an emerging class of drugs targeting the enzyme phosphatidylinositol-3-kinase (PI3K), and specifically its catalytic subunit p110. Mechanism-based side effects, observed pre-clinically as well as clinically, include hyperglycemia and hyperinsulinemia (Busaidy et al, 2012, J. Clin. Oncol. 30:2919-2928; Hopkins et al, 2018, Nature, 560(7719):499-503). In normal mice, Compound A (dosed subcutaneously, Q4D over a span of 10 days prior to dosing with the PI3k inhibitor alpelisib/BYL-719) attenuated acute hyperglycemia induced by alpelisib/BYL-719 (45 mg/kg, po; FIG. 16A). FIGS. 20 and 21 show the time course improvements in hyperinsulinemia (measured via both direct insulin and its surrogate C-peptide). While glucose levels were generally attenuated regardless of when the animals were pre-treated with Compound A before alpelisib/BYL-719, insulin levels showed a surprising time-dependent and significant improvement in hyperinsulinemia, which was confirmed by C-peptide levels.

Annexins are a family of calcium-dependent phospholipid-binding proteins that preferentially bind phosphatidylserine (PS). Under normal physiological conditions, PS is predominantly located in the inner leaflet of the plasma membrane (FIG. 1). Upon initiation of apoptosis, PS loses its asymmetric distribution across the phospholipid bilayer and is translocated to the extracellular membrane leaflet, marking cells as targets of phagocytosis. Once on the outer surface of the membrane, PS can be detected by fluorescently labelled Annexin V in a calcium-dependent manner.

In early-stage apoptosis, the plasma membrane excludes viability dyes such as 7-aminoactinomycin D (7-AAD). Cells at this stage will stain with Annexin V but not a viability dye, thus distinguishing cells in early apoptosis.

Figure 17:
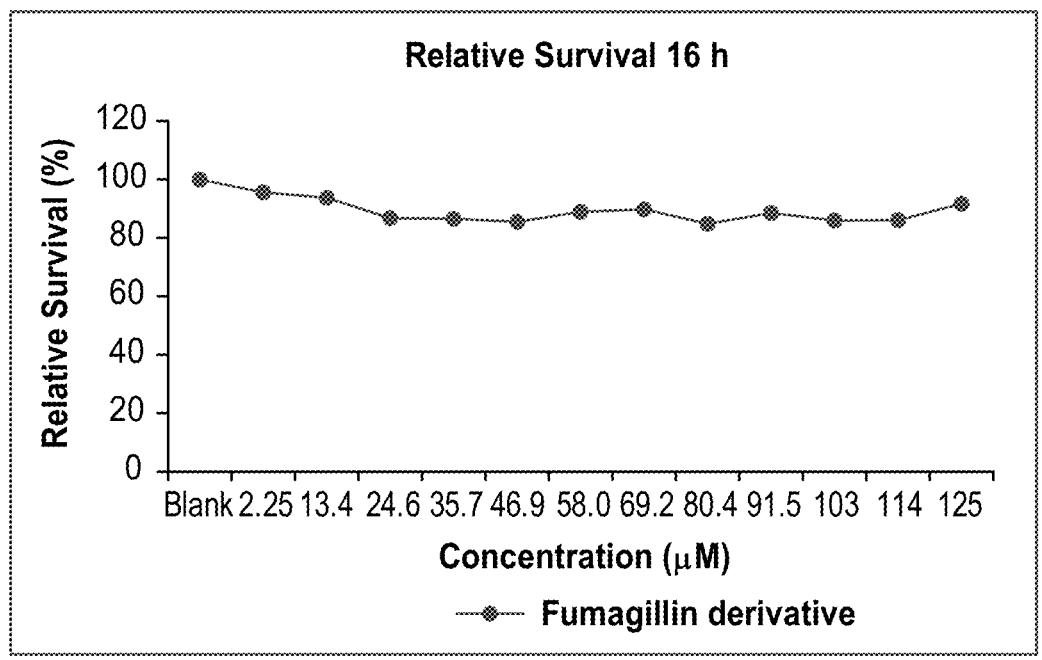
FIG. 17 shows time course increasing apoptosis of cultured human lymphoblastoid cell line TK6, seeded at $2\times10^5$ cells per ml over a 16 hour (top panel) and 24 hour period (bottom panel) treated with a small molecule fumagillin derivative of the present disclosure.
Figure 17:
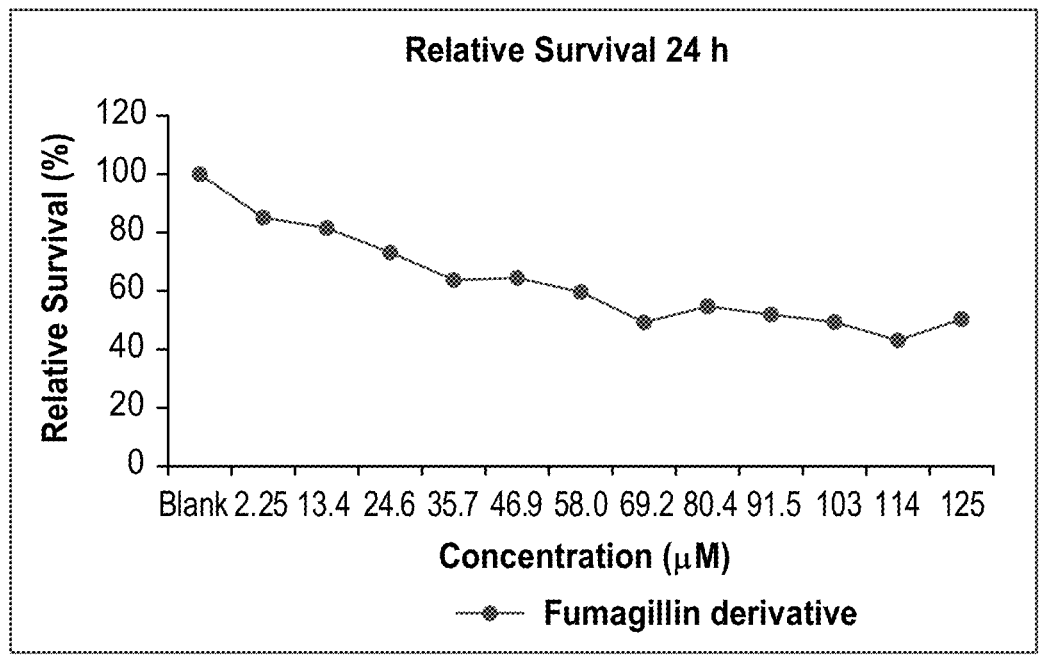

However, in late-stage apoptosis, the cell membrane loses integrity thereby allowing Annexin V to also access PS in the interior of the cell. A viability dye can be used to resolve these late-stage apoptotic and necrotic cells (Annexin V and viability dye positive) from the early-stage apoptotic cells (Annexin V positive, viability dye negative). In this study Annexin V expression was assessed using the Annexin V PE Apoptosis Detection Kit provided by BioLegend (catalogue #640934) using a BD FACSCanto II flow cytometer. FIG. 17 shows decreasing cell survival via apoptosis using a small molecule fumagillin derivative of the present invention in a time dependent manner.

The Caspase-Glo® 3/7 Assay from Promega Corp is a homogeneous, luminescent assay that measures caspase-3 and -7 activities. These members of the cysteine aspartic acid-specific protease (caspase) family play key effector roles in apoptosis in mammalian cells.

Figure 18:
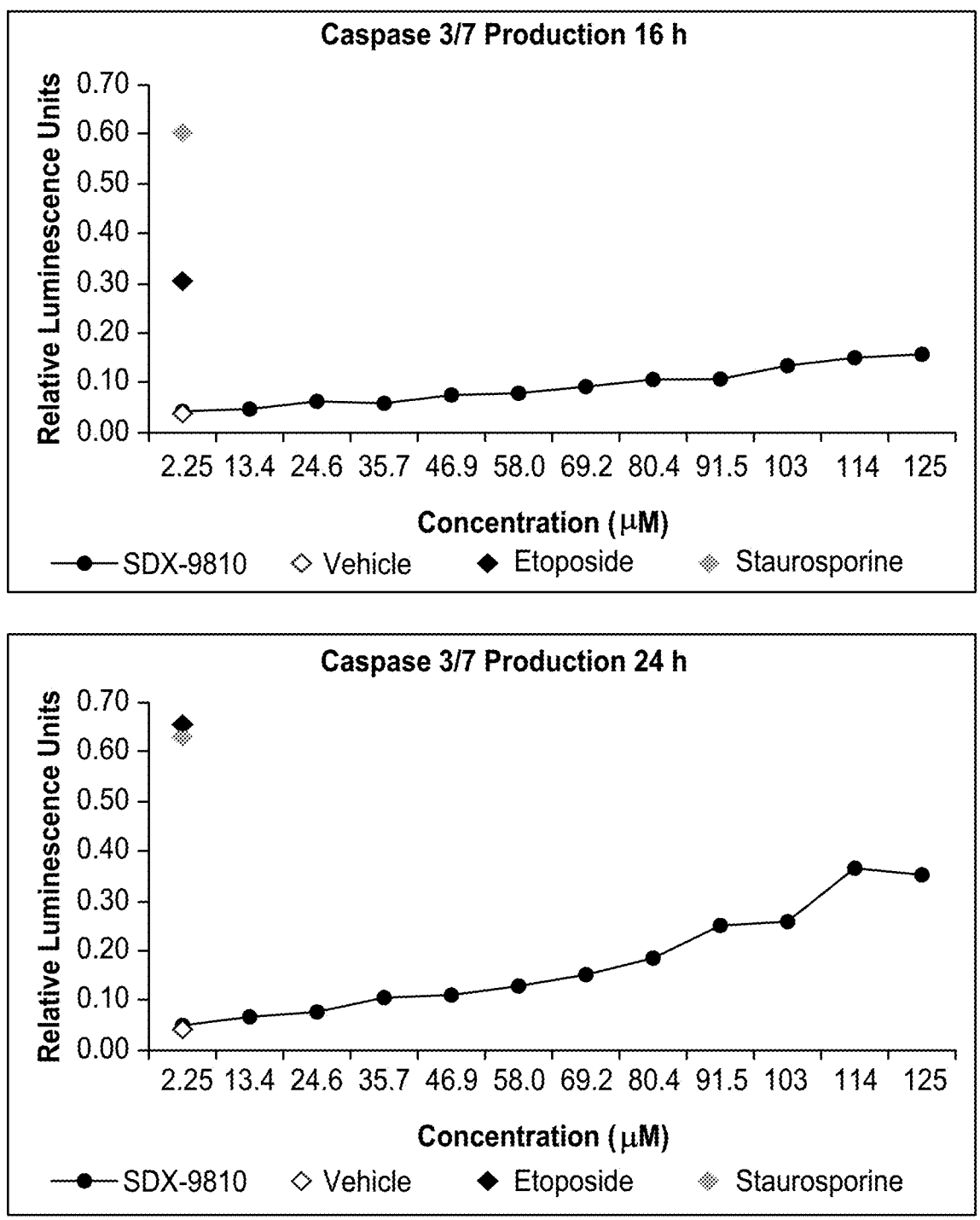
FIG. 18 shows increasing induction of caspase 3/7 markers of apoptosis over time (16 hours, top panel; 24 hours, bottom panel) in cultured human lymphoblastoid cell line TK6, seeded at $2\times10^5$ cells per ml and treated with a small molecule fumagillin derivative of the present disclosure.

The assay provides a luminogenic caspase-3/7 substrate, which contains the tetrapeptide sequence DEVD, in a reagent optimized for caspase activity, luciferase activity and cell lysis. Addition of a single Caspase-Glo® 3/7 reagent in an "add-mix-measure" format results in cell lysis, followed by caspase cleavage of the substrate and generation of a "glow-type" luminescent signal, produced by luciferase. Luminescence is proportional to the amount of caspase activity present. FIG. 18 shows a time1-dependent induction of caspase 3/7 signalling apoptosis at increasing concentrations of a small molecule of the present invention.

Example 4: Treating Cancer Using a Combination of Compound 20 (Shown in the Figures as Compound A) and a PI3K Inhibitor The following is an example showing that MetAP2 inhibitors, specifically Compound 20 (herein referred to as Compound A) can be used in combination with PI3K inhibitors, specifically alpelisib/BYL-719 to treat cancer. In this example, female nu/nu mice, age 8-10 weeks, with estrogen pellets implanted into the intra-scapular region, were used. First, the mice (n=10/treatment group) were injected with $2.5 \times 10^6$ MCF-7 cells (suspended in Matrigel) into the fourth mammary gland. When the MCF-7 mammary gland tumors reached approximately 50 mm3, the mice were subdivided into treatment groups of n=10 mice and administered the doses of Compound A indicated in Table 2. 24 hours after receiving Compound A, a subset of the treatment groups were administered the doses of BYL-719 indicated in Table 2. The dosing route and schedule for Compound A was subcutaneous injection (SC) and Q4D (once every four days) respectively. The dosing route and schedule for BYL-719 was oral (per os, PO) and QD (once daily) respectively. The vehicle control was administered once daily (QD) orally (PO).

TABLE 2

| Treatment Group Name | N (mice/treatment group) | Dose of Compound A | Dosing Schedule of Compound A | Dosing Route of Compound A | Dose of BYL-719 | Dosing Schedule of BYL-719 | Dosing Route of BYL-719 |
| --- | --- | --- | --- | --- | --- | --- | --- |
| Vehicle | 10 | — | — | — | — | — | — |
| Compound A (8 mg/kg) | 10 | 8 | Q4D | SC | — | — | — |
| Compound A (16 mg/kg) | 10 | 16 | Q4D | SC | — | — | — |
| Compound A (8 mg/kg) + BYL-719 (25 mg/kg) | 10 | 8 | Q4D | SC | 25 | QD | PO |
| Compound A (8 mg/kg) + BYL-719 (45 mg/kg) | 10 | 8 | Q4D | SC | 45 | QD | PO |
| BYL-719 (25 mg/kg) | 10 | — | — | — | 25 | QD | PO |
| BYL-719 (45 mg/kg) | 10 | — | — | — | 45 | QD | PO |

Blood glucose levels were assessed at baseline using a glucometer, once each week (4 hours post-BYL administration) and also when mice were euthanized, using blood taken from the tail of the mice. Upon euthanasia of viable mice, a terminal blood sample was obtained (cardiac puncture) and plasma was prepared from the remaining blood for biomarker analysis. Upon euthanasia, tumors were dissected, weighed and split into two portions-half were placed into buffered formalin and half were homogenized in RIPA buffer containing phosphatase and protease inhibitors, then frozen at −70° C.

Figure 22:
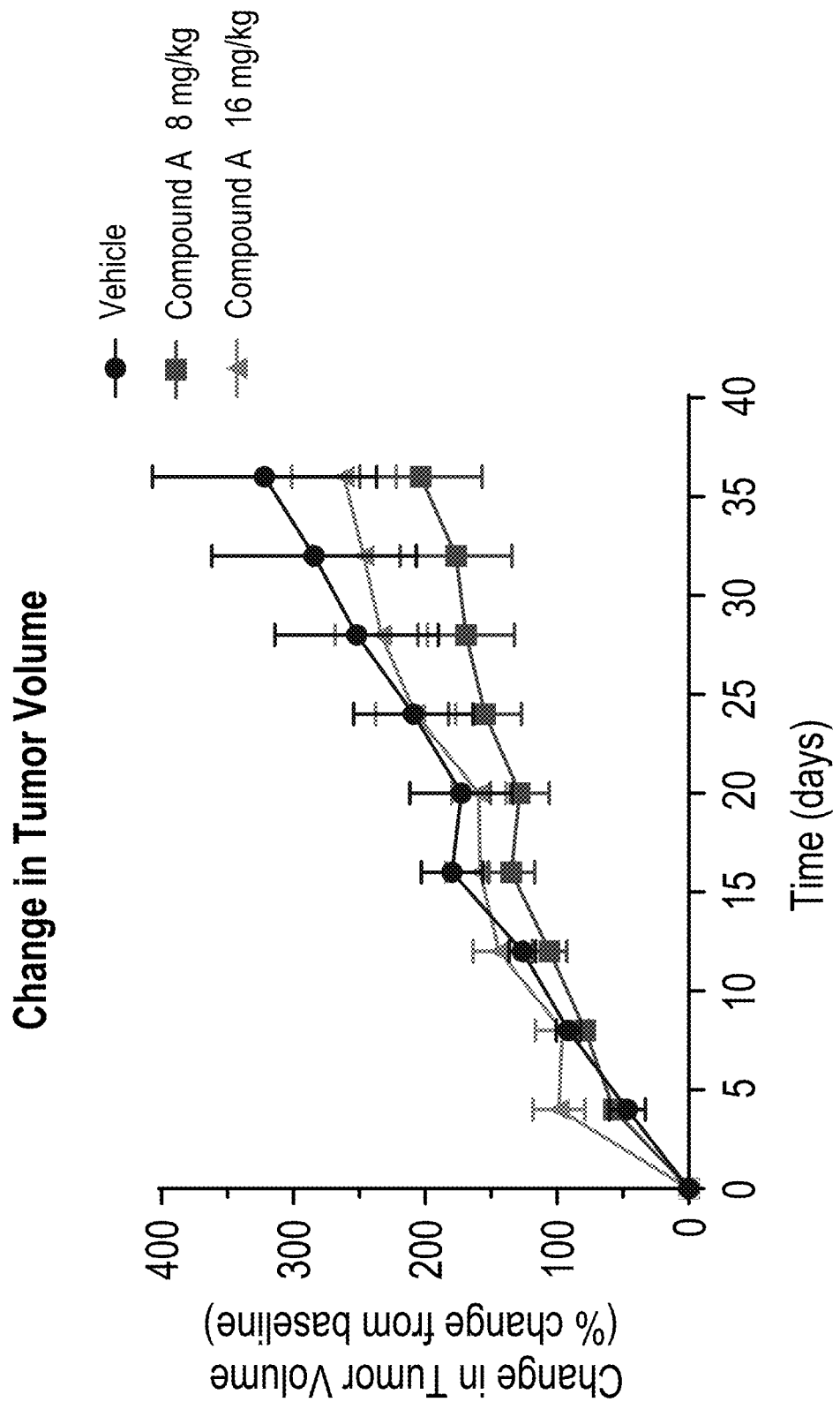
FIG. 22 is a graph showing the change in MCF-7 tumor volume (% change from baseline) in mice treated with either vehicle control, Compound 20 (referred to as Compound A) at 8 mg/kg or Compound 20 at 16 mg/kg.
Figure 23:
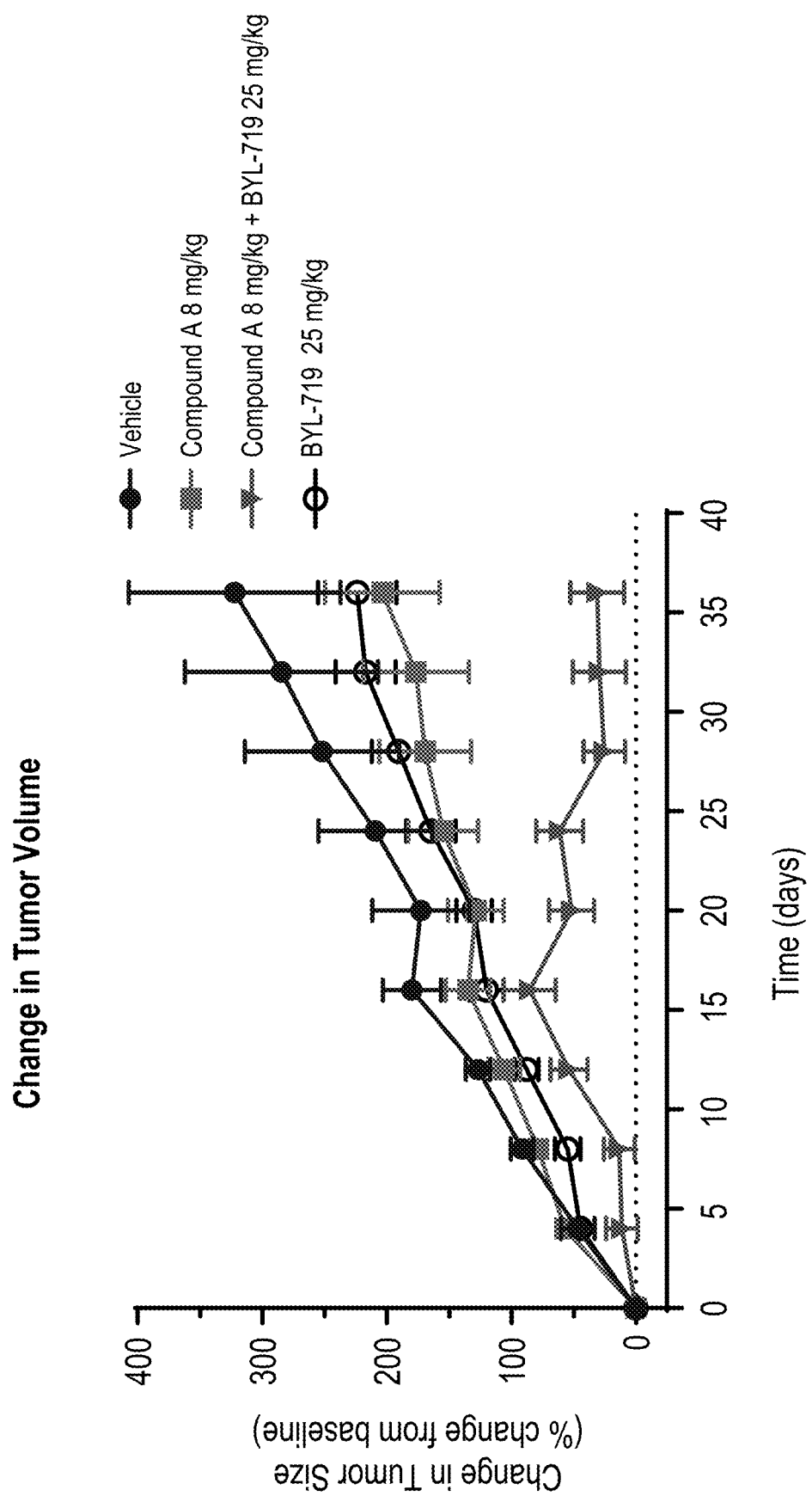
FIG. 23 is a graph showing the change in MCF-7 tumor volume (% change from baseline) in mice treated with either vehicle control, Compound 20 (referred to as Compound A) at 8 mg/kg, Compound 20 at 8 mg/kg in combination with BYL-719 at 25 mg/kg or BYL-719 alone at 25 mg/kg.
Figure 24:
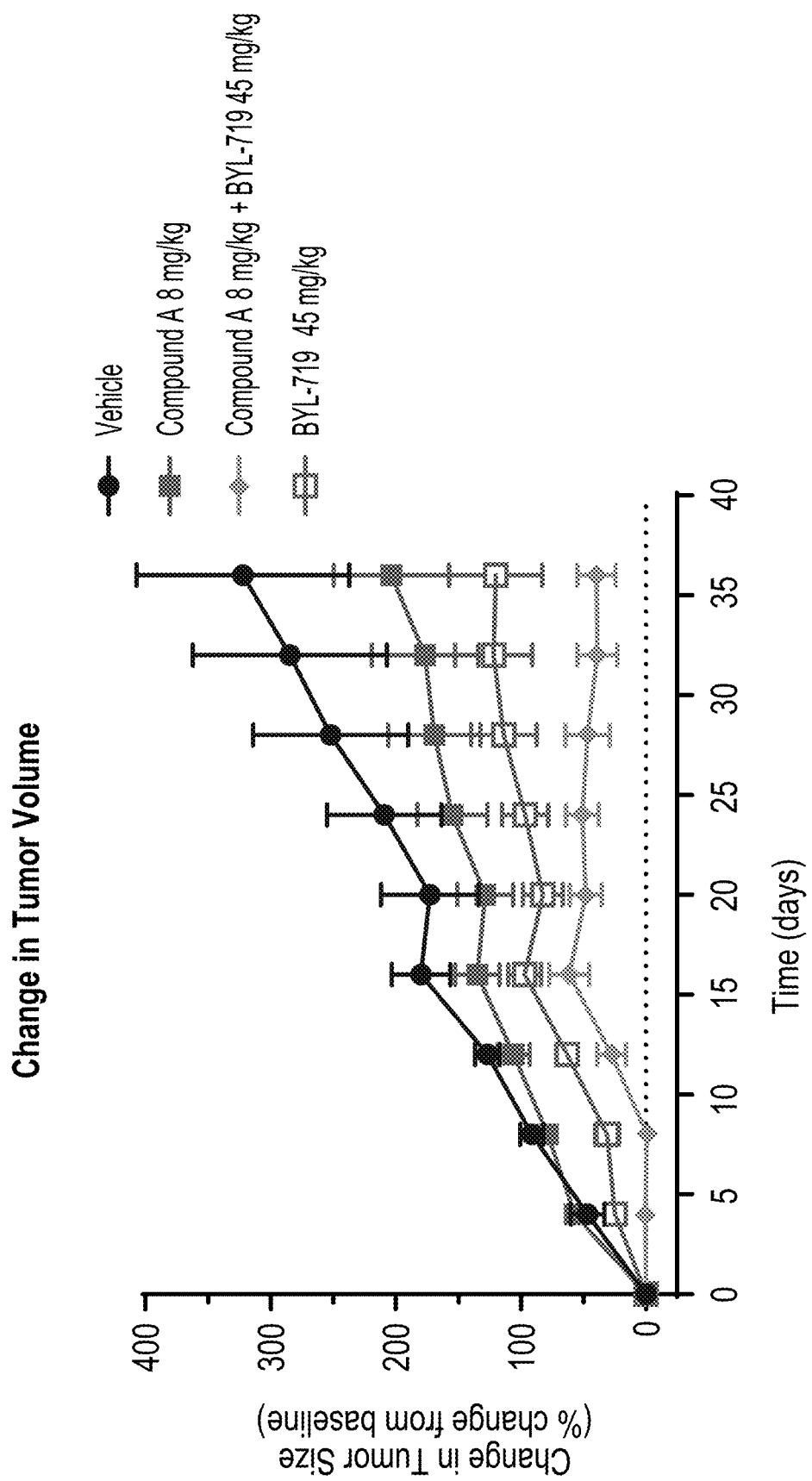
FIG. 24 is a graph showing the change in MCF-7 tumor volume (% change from baseline) in mice treated with either vehicle control, Compound 20 (referred to as Compound A) at 8 mg/kg, Compound A at 8 mg/kg in combination with BYL-719 at 45 mg/kg or BYL-719 alone at 45 mg/kg.

FIG. 22 shows the change in MCF-7 tumor volume (% change from baseline) in mice treated with either vehicle control, Compound A at 8 mg/kg or Compound A at 16 mg/kg. FIG. 23 shows the change in MCF-7 tumor volume in mice treated with either vehicle control, Compound A at 8 mg/kg, Compound A at 8 mg/kg in combination with BYL-719 at 25 mg/kg or BYL-719 alone at 25 mg/kg. FIG. 24 shows the change in MCF-7 tumor volume in mice treated with either vehicle control, Compound A at 8 mg/kg, Compound A at 8 mg/kg in combination with BYL-719 at 45 mg/kg or BYL-719 alone at 45 mg/kg. Comparison of FIGS. 22, 23 and 24 show that the effect of treatment with Compound A alone was smaller than the effect seen when Compound A was used in combination with BYL-719. The effect of using Compound A in combination with BYL-719 appeared either synergistic (with 25 mg/kg BYL-719) or additive (with 45 mg/kg BYL-719).

Figure 25:
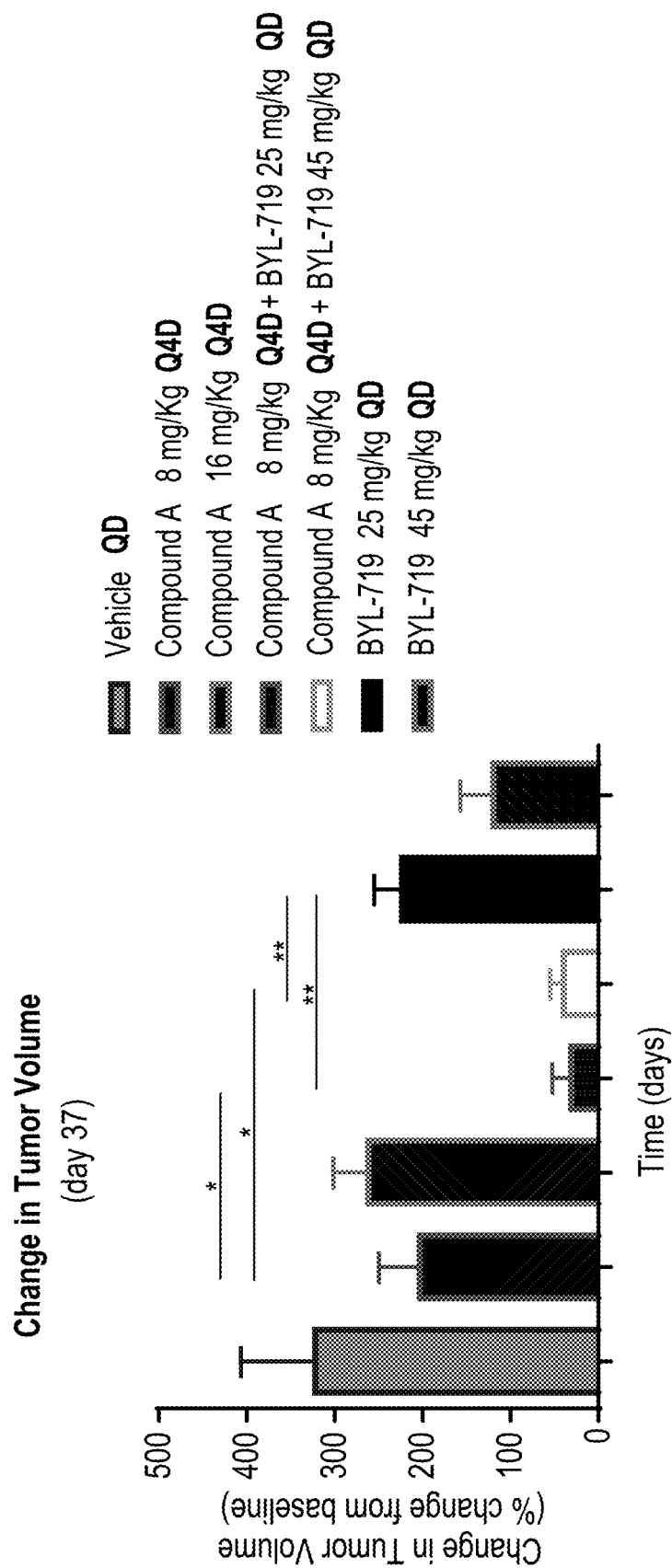
FIG. 25 is a graph showing the change in tumor volume at day 37 in mice treated either with a vehicle control, Compound 20 (referred to as Compound A) alone, BYL-719 alone or Compound 20 in combination with BYL-719.

FIG. 25 shows the change in tumor volume at day 37 in all treatment groups. FIG. 25 shows that when compared to single agent activity of Compound A or BLY-719 alone, the combination of Compound A and BYL-719 at either low BYL-719 doses (25 mg/kg) or high BYL-719 doses (45 mg/kg) significantly attenuated tumor growth. Thus, the results of this example show that MetAP2 inhibitors can be used in combination with PI3K inhibitors to treat cancer.

Figure 26:
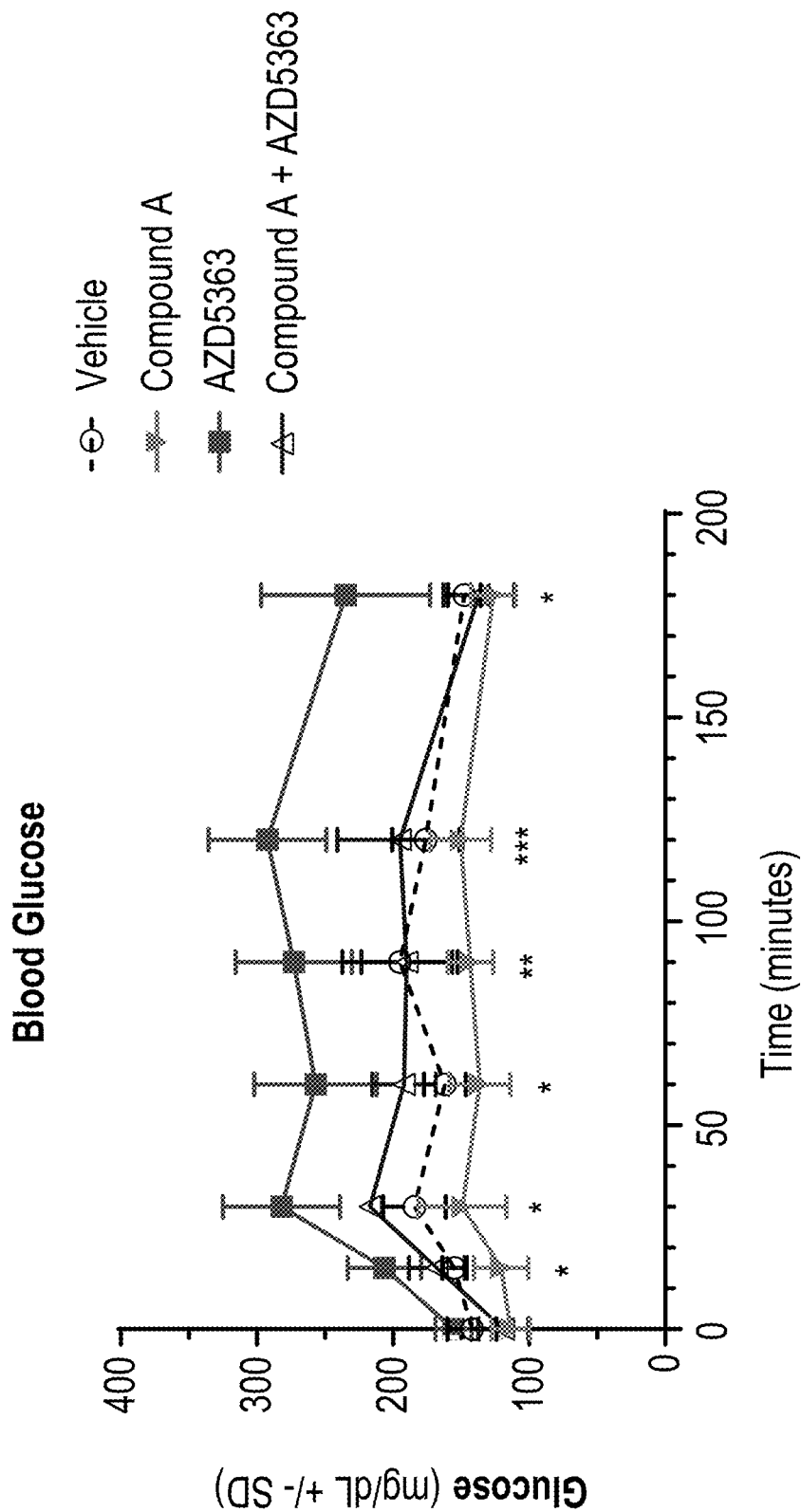
FIG. 26 is a graph showing the glucose levels in mice treated either with Compound 20 (referred to as Compound A) along, the Akt inhibitor AZD5363 alone, or a combination of compound 20 and AZD5363.

Example 5: Treating Cancer Using a Combination of Compound 20 (Shown in the Figures as Compound A) and an AKT Inhibitor The following is an example showing that MetAP2 inhibitors, specifically Compound 20 (herein referred to as Compound A) can be used in combination with AKT inhibitors, specifically AZD5363/capavasertib to treat cancer. In this example, male C57Bl/6 mice, age 8-10 weeks, were used. The mice (n=8/treatment group) were administered doses of either vehicle control (5% mannitol), Compound A alone, Compound A in combination with AZD5363 or AZD5363 alone, as indicated in Table 3. The dosing route and schedule for Compound A was subcutaneous injection (SC) and Q4D (once every four days) respectively, with a dose of 8 mg/kg. The dosing route and schedule for AZD5363 was oral (per os, PO) and QD (once daily) respectively, with a dose of 200 mg/kg. The vehicle control was administered once daily (QD) orally (PO). Blood glucose was monitored using 10 ul of blood taken from the tail of the mice and a glucometer, starting prior to the AZD5363 administration (time 0) and then again at various times points (15, 30, 60, 90, 120 and 180 minutes) after the administration of AZD5363. As shown in FIG. 26, a single dose of AZD5363 (200 mg/kg, P.O.) to normal adult male C57Bl/6 mice rapidly increased blood glucose significantly compared to vehicle, while pre-treatment of mice with SDX-7320 (8 mg/kg, S.C., Q4D, 4 doses total) significantly attenuated the rise in glucose elicited by AZD5363.

TABLE 3

| | N (mice/group) | Dose (mg/kg) | Route | Pre-Dose Time (h, d) | Number of doses |
|---|---|---|---|---|---|
| Vehicle | 8 | — | PO | | |
| Compound A | 8 | 8 (Q4D) | SC | −14 d | 3 |
| Compound A + AZD5363 | 8 | 8(Q4D)/200 (QD) | SC/PO | −14 d | 3/1 |
| AZD5363 | 8 | 200 (QD) | PO | 0 | 1 |
| Total = 32 | | | | | |

Without wishing to be bound by theory, inhibitors of the PI3K/Akt/mTOR pathway can disrupt insulin signaling and which can confer therapeutic benefit by inhibiting growth of certain tumors, especially those with activating mutations in this pathway. However due to concurrent effects on normal physiologic control of systemic glucose homeostasis, such inhibitors can also cause hyperglycemia and subsequent hyperinsulinemia. The side effect of hyperglycemia/hyperinsulinemia has been observed both in preclinical models as well as in patients participating in clinical trials of novel PI3K/Akt/mTOR inhibitors. Attenuating the induced hyperglycemia/hyperinsulinemia may provide a benefit in terms of greater reductions in tumor growth and increased survival compared to the PI3K inhibitor alone Thus, this example demonstrate that the conjugates and compounds of the present disclosure, including Compound A, attenuate the hyperglycemia induced by Akt inhibitors such as AZD5363. Attenuation of such a side effect by Compound A can provide a benefit in terms of enhanced anti-tumor activity when dosed in combination with AZD5363, making the combination of the conjugates/compounds of the present disclosure and Akt inhibitors a powerful method of treating cancer in a subject.

Example 6—Treating Cancer Using a Combination of a MetAP2 Inhibitor and a PI3K Inhibitor The following is an example showing that MetAP2 inhibitors, specifically ZGN-1061 can be used in combination with PI3K inhibitors, specifically BYL-719, to treat cancer and to attenuate treatment-induced metabolic dysfunction. In this example, male C57Bl/6 mice, age 10-12 weeks, were used. The mice (n=8/treatment group) were administered doses of either vehicle control (10 mM phosphate in 5% mannitol, pH 7.2), ZGN-1061 alone, ZGN-1061 in combination with BYL-719 or BYL-719 alone, as indicated in Table 4. The dosing route and schedules for each compound/combination of compounds are shown in Table 4. In Table 4, the time of dose indicates the time relative to the administration of BYL-719. Blood glucose was monitored using 10 ul of blood taken from the tail of the mice and a glucometer, starting prior to the BYL-719 administration (time 0) and then again at various times points (15, 30, 60, 90, 120 and 180 minutes) after the administration of BYL-719.

TABLE 4

| | N (mice/group) | Dose (mg/kg) | Route | Time of Dose (hours, relative to BYL-719) | Number of Doses |
|---|---|---|---|---|---|
| Vehicle | 8 | — | PO | 0 | |
| ZGN-1061 | 8 | 0.5 | SC | −24 h | 1 |
| ZGN-1061 | 8 | 0.5 (QD) | SC | −72 h | 3 (QD) |
| ZGN-1061 + BYL-719 | 8 | 0.5/45 | SC/PO | −4 h/0 | 1/1 |
| ZGN-1061 + BYL-719 | 8 | 0.5/45 | SC/PO | −24 h/0 | 1/1 |
| ZGN-1061 + BYL-719 | 8 | 0.5/45 | SC/PO | −72 h/0 | 3 (QD)/1 |
| BYL-719 | 8 | 45 | PO | 0 | 1 |
| Total = 56 | | | | | |

Figure 27:
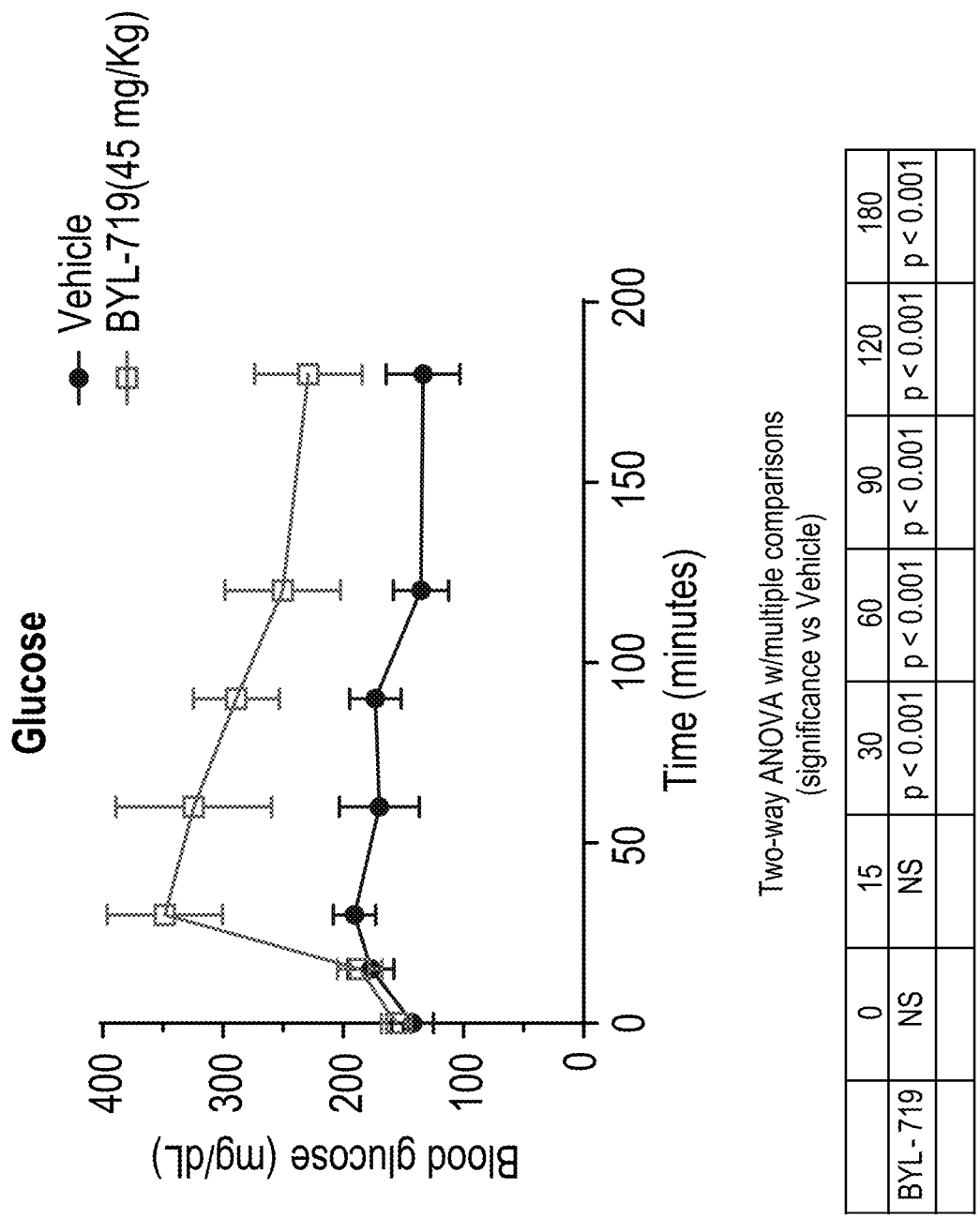
FIG. 27 is a graph showing blood glucose levels in mice treated either with vehicle control or the PI3K inhibitor BYL-719.
Figure 28:
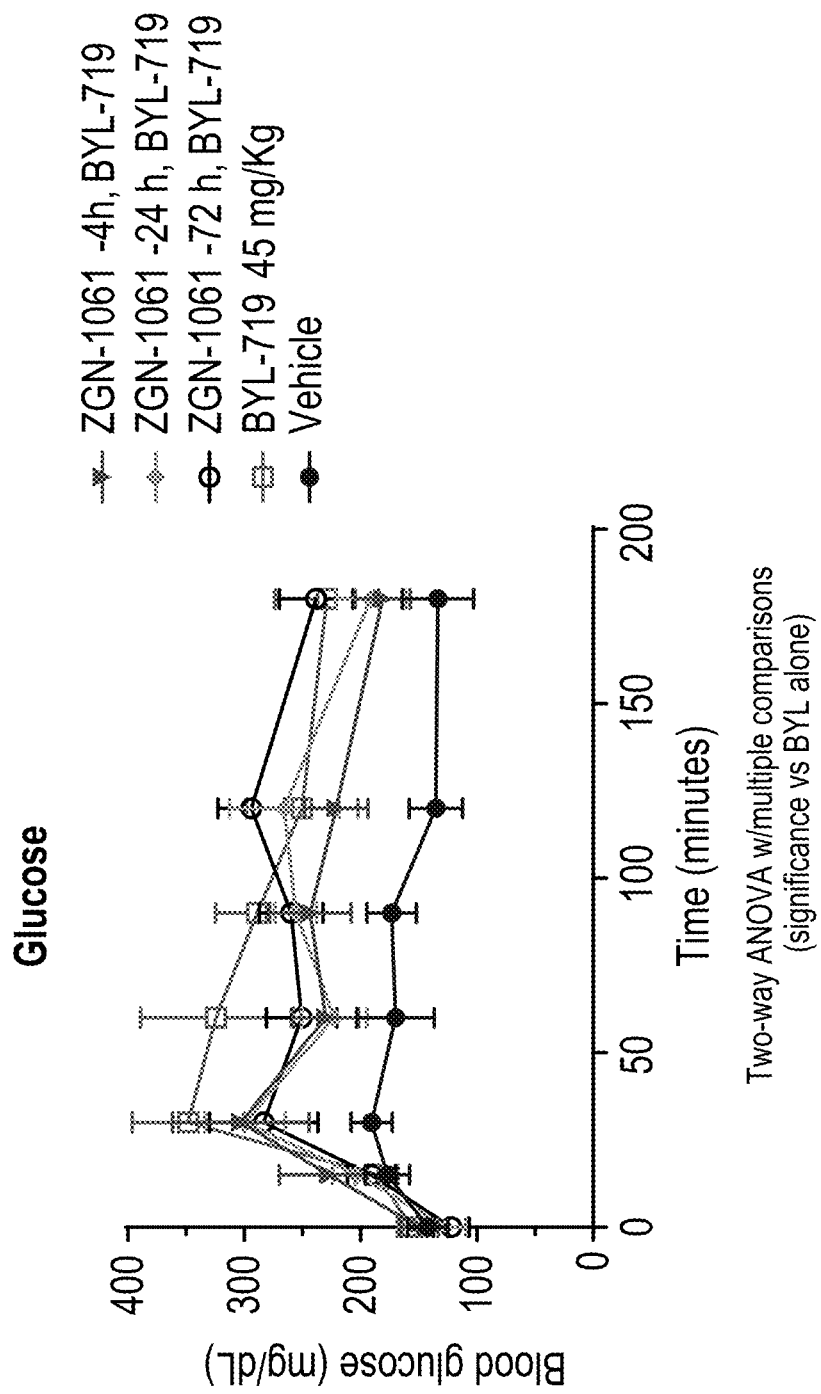
FIG. 28 is a graph showing blood glucose levels in mice treated either with a vehicle control, ZGN-1061 alone, BYL-719 alone or a combination of ZGN-1061 and BYL-719.

As shown in FIG. 27, a of BYL-719 elicited robust hyperglycemia. However, as shown in of FIG. 28, pre-treatment of mice with the MetAP2 inhibitor (ZGN-1061) for various times prior to dosing with BYL-719 attenuated hyperglycemia induced by BYL-719. These results indicated that MetAP2 inhibitors, such as ZGN-1061, can attenuate PI3K inhibitor-induced hyperglycemic, indicating that a combination of MetAP2 inhibitors and PI3K inhibitors are useful in treating cancer patients, particularly cancer patients with treatment-induced hyperglycemia.

What is claimed is:

1. A method for treating, or ameliorating at least one symptom of, cancer in a subject in need thereof comprising administering a therapeutically effective amount of at least one compound of the Formula

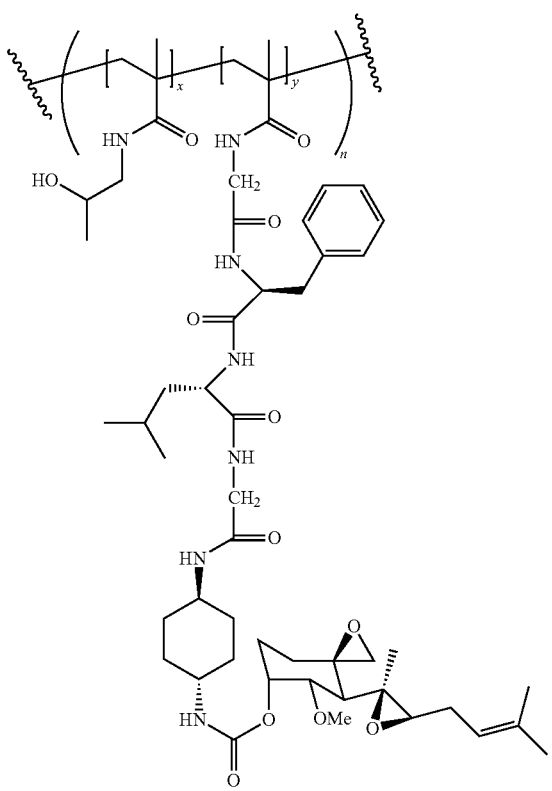

wherein,
x is in the range of 1 to about 450;
y is in the range of 1 to about 30;
n is in the range of 1 to about 100;
or a pharmaceutically acceptable salt thereof, in combination with a therapeutically effective amount of alpelisib (BYL-719), wherein the subject is pre-treated by administering at least one therapeutically effective amount of the at least one compound at least 10 days prior to the administration of alpelisib, wherein administration of the at least one compound attenuates alpelisib-induced hyperglycemia.

2. The method of claim 1, wherein the at least one compound is administered in an amount from about 0.0001 mg/kg to about 5 mg/kg of body weight per day.

3. The method of claim 1, wherein the at least one compound is administered in an amount from about 0.001 to about 0.1 mg/kg of body weight per day.

4. The method of claim 1, wherein that at least one compound and the alpelisib (BYL-719) are administered sequentially or in a substantially simultaneous manner after pre-treatment with the at least one compound.

5. The method of claim 1, wherein that at least one compound is administered on a q4d dosing schedule.

6. The method of claim 1, wherein that at least one compound is administered on a q7d dosing schedule.

7. The method of claim 1, wherein that at least one compound is administered once every two weeks.

8. The method of claim 1, wherein that at least one compound is administered about 1 to 4 times per month.

9. The method of claim 1, wherein said subject is treated for at least about six months, for at least about one year, at least about two years, or at least about three years.

10. The method of claim 1, wherein the at least one compound is administered parenterally or subcutaneously.

11. The method of claim 1, wherein the cancer is postmenopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof.

12. The method of claim 1, wherein the cancer is breast cancer.

13. The method of claim 1, wherein the cancer is HR+/Her2− breast cancer.

14. The method of claim 1, wherein the cancer is postmenopausal HR+/Her2− breast cancer.

* * * * *

UNITED STATES PATENT AND TRADEMARK OFFICE
CERTIFICATE OF CORRECTION

| | |
|---|---|
| PATENT NO. | : 11,612,577 B2 |
| APPLICATION NO. | : 16/666249 |
| DATED | : March 28, 2023 |
| INVENTOR(S) | : Cornelius et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 314 days.

Signed and Sealed this
Twelfth Day of November, 2024

*Katherine Kelly Vidal*

Katherine Kelly Vidal
*Director of the United States Patent and Trademark Office*